(12) United States Patent
Ghidini et al.

(10) Patent No.: US 8,481,517 B2
(45) Date of Patent: Jul. 9, 2013

(54) PYRROLIDINE COMPOUNDS, PHARMACEUTICAL COMPOSITIONS CONTAINING THE SAME, DEVICES CONTAINING THE SAME, AND METHODS OF TREATING ASTHMA OR CHRONIC OBSTRUCTIVE PULMONARY DISEASE BY ADMINISTERING THE SAME

(75) Inventors: Eleonora Ghidini, Parma (IT); Andrea Rizzi, Parma (IT); Andrea Virdis, Parma (IT); Fabio Rancati, Parma (IT); Anna Rencurosi, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 50 days.

(21) Appl. No.: 13/020,988

(22) Filed: Feb. 4, 2011

(65) Prior Publication Data
US 2011/0201580 A1 Aug. 18, 2011

(30) Foreign Application Priority Data
Feb. 5, 2010 (EP) .................................... 10152731

(51) Int. Cl.
*A61K 31/58* (2006.01)
*C07J 71/00* (2006.01)

(52) U.S. Cl.
USPC ........................................... 514/176; 540/49

(58) Field of Classification Search
CPC .................................. C07J 71/00; A61K 31/58
USPC ............................................. 540/49; 514/176
See application file for complete search history.

(56) References Cited

U.S. PATENT DOCUMENTS

| 4,018,757 A | 4/1977 | Varma et al. |
| 4,474,702 A | 10/1984 | Karanewsky et al. |
| 2011/0065678 A1 | 3/2011 | Armani et al. |

FOREIGN PATENT DOCUMENTS

| GB | 1 578 446 | 11/1980 |
| WO | 2006/005611 | 1/2006 |

OTHER PUBLICATIONS

U.S. Appl. No. 13/421,128, filed Mar. 15, 2012, Ghidini, et al.
U.S. Appl. No. 13/421,150, filed Mar. 15, 2012, Ghidini, et al.
European Search Report in Application No. 10152731.5, issued Jun. 29, 2010.
Green, M.J. et al., "Journal of Medicinal Chemistry", vol. 25. No. 12 (1982), p. 1492-1495.
U.S. Appl. No. 13/561,134, filed Jul. 30, 2012, Ghidini, et al.

*Primary Examiner* — Barbara P Badio
(74) *Attorney, Agent, or Firm* — Oblon, Spivak, McClelland, Maier & Neustadt, L.L.P.

(57) ABSTRACT

The present invention relates to novel anti-inflammatory and antiallergic compounds of the glucocorticosteroid series, methods of preparing such compounds, pharmaceutical compositions comprising them, combinations and therapeutic uses thereof. More particularly, the invention relates to glucocorticosteroids that are derivatives of pyrrolidine.

15 Claims, No Drawings

PYRROLIDINE COMPOUNDS, PHARMACEUTICAL COMPOSITIONS CONTAINING THE SAME, DEVICES CONTAINING THE SAME, AND METHODS OF TREATING ASTHMA OR CHRONIC OBSTRUCTIVE PULMONARY DISEASE BY ADMINISTERING THE SAME

CROSS REFERENCES TO RELATED APPLICATIONS

This application claims priority to European Patent Application No. 10152731.5 filed on Feb. 5, 2010, which is incorporated herein by reference in its entirety.

BACKGROUND OF THE INVENTION

1. Field of the Invention

The present invention relates to novel anti-inflammatory and antiallergic compounds of the glucocorticosteroid series. The present invention also relates to methods of preparing such a compound, pharmaceutical compositions which contain such a compound, combinations which contain such a compound, and therapeutic uses of such a compound, composition, or combination. More particularly, the present invention relates to glucocorticosteroids that are derivatives of pyrrolidine.

2. Discussion of the Background

Corticosteroids are potent anti-inflammatory agents, which are able to decrease the number, activity, and movement of inflammatory cells. Corticosteroids are commonly used to treat a wide range of chronic and acute inflammatory conditions including asthma, chronic obstructive pulmonary disease (COPD), allergic rhinitis, rheumatoid arthritis, inflammatory bowel disease, and autoimmune diseases.

Corticosteroids mediate their effects through the glucocorticoid receptor (GR). The binding of corticosteroids to GR induces its nuclear translocation which, in turn, affects a number of downstream pathways via DNA-binding-dependent (e.g. transactivation) and -independent (e.g. transrepression) mechanisms.

Corticosteroid, for treating chronic inflammatory conditions in the lung such as asthma and COPD, are currently administered through inhalation. One of the advantages of employing inhaled corticosteroids (ICS) is the possibility of delivering the drug directly at the site of action, limiting systemic side-effects, thus resulting in a more rapid clinical response and a higher therapeutic ratio.

Although ICS treatment can yield important benefits, especially in asthma, it is important to minimise ICS systemic exposure which leads to the occurrence and severity of unwanted side effects that may be associated with chronic administration. Moreover, the limited duration of action of ICS currently available in the clinical practice contributes to suboptimal management of the disease. While the inhaler technology is the key point to target the lung, the modulation of the substituents on the corticosteroids molecular scaffold is important for the optimization of pharmacokinetic and pharmacodynamic properties in order to decrease oral bioavailability, confine pharmacological activity only in the lung (prodrugs and soft drugs) and increase systemic clearance. Moreover, long-lasting ICS activity in the lung is highly desirable, as once daily administration of ICS would allow the reduction of the frequency of administration and, thus, substantially improve patient compliance and, as a result, disease management and control. In sum, there is a pressing medical need for developing ICS with improved pharmacokinetic and pharmacodynamic characteristics.

Fluticasone furoate is an example of enhanced affinity glucocorticoid that has been developed as topical therapy for allergic rhinitis with a unique combination of pharmacodynamic and physicochemical properties which render this compound long acting in the lung and rapidly inactivated by hepatic metabolism to reduce systemic side effects (see, Salter et al., American Journal of Physiology, vol. 293, no. 3, L660-L667, 2007).

To the extent of our knowledge, glucocorticoids pyrrolidine derivatives have never been described in the literature.

SUMMARY OF THE INVENTION

Accordingly, it is one object of the present invention to provide novel anti-inflammatory and antiallergic compounds of the glucocorticosteroid series.

It is another object of the present invention to provide novel anti-inflammatory and antiallergic compounds of the glucocorticosteroid series with improved pharmacological properties.

It is another object of the present invention to provide novel methods of preparing such a compound.

It is another object of the present invention to provide novel pharmaceutical compositions which contain such a compound.

It is another object of the present invention to provide novel combinations which contain such a compound.

It is another object of the present invention to provide novel therapeutic uses of such a compound, composition, or combination.

It is another object of the present invention to provide novel methods of treating certain diseases and conditions by administering such a compound, composition, or combination.

These and other objects, which will become apparent during the following detailed description, have been achieved by the inventors' discovery that compounds of general formula (I), and to the corresponding compounds of general formula (I') wherein the configuration of some stereogenic centers is fixed, which are novel pyrrolidine derivatives, belonging to glucocorticosteroid series, exhibit good pharmacological properties.

The present invention is also directed to pharmaceutically acceptable acid addition salts of compounds of general formula (I) and (I'), to methods of preparing such compounds, to combinations with one or more active ingredients selected from the classes of β2-agonist, antimuscarinic agents, PDE4 inhibitors, P38 MAP kinase inhibitors and IKK2 inhibitors, to pharmaceutical compositions comprising them and to therapeutic uses thereof.

The pyrrolidine glucocorticoids of the present invention are profiled in vitro by potency and efficacy in: a) binding to the GR; b) inducing nuclear translocation of GR; and c) inhibiting inflammatory responses in macrophages. In addition, the optimization of pharmacokinetics/pharmacodynamic properties is pursued with the aim of improving the anti-inflammatory potency, efficacy and duration of action in the lung and to reduce systemic side effects. When administered topically in the lung in experimental animal models the pyrrolidine glucocorticoids of the present invention are characterized by a good anti-inflammatory potency and efficacy which is associated with a long duration of action and a limited systemic exposure.

DETAILED DESCRIPTION OF THE PREFERRED EMBODIMENTS

According to a first aspect, the present invention is directed to compounds of general formula (I):

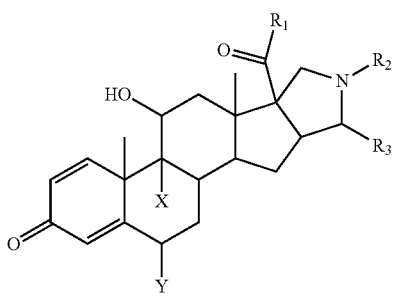

wherein:
$R_1$ is $(CH_2)_n$—V—$(CH_2)_{n'}$—Z—$R_4$, wherein:
n and n' are independently 0, 1 or 2;
V is absent or is selected from the group consisting of —O—, —S—, —OCOO, and NH;
Z is a single bond or is selected from the group consisting of —S—, —O—, carbonyl, carboxyl, $(C_3$-$C_8)$cycloalkyl, —$NR_5$—, and —$NR_5C(O)$—, wherein $R_5$ is H or is selected from the group consisting of $(C_1$-$C_6)$alkyl, $(C_3$-$C_8)$cycloalkyl, aryl, aryl$(C_1$-$C_6)$alkyl, aryl$(C_3$-$C_8)$cycloalkylene, and heteroaryl, optionally substituted by CN;
$R_4$ is selected from the group consisting of:
—H, —OH, —CN, —SH or halogen;
$(C_1$-$C_6)$alkyl, $(C_1$-$C_6)$alkylsulfonyl, $(C_1$-$C_6)$alkylcarboxyl, $(C_1$-$C_6)$alkylcarbonyl and $(C_3$-$C_8)$cycloalkyl, wherein one or more of the hydrogen atoms of the alkyl groups may be optionally substituted by one or more groups selected from oxo, —CN, —SH or halogen;
a mono-, bi- or tricyclic saturated, partially saturated or fully unsaturated ring, such as $(C_3$-$C_8)$cycloalkyl, hetero$(C_3$-$C_8)$cycloalkyl, aryl or heteroaryl optionally substituted by one or more halogen atoms or oxo groups; and
wherein when $R_4$ and $R_5$ are both $(C_1$-$C_6)$alkyl, they may form a 4-8 membered heterocycle together with the nitrogen atom to which they are bonded;
$R_2$ is $(CH_2)_m$—W—W'-M-$R_6$, wherein:
m=0 or 1 to 6;
W is a single bond or is selected from the group consisting of —S—, —O—, carbonyl, and thiocarbonyl;
W' is absent, NH or arylene group;
M is absent or is selected from the group consisting of $(C_1$-$C_6)$alkylsulfanyl, $(C_1$-$C_6)$alkylsulfonyl and $(C_1$-$C_6)$alkylsulfinyl;
$R_6$ is selected from the group consisting of:
—H;
$(C_1$-$C_6)$alkyl;
a mono-, bi-, or tricyclic saturated, partially unsaturated or fully unsaturated ring, such as $(C_3$-$C_8)$cycloalkyl, aryl, hetero$(C_3$-$C_8)$cycloalkyl, or heteroaryl having 3 to 10 ring atoms wherein the hetero$(C_3$-$C_8)$cycloalkyl and the heteroaryl have at least one ring atom which is a heteroatomic group selected from the group consisting of N, NH, S, and O, and wherein any of the above rings is optionally substituted by one or more groups selected from oxo, OH, CN, COOH, $(C_1$-$C_6)$alkoxy, halo$(C_1$-$C_6)$alkoxy, aryl$(C_1$-$C_6)$alkyl, $(C_1$-$C_6)$alkyl, halo$(C_1$-$C_6)$alkyl, cyano, OCO$(C_1$-$C_6)$alkyl and halogen;
—$OR_7$
—$OCOR_7$
—$COR_7$
—$COOR_8$
—$CONR_9R_{10}$
—$CSNR_9R_{10}$
—$S(O)_2R_{11}$
wherein $R_7$, $R_8$ and $R_{11}$ are independently selected from the group consisting of $(C_1$-$C_6)$alkyl, $(C_2$-$C_6)$alkenyl, $(C_3$-$C_8)$cycloalkyl, $(C_1$-$C_6)$alkylaryl, aryl$(C_1$-$C_6)$alkyl, and a saturated, partially unsaturated or fully unsaturated optionally fused ring such as aryl, heterocyclo$(C_1$-$C_6)$alkyl or heteroaryl having 3 to 10 ring atoms wherein at least one ring atom is a heteroatomic group selected from the group consisting of N, NH, S, and O, which groups may be optionally substituted with one or more substituents selected from the group consisting of halogen, cyano, nitro, $(C_1$-$C_6)$ alkyl, aryl, heteroaryl, hydroxy, amino or alkoxy;
and wherein $R_9$ and $R_{10}$ are independently selected from the group consisting of H, $(C_1$-$C_6)$alkyl, $(C_3$-$C_8)$cycloalkyl, aryl$(C_1$-$C_6)$alkyl, and a saturated, partially unsaturated or fully unsaturated optionally fused ring such as aryl, heterocyclo$(C_1$-$C_6)$alkyl or heteroaryl having 3 to 10 ring atoms wherein at least one ring atom is a heteroatomic group selected from the group consisting of N, NH, S, and O, which groups may be optionally substituted with one or more substituents selected from the group consisting of halogen, cyano, nitro, $(C_1$-$C_6)$ alkyl, hydroxyl, and when $R_9$ and $R_{10}$ are both $(C_1$-$C_6)$ alkyl, they may form a 4-8 membered heterocycle together with the nitrogen atom to which they are bonded;
$R_3$ is selected from the group consisting of:
—H;
aryl;
$C(O)OR_{12}$ wherein $R_{12}$ is selected from the group consisting of H, $(C_1$-$C_6)$alkyl, $(C_3$-$C_8)$cycloalkyl, aryl and heteroaryl;
$C(O)NR_{13}R_{14}$ wherein $R_{13}$ and $R_{14}$ are independently selected from the group consisting of H, $(C_1$-$C_6)$alkyl, $(C_3$-$C_8)$cycloalkyl, aryl$(C_1$-$C_6)$alkyl and a saturated, partially unsaturated or fully unsaturated optionally fused ring such as aryl, hetero$(C_3$-$C_8)$cycloalkyl or heteroaryl having 3 to 10 ring atoms wherein at least one ring atom is a heteroatomic group selected from the group consisting of N, NH, S, and O, which groups may be optionally substituted with one or more substituents selected from the group consisting of halogen, cyano, nitro, $(C_1$-$C_6)$alkyl, hydroxyl, and when $R_{13}$ and $R_{14}$ are both $(C_1$-$C_6)$alkyl, they may form a 4-8 membered heterocycle together with the nitrogen atom to which they are bonded;
X and Y are independently selected from the group consisting of H and halogen;
and pharmaceutically acceptable salts thereof.

The term "halogen atoms" as used herein includes fluorine, chlorine, bromine and iodine.

As used herein, the expression "$(C_1$-$C_6)$alkyl" refers to linear or branched alkyl groups wherein the number of constituent carbon atoms is in the range 1 to 6. Examples of alkyl groups are methyl, ethyl, n-propyl, isopropyl, t-butyl, n-pentyl and n-hexyl.

The term "($C_1$-$C_6$)alkoxy" refers to alkyl-oxy (e.g. alkoxy) groups.

The expression "halo($C_1$-$C_6$)alkyl" refers to ($C_1$-$C_6$)alkyl wherein one or more hydrogen atoms are replaced by halogen atoms.

The expression "halo($C_1$-$C_6$)alkoxy" refers to ($C_1$-$C_6$) alkoxy wherein one or more hydrogen atoms are replaced by halogen atoms.

The expression "($C_2$-$C_6$)alkenyl" refers to unsaturated straight or branched carbon chains wherein the number atoms is in the range 2 to 6.

The derived expressions "halo($C_2$-$C_6$)alkenyl", "($C_2$-$C_6$) alkynyl" and halo($C_2$-$C_6$)alkynyl" are to be construed in an analogous manner.

As used herein, the expression "($C_3$-$C_8$)cycloalkyl" refers to cyclic non-aromatic hydrocarbon groups. Examples include cyclopropyl, cyclobutyl, cyclopentyl, cyclohexyl and cycloheptyl.

As used herein, the expression "hetero($C_3$-$C_8$)cycloalkyl" refers to "($C_3$-$C_8$)cycloalkyl" in which at least one ring atom is a heteroatomic group selected from the group consisting of N, NH, S, and O.

The expressions "($C_1$-$C_6$)alkylsulfanyl", "($C_1$-$C_6$)alkylsulfinyl" and "($C_1$-$C_6$)alkylsulfinyl" refer, respectively, to alkyl-S—, alkyl-SO— and alkyl-$SO_2$-groups.

As used herein, the expression "aryl" refers to mono, bi- or tricyclic ring systems which have 5 to 20 ring atoms, preferably from 5 to 15 and wherein at least one ring is aromatic.

As used herein, the expression "heteroaryl" refers to mono, bi- or tricyclic ring systems which have 5 to 20 ring atoms, preferably from 5 to 15, in which at least one ring is aromatic and in which at least one ring atom is a heteroatomic group selected from the group consisting of N, NH, S, and O.

Examples of suitable monocyclic systems include thiophene, cyclopentadiene, benzene, pyrrole, pyrazole, imidazole, isoxazole, oxazole, isothiazole, thiazole, pyridine, imidazolidine, piperidine and furan radicals such as tetrahydrofuran.

Examples of suitable bicyclic systems include naphthalene, biphenyl, purine, pteridine, benzotriazole, quinoline, isoquinoline, indole, isoindole, benzofuran, benzodioxane and benzothiophene radicals.

Examples of suitable tricyclic systems include fluorene radicals.

As used herein, the expressions "arylalkyl" and "aryl($C_3$-$C_8$)cycloalkyl" refer to a "($C_1$-$C_6$)alkyl" and "($C_3$-$C_8$)cycloalkyl" being substituted by aryl as above defined.

Examples of suitable arylalkyl groups include benzyl and diphenylmethyl.

Examples of suitable heteroarylalkyl groups include thiophenylmethyl.

Optionally in any of the said rings including ($C_3$-$C_8$)cycloalkyl, aryl, heteroaryl and the like, one or more hydrogen atoms can be replaced by a group selected from halogen atoms, hydroxy, nitrile, amino, ($C_1$-$C_6$)alkylamino, dialkylamino, ($C_1$-$C_6$)alkyl, halo($C_1$-$C_6$)alkyl, ($C_1$-$C_6$)alkylsulfonyl, carboxy($C_1$-$C_6$)alkyl, ($C_1$-$C_6$)alkylcarbonyloxy, ($C_1$-$C_6$) alkyloxy, ($C_1$-$C_6$)alkylsulfinyl, ($C_1$-$C_6$)alkyloxycarbonyl, ($C_1$-$C_6$)alkylaminocarbonyl, ($C_1$-$C_6$)arylalkoxy and oxo.

It will be apparent to those skilled in the art that compounds of general formula (I) contain at least asymmetric centers at the positions 4a, 4b, 5, 6a, 6b, 9a, 10a, 10b and, depending on substituents, also at position 9 and 12. As a consequence, compounds of general formula (I) may exist as many optical stereoisomers and mixtures thereof.

Therefore the invention is also directed to all of these forms of the compounds of formula (I) and mixtures thereof.

Preferred compounds, however, are those of general formula (I) wherein the configuration of some of stereogenic centers is fixed and specifically wherein the configuration of the carbon atom in position 5 is S, in position 6a is S, in position 6b is S, in position 9a is R, in position 10a is S, in position 10b is S, in position 4a is S when X is halogen or 4a is R when X is hydrogen, in position 4b is R when X is halogen or 4b is S when X is hydrogen, and in position 12 is S when X is halogen, which are represented by the formula (I') below:

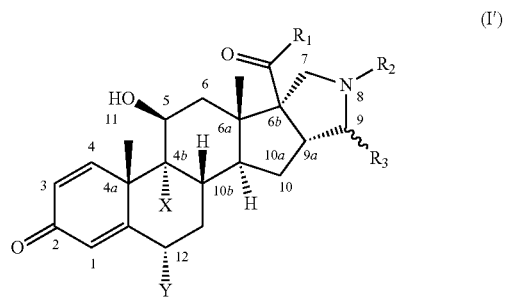

wherein the symbol (⸹)

represents an unspecified bond, which indicates an asymmetric carbon atom in position 9, wherein the configuration may be R or S, and wherein the values of $R_1$, $R_2$, $R_3$, X, and Y are as defined above in free or salt form.

Compounds of general formula (I) and (I') may be capable of forming acid addition salts, particularly pharmaceutically acceptable acid addition salts. Pharmaceutically acceptable acid addition salts of the compounds of formula (I) and (I') include those of inorganic acids, for example hydrohalic acids such as hydrofluoric acid, hydrochloric acid, hydrobromic acid or hydroiodic acid, as well as nitric acid, sulfuric acid, phosphoric acid; and organic acids, for example aliphatic monocarboxylic acids such as formic acid, acetic acid, trifluoroacetic acid, and propionic acid; aliphatic hydroxyl acids such as lactic acid, citric acid, tartaric acid or malic acid; dicarboxylic acids such as maleic acid or succinic acid; aromatic carboxylic acids such as benzoic acid; aromatic hydroxyl acids, and sulfonic acids.

Likewise, pharmaceutically acceptable salts of the compounds of formula (I) and (I') include those of bases, such as amines.

These salts may be prepared from compounds of formula (I) and (I') by known salt-forming procedures.

A preferred group of compounds of general formula (I') is that wherein $R_1$ is $(CH_2)_n$—V—$(CH_2)_{n'}$—Z—$R_4$, n and n' are independently 0, 1 or 2; V is absent or is selected from the group consisting of O, S, OCOO and NH; Z is a single bond or is selected from the group consisting of O, carbonyl, carboxyl, ($C_3$-$C_8$)cycloalkyl, —S— and —$NR_5$, wherein $R_5$ is H or is selected from the group consisting of ($C_1$-$C_6$)alkyl, ($C_3$-$C_8$)cycloalkyl, aryl, aryl($C_1$-$C_6$)alkyl, aryl($C_3$-$C_8$)cycloalkyl and heteroaryl, optionally substituted by CN; $R_4$ is selected from the group consisting of H, CN, OH, $COR_8$, halogen, ($C_1$-$C_6$)alkyl, aryl and hetero($C_3$-$C_8$)cycloalkyl which may be optionally substituted by one or more halogen atoms or oxo and wherein $R_8$ is ($C_1$-$C_6$)alkyl optionally substituted by halogen; $R_2$ is $(CH_2)_m$—W—W'-M-$R_6$ wherein m=0 to 4; W is a single bond or is selected from the group consisting of —O—, carbonyl or thiocarbonyl; W' is absent, NH or is aryl; M is absent or is selected from the group consisting of $(C_1-C_6)$alkylsulfanyl and $(C_1-C_6)$alkylsulfinyl; $R_6$ is selected from the group consisting of H, $(C_1-C_6)$alkyl, $(C_3-C_8)$cycloalkyl, hetero$(C_3-C_8)$cycloalkyl, aryl and heteroaryl, wherein $(C_3-C_8)$cycloalkyl, hetero$(C_3-C_8)$cycloalkyl, aryl and heteroaryl are optionally substituted by one or more groups selected from halogen atoms, oxo, OH, CN, COOH, $(C_1-C_6)$alkoxy, halo$(C_1-C_6)$alkoxy, aryl$(C_1-C_6)$alkyl, $(C_1-C_6)$alkyl, halo$(C_1-C_6)$alkyl, —OCO$(C_1-C_6)$alkyl or halogen; —OR$_7$, —OCOR$_7$, —COR$_7$, —COOR$_8$, —CONR$_9$R$_{10}$, —CSNR$_9$R$_{10}$, —S(O)$_2$R$_{11}$ wherein R$_7$, R$_8$ and R$_{11}$ are independently selected from the group consisting of $(C_1-C_6)$alkyl, $(C_2-C_6)$alkenyl, $(C_3-C_8)$cycloalkyl, aryl$(C_1-C_6)$alkyl, $(C_1-C_6)$alkylheteroaryl, aryl, hetero$(C_3-C_8)$cycloalkyl and heteroaryl having 3 to 10 ring atoms wherein at least one ring atom is a heteroatomic group selected from the group consisting of N, NH, S, and O, which groups may be optionally substituted with one or more substituents selected from the group consisting of halogen and $(C_1-C_6)$alkyl; R$_9$ and R$_{10}$ are independently selected from the group consisting of $(C_1-C_6)$alkyl and $(C_3-C_8)$cycloalkyl; R$_3$ is selected from the group consisting of H and C(O)OR$_{12}$ wherein R$_{12}$ is H or $(C_1-C_6)$alkyl; X and Y are independently selected from the group consisting of H and fluorine.

An even more preferred group of compounds of general formula (I') is that wherein R$_1$ is hydroxy-methyl, acetoxy, carboxyl 2-methoxy-ethyl ester, carbonyl 2-oxo ethyl ester, carboxyl 2-hydroxy-ethyl ester, carboxylbenzyl amide, carboxyl (1-phenyl-cyclopropyl)-amide or chloromethyloxy; R$_2$ is H, benzyl, ethyl butyl, chloro-benzyl, propionyl 2 oxo-ethyl, 4-chloro-benzyl, 3-chloro-benzyl, phenylpropyl, thiophen-2-ylmethyl, benzoyl, methyl-furan-2-ylmethyl, 3-fluoro-benzyl, 4-fluoro-benzyl, 4-trifluoromethyl-benzyl, 4-methoxybenzyl, difluorobenzyl, 2-oxo-2-phenyl-ethyl, 2-oxo-2-thiophen-2-yl-ethyl, 3-methyl-butyl, benzoyl, thiophene-2-carbonyl, methoxy-benzoyl, pyridine-3-carbonyl, propyl-2-sulfonyl, carbothioic cyclohexylamide, carboxyl-phenylamide, carboxyl isopropyl, carbox benzyl, benzooxazol, pyrimidin-2-yl, 2-phenoxy-ethyl, thiophen-2-sulfonyl, 2-oxo-phenyl-carbamoyl, 2-oxo-phenyl thiocarbamoyl, cyclohexylcarbamoyl, methylsulfonyl, benzylsulfonyl, furan-2-ylmethyl, thiophen-2-ylmethyl, 3-methylbutyl, butyl, furan-2-carbonyl, 2-phenylsulfanyl, phenylsulfanylethyl, phenylacetyl, thiophen-2-yl-acetyl, 2-phenoxyethyl, 2-phenylethyl, pyridin-3-ylmethyl, 3-methoxybenzyl, phenylmethanesulfonyl, cyclohexylthiocarbamoyl, acetoxyacetyl, difluoromethoxybenzyl, 4-hydroxy-phenylsulfanylmethyl)-benzyl, 4-hydroxy-phenylsulfinylmethyl)-benzyl; R$_3$ is H, carboxyethyl or carboxyl.

Another preferred group of compounds of general formula (I') is that wherein R$_1$ is $(CH_2)_n$—V—$(CH_2)_{n'}$—Z—R$_4$, wherein V is absent, n=0, n'=1 or 2, Z is a bond or carboxyl, R$_4$=OH; R$_2$ is $(CH_2)_m$—W—W'-M-R$_6$, wherein m=0, 1 or 3, W is a bond, —O—, —S—, carbonyl or thiocarbonyl, W' and M are absent; R$_6$ is H; $(C_1-C_6)$alkyl; $(C_3-C_8)$cycloalkyl; S(O)$_2$R$_{11}$, wherein R$_{11}$ is $(C_1-C_6)$alkyl, $(C_1-C_6)$alkylaryl or heteroaryl; aryl; heteroaryl; CSNR$_9$R$_{10}$ or CONR$_9$R$_{10}$, wherein R$_9$ is H and R$_{10}$ is aryl or heteroaryl, wherein in both aryl or heteroaryl, one or more hydrogen atoms may be optionally substituted by halogen or O$(C_1-C_6)$alkyl; R$_3$=H or COOR$_{12}$, wherein R$_{12}$ is $(C_1-C_6)$alkyl; X and Y are independently selected from hydrogen or fluorine.

Another preferred group of compounds of general formula (I') is that wherein R$_1$ is $(CH_2)_n$—V—$(CH_2)_{n'}$—Z—R$_4$, wherein n=1, n'=0, Z is —O—, R$_4$ is $(C_1-C_6)$alkylcarbonyl or $(C_1-C_6)$alkylcarboxyl; R$_2$ is $(CH_2)_m$—W—W'-M-R$_6$, wherein m=0 or 1, W is a bond, carbonyl or thiocarbonyl, W' and M are absent, R$_6$ is H, $(C_1-C_6)$alkyl, $(C_3-C_8)$cycloalkyl, aryl, heteroaryl, or —OR$_7$, wherein R$_7$ is $(C_1-C_6)$alkyl or $(C_1-C_6)$alkylaryl.

Another preferred group of compounds of general formula (I') is that wherein R$_1$ is $(CH_2)_n$—V—$(CH_2)_{n'}$—Z—R$_4$, wherein n=1, n'=0, V is absent, Z is —O— and R$_4$ is $(C_1-C_6)$ alkylcarbonyl; R$_2$ is $(CH_2)_m$—W—W'-M-R$_6$, wherein m=0, W is carbonyl and R$_6$ is —OR$_7$, wherein R$_7$ is $(C_1-C_6)$alkylaryl, W' and M are absent.

Another preferred group of compounds of general formula (I') is that wherein R$_2$ is $(CH_2)_m$—W—W'-M-R$_6$, wherein m=1, W is a single bond, W' is aryl, M is $(C_1-C_6)$alkylsulfanyl or $(C_1-C_6)$alkylsulfinyl and R$_6$ is aryl optionally substituted by OH.

Another preferred group of compounds of general formula (I') is that wherein R$_1$ is $(CH_2)_n$—V—$(CH_2)_{n'}$—Z—R$_4$, wherein n and n'=0, V is absent, Z is —O— and R$_4$ is $(C_1-C_6)$alkyl, wherein one or more hydrogen atoms are substituted by halogen.

Another preferred group of compounds of general formula (I') is that wherein R$_1$ is $(CH_2)_n$—V—$(CH_2)_{n'}$—Z—R$_4$, wherein n and n'=0, V is absent, Z is —NR$_5$, wherein R$_5$ is H or is selected from the group consisting of $(C_1-C_6)$alkyl, $(C_3-C_8)$cycloalkyl, aryl, aryl$(C_1-C_6)$alkyl, aryl$(C_3-C_8)$cycloalkyl and heteroaryl, optionally substituted by CN.

The compounds of general formula (I') may be prepared conventionally according to methods disclosed in the art. Some of the processes which can be used are described below and reported in Scheme 1.

The present invention is directed to a process for the preparation of compounds of general formula (I') wherein R$_1$=$(CH_2)_n$—V—$(CH_2)_{n'}$—Z—R$_4$, n=0, n'=1, V is absent, Z is a bond, R$_4$=OH, R$_2$=$(CH_2)_m$—W—W'-M-R$_6$, m is 1 to 6, W is a single bond, W' and M are absent, which comprises the reaction of a compound of general formula (IX):

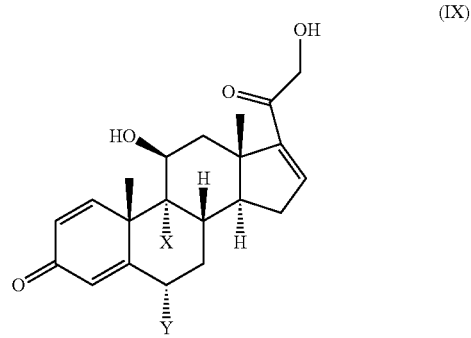

(IX)

with a compound of general formula (V):

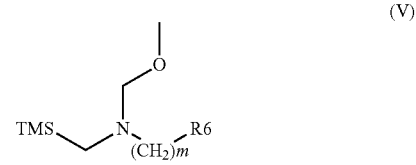

(V)

wherein X, Y, m and R$_6$ are as defined above and TMS represents trimethylsilyl.

The present invention is also directed to a process for the preparation of compounds of general formula (I') wherein $R_1=(CH_2)_n-V-(CH_2)_{n'}-Z-R_4$, n=0, n'=1, V is absent, Z is a bond, $R_4$ is OH and $R_3=H$, by reacting a compound of general formula (IV):

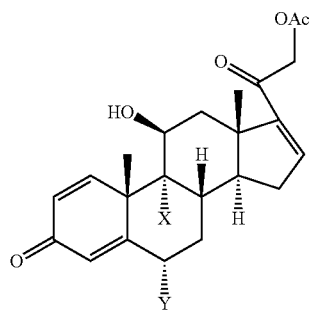

(IV)

with a compound of formula (V) wherein m=1 and $R_6$=phenyl, to obtain a compound of formula (VI):

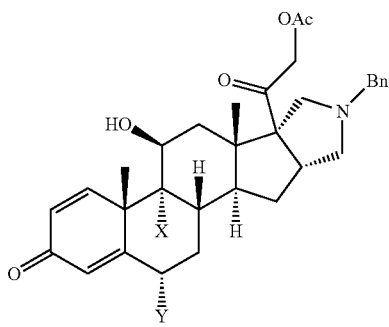

(VI)

wherein the benzyl group (Bn) can be removed by catalytic hydrogenation or through chemical dealkylation of tertiary amines and in presence of a base, to obtain compounds of formula (VII):

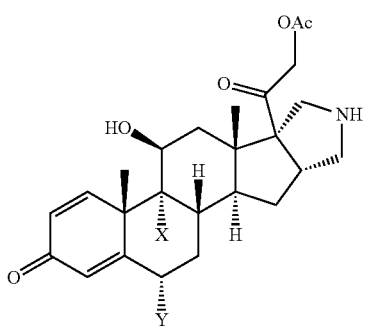

(VII)

which can be converted into (I') wherein X, Y, $R_1$ and $R_3$ are as defined above.

The present invention is also directed to a process for the preparation of compounds of general formula (I') wherein $R_1=(CH_2)_n-V-(CH_2)_{n'}-Z-R_4$, n=1, V is O, n'=0, Z is carbonyl or carboxyl, $R_4$ is $(C_1-C_6)$alkyl and $R_3=H$ which comprises the conversion of the hydroxyl group of 2-hydroxy acetyl moiety at position 6b of compounds of general formula (I') wherein n=0, V is absent, n'=1, Z is a bond, $R_4=OH$ and $R_3=H$, by reaction with acylating agents.

The present invention is also directed to a process for the preparation of compounds of general formula (I') wherein $R_1=(CH_2)_n-V-(CH_2)_{n'}-Z-R_4$, n=0, V is absent and n'=1, which comprises the conversion of the hydroxyl group of 2-hydroxy acetyl moiety at position 6b of compounds of general formula (I') wherein n=0, V is absent, n'=1, Z is a bond, $R_4=OH$ and $R_3=H$.

The present invention is also directed to a process for the preparation of compounds of general formula (I') wherein $R_1=(CH_2)_n-V-(CH_2)_{n'}-Z-R_4$, n and n'=0, V is absent, Z=S and $R_3=H$, which comprises the reaction of compounds of formula (I') wherein n=0, V is absent, n'=1, Z is a bond, $R_4=OH$ and $R_3=H$ in the presence of an aqueous solution of an inorganic base, to obtain the compounds of general formula (XI), wherein X, Y and $R_2$ are as defined above,

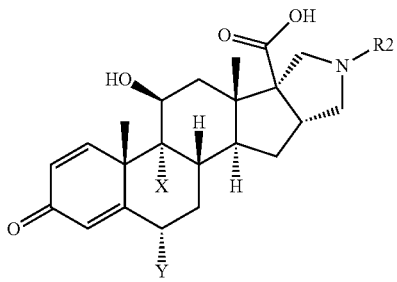

(XI)

and then treatment with dimethyl thiocarbamoyl chloride and diethyl amine.

The present invention is also directed to a process for the preparation of compounds of general formula (I') wherein $R_1=(CH_2)_n-V-(CH_2)_{n'}-Z-R_4$, n and n'=0, V is absent and $R_3=H$, which comprises the reaction of the compounds of formula (XI) with one or more equivalents of an acid activating agent followed by displacement by a nucleophile.

The present invention is also directed to a process for the preparation of compounds of general formula (I') wherein $R_1=(CH_2)_n-V-(CH_2)_{n'}-Z-R_4$, n and n'=0, V is absent, Z=S, $R_3=H$, which comprises the reaction of compounds of formula (XI) with an activating agent and then with the sodium salt of thioacetic acid or with sodium hydrogensulfide to obtain compounds of general formula (XII), wherein X, Y and $R_2$ are as defined above,

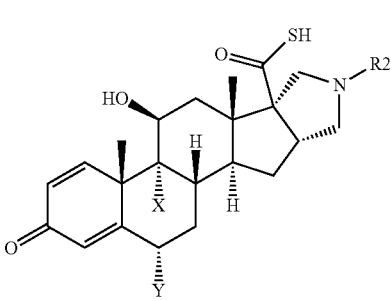

(XII)

which is reacted with an alkylating reagent.

The present invention is also directed to a process for the preparation of compounds of general formula (I') wherein $R_1=(CH_2)_n-V-(CH_2)_{n'}-Z-R_4$, n and n'=0, V is absent, Z=O, $R_4$ is $(C_1-C_6)$alkyl and $R_3=H$, which comprises the reaction of compounds of formula (XI) with dimethylcarbonate or an alkylating reagent in the presence of an inorganic base.

The present invention is also directed to a process for the preparation of compounds of general formula (I') wherein $R_3$=COOH, by reacting a compound of formula (IX):

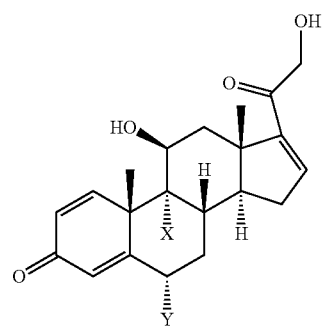

(IX)

with ethylisocyanoacetate to obtain a compound of formula (XIII), wherein X and Y are as defined above,

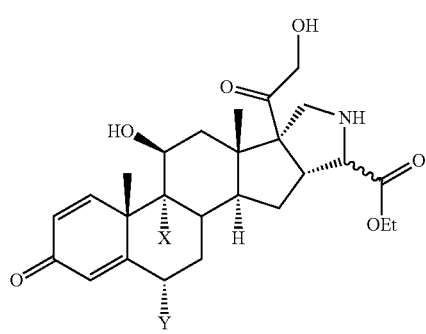

(XIII)

which can be hydrolized and converted into compounds of general formula (I') wherein $R_3$ is $C(O)OR_{13}$ with $R_{13}$=H, which can be further converted into compounds of general formula (I') wherein $R_3$=$CONR_{13}R_{14}$.

The present invention is also directed to a process for the preparation of compounds of general formula (I') wherein $R_1$=$(CH_2)_n$—V—$(CH_2)_{n'}$—Z—$R_4$, n=0, V is absent, n'=1, Z is a bond, $R_4$ is halide and $R_3$=H, starting from the conversion of the hydroxyl group of 2-hydroxy acetyl moiety at position 6b of compounds of general formula (IX), wherein n=0, V is absent, n'=1, Z is a bond, $R_4$=OH and $R_3$=H, into a leaving group (LG), followed by the displacement of the LG by using a nucleophile such as an halide salt to obtain compounds of general formula (XIV), wherein X and Y are as defined above,

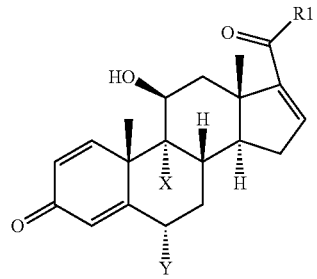

(XIV)

and by reacting a compound of general formula (XIV) with a compound of general formula (V).

The present invention is also directed to a process for the preparation of compounds of general formula (I') wherein $R_1$=$(CH_2)_n$—V—$(CH_2)_{n'}$—Z—$R_4$, n=0, V is absent, n'=1, Z is a bond, $R_4$ is halide, hydrogen or thioalkyl and $R_3$=H, which comprises the reaction of compounds of general formula (VI), wherein X and Y are as defined above,

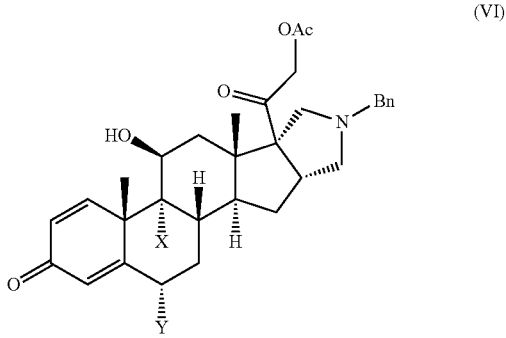

(VI)

with vinylchloroformate, the hydrolysis of the acetyl group to obtain compounds of formula (XV):

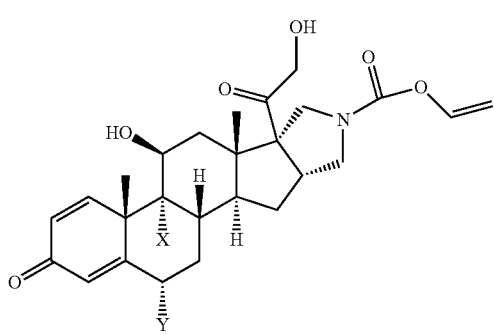

(XV)

the conversion of the hydroxyl group of 2-hydroxy acetyl moiety at position 6b of compounds of general formula (XV) into a leaving group (LG), followed by the displacement of the LG by using a nucleophile to obtain compounds of general formula (XVI):

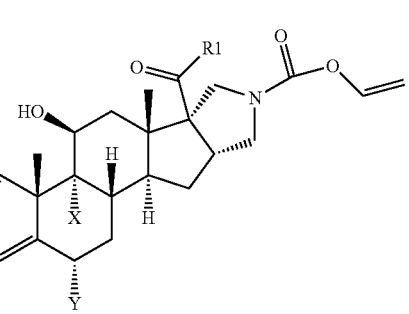

(XVI)

The present invention is also directed to a process for the preparation of compounds of general formula (XVI) wherein $R_4$=H, by generating a compound of general formula (XVI) with $R_4$=I and by reducing this intermediate in the presence of iodide salts.

The present invention is also directed to the preparation of compounds of general formula (I), starting from a suitable different stereoisomer of compounds of formula (II) and following the same synthetic routes described in Scheme 1 for compounds of general formula (I').

Scheme 1
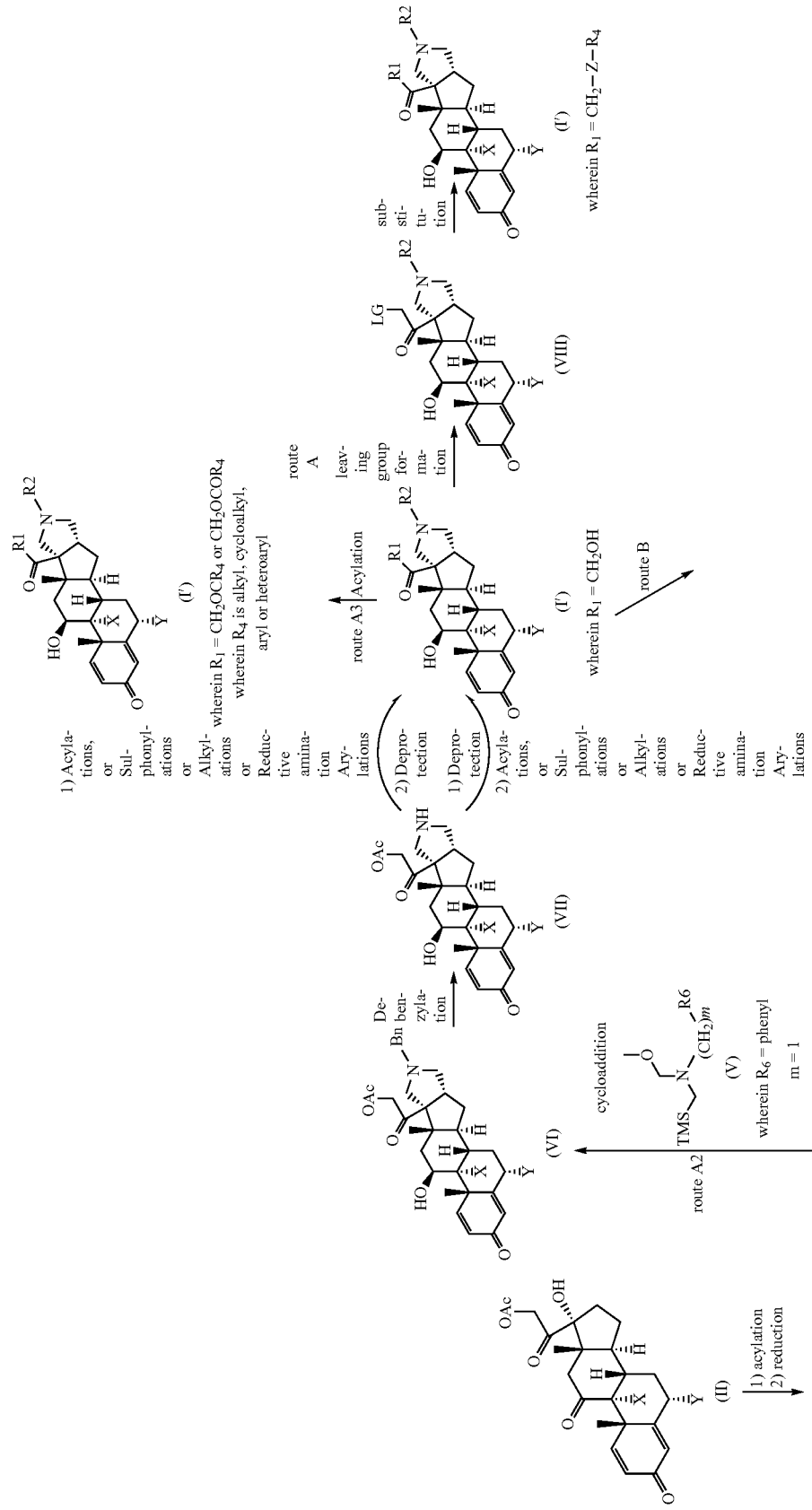

-continued
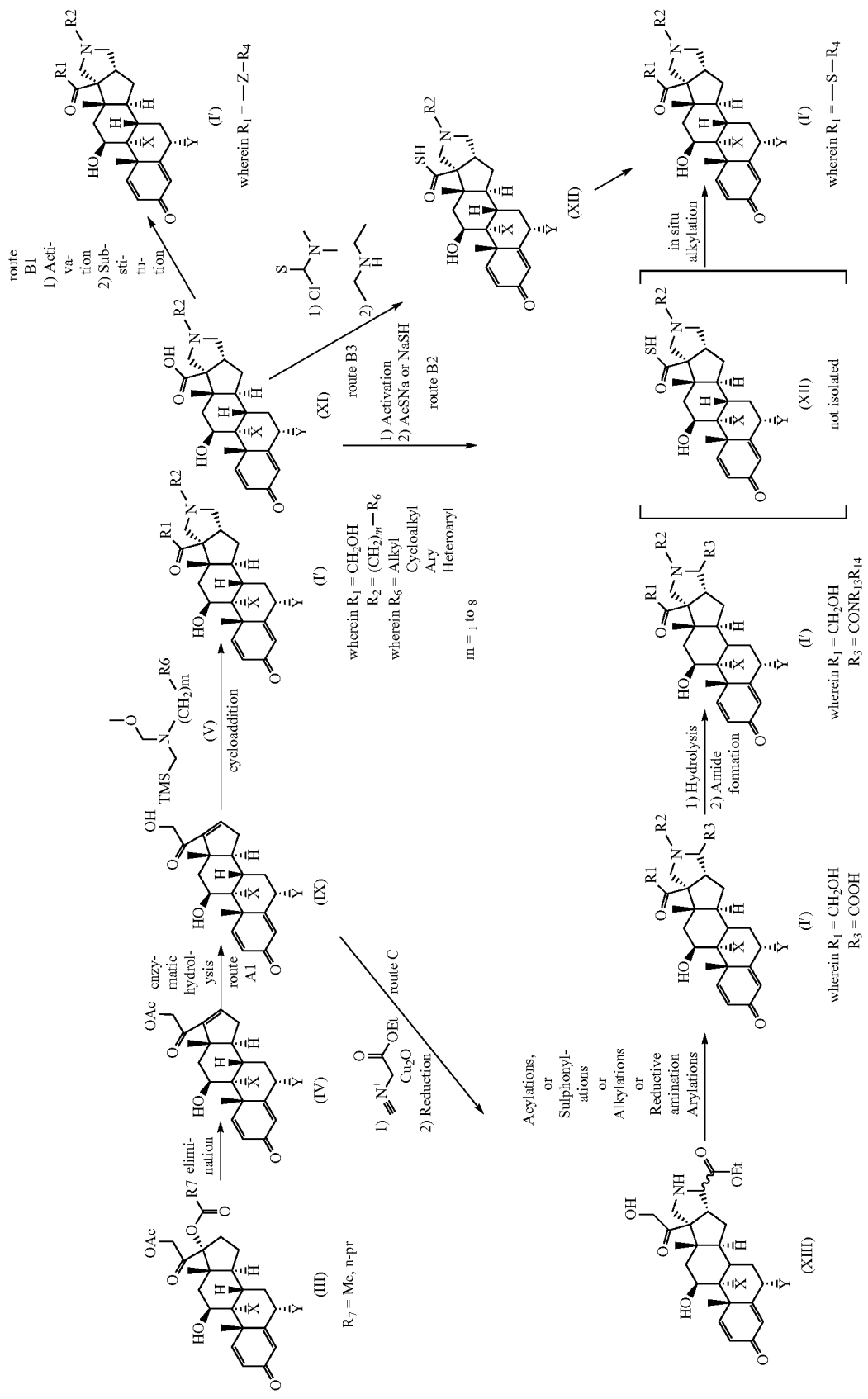

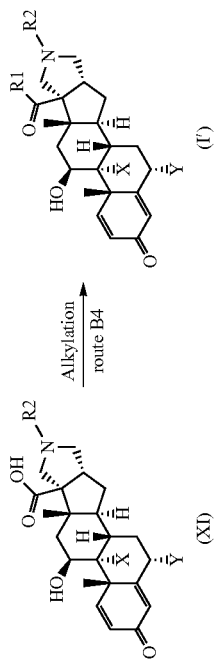
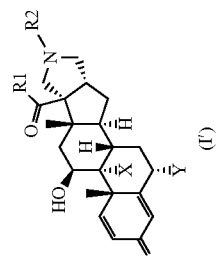
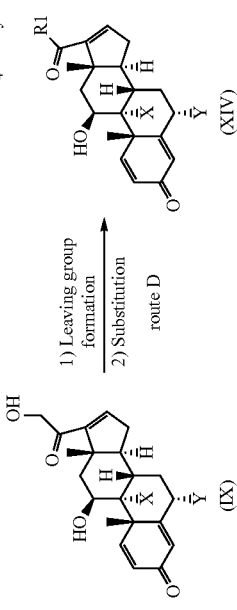
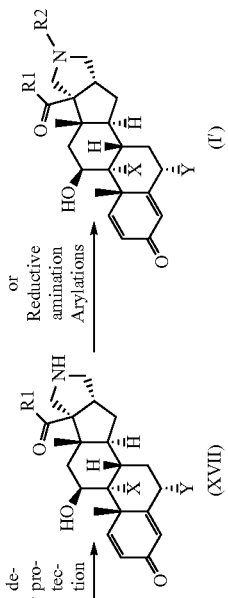
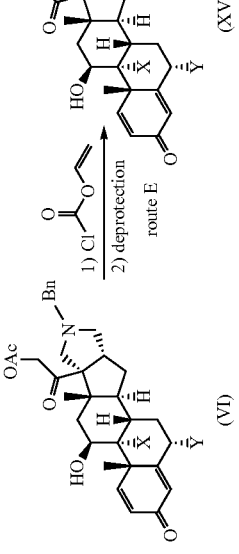

The present invention also provides pharmaceutical compositions comprising a compound of general formula (I) or (I') and one or more pharmaceutically acceptable carriers and/or excipients.

The present invention also provides combinations of a compound of general formula (I) or (I') with one or more active ingredients selected from the classes of β2-agonists, antimuscarinic agents, PDE4 inhibitors, P38 MAP kinase inhibitors, and IKK2 inhibitors.

The present invention also provides combinations of a compound of general formula (I) or (I') with a β2-agonist selected from the group consisting carmoterol, GSK-642444, indacaterol, milveterol, arformoterol, formoterol, salbutamol, levalbuterol, terbutaline, AZD-3199, BI-1744-CL, LAS-100977, bambuterol, isoproterenol, procaterol, clenbuterol, reproterol, fenoterol, and ASF-1020.

The present invention also provides combinations of a compound of general formula (I) or (I') with an antimuscarinic agent selected from the group consisting of aclidinium, tiotropium, ipratropium, trospium, glycopyrronium, and oxitropium.

The present invention also provides combinations of a compound of general formula (I) or (I') with a PDE4 inhibitor selected from the group consisting of cilomilast, roflumilast, BAY19-8004, and SCH-351591.

The present invention also provides combinations of a compound of general formula (I) or (I') with a P38 inhibitor selected from the group consisting of semapimod, talmapimod, pirfenidone, PH-797804, GSK-725, minokine, and losmapimod.

In a preferred embodiment, the present invention provides combinations of a compound of general formula (I) or (I') with a IKK2 inhibitor.

The present invention also provides compounds of general formula (I) or (I') for use as a medicament.

Also provided is the use of compounds of general formula (I) or (I'), alone or combined with one or more active ingredients, for the preparation of a medicament for the prevention or treatment of any disease wherein the decrease in the number, activity and movement of inflammatory cells is implicated.

In particular, also provided, is the use of compounds of general formula (I) or (I'), alone or combined with one or more active ingredients, for the preparation of a medicament for the prevention and/or treatment of a disease of the respiratory tract characterized by airway obstruction such as asthma and COPD.

Moreover the present invention provides a method for prevention and/or treatment of any disease wherein the decrease in the number, activity and movement of inflammatory cells is implicated, said method comprising administering to a patient in need of such treatment a therapeutically effective amount of a compound of general formula (I) or (I'), alone or combined with one or more active ingredients.

The above diseases, wherein the decrease in the number, activity and movement of inflammatory cells is implicated, comprise diseases of the respiratory tract characterized by airway obstruction such as asthma and COPD.

The present invention also provides pharmaceutical preparations of compounds of general formula (I) or (I') suitable for administration by inhalation, by injection, orally or intranasally.

Inhalable preparations include inhalable powders, propellant-containing metering aerosols or propellant-free inhalable formulations.

The present invention is also directed to a device which may be a single- or multi-dose dry powder inhaler, a metered dose inhaler or a soft mist nebulizer comprising a compound of general formula (I) or (I').

The present invention is also directed to a kit comprising the pharmaceutical compositions of compounds of general formula (I) or (I') alone or in combination with or in admixture with one or more pharmaceutically acceptable carriers and/or excipients, and a device which may be a single- or multi-dose dry powder inhaler, a metered dose inhaler or a soft mist nebulizer.

Most of the compounds of the invention were found to show an in vitro activity ranging from $10^{-8}$ to $10^{-10}$ M in all the cell free and cell based assays employed and some of them turned out to be endowed with a long duration of anti-inflammatory action in the lung in rodent experimental models in vivo.

According to preferred embodiments the present invention provides the compounds reported below:

| Compound | Chemical Name |
|---|---|
| 8 | (4aS,4bR,5S,6aS,6bS,9aR,10aS,10bS,12S)-8-benzyl-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 9 | (4aS,4bR,5S,6aS,6bS,9aR,8R,10aS,10bS,12S)-8-(4-chloro-benzyl)-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 10 | acetic acid 2-((4aR,4bS,5S,6aS,6bS,9aR,10aS,10bS)-8-benzyl-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl)-2-oxo-ethyl ester |
| 11 | acetic acid 2-((4aS,4bR,5S,6aS,6bS,9aR,10aS,10bS,12S)-8-benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl)-2-oxo-ethyl ester |
| 12 | (4aS,4bR,5S,6aS,6bS,9aR,10aS,10bS,12S)-4b,12-difluoro-5-hydroxy-6b-(2-hydroxy-acetyl)-4a,6a-dimethyl-8-(3-phenyl-propyl)-4b,5,6,6a,6b,7,8,9,9a,10,10a,10b,11,12-tetradecahydro-4aH-8-aza-pentaleno[2,1-a]phenanthren-2-one |
| 13 | (4aS,4bR,5S,6aS,6bS,9aR,10aS,10bS,12S)-4b,12-difluoro-5-hydroxy-6b-(2-hydroxy-acetyl)-4a,6a-dimethyl-8-thiophen-2-ylmethyl-4b,5,6,6a,6b,7,8,9,9a,10,10a,10b,11,12-tetradecahydro-4aH-8-aza-pentaleno[2,1-a]phenanthren-2-one |

-continued

| Compound | Chemical Name |
|---|---|
| 14 | (4aS,4bR,5S,6aS,6bS,9aR,10aS,10bS,12S)-4b,12-difluoro-8-furan-2-ylmethyl-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 15 | (4aS,4bR,5S,6aS,6bS,9aR,10aS,10bS,12S)-4b,12-difluoro-5-hydroxy-6b-(2-hydroxy-acetyl)-4a,6a-dimethyl-8-(5-methyl-furan-2-ylmethyl)-4b,5,6,6a,6b,7,8,9,9a,10,10a,10b,11,12-tetradecahydro-4aH-8-aza-pentaleno[2,1-a]phenanthren-2-one |
| 16 | (4aS,4bR,5S,6aS,6bS,9aR,10aS,10bS,12S)-4b,12-difluoro-8-(3-fluoro-benzyl)-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 17 | (4aS,4bR,5S,6aS,6bS,9aR,10aS,10bS,12S)-8-(3,5-difluoro-benzyl)-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 18 | (4aR,4bS,5S,6aS,6bS,9aR,10aS,10bS)-8-benzyl-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 19 | (4aS,4bR,5S,6aS,6bS,9aR,10aS,10bS,12S)-6b-(2-acetoxy-acetyl)-4b,12-difluoro-5-hydroxy-4a,6a-dimethyl-2-oxo-2,4b,5,6,6a,6b,7,9,9a,10,10a,10b,11,12-tetradecahydro-4aH-8-aza-pentaleno[2,1-a]phenanthrene-8-carboxylic acid vinyl ester |
| 20 | acetic acid 2-((4aS,4bR,5S,6aS,6bS,9aR,10aS,10bS,12S)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl)-2-oxo-ethyl ester hydrochloride |
| 21 | (4aR,4bS,5S,6aS,6bS,9aR,10aS,10bS)-6b-(2-acetoxy-acetyl)-5-hydroxy-4a,6a-dimethyl-2-oxo-2,4b,5,6,6a,6b,7,9,9a,10,10a,10b,11,12-tetradecahydro-4aH-8-aza-pentaleno[2,1-a]phenanthrene-8-carboxylic acid vinyl ester |
| 22 | acetic acid 2-((4aR,4bS,5S,6aS,6bS,9aR,10aS,10bS)-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl)-2-oxo-ethyl ester hydrochloride |
| 23 | acetic acid 2-[(4aS,4bR,5S,6aS,6bS,9aR,10aS,10bS,12S)-4b,12-difluoro-5-hydroxy-4a,6a-dimethyl-2-oxo-8-(2-oxo-2-phenyl-ethyl)-2,4b,5,6,6a,7,8,9,9a,10,10a,10b,11,12-tetradecahydro-4aH-8-aza-pentaleno[2,1-a]phenanthren-6b-yl]-2-oxo-ethyl ester |
| 24 | (4aS,4bR,5S,6aS,6bS,9aR,10aS,10bS,12S)-4b,12-difluoro-5-hydroxy-6b-(2-hydroxy-acetyl)-4a,6a-dimethyl-8-(2-oxo-2-phenyl-ethyl)-4b,5,6,6a,6b,7,8,9,9a,10,10a,10b,11,12-tetradecahydro-4aH-8-aza-pentaleno[2,1-a]phenanthren-2-one |
| 25 | acetic acid 2-((4aS,4bR,5S,6aS,6bS,9aR,10aS,10bS,12S)-4b,12-difluoro-5-hydroxy-4a,6a-dimethyl-2-oxo-8-pyridin-3-ylmethyl-2,4b,5,6,6a,7,8,9,9a,10,10a,10b,11,12-tetradecahydro-4aH-8-aza-pentaleno[2,1-a]phenanthren-6b-yl)-2-oxo-ethyl ester |
| 26 | acetic acid 2-[(4aS,4bR,5S,6aS,6bS,9aR,10aS,10bS,12S)-8-(3,5-difluoro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl]-2-oxo-ethyl ester |
| 27 | 3-[(4aS,4bR,5S,6aS,6bS,9aR,10aS,10bS,12S)-6b-(2-Acetoxy-acetyl)-4b,12-difluoro-5-hydroxy-4a,6a-dimethyl-2-oxo-2,4b,5,6,6a,6b,7,9,9a,10,10a,10b,11,12-tetradecahydro-4aH-8-aza-pentaleno[2,1-a]phenanthren-8-ylmethyl]-benzoic acid methyl ester |
| 28 | 3-[(4aS,4bR,5S,6aS,6bS,9aR,10aS,10bS,12S)-6b-(2-Acetoxy-acetyl)-4b,12-difluoro-5-hydroxy-4a,6a-dimethyl-2-oxo-2,4b,5,6,6a,6b,7,9,9a,10,10a,10b,11,12-tetradecahydro-4aH-8-aza-pentaleno[2,1-a]phenanthren-8-ylmethyl]-benzoic acid |
| 29 | (4aS,4bR,5S,6aS,6bS,9aR,10aS,10bS,12S)-8-(3-chloro-benzyl)-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 30 | (4aS,4bR,5S,6aS,6bS,9aR,10aS,10bS,12S)-4b,12-difluoro-8-(4-fluoro-benzyl)-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 31 | (4aS,4bR,5S,6aS,6bS,9aR,10aS,10bS,12S)-4b,12-difluoro-5-hydroxy-6b-(2-hydroxy-acetyl)-4a,6a-dimethyl-8-(4-trifluoromethyl-benzyl)-4b,5,6,6a,6b,7,8,9,9a,10,10a,10b,11,12-tetradecahydro-4aH-8-aza-pentaleno[2,1-a]phenanthren-2-one |
| 32 | (4aS,4bR,5S,6aS,6bS,9aR,10aS,10bS,12S)-4b,12-difluoro-5-hydroxy-6b-(2-hydroxy-acetyl)-8-(4-methoxy-benzyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 33 | (4aS,4bR,5S,6aS,6bS,9aR,10aS,10bS,12S)-4b,12-difluoro-5-hydroxy-6b-(2-hydroxy-acetyl)-4a,6a-dimethyl-8-(2-oxo-2-thiophen-2-yl-ethyl)-4b,5,6,6a,6b,7,8,9,9a,10,10a,10b,11,12-tetradecahydro-4aH-8-aza-pentaleno[2,1-a]phenanthren-2-one |

| Compound | Chemical Name |
|---|---|
| 34 | (4aS,4bR,5S,6aS,6bS,9aR,10aS,10bS,12S)-4b,12-difluoro-5-hydroxy-6b-(2-hydroxy-acetyl)-8-(3-methoxy-benzyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 35 | (4aR,4bS,5S,6aS,6bS,9aR,10aS,10bS)-8-(3-chloro-benzyl)-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 36 | (4aS,4bR,5S,6aS,6bS,9aR,10aS,10bS,12S)-4b,12-difluoro-5-hydroxy-6b-(2-hydroxy-acetyl)-4a,6a-dimethyl-8-(pyridin-3-ylmethyl-4b,5,6,6a,6b,7,8,9,9a,10,10a,10b,11,12-tetradecahydro-4aH-8-aza-pentaleno[2,1-a]phenanthren-2-one |
| 37 | (4aS,4bR,5S,6aS,6bS,9aR,10aS,10bS,12S)-4b,12-difluoro-5-hydroxy-6b-(2-hydroxy-acetyl)-4a,6a-dimethyl-8-(3-methyl-butyl)-4b,5,6,6a,6b,7,8,9,9a,10,10a,10b,11,12-tetradecahydro-4aH-8-aza-pentaleno[2,1-a]phenanthren-2-one |
| 38 | (4aS,4bR,5S,6aS,6bS,9aR,10aS,10bS,12S)-4b,12-Difluoro-5-hydroxy-6b-(2-hydroxy-acetyl)-4a,6a-dimethyl-8-(3-trifluoromethoxy-benzyl)-4b,5,6,6a,6b,7,8,9,9a,10,10a,10b,11,12-tetradecahydro-4aH-8-aza-pentaleno[2,1-a]phenanthren-2-one |
| 39 | 4-[(4aS,4bR,5S,6aS,6bS,9aR,10aS,10bS,12S)-4b,12-Difluoro-5-hydroxy-6b-(2-hydroxy-acetyl)-4a,6a-dimethyl-2-oxo-2,4b,5,6,6a,6b,7,9,9a,10,10a,10b,11,12-tetradecahydro-4aH-8-aza-pentaleno[2,1-a]phenanthren-8-ylmethyl]-benzonitrile |
| 40 | 3-[(4aS,4bR,5S,6aS,6bS,9aR,10aS,10bS,12S)-4b,12-Difluoro-5-hydroxy-6b-(2-hydroxy-acetyl)-4a,6a-dimethyl-2-oxo-2,4b,5,6,6a,6b,7,9,9a,10,10a,10b,11,12-tetradecahydro-4aH-8-aza-pentaleno[2,1-a]phenanthren-8-ylmethyl]-benzonitrile |
| 41 | bis((4aS,4bR,5S,6aS,6bS,9aR,10aS,10bS,12S)-8-(3-Chloro-benzyl)-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one) naphtalen disulfonate salt |
| 42 | (4aS,4bR,5S,6aS,6bS,9aR,10aS,10bS,12S)-8-(3-Chloro-benzyl)-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one methane sulfonate |
| 43 | (4aS,4bR,5S,6aS,6bS,9aR,10aS,10bS,12S)-8-(3-Chloro-benzyl)-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one hydrochloride |
| 44 | acetic acid 2-((4aS,4bR,5S,6aS,6bS,9aR,10aS,10bS,12S)-8-cyclopropylmethyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl)-2-oxo-ethyl ester |
| 45 | (4aS,4bR,5S,6aS,6bS,9aR,10aS,10bS,12S)-8-cyclopropylmethyl-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 46 | 3-[(4aS,4bR,5S,6aS,6bS,9aR,10aS,10bS,12S)-4b,12-Difluoro-5-hydroxy-6b-(2-hydroxy-acetyl)-4a,6a-dimethyl-2-oxo-2,4b,5,6,6a,6b,7,9,9a,10,10a,10b,11,12-tetradecahydro-4aH-8-aza-pentaleno[2,1-a]phenanthren-8-ylmethyl]-benzoic acid methyl ester |
| 47 | 3-[(4aS,4bR,5S,6aS,6bS,9aR,10aS,10bS,12S)-4b,12-Difluoro-5-hydroxy-6b-(2-hydroxy-acetyl)-4a,6a-dimethyl-2-oxo-2,4b,5,6,6a,6b,7,9,9a,10,10a,10b,11,12-tetradecahydro-4aH-8-aza-pentaleno[2,1-a]phenanthren-8-ylmethyl]-benzoic acid trifluoroacetate |
| 48 | Propionic acid 2-[(4aS,4bR,5S,6aS,6bS,9aR,10aS,10bS,12S)-8-(3-chloro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl]-2-oxo-ethyl ester |
| 49 | Carbonic acid 2-((4aS,4bR,5S,6aS,6bS,9aR,10aS,10bS,12S)-8-benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl)-2-oxo-ethyl ester ethyl ester |
| 50 | acetic acid 2-((4aS,4bR,5S,6aS,6bS,9aR,10aS,10bS,12S)-4b,12-difluoro-5-hydroxy-4a,6a,8-trimethyl-2-oxo-2,4b,5,6,6a,7,8,9,9a,10,10a,10b,11,12-tetradecahydro-4aH-8-aza-pentaleno[2,1-a]phenanthren-6b-yl)-2-oxo-ethyl ester |
| 51 | (4aS,4bR,5S,6aS,6bS,9aR,10aS,10bS,12S)-4b,12-difluoro-5-hydroxy-6b-(2-hydroxy-acetyl)-4a,6a,8-trimethyl-4b,5,6,6a,6b,7,8,9,9a,10,10a,10b,11,12-tetradecahydro-4aH-8-aza-pentaleno[2,1-a]phenanthren-2-one |
| 52 | acetic acid 2-((4aS,4bR,5S,6aS,6bS,9aR,10aS,10bS,12S)-4b,12-difluoro-5-hydroxy-8-isopropyl-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl)-2-oxo-ethyl ester |

| Compound | Chemical Name |
|---|---|
| 53 | acetic acid 2-((4aS,4bR,5S,6aS,6bS,9aR,10aS,10bS,12S)-8-cyclohexyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl)-2-oxo-ethyl ester |
| 54 | (4aS,4bR,5S,6aS,6bS,9aR,10aS,10bS,12S)-4b,12-Difluoro-5-hydroxy-6b-(2-hydroxy-acetyl)-8-isopropyl-4a,6a-dimethyl-4b,5,6,6a,6b,7,8,9,9a,10,10a,10b,11,12-tetradecahydro-4aH-8-aza-pentaleno[2,1-a]phenanthren-2-one |
| 55 | 4aS,4bR,5S,6aS,6bS,9aR,10aS,10bS,12S)-8-Cyclohexyl-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 56 | acetic acid 2-[(4aS,4bR,5S,6aS,6bS,9aR,10aS,10bS,12S)-8-(3,3-dimethyl-butyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl]-2-oxo-ethyl ester |
| 57 | (4aS,4bR,5S,6aS,6bS,9aR,10aS,10bS,12S)-8-(3,3-Dimethyl-butyl)-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 58 | acetic acid 2-[(4aS,4bR,5S,6aS,6bS,9aR,10aS,10bS,12S)-4b,12-difluoro-5-hydroxy-4a,6a-dimethyl-2-oxo-8-(1-propyl-butyl)-2,4b,5,6,6a,7,8,9,9a,10,10a,10b,11,12-tetradecahydro-4aH-8-aza-pentaleno[2,1-a]phenanthren-6b-yl]-2-oxo-ethyl ester |
| 59 | acetic acid 2-[(4aS,4bR,5S,6aS,6bS,9aR,10aS,10bS,12S)-8-(2-ethyl-butyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl]-2-oxo-ethyl ester |
| 60 | acetic acid 2-[(4aS,4bR,5S,6aS,6bS,9aR,10aS,10bS,12S)-8-(4-benzyl-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl]-2-oxo-ethyl ester |
| 61 | acetic acid 2-[(4aS,4bR,5S,6aS,6bS,9aR,10aS,10bS,12S)-4b,12-difluoro-5-hydroxy-4a,6a-dimethyl-8-(5-methyl-furan-2-ylmethyl)-2-oxo-2,4b,5,6,6a,7,8,9,9a,10,10a,10b,11,12-tetradecahydro-4aH-8-aza-pentaleno[2,1-a]phenanthren-6b-yl]-2-oxo-ethyl ester |
| 62 | acetic acid 2-[(4aS,4bR,5S,6aS,6bS,9aR,10aS,10bS,12S)-4b,12-difluoro-5-hydroxy-4a,6a-dimethyl-8-(3-methyl-butyl)-2-oxo-2,4b,5,6,6a,7,8,9,9a,10,10a,10b,11,12-tetradecahydro-4aH-8-aza-pentaleno[2,1-a]phenanthren-6b-yl]-2-oxo-ethyl ester |
| 63 | acetic acid 2-[(4aS,4bR,5S,6aS,6bS,9aR,10aS,10bS,12S)-4b,12-difluoro-5-hydroxy-6b-(2-hydroxy-acetyl)-8-[4-(4-hydroxy-phenylsulfanylmethyl)-benzyl]-4a,6a-dimethyl-4b,5,6,6a,6b,7,8,9,9a,10,10a,10b,11,12-tetradecahydro-4aH-8-aza-pentaleno[2,1-a]phenanthren-6b-yl]-2-oxo-ethyl ester |
| 64 | (4aS,4bR,5S,6aS,6bS,9aR,10aS,10bS,12S)-4b,12-difluoro-5-hydroxy-6b-(2-hydroxy-acetyl)-4a,6a-dimethyl-8-(1-propyl-butyl)-4b,5,6,6a,6b,7,8,9,9a,10,10a,10b,11,12-tetradecahydro-4aH-8-aza-pentaleno[2,1-a]phenanthren-2-one |
| 65 | (4aS,4bR,5S,6aS,6bS,9aR,10aS,10bS,12S)-8-(2-Ethyl-butyl)-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 66 | (4aS,4bR,5S,6aS,6bS,9aR,10aS,10bS,12S)-8-(4-Benzyl-benzyl)-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 67 | (4aS,4bR,5S,6aS,6bS,9aR,10aS,10bS,12S)-4b,12-Difluoro-5-hydroxy-6b-(2-hydroxy-acetyl)-8-[4-(4-hydroxy-phenylsulfanylmethyl)-benzyl]-4a,6a-dimethyl-4b,5,6,6a,6b,7,8,9,9a,10,10a,10b,11,12-tetradecahydro-4aH-8-aza-pentaleno[2,1-a]phenanthren-2-one |
| 68 | (4aS,4bR,5S,6aS,6bS,9aR,10aS,10bS,12S)-4b,12-difluoro-5-hydroxy-6b-(2-hydroxy-acetyl)-8-[4-(4-hydroxy-phenylsulfinylmethyl)-benzyl]-4a,6a-dimethyl-4b,5,6,6a,6b,7,8,9,9a,10,10a,10b,11,12-tetradecahydro-4aH-8-aza-pentaleno[2,1-a]phenanthren-2-one |
| 69 | (4aS,4bR,5S,6aS,6bS,9aR,10aS,10bS,12S)-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one hydrochloride |
| 70 | (4aS,4bR,5S,6aS,6bS,9aR,10aS,10bS,12S)-8-benzyl-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one hydrochloride |
| 71 | acetic acid 4-[(4aS,4bR,5S,6aS,6bS,9aR,10aS,10bS,12S)-4b,12-difluoro-5-hydroxy-6b-(2-hydroxy-acetyl)-4a,6a-dimethyl-2-oxo-2,4b,5,6,6a,6b,7,9,9a,10,10a,10b,11,12-tetradecahydro-4aH-8-aza-pentaleno[2,1-a]phenanthren-8-ylmethyl]-phenyl ester |

-continued

| Compound | Chemical Name |
|---|---|
| 72 | acetic acid 2-((4aS,4bR,5S,6aS,6bS,9aR,10aS,10bS,12S)-8-benzoyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl)-2-oxo-ethyl ester |
| 73 | (4aS,4bR,5S,6aS,6bS,9aR,10aS,10bS,12S)-8-benzoyl-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 74 | (4aS,4bR,5S,6aS,6bS,9aR,10aS,10bS,12S)-4b,12-difluoro-8-(furan-2-carbonyl)-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 75 | 4aS,4bR,5S,6aS,6bS,9aR,10aS,10bS,12S)-4b,12-difluoro-5-hydroxy-6b-(2-hydroxy-acetyl)-4a,6a-dimethyl-8-(thiophene-2-carbonyl)-4b,5,6,6a,6b,7,8,9,9a,10,10a,10b,11,12-tetradecahydro-4aH-8-aza-pentaleno[2,1-a]phenanthren-2-one |
| 76 | (4aS,4bR,5S,6aS,6bS,9aR,10aS,10bS,12S)-4b,12-difluoro-5-hydroxy-6b-(2-hydroxy-acetyl)-8-(3-methoxy-benzoyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 77 | (4aS,4bR,5S,6aS,6bS,9aR,10aS,10bS,12S)-4b,12-difluoro-5-hydroxy-6b-(2-hydroxy-acetyl)-4a,6a-dimethyl-8-(pyridine-3-carbonyl)-4b,5,6,6a,6b,7,8,9,9a,10,10a,10b,11,12-tetradecahydro-4aH-8-aza-pentaleno[2,1-a]phenanthren-2-one |
| 78 | (4aS,4bR,5S,6aS,6bS,9aR,10aS,10bS,12S)-8-benzenesulfonyl-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 79 | (4aS,4bR,5S,6aS,6bS,9aR,10aS,10bS,12S)-4b,12-difluoro-5-hydroxy-6b-(2-hydroxy-acetyl)-4a,6a-dimethyl-8-(propane-2-sulfonyl)-4b,5,6,6a,6b,7,8,9,9a,10,10a,10b,11,12-tetradecahydro-4aH-8-aza-pentaleno[2,1-a]phenanthren-2-one |
| 80 | (4aS,4bR,5S,6aS,6bS,9aR,10aS,10bS,12S)-4b,12-difluoro-5-hydroxy-6b-(2-hydroxy-acetyl)-4a,6a-dimethyl-8-(thiophene-2-sulfonyl)-4b,5,6,6a,6b,7,8,9,9a,10,10a,10b,11,12-tetradecahydro-4aH-8-aza-pentaleno[2,1-a]phenanthren-2-one |
| 81 | (4aS,4bR,5S,6aS,6bS,9aR,10aS,10bS,12S)-4b,12-difluoro-5-hydroxy-6b-(2-hydroxy-acetyl)-4a,6a-dimethyl-8-phenylmethanesulfonyl-4b,5,6,6a,6b,7,8,9,9a,10,10a,10b,11,12-tetradecahydro-4aH-8-aza-pentaleno[2,1-a]phenanthren-2-one |
| 82 | acetic acid 2-((4aS,4bR,5S,6aS,6bS,9aR,10aS,10bS,12S)-8-cyclohexylthiocarbamoyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl)-2-oxo-ethyl ester |
| 83 | (4aS,4bR,5S,6aS,6bS,9aR,10aS,10bS,12S)-4b,12-difluoro-5-hydroxy-6b-(2-hydroxy-acetyl)-4a,6a-dimethyl-2-oxo-2,4b,5,6,6a,6b,7,9,9a,10,10a,10b,11,12-tetradecahydro-4aH-8-aza-pentaleno[2,1-a]phenanthrene-8-carbothioic acid cyclohexylamide |
| 84 | (4aS,4bR,5S,6aS,6bS,9aR,10aS,10bS,12S)-4b,12-difluoro-5-hydroxy-6b-(2-hydroxy-acetyl)-4a,6a-dimethyl-2-oxo-2,4b,5,6,6a,6b,7,9,9a,10,10a,10b,11,12-tetradecahydro-4aH-8-aza-pentaleno[2,1-a]phenanthrene-8-carboxylic acid phenylamide |
| 85 | (4aS,4bR,5S,6aS,6bS,9aR,10aS,10bS,12S)-4b,12-difluoro-5-hydroxy-6b-(2-hydroxy-acetyl)-4a,6a-dimethyl-2-oxo-2,4b,5,6,6a,6b,7,9,9a,10,10a,10b,11,12-tetradecahydro-4aH-8-aza-pentaleno[2,1-a]phenanthrene-8-carbothioic acid phenylamide |
| 86 | (4aS,4bR,5S,6aS,6bS,9aR,10aS,10bS,12S)-4b,12-difluoro-5-hydroxy-6b-(2-isopropoxycarbonyloxy-acetyl)-4a,6a-dimethyl-2-oxo-2,4b,5,6,6a,6b,7,9,9a,10,10a,10b,11,12-tetradecahydro-4aH-8-aza-pentaleno[2,1-a]phenanthrene-8-carboxylic acid isopropyl ester |
| 87 | (4aS,4bR,5S,6aS,6bS,9aR,10aS,10bS,12S)-4b,12-difluoro-5-hydroxy-6b-(2-hydroxy-acetyl)-4a,6a-dimethyl-2-oxo-2,4b,5,6,6a,6b,7,9,9a,10,10a,10b,11,12-tetradecahydro-4aH-8-aza-pentaleno[2,1-a]phenanthrene-8-carboxylic acid isopropyl ester |
| 88 | (4aS,4bR,5S,6aS,6bS,9aR,10aS,10bS,12S)-6b-(2-acetoxy-acetyl)-4b,12-difluoro-5-hydroxy-4a,6a-dimethyl-2-oxo-2,4b,5,6,6a,6b,7,9,9a,10,10a,10b,11,12-tetradecahydro-4aH-8-aza-pentaleno[2,1-a]phenanthrene-8-carboxylic acid benzyl ester |
| 89 | (4aS,4bR,5S,6aS,6bS,9aR,10aS,10bS,12S)-4b,12-difluoro-5-hydroxy-6b-(2-hydroxy-acetyl)-4a,6a-dimethyl-2-oxo-2,4b,5,6,6a,6b,7,9,9a,10,10a,10b,11,12-tetradecahydro-4aH-8-aza-pentaleno[2,1-a]phenanthrene-8-carboxylic acid benzyl ester |
| 90 | acetic acid 2-((4aS,4bR,5S,6aS,6bS,9aR,10aS,10bS,12S)-8-(benzooxazol-2-yl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl)-2-oxo-ethyl ester |

| Compound | Chemical Name |
| --- | --- |
| 91 | (4aS,4bR,5S,6aS,6bS,9aR,10aS,10bS,12S)-8-(benzooxazol-2-yl-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 92 | (4aS,4bR,5S,6aS,6bS,9aR,10aS,10bS,12S)-4b,12-difluoro-5-hydroxy-6b-(2-hydroxy-acetyl)-4a,6a-dimethyl-8-(pyrimidin-2-yl-4b,5,6,6a,6b,7,8,9,9a,10,10a,10b,11,12-tetradecahydro-4aH-8-aza-pentaleno[2,1-a]phenanthren-2-one |
| 93 | (4aS,4bR,5S,6aS,6bS,9aR,10aS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid |
| 94 | (4aS,4bR,5S,6aS,6bS,9aR,10aS,10bS,12S)-8-benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid chloromethyl ester |
| 95 | (4aS,4bR,5S,6aS,6bS,9aR,10aS,10bS,12S)-8-(3-Chloro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid |
| 96 | (4aS,4bR,5S,6aS,6bS,9aR,10aS,10bS,12S)-8-(3-Chloro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid chloromethyl ester |
| 97 | (4aS,4bR,5S,6aS,6bS,9aR,10aS,10bS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid 2-methoxy-ethyl ester |
| 98 | (4aS,4bR,5S,6aS,6bS,9aR,10aS,10bS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid 2-hydroxy-ethyl ester |
| 99 | (4aS,4bR,5S,6aS,6bS,9aR,10aS,10bS,12S)-4b,12-Difluoro-5-hydroxy-4a,6a-dimethyl-8-(3-methyl-butyl)-2-oxo-2,4b,5,6,6a,7,8,9,9a,10,10a,10b,11,12-tetradecahydro-4aH-8-aza-pentaleno[2,1-a]phenanthrene-6b-carboxylic acid |
| 100 | (4aS,4bR,5S,6aS,6bS,9aR,10aS,10bS,12S)-8-(3,5-Difluoro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid |
| 101 | (4aS,4bR,5S,6aS,6bS,9aR,10aS,10bS,12S)-4b,12-Difluoro-5-hydroxy-4a,6a-dimethyl-8-(5-methyl-furan-2-ylmethyl)-2-oxo-2,4b,5,6,6a,7,8,9,9a,10,10a,10b,11,12-tetradecahydro-4aH-8-aza-pentaleno[2,1-a]phenanthrene-6b-carboxylic acid |
| 102 | (4aS,4bR,5S,6aS,6bS,9aR,10aS,10bS,12S)-8-(3,3-Dimethyl-butyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid |
| 103 | (4aS,4bR,5S,6aS,6bS,9aR,10aS,10bS,12S)-4b,12-Difluoro-5-hydroxy-4a,6a-dimethyl-2-oxo-8-(3-phenyl-propyl)-2,4b,5,6,6a,7,8,9,9a,10,10a,10b,11,12-tetradecahydro-4aH-8-aza-pentaleno[2,1-a]phenanthrene-6b-carboxylic acid |
| 104 | (4aS,4bR,5S,6aS,6bS,9aR,10aS,10bS,12S)-8-(3-Chloro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid fluoromethyl ester |
| 105 | (4aS,4bR,5S,6aS,6bS,9aR,10aS,10bS,12S)-4b,12-Difluoro-5-hydroxy-4a,6a-dimethyl-8-(3-methyl-butyl)-2-oxo-2,4b,5,6,6a,7,8,9,9a,10,10a,10b,11,12-tetradecahydro-4aH-8-aza-pentaleno[2,1-a]phenanthrene-6b-carboxylic acid fluoromethyl ester |
| 106 | (4aS,4bR,5S,6aS,6bS,9aR,10aS,10bS,12S)-8-(3,5-Difluoro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid fluoromethyl ester |
| 107 | (4aS,4bR,5S,6aS,6bS,9aR,10aS,10bS,12S)-4b,12-Difluoro-5-hydroxy-4a,6a-dimethyl-8-(5-methyl-furan-2-ylmethyl)-2-oxo-2,4b,5,6,6a,7,8,9,9a,10,10a,10b,11,12-tetradecahydro-4aH-8-aza-pentaleno[2,1-a]phenanthrene-6b-carboxylic acid fluoromethyl ester |
| 108 | (4aS,4bR,5S,6aS,6bS,9aR,10aS,10bS,12S)-8-(3,3-Dimethyl-butyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid fluoromethyl ester |
| 109 | (4aS,4bR,5S,6aS,6bS,9aR,10aS,10bS,12S)-4b,12-Difluoro-5-hydroxy-4a,6a-dimethyl-8-(5-methyl-furan-2-ylmethyl)-2-oxo-2,4b,5,6,6a,7,8,9,9a,10,10a,10b,11,12-tetradecahydro-4aH-8-aza-pentaleno[2,1-a]phenanthrene-6b-carboxylic acid cyanomethyl ester |

-continued

| Compound | Chemical Name |
|---|---|
| 110 | (4aS,4bR,5S,6aS,6bS,9aR,10aS,10bS,12S)-8-(3,3-Dimethyl-butyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid cyanomethyl ester |
| 111 | acetic acid 2-((4aS,4bR,5S,6aS,6bS,9aR,10aS,10bS,12S)-4b,12-difluoro-5-hydroxy-4a,6a-dimethyl-2-oxo-8-phenyl-2,4b,5,6,6a,7,8,9,9a,10,10a,10b,11,12-tetradecahydro-4aH-8-aza-pentaleno[2,1-a]phenanthren-6b-yl)-2-oxo-ethyl ester |
| 112 | (4aS,4bR,5S,6aS,6bS,9aR,10aS,10bS,12S)-4b,12-difluoro-5-hydroxy-6b-(2-hydroxy-acetyl)-4a,6a-dimethyl-8-phenyl-2-yl-4b,5,6,6a,6b,7,8,9,9a,10,10a,10b,11,12-tetradecahydro-4aH-8-aza-pentaleno[2,1-a]phenanthren-2-one |
| 113 | acetic acid 2-[(4aS,4bR,5S,6aS,6bS,9aR,10aS,10bS,12S)-4b,12-difluoro-5-hydroxy-8-(3-methoxy-phenyl)-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl]-2-oxo-ethyl ester |
| 114 | Acetic acid 2-[(4aS,4bR,5S,6aS,6bS,9aR,10aS,10bS,12S)-4b,12-difluoro-5-hydroxy-8-(4-methoxy-phenyl)-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl]-2-oxo-ethyl ester |
| 115 | (4aS,4bR,5S,6aS,6bS,9aR,10aS,10bS,12S)-4b,12-Difluoro-5-hydroxy-6b-(2-hydroxy-acetyl)-8-(3-methoxy-phenyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 116 | 4aS,4bR,5S,6aS,6bS,9aR,10aS,10bS,12S)-4b,12-Difluoro-5-hydroxy-6b-(2-hydroxy-acetyl)-8-(4-methoxy-phenyl)-4a,6a-dimethyl-4b,5,6,6a,6b,7,8,9,9a,10,10a,10b,11,12-tetradecahydro-4aH-8-aza-pentaleno[2,1-a]phenanthren-2-one |
| 117 | 4aS,4bR,5S,6aS,6bS,9aR,10aS,10bS,12S)-4b,12-Difluoro-5-hydroxy-6b-(2-hydroxy-acetyl)-4a,6a-dimethyl-8-m-tolyl-4b,5,6,6a,6b,7,8,9,9a,10,10a,10b,11,12-tetradecahydro-4aH-8-aza-pentaleno[2,1-a]phenanthren-2-one and 4aS,4bR,5S,6aS,6bS,9aR,10aS,10bS,12S)-4b,12-Difluoro-5-hydroxy-6b-(2-hydroxy-acetyl)-4a,6a-dimethyl-8-p-tolyl-4b,5,6,6a,6b,7,8,9,9a,10,10a,10b,11,12-tetradecahydro-4aH-8-aza-pentaleno[2,1-a]phenanthren-2-one |
| 118 | (4aS,4bR,5S,6aS,6bS,9aR,10aS,10bS,12S)-4b,12-Difluoro-5-hydroxy-6b-(2-hydroxy-acetyl)-4a,6a-dimethyl-2-oxo-2,4a,4b,5,6,6a,6b,9,9a,10,10a,10b,11,12-tetradecahydro-8-aza-pentaleno[2,1-a]phenanthrene-9-carboxylic acid ethyl ester |
| 119 | (4aS,4bR,5S,6aS,6bS,9aR,10aS,10bS,12S)-4b,12-difluoro-5-hydroxy-6b-(2-hydroxy-acetyl)-4a,6a-dimethyl-2-oxo-2,4a,4b,5,6,6a,6b,7,8,9,9a,10,10a,10b,11,12-hexadecahydro-8-aza-pentaleno[2,1-a]phenanthrene-9-carboxylc acid ethyl ester |
| 120 | (4aS,4bR,5S,6aS,6bS,9aR,10aS,10bS,12S)-8-(thiophene-2-carbonyl)-4b,12-difluoro-5-hydroxy-6b-(2-hydroxy-acetyl)-4a,6a-dimethyl-2-oxo-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 121 | (4aR,4bS,5S,6aS,6bS,9aR,10aS,10bS)-8-benzoyl-5-hydroxy-6b-(2-hydroxy-acetyl)-4a,6a-dimethyl-2-oxo-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 122 | (4aS,4bR,5S,6aS,6bS,9aR,10aS,10bS,12S)-8-benzoyl-4b,12-difluoro-5-hydroxy-6b-(2-hydroxy-acetyl)-4a,6a-dimethyl-2-oxo-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 123 | (4aS,4bR,5S,6aS,6bS,9aR,10aS,10bS,12S)-8-(furan-2-carbonyl)-4b,12-difluoro-5-hydroxy-6b-(2-hydroxy-acetyl)-4a,6a-dimethyl-2-oxo-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 124 | (4aS,4bR,5S,6aS,6bS,9aR,10aS,10bS,12S)-4b,12-difluoro-5-hydroxy-6b-(2-hydroxy-acetyl)-4a,6a-dimethyl-2-oxo-8-phenylacetyl-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 125 | (4aS,4bR,5S,6aS,6bS,9aR,10aS,10bS,12S)-4b,12-difluoro-5-hydroxy-6b-(2-hydroxy-acetyl)-4a,6a-dimethyl-2-oxo-8-(2-thiophen-2-yl-ac ethyl)-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 126 | (4aS,4bR,5S,6aS,6bS,9aR,10aS,10bS,12S)-4b,12-difluoro-8-(furan-2-ylmethyl-5-hydroxy-6b-(2-hydroxy-acetyl)-4a,6a-dimethyl-2-oxo-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 127 | (4aS,4bR,5S,6aS,6bS,9aR,10aS,10bS,12S)-4b,12-difluoro-5-hydroxy-6b-(2-hydroxy-acetyl)-4a,6a-dimethyl-2-oxo-8-(thiophen-2-ylmethyl-2,4a,4b,5,6,6a,6b,7,8,9,9a,10,10a,10b,11,12-hexadecahydro-8-aza-pentaleno[2,1-a]phenanthrene-9-carboxylic acid ethyl ester |

-continued

| Compound | Chemical Name |
|---|---|
| 128 | (4aR,5S,6aS,6bS,9aR,10aS,10bS)-8-furan-2-ylmethyl-5-hydroxy-6b-(2-hydroxy-acetyl)-4a,6a-dimethyl-2-oxo-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 129 | (4aR,5S,6aS,6bS,9aR,10aS,10bS)-5-hydroxy-6b-(2-hydroxy-acetyl)-4a,6a-dimethyl-2-oxo-8-thiophen-2-ylmethyl-2,4a,4b,5,6,6a,6b,7,8,9,9a,10,10a,10b,11,12-hexadecahydro-8-aza-pentaeno[2,1-a]phenanthrene-9-carboxylic acid ethyl ester |
| 130 | (4aR,4bS,5S,6aS,6bS,9aR,10aS,10bS)-5-hydroxy-6b-(2-hydroxy-acetyl)-4a,6a-dimethyl-2-oxo-8-(3-phenyl-propyl)-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 131 | (4aR,4bS,5S,6aS,6bS,9aR,10aS,10bS)-8-butyl-5-hydroxy-6b-(2-hydroxy-acetyl)-4a,6a-dimethyl-2-oxo-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 132 | (4aS,4bR,5S,6aS,6bS,9aR,10aS,10bS,12S)-8-butyl-4b,12-difluoro-5-hydroxy-6b-(2-hydroxy-acetyl)-4a,6a-dimethyl-2-oxo-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 133 | (4aR,4bS,5S,6aS,6bS,9aR,10aS,10bS)-8-benzyl-5-hydroxy-6b-(2-hydroxy-acetyl)-4a,6a-dimethyl-2-oxo-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 134 | (4aS,4bR,5S,6aS,6bS,9aR,10aS,10bS,12S)-8-benzyl-4b,12-difluoro-5-hydroxy-6b-(2-hydroxy-acetyl)-4a,6a-dimethyl-2-oxo-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 135 | (4aS,4bR,5S,6aS,6bS,9aR,10aS,10bS,12S)-4b,12-difluoro-5-hydroxy-6b-(2-hydroxy-acetyl)-4a,6a-dimethyl-2-oxo-8-(2-phenylsulfanyl-ethyl)-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 136 | (4aS,4bR,5S,6aS,6bS,9aR,10aS,10bS,12S)-4b,12-difluoro-5-hydroxy-6b-(2-hydroxy-acetyl)-4a,6a-dimethyl-2-oxo-8-(2-phenoxy-ethyl)-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 137 | (4aS,4bR,5S,6aS,6bS,9aR,10aS,10bS,12S)-4b,12-difluoro-5-hydroxy-6b-(2-hydroxy-acetyl)-4a,6a-dimethyl-2-oxo-8-(3-phenyl-propyl)-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 138 | (4aS,4bR,5S,6aS,6bS,9aR,10aS,10bS,12S)-4b,12-difluoro-5-hydroxy-6b-(2-hydroxy-acetyl)-4a,6a-dimethyl-2-oxo-8-phenylcarbamoyl-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 139 | (4aR,4bS,5S,6aS,6bS,9aR,10aS,10bS)-5-hydroxy-6b-(2-hydroxy-acetyl)-4a,6a-dimethyl-2-oxo-8-phenylcarbamoyl-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 140 | (4aR,4bS,5S,6aS,6bS,9aR,10aS,10bS)-5-hydroxy-6b-(2-hydroxy-acetyl)-4a,6a-dimethyl-2-oxo-8-phenylthiocarbamoyl-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 141 | (4aR,4bS,5S,6aS,6bS,9aR,10aS,10bS)-8-cyclohexylcarbamoyl-5-hydroxy-6b-(2-hydroxy-acetyl)-4a,6a-dimethyl-2-oxo-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 142 | (4aS,4bR,5S,6aS,6bS,9aR,10aS,10bS,12S)-8-benzenesulfonyl-4b,12-difluoro-5-hydroxy-6b-(2-hydroxy-acetyl)-4a,6a-dimethyl-2-oxo-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 143 | (4aR,4bS,5S,6aS,6bS,9aR,10aS,10bS)-5-hydroxy-6b-(2-hydroxy-acetyl)-8-methanesulfonyl-4a,6a-dimethyl-2-oxo-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 144 | (4aR,4bS,5S,6aS,6bS,9aR,10aS,10bS)-8-benzenesulfonyl-5-hydroxy-6b-(2-hydroxy-acetyl)-4a,6a-dimethyl-2-oxo-2,4a,4b,5,6,6a,6b,7,8,9,9a,10,10a,10b,11,12-hexadecahydro-8-aza-pentaleno[2,1-a]phenanthrene-9-carboxylic acid ethyl ester |
| 145 | (4aS,4bR,5S,6aS,6bS,9aR,10aS,10bS,12S)-8-benzyl-4b,12-difluoro-5-hydroxy-6b-(2-hydroxy-acetyl)-4a,6a-dimethyl-2-oxo-2,4a,4b,5,6,6a,6b,7,8,9,9a,10,10a,10b,11,12-hexadecahydro-8-aza-pentaleno[2,1-a]phenanthrene-9-carboxylic acid |
| 146 | (4aS,4bR,5S,6aS,6bS,9aR,10aS,10bS,12S)-4b,12-Difluoro-5-hydroxy-4a,6a-dimethyl-8-(5-methyl-furan-2-ylmetyl)-2-oxo-2,4b,5,6,6a,7,8,9,9a,10,10a,10b,11,12-tetradecahydro-4aH-8-aza-pentaleno[2,1-a]phenanthrene-6b-carboxylic acid dimethylamide |

-continued

| Compound | Chemical Name |
|---|---|
| 147 | 4aS,4bR,5S,6aS,6bS,9aR,10aS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid ethyl amide |
| 148 | (4aS,4bR,5S,6aS,6bS,9aR,10aS,10bS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid ethyl-methyl-amide |
| 149 | (4aS,4bR,5S,6aS,6bS,9aR,10aS,10bS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid benzyl amide |
| 150 | (4aS,4bR,5S,6aS,6bS,9aR,10aS,10bS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid (1-phenyl-cyclopropyl)-amide |
| 151 | (4aS,4bR,5S,6aS,6bS,9aR,10aS,10bS,12S)-8-(3-Chloro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid cyanomethyl-amide |
| 152 | (4aS,4bR,5S,6aS,6bS,9aR,10aS,10bS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid dimethylamide |
| 153 | (4aS,4bR,5S,6aS,6bS,9aR,10aS,10bS,12S)-8-(3-Chloro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid dimethylamide |
| 154 | (4aS,4bR,5S,6aS,6bS,9aR,10aS,10bS,12S)-8-(3,5-Difluoro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid dimethylamide |
| 155 | (4aS,4bR,5S,6aS,6bS,9aR,10aS,10bS,12S)-8-(3,3-Dimethyl-butyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid dimethylamide |
| 156 | (4aS,4bR,5S,6aS,6bS,9aR,10aS,10bS,12S)-4b,12-Difluoro-5-hydroxy-4a,6a-dimethyl-2-oxo-8-(3-phenyl-propyl)-2,4b,5,6,6a,7,8,9,9a,10,10a,10b,11,12-tetradecahydro-4aH-8-aza-pentaleno[2,1-a]phenanthrene-6b-carboxylic acid dimethylamide |
| 157 | (4aS,4bR,5S,6aS,6bS,9aR,10aS,10bS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid methyl ester trifluoroacetate |
| 158 | [(4aS,4bR,5S,6aS,6bS,9aR,10aS,10bS,12S)-6b-(2-Acetoxy-acetyl)-4b,12-difluoro-5-hydroxy-4a,6a-dimethyl-2-oxo-2,4b,5,6,6a,6b,7,9,9a,10,10a,10b,11,12-tetradecahydro-4aH-8-aza-pentaleno[2,1-a]phenanthren-8-yl]-acetic acid ethyl ester |
| 159 | [(4aS,4bR,5S,6aS,6bS,9aR,10aS,10bS,12S)-4b,12-Difluoro-5-hydroxy-6b-(2-hydroxy-acetyl)-4a,6a-dimethyl-2-oxo-2,4b,5,6,6a,6b,7,9,9a,10,10a,10b,11,12-tetradecahydro-4aH-8-aza-pentaleno[2,1-a]phenanthren-8-yl]-acetic acid ethyl ester |
| 160 | (6S,8S,9R,10S,11S,13S,14S)-6,9-difluoro-17-(2-fluoroacetyl)-11-hydroxy-10,13-dimethyl-6,7,8,9,10,11,12,13,14,15-decahydro-3H-cyclopenta[a]phenanthren-3-one |
| 161 | (4aS,4bR,5S,6aS,6bS,9aR,10aS,10bS,12S)-8-Benzyl-4b,12-difluoro-6b-(2-fluoro-acetyl)-5-hydroxy-4a,6a-dimethyl-4b,5,6,6a,6b,7,8,9,9a,10,10a,10b,11,12-tetradecahydro-4aH-8-aza-pentaleno[2,1-a]phenanthren-2-one |
| 162 | (4aS,4bR,5S,6aS,6bS,9aR,10aS,10bS,12S)-8-(3-Chloro-benzyl)-4b,12-difluoro-6b-(2-fluoro-acetyl)-5-hydroxy-4a,6a-dimethyl-4b,5,6,6a,6b,7,8,9,9a,10,10a,10b,11,12-tetradecahydro-4aH-8-aza-pentaleno[2,1-a]phenanthren-2-one |
| 163 | (4aS,4bR,5S,6aS,6bS,9aR,10aS,10bS,12S)-4b,12-Difluoro-6b-(2-fluoro-acetyl)-5-hydroxy-4a,6a-dimethyl-2-oxo-2,4b,5,6,6a,6b,7,9,9a,10,10a,10b,11,12-tetradecahydro-4aH-8-aza-pentaleno[2,1-a]phenanthrene-8-carboxylic acid vinyl ester |
| 164 | (4aS,4bR,5S,6aS,6bS,9aR,10aS,10bS,12S)-4b,12-Difluoro-5-hydroxy-6b-(2-hydroxy-acetyl)-4a,6a-dimethyl-2-oxo-2,4b,5,6,6a,6b,7,9,9a,10,10a,10b,11,12-tetradecahydro-4aH-8-aza-pentaleno[2,1-a]phenanthrene-8-carboxylic acid vinyl ester |
| 165 | (4aS,4bR,5S,6aS,6bS,9aR,10aS,10bS,12S)-4b,12-Difluoro-5-hydroxy-6b-(2-methanesulfonyloxy-acetyl)-4a,6a-dimethyl-2-oxo-2,4b,5,6,6a,6b,7,9,9a,10,10a,10b,11,12-tetradecahydro-4aH-8-aza-pentaleno[2,1-a]phenanthrene-8-carboxylic acid vinyl ester |

-continued

| Compound | Chemical Name |
|---|---|
| 166 | (4aS,4bR,5S,6aS,6bS,9aR,10aS,10bS,12S)-4b,12-Difluoro-6b-(2-fluoro-acetyl)-5-hydroxy-4a,6a-dimethyl-4b,5,6,6a,6b,7,8,9,9a,10,10a,10b,11,12-tetradecahydro-4aH-8-aza-pentaleno[2,1-a]phenanthren-2-one hydrochloride |
| 167 | (4aS,4bR,5S,6aS,6bS,9aR,10aS,10bS,12S)-4b,12-Difluoro-6b-(2-fluoro-acetyl)-8-(4-fluoro-benzyl)-5-hydroxy-4a,6a-dimethyl-4b,5,6,6a,6b,7,8,9,9a,10,10a,10b,11,12-tetradecahydro-4aH-8-aza-pentaleno[2,1-a]phenanthren-2-one |
| 168 | (4aS,4bR,5S,6aS,6bS,9aR,10aS,10bS,12S)-8-(3,5-Difluoro-benzyl)-4b,12-difluoro-6b-(2-fluoro-acetyl)-5-hydroxy-4a,6a-dimethyl-4b,5,6,6a,6b,7,8,9,9a,10,10a,10b,11,12-tetradecahydro-4aH-8-aza-pentaleno[2,1-a]phenanthren-2-one |
| 169 | (4aS,4bR,5S,6aS,6bS,9aR,10aS,10bS,12S)-8-(3,3-Dimethyl-butyl)-4b,12-difluoro-6b-(2-fluoro-acetyl)-5-hydroxy-4a,6a-dimethyl-4b,5,6,6a,6b,7,8,9,9a,10,10a,10b,11,12-tetradecahydro-4aH-8-aza-pentaleno[2,1-a]phenanthren-2-one |
| 170 | (4aS,4bR,5S,6aS,6bS,9aR,10aS,10bS,12S)-4b,12-Difluoro-6b-(2-fluoro-acetyl)-5-hydroxy-4a,6a-dimethyl-8-(3-methyl-butyl)-4b,5,6,6a,6b,7,8,9,9a,10,10a,10b,11,12-tetradecahydro-4aH-8-aza-pentaleno[2,1-a]phenanthren-2-one |
| 171 | (4aS,4bR,5S,6aS,6bS,9aR,10aS,10bS,12S)-4b,12-Difluoro-6b-(2-fluoro-acetyl)-5-hydroxy-4a,6a-dimethyl-8-(5-methyl-furan-2-ylmethyl)-4b,5,6,6a,6b,7,8,9,9a,10,10a,10b,11,12-tetradecahydro-4aH-8-aza-pentaleno[2,1-a] phenanthren-2-one |
| 172 | (4aS,4bR,5S,6aS,6bS,9aR,10aS,10bS,12S)-4b,12-Difluoro-6b-(2-fluoro-acetyl)-5-hydroxy-4a,6a-dimethyl-8-(3-phenyl-propyl)-4b,5,6,6a,6b,7,8,9,9a,10,10a,10b,11,12-tetradecahydro-4aH-8-aza-pentaleno[2,1-a]phenanthren-2-one |
| 173 | (4aS,4bR,5S,6aS,6bS,9aR,10aS,10bS,12S)-8-[4-(4-hydroxy-phenylsulfanylmethyl)-benzyl]-4b,12-difluoro-6b-(2-fluoro-acetyl)-5-hydroxy-4a,6a-dimethyl-4b,5,6,6a,6b,7,8,9,9a,10,10a,10b,11,12-tetradecahydro-4aH-8-aza-pentaleno[2,1-a]phenanthren-2-one |
| 174 | (4aS,4bR,5S,6aS,6bS,9aR,10aS,12S)-4b,12-Difluoro-6b-(2-fluoro-acetyl)-5-hydroxy-4a,6a-dimethyl-8-thiophen-2-ylmethyl-4b,5,6,6a,6b,7,8,9,9a,10,10a,10b,11,12-tetradecahydro-4aH-8-aza-pentaleno[2,1-a]phenanthren-2-one |
| 175 | (4aS,4bR,5S,6aS,6bS,9aR,10aS,10bS,12S)-8-(2-Ethyl-butyl)-4b,12-difluoro-6b-(2-fluoro-acetyl)-5-hydroxy-4a,6a-dimethyl-4b,5,6,6a,6b,7,8,9,9a,10,10a,10b,11,12-tetradecahydro-4aH-8-aza-pentaleno[2,1-a]phenanthren-2-one |
| 176 | (4aS,4bR,5S,6aS,6bS,9aR,10aS,10bS,12S)-6b-Acetyl-4b,12-difluoro-5-hydroxy-4a,6a-dimethyl-2-oxo-2,4b,5,6,6a,6b,7,9,9a,10,10a,10b,11,12-tetradecahydro-4aH-8-aza-pentaleno[2,1-a]phenanthrene-8-carboxylic acid vinyl ester |
| 177 | (4aS,4bR,5S,6aS,6bS,9aR,10aS,10bS,12S)-6b-Acetyl-4b,12-difluoro-5-hydroxy-4a,6a-dimethyl-4b,5,6,6a,6b,7,8,9,9a,10,10a,10b,11,12-tetradecahydro-4aH-8-aza-pentaleno[2,1-a]phenanthren-2-one hydrochloride |
| 178 | (4aS,4bR,5S,6aS,6bS,9aR,10aS,10bS,12S)-6b-Acetyl-8-(3-chloro-benzyl)-4b,12-difluoro-5-hydroxy-4a,6a-dimethyl-4b,5,6,6a,6b,7,8,9,9a,10,10a,10b,11,12-tetradecahydro-4aH-8-aza-pentaleno[2,1-a]phenanthren-2-one |
| 179 | (4aS,4bR,5S,6aS,6bS,9aR,10aS,10bS,12S)-6b-Acetyl-8-(3,5-difluoro-benzyl)-4b,12-difluoro-5-hydroxy-4a,6a-dimethyl-4b,5,6,6a,6b,7,8,9,9a,10,10a,10b,11,12-tetradecahydro-4aH-8-aza-pentaleno[2,1-a]phenanthren-2-one |
| 180 | (4aS,4bR,5S,6aS,6bS,9aR,10aS,10bS,12S)-6b-Acetyl-4b,12-difluoro-5-hydroxy-4a,6a-dimethyl-8-(5-methyl-furan-2-ylmethyl)-4b,5,6,6a,6b,7,8,9,9a,10,10a,10b,11,12-tetradecahydro-4aH-8-aza-pentaleno[2,1-a]phenanthren-2-one |
| 181 | (4aS,4bR,5S,6aS,6bS,9aR,10aS,10bS,12S)-6b-Acetyl-8-(3,3-dimethyl-butyl)-4b,12-difluoro-5-hydroxy-4a,6a-dimethyl-4b,5,6,6a,6b,7,8,9,9a,10,10a,10b,11,12-tetradecahydro-4aH-8-aza-pentaleno[2,1-a]phenanthren-2-one |
| 182 | (4aS,4bR,5S,6aS,6bS,9aR,10aS,10bS,12S)-6b-Acetyl-4b,12-difluoro-5-hydroxy-4a,6a-dimethyl-8-(3-methyl-butyl)-4b,5,6,6a,6b,7,8,9,9a,10,10a,10b,11,12-tetradecahydro-4aH-8-aza-pentaleno[2,1-a]phenanthren-2-one |
| 183 | (4aS,4bR,5S,6aS,6bS,9aR,10aS,10bS,12S)-6b-Acetyl-4b,12-difluoro-5-hydroxy-4a,6a-dimethyl-8-(3-phenyl-propyl)-4b,5,6,6a,6b,7,8,9,9a,10,10a,10b,11,12-tetradecahydro-4aH-8-aza-pentaleno[2,1-a]phenanthren-2-one |
| 184 | (4aS,4bR,5S,6aS,6bS,9aR,10aS,10bS,12S)-6b-Acetyl-4b,12-difluoro-5-hydroxy-4a,6a-dimethyl-8-thiophen-2-ylmethyl-4b,5,6,6a,6b,7,8,9,9a,10,10a,10b,11,12-tetradecahydro-4aH-8-aza-pentaleno[2,1-a]phenanthren-2-one |

| Compound | Chemical Name |
|---|---|
| 185 | (4aS,4bR,5S,6aS,6bS,9aR,10aS,10bS,12S)-4b,12-Difluoro-5-hydroxy-4a,6a-dimethyl-6b-(2-methylsulfanyl-acetyl)-2-oxo-2,4b,5,6,6a,6b,7,9,9a,10,10a,10b,11,12-tetradecahydro-4aH-8-aza-pentaleno[2,1-a]phenanthrene-8-carboxylic acid vinyl ester |
| 186 | (4aS,4bR,5S,6aS,6bS,9aR,10aS,10bS,12S)-4b,12-Difluoro-5-hydroxy-4a,6a-dimethyl-6b-(2-methylsulfanyl-acetyl)-4b,5,6,6a,6b,7,8,9,9a,10,10a,10b,11,12-tetradecahydro-4aH-8-aza-pentaleno[2,1-a]phenanthren-2-one hydrochloride |
| 187 | (4aS,4bR,5S,6aS,6bS,9aR,10aS,10bS,12S)-8-(3-Chloro-benzyl)-4b,12-difluoro-5-hydroxy-4a,6a-dimethyl-6b-(2-methylsulfanyl-acetyl)-4b,5,6,6a,6b,7,8,9,9a,10,10a,10b,11,12-tetradecahydro-4aH-8-aza-pentaleno[2,1-a]phenanthren-2-one |
| 188 | (4aS,4bR,5S,6aS,6bS,9aR,10aS,10bS,12S)-8-(3,3-Dimethyl-butyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carbothioic acid S-fluoromethyl ester |
| 189 | (4aS,4bR,5S,6aS,6bS,9aR,10aS,10bS,12S)-4b,12-Difluoro-5-hydroxy-4a,6a-dimethyl-8-(3-methyl-butyl)-2-oxo-2,4b,5,6,6a,7,8,9,9a,10,10a,10b,11,12-tetradecahydro-4aH-8-aza-pentaleno[2,1-a]phenanthrene-6b-carbothioic acid S-fluoromethyl ester |
| 190 | (4aS,4bR,5S,6aS,6bS,9aR,10aS,10bS,12S)-4b,12-Difluoro-5-hydroxy-4a,6a-dimethyl-8-(5-methyl-furan-2-ylmethyl)-2-oxo-2,4b,5,6,6a,7,8,9,9a,10,10a,10b,11,12-tetradecahydro-4aH-8-aza-pentaleno[2,1-a]phenanthrene-6b-carbothioic acid S-fluoromethyl ester |
| 191 | (4aS,4bR,5S,6aS,6bS,9aR,10aS,10bS,12S)-8-(3,5-Difluoro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carbothioic acid S-fluoromethyl ester |
| 192 | (4aS,4bR,5S,6aS,6bS,9aR,10aS,10bS,12S)-8-(3-Chloro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carbothioic acid S-chloromethyl ester |
| 193 | (4aS,4bR,5S,6aS,6bS,9aR,10aS,10bS,12S)-8-(3-Chloro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carbothioic acid S-iodomethyl ester |
| 194 | (4aS,4bR,5S,6aS,6bS,9aR,10aS,10bS,12S)-8-(3-Chloro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carbothioic acid S-fluoromethyl ester trifluoroacetate |
| 195 | (4aS,4bR,5S,6aS,6bS,9aR,10aS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carbothioic acid S-chloromethyl ester |
| 196 | (4aS,4bR,5S,6aS,6bS,9aR,10aS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carbothioic acid S-iodomethyl ester |
| 197 | (4aS,4bR,5S,6aS,6bS,9aR,10aS,10bS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carbothioic acid S-fluoromethyl ester trifluoroacetate |
| 198 | (4aS,4bR,5S,6aS,6bS,9aR,10aS,10bS,12S)-8-(3-Chloro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carbothioic acid S-(2-oxo-propyl) ester |
| 199 | (4aS,4bR,5S,6aS,6bS,9aR,10aS,10bS,12S)-8-(3-Chloro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carbothioic acid S-(2-fluoro-ethyl) ester |
| 200 | (4aS,4bR,5S,6aS,6bS,9aR,10aS,10bS,12S)-8-(3-Chloro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carbothioic acid S-cyanomethyl ester |
| 201 | (4aS,4bR,5S,6aS,6bS,9aR,10aS,10bS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carbothioic acid S-cyanomethyl ester |
| 202 | (4aS,4bR,5S,6aS,6bS,9aR,10aS,10bS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carbothioic acid S-(2-oxo-tetrahydro-furan-3-yl) ester |
| 203 | (4aS,4bR,5S,6aS,6bS,9aR,10aS,10bS,1S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carbothioic acid S-ethyl ester |

Procedure for the Preparation of Compounds of Formula (I) and (I').

According to a particular embodiment of the present invention, the compounds of general formula (I') may be prepared, for example, following synthetic pathways described in Scheme 1.

The compounds of general formula (I') may be prepared according to different routes described in Scheme 1, depending on the substituents $R_1$, $R_2$, $R_3$, X and Y.

Route A1—Compounds of general formula I' wherein $R_1=(CH_2)_n$—V—$(CH_2)_{n'}$—Z—$R_4$, wherein n=0, n'=1, V is absent, Z is a bond, $R_4$=OH, $R_2=(CH_2)_m$—W—W'-M-$R_6$ wherein m is 1 to 6, W is a single bond, W' and M are absent and $R_3$=H, may be conveniently prepared reacting a compound of general formula (IX) under well described conditions for the synthesis of pyrrolidine through the 1,3-dipolar cycloaddition (1,3-DC) of unsaturated compounds and azomethine ylides. The ylide is generated in situ from a suitable precursor for example a compound of general formula (V). The reaction involves the use of 1 to 7 equivalents of azomethine ylide precursor and it is usually performed in a high boiling point solvent such as THF, dioxane, toluene, or xylene. The reaction usually proceeds in a range of temperature from 50 to 150° C. over a period of 1 to 5 hours and may be promoted by an acid such as trifluoroacetic acid, trimethylsilyl iodide or trimethylsilyl trifluoromethanesulfonate. Sodium, potassium or cesium fluoride could also be effective in catalyzing the reaction.

The 1,3-DC reaction can be performed under classical batch reaction conditions, or can be conducted under flow conditions. A flowing solution of compound of general formula (IX) in a suitable solvent such as for example THF or dioxane, containing 0.01 to 1% of TFA or other acid, is mixed with a flowing solution of compound of general formula (V) and quickly pumped through a hot reaction chamber at such a rate that allows the reaction mixture to spend from 1 to 10 minutes at the reaction temperature.

Azomethine ylide precursors of general formula (V) are commercially available or can be prepared as described in the literature, for example following the procedure described in *J. Chem.-Soc., Perkin Trans.*, 1, 1998, pp. 3867-3872, which is incorporated herein by reference in its entirety.

The compounds of formula (IX) may be prepared hydrolyzing the compounds of formula (IV). This reaction is preferably carried out by subjecting compounds (IV) to the action of an enzyme, such as for example immobilized Lipase from *Candida Antarctica* (Sigma Aldrich) (*Tetrahedron*, 1994, Vol. 50, No. 46, 13165-13172), which is incorporated herein by reference in its entirety.

Compounds of general formula (IV) may be conveniently prepared according to standard procedures reported in the literature. For instance they may be prepared by treatment of compounds of general formula (III) with a base such as potassium acetate. This reaction is usually performed in a suitable polar solvent (e.g. DMF) and typically proceeds at a temperature range from 80 to 110° C., over a period of 0.5 to 4 hours.

Compounds of formula (III) may be readily prepared from known compounds by methods well known to those skilled in the art, starting from compounds of general formula (II) (*J. Med. Chem.*, 1982, 25, 1492-1495, which is incorporated herein by reference in its entirety).

Alternatively compounds of general formula (I') wherein $R_1=(CH_2)_n$—V—$(CH_2)_{n'}$—Z—$R_4$, n=0, n'=1, V is absent, Z is a bond, $R_4$ is OH and $R_3$=H, can be prepared following Route A2, starting from the reaction of compound of general formula (IV) with the N-benzyl-N-(trimethylsilylmethyl) aminomethyl ether (V), wherein m=1 and $R_6$=phenyl, under the 1,3-DC conditions described in Route A1, to obtain a compound of formula (VI). The benzyl group can be removed by catalytic hydrogenation, using palladium on charcoal as catalyst, or through chemical dealkylation of tertiary amines with acyl chlorides, phosgene analogues or preferably chloroformates such as vinylchloroformate. The reaction is usually performed in a suitable solvent such as dichloromethane (DCM), tetrahydrofuran (THF) or acetonitrile at temperature range from room temperature (RT) to 60° C. The reaction requires the presence of a base such as alkali carbonates or bicarbonates or an organic base such as pyridine and usually completes over a time range from 0.5 to 2 hours. The carbamate obtained from the first step of the reaction is deprotected under carbamate deprotection of amine, conditions well known for those skilled in the art and well described in the literature (Wiley-VCH; Wuts, Peter G. M./Greene, Theodora W., *Greene's Protective Groups in Organic Synthesis*, Fourth Edition, John Wiley and Sons, 2007, p 503 and following, which is incorporated herein by reference in its entirety).

Compounds of general formula (VII) can be easily further functionalized. For example a compound of general formula (VII) can be treated with acyl chloride and converted into corresponding amide. The conditions for the reaction of pyrrolidines with acyl chlorides are widely described in the literature and involve the use of a solvent such as DCM or THF. The reaction normally requires a base such as triethylamine (TEA), N,N-diisopropylethylamine (DIPEA) or pyridine and it is performed at RT over a period of 1 to 24 hours. In the case the acyl chloride is not available it could be easily obtained from the corresponding carboxylic acid by treatment with for example oxalyl chloride or thionyl chloride. The reaction is performed in a solvent such as DCM, a temperature from 0 to 40° C. and can be accelerated by traces of dimethylformamide.

The same compounds can be obtained by activating a carboxylic acid with an acid activating agent such as carbonyldiimidazole (CDI). The activation with CDI is a well known reaction of carboxylic acids and it is usually performed at temperature range from 0 to 80° C. in a suitable solvent such as DCM, THF or DMF.

It is well know for those skilled in the art that the conversion described above can be accomplished applying variety of other synthetic methodologies which involve the activation of the acid with specific activating reactant or mixture of reactants such as, but not limited to dicyclohexylcarbodiimide (DCC), 1-ethyl-3-(3-dimethylaminopropyl) carbodiimide (EDC), hydroxybenzotriazole (HOBT), 2-(1H-Benzotriazole-1-yl)-1,1,3,3-tetramethyluronium hexafluorophosphate (HBTU), and benzotriazol-1-yl-oxytripyrrolidinophosphonium hexafluorophosphate (PyBROP).

The reaction of compounds of general formula (VII) with chloroformates can be performed as described for the reaction of acyl chloride in a solvent such as DCM or THF in the presence of a base (e.g. TEA or DIPEA). The reaction usually proceeds at RT and over 0.5 to 24 hours.

The reaction of compounds of general formula (VII) with isocyanates or isothiocyanates can be accomplished by dissolving reagents in suitable solvent such DCM, THF, acetonitrile at RT or up to 80° C. The reaction can be facilitated by the presence of a base (e.g. TEA, DIPEA or pyridine) and completes in 1 to 24 hours.

The treatment of compounds of general formula (VII) with sulfonyl chlorides is the standard reaction for the preparation of sulfonamides. The reaction occurs in a solvent such as DCM, THF or pyridine and may require the presence of a base (e.g. TEA or DIPEA) and completes over a period of 0.5 to 4 hours at RT.

Aryl or heteroaryl groups can be introduced at N atom of pyrrolidine ring by following described procedures for the N arylation of pyrrolidines. Compounds of general formula (VII) can be reacted under metal catalyzed arylation conditions. The reaction is promoted by copper (I) salts, nickel(II) phosphine complexes and palladium complexes and often a base such as sodium or potassium terbutylate is required. The reaction occurs in a solvent such as DMF, dimetilacetamide (DMA), acetonitrile, dioxane, THF, toluene, N-methylpyrrolidone (NMP) at a temperature range from 40 to 200° C. by conventional thermal heating or by microwaves. In some cases the reaction can occur by simple heating, from 20 to 150° C., of a solution of compound of general formula (VII) and a suitable aryl or heteroaryl derivative, such as halides or trifluoromethane sulfonates (triflate), in a solvent such as ethanol, THF, acetonitrile, DMF, DMA, dioxane or NMP for a period of time from 0.5 to 24 hours. Alternatively this compound can be prepared by reacting the pyrrolidine intermediate of general formula (VII) with a benzyne. This very reactive species can be generated in situ from a suitable precursor following methods described in the literature. A valid protocol involves the treatment of 2-trimethylsilyl-phenyl trifluoromethane sulfonates with cesium fluoride. The reaction occurs at RT in a polar solvent such as acetonitrile and completes over a period from 1 to 72 hours. In the case the benzyne precursor features substituents on the benzene ring, the reaction can lead to a mixture of two regioisomers.

The alkylation of compounds of general formula (VII) can be performed applying the conditions for the alkylation of pyrrolidines. The reaction involves the use of alkyl halides, methane sulfonates, tosylates or other alkyl derivatives suitable for amine alkylation and requires the presence of a base such as TEA, DIPEA or pyridine to complete. It proceeds at a temperature from RT to 100° C. over 1 to 48 hours in a suitable solvent such as DCM, THF, acetonitrile or DMF. The presence of sodium or potassium iodide can in some cases accelerate the reaction rate.

The same class of derivatives can be obtained reacting compounds of general formula (VII) under reductive amination reaction conditions with a suitable aldehyde in a solvent such as methanol, ethanol, THF, DCM, toluene, acetonitrile or mixture of them. The imine intermediate is usually in situ reduced by treatment with reducing agents, such as sodium borohydride, sodium cyanoborohydride, sodium triacetoxyborohydride at a temperature range from 0 to 20° C., over 1 to 48 hours, or such as formic acid and its salts at a temperature range from 70 to 150° C., over 10 to 30 minutes.

In all cases products obtained feature an acetoxy moiety at position 6b of the steroid scaffold. This moiety can be easily hydrolyzed by treatment with a base such as LiOH, NaOH, KOH, or $K_2CO_3$ solid or dissolved in water, in organic solvents such as methanol, ethanol or THF or alternatively with an aqueous acid solution (for example HCl) in a suitable organic solvent such as THF or dioxane at 40 to 80° C. over a period of 1 to 8 hours.

It will be apparent for those skilled in the art that the sequence of reactions can be inverted performing first the hydrolysis of the acetyl group at position 6b of the steroid scaffold and then one of the functionalizations described above, if the second step is compatible with the presence of a primary alcohol moiety.

It will be even more apparent for those skilled in the art that the N-alkyl derivatives of compounds of formula (VII) obtained through its alkylation and subsequent hydrolysis of acetic ester at position 6b of steroid scaffold as described above in Route A2, can be obtained by 1,3-dipolar cycloaddition from intermediates (IX) and (V) as described in Route A1. All compounds obtained through Route A1 or Route A2 can undergo the sequence of reactions shown in Scheme 1 Route A that describes the functionalization of the hydroxyl moiety at position 6b of the steroid scaffold.

Route A—conversion of the hydroxyl group of 2-hydroxy acetyl moiety at position 6b of compounds of general formula (I') wherein $R_1=(CH_2)_n-V-(CH_2)_{n'}-Z-R_4$, wherein n=0, V is absent, n'=1, Z is a bond, $R_4$=OH and $R_3$=H into a leaving group (LG) of compounds of general formula (VIII) can be carried out by treating compounds of formula (I') with methanesulphonyl chloride or p-toluenesulphonyl chloride (March's, "Advanced Organic Chemistry" Fifth Edition, Michael B. Smith and Jerry March, John Wiley & Sons, Wiley-Interscience), which is incorporated herein by reference in its entirety), in a suitable solvent, for example pyridine. This reaction is usually performed at RT over a period of 1 to 5 hours.

The LG of compounds of general formula (VIII) may be easily displaced by nucleophiles such as halide anions, alcohols, thiols, thioacids, amines, amides and carbanions (*J. Org. Chem.*, 1999, 1042; *J. Steroid. Biochem.*, 13 1980, 311-322, which are incorporated herein by reference in their entireties), to obtain compounds of general formula (I') wherein n=0, V is absent and n'=1. The reaction is usually performed in a suitable solvent (e.g. DCM, THF or DMF), in a range of temperature from −40 to 80° C. over a period of 1 to 5 hours and may be promoted by a base such as sodium or potassium carbonate or sodium hydride. The obtained product may be further functionalized modifying the moiety introduced by the described nucleophilic substitution reaction.

Route A3—the acylation of the hydroxyl group of 2-hydroxy acetyl moiety at position 6b of compounds of general formula (I') wherein $R_1=(CH_2)_n-V-(CH_2)_{n'}-Z-R_4$, wherein n=0, V is absent, n'=1, Z is a bond, $R_4$=OH and $R_3$=H to obtain compounds of general formula (I') wherein n=1, V is O, n'=0, Z is carbonyl or carboxyl, $R_4$ is $(C_1-C_6)$ alkyl, $(C_3-C_8)$cycloalkyl, aryl or heteroaryl and $R_3$=H, is performed by reaction with the suitable acylating agents such as acetylchloride or ethylchloroformate in a suitable solvent such as DCM in the presence of an organic base, such as for example triethylamine.

Route B—reaction of compounds of formula (I') wherein $R_1=(CH_2)_n-V-(CH_2)_{n'}-Z-R_4$, wherein n=0, V is absent, n'=1, Z is a bond, $R_4$=OH and $R_3$=H under well known oxidation conditions to afford the compounds of general formula (XI). This reaction is usually performed in open air at RT over a period of 12 to 48 hours, in a suitable solvent such as THF in the presence of an aqueous solution of an inorganic base, such as for example sodium or potassium hydroxide.

Route B1—conversion of the compounds of formula (XI) into compounds of general formula (I') wherein $R_1=(CH_2)_n-V-(CH_2)_{n'}-Z-R_4$, wherein n and n'=0, V is absent and $R_3$=H, can be obtained by treating the acid (XI) with one or more equivalents of an acid activating agent such as carbonyldiimidazole. The reaction is usually performed in a suitable polar solvent (e.g. DMF), in a range of temperature from 0 to 80° C. over a period of 1 to 2 hours. The activated acid may be reacted with a nucleophile, readily apparent to those skilled in the art, such as alcohols, thiols, thioacids and amines. The reaction may be promoted by a base such as sodium or potassium carbonate, sodium hydride and proceeds at a temperature ranging from 0 to 20° C. over a period of 1 to 24 hours.

Alternatively, the compounds of formula (XI) may be converted into the corresponding acyl chloride under well known conditions, using for example oxalyl chloride in a suitable solvent such as DCM. The activated compound may be reacted with a nucleophile, readily apparent to those skilled in the art, such as alcohols, thiols, thioacids, amines and carbanions such as alkyl, aryl and heteroaryl cuprates or other metalloorganic compounds reported in the literature to be suitable for the conversion of acyl chlorides into the corresponding ketones. The use of protecting groups must be considered in this reaction in order to avoid undesired reactions.

Route B2—conversion of compounds of formula (XI) into compounds of general formula (XII), derived from reaction of acid (XI) with for example carbonyldiimidazole or N-[(dimethylamino)-1H-1,2,3-triazolo[4,5-b]pyridine-1-yl-methylene]-N-methylmethanaminium hexafluorophosphate N-oxide (HATU), followed by reaction with the sodium salt of thioacetic acid or with sodium hydrogensulfide. The reaction is usually performed adding the solution of the preformed salt in the reaction solvent to the solution of the activated acid, at a temperature ranging from 0 to 20° C. The thioacid compounds of formula (XII) readily formed is in situ reacted with an alkylating reagent, such as bromoalkanes, leading to thioesters of general formula (I') wherein $R_1$=$(CH_2)_n$—V—$(CH_2)_{n'}$—Z—$R_4$, wherein n and n'=0, V is absent, Z=S, $R_3$=H. The choice of suitable bromoalkane, such as bromo-chloromethane, may allow the preparation of compounds of formula (I') wherein $R_1$=$(CH_2)_n$—V—$(CH_2)_{n'}$—Z—$R_4$, wherein n and n'=0, V is absent, Z=S, $R_3$=H that may be further modified. For example, the reaction of these compounds in which $R_4$=chloromethyl with potassium iodide, followed by treatment with silver fluoride, may allow the preparation of compounds of formula (I') in which $R_4$=fluoromethyl. These reactions are carried out as described in the literature for the synthesis of well known compounds such as fluticasone derivatives and are well known to those skilled in the art (*J. Med. Chem.*, 1994, 37, 3717-3729, which is incorporated herein by reference in its entirety).

Route B3—Alternatively compounds of general formula (I') wherein $R_1$=$(CH_2)_n$—V—$(CH_2)_{n'}$—Z—$R_4$, n and n'=0, V is absent, Z=S and $R_3$=H can be obtained applying the reaction conditions for the conversion of carboxylic acids into corresponding thioacids with dimethyl thiocarbamoyl chloride. The reaction is performed in DCM at RT over a period of time from 36 to 72 hours. The obtained compound is treated with diethyl amine at reflux temperature for a period of time from 8 to 12 hours to give a compound of general formula (XII) that may be further functionalized as described above.

Route B4—Conversion of the compounds of formula (XI) into compounds of general formula (I') wherein $R_1$=$(CH_2)_n$—V—$(CH_2)_{n'}$—Z—$R_4$, wherein n and n'=0, V is absent, Z=O, $R_4$ is $(C_1-C_6)$alkyl and $R_3$=H can be obtained by treating the acid (XI) with dimethylcarbonate at reflux or with an alkylating reagent such as bromofluoromethane in a suitable solvent such as DMF, at RT, in the presence of an inorganic base such as sodium carbonate over a period of 1 to 24 hours. These reactions are carried out as described in the literature for the synthesis of similar compounds and are well known to those skilled in the art.

Route C—In another embodiment of the present invention, compound of general formula (XIII) can be prepared by a two step reaction of intermediate of general formula (IX) with ethylisocyanoacetate followed by reduction of the pyrroline so formed. The cycloaddition of the isonitrile occurs in solvents such as tetrahydrofuran or dioxane at a temperature from 50 to 90° C. over a period of time from 1 to 5 hours. It is catalyzed by a base such as cuprous oxide. The reduction of the formed pyrroline can be performed by treating this intermediate with a suitable reducing agent such as $NaCNBH_3$ in methanol or ethanol in a temperature range from 0° C. to RT. It will be apparent to those skilled in the art that following the procedure described a mixture of stereoisomers is obtained.

Compounds of general formula (XIII) can be further functionalized. For example they can undergo all reactions already described for the functionalization of compound (VII) and well known for those skilled in the art.

The ethyl ester at position 9 of compound of general formula (XIII) can be hydrolyzed and converted into the corresponding carboxylic acid. The reaction can be conveniently performed treating with a base such as sodium of potassium hydroxide in suitable solvent such as methanol, ethanol or THF. The reaction occurs at a temperature from 0° C. to RT over a period of time ranging from 4 to 24 hours.

The obtained acid of general formula (I') wherein $R_3$=COOH can be easily further functionalized for example converted into compound of general formula (I') wherein $R_3$=$CONR_{13}R_{14}$ using one of the methods for the preparation of amides described herein Route A for the conversion of compound of general formula (VII) into compound of general formula (I') (wherein $R_2$=$(CH_2)_m$—W—W'-M-$R_6$, wherein m=0, W is a bond, W' and M are absent and $R_6$=$COR_7$), well known for those skilled in the art.

Route D—In another embodiment of the present invention, compounds of general formula (I') wherein $R_1$=$(CH_2)_n$—V—$(CH_2)_{n'}$—Z—$R_4$, n=0, V is absent, n'=1, Z is a bond, $R_4$=OH and $R_3$=H can be prepared by a two step procedure, starting from the conversion of the hydroxyl group of 2-hydroxy acetyl moiety at position 6b of compounds of general formula (IX) into a leaving group (LG) using methanesulphonyl chloride or p-toluenesulphonyl chloride (March's, "*Advanced Organic Chemistry*" Fifth Edition, Michael B. Smith and Jerry March, John Wiley & Sons, Wiley-Interscience), in a suitable solvent, for example acetonitrile in the presence of an organic base such as DIPEA. This reaction is usually performed at RT over a period of 1 to 24 hours and the obtained activate intermediates are submitted to the displacement of the LG by using a nucleophile such as an halide salt to obtain compounds of general formula (XIV). This displacement is usually performed in situ for example by the addition of TBAF and/or potassium carbonate and refluxing the reaction mixture over a period of 24-26 hours. The second step is the 1-3 dipolar cycloaddition reaction of compounds of general formula (XIV) with a compound of general formula (V) performed as described above (Route A1).

Route E—In another embodiment of the present invention, compounds of general formula (I') wherein $R_1$=$(CH_2)_n$—V—$(CH_2)_{n'}$—Z—$R_4$, n=0, V is absent, n'=1, Z is a bond, $R_4$ is halide, hydrogen or a thioalkyl and $R_3$=H, are obtained by a four step procedure. The sequence comprises the reaction of compounds of general formula (VI) with vinylchloroformate as previously described (Route A1), the hydrolysis of the acetyl group is performed under basic conditions using potassium carbonate in methanol at 0° C. to obtain compounds of formula (XV), the conversion of the hydroxyl group of 2-hydroxy acetyl moiety at position 6b of compounds of general formula (XV) into a leaving group (LG) such as a mesylated as previously described (Route E), the displacement of the LG by using a nucleophile such as an halide salt or an alkylthiolate salt to obtain compounds of general formula (XVI). This displacement is preformed in a suitable solvent such as acetonitrile or DMF and using potassium fluoride, TBAF or sodium methylthiolate as possible nucleofiles. Alternatively compounds of general formula (XVI) with $R_4$=I are generated and reduced in situ in the presence of sodium iodide in a suitable solvent such as acetonitrile, under microwave irradiation at 100° C. in a period of 2 to 6 hours. While the reduction of α-iodo-ketones is well known using for example reducing agents such as zinc in acetic acid (see, U.S. Pat. No. 2,864,838; 1958, which is incorporated herein by reference in its entirety) or sodium thiosulfate in acetic acid (see, U.S. Pat. No. 2,838,545; 1958, which is incorporated herein by reference in its entirety) this iodide promoted reduction reaction is unprecedented. Compounds of general formula (XVI) are deprotected to obtain compounds of general formula (XVII)

which may be further N-functionalized by acylation, alkylation, sulfonylation, reductive amination and arylation to obtain compounds of general formula (I').

Compounds of general formula (XVII) can be easily further functionalized as previously described for intermediate (VII) (Route A2).

Advantageously, the compounds of general formula (I') may be administered for example, at a dosage of 0.001 to 1000 mg/day, preferably 0.1 to 500 mg/day.

When they are administered by inhalation route, the dosage of the compounds of general formula (I) is advantageously 0.01 to 20 mg/day, preferably 0.1 to 10 mg/day.

Preferably, the compounds of general formula (I) alone or combined with other active ingredients may be administered for the prevention and/or treatment of any obstructive respiratory disease such as asthma, chronic bronchitis, and chronic obstructive pulmonary disease (COPD).

However the compounds of general formula (I) may be administered for the prevention and/or treatment of any disease wherein the decrease in the number, activity and movement of inflammatory cells is implicated.

Examples of such diseases include: diseases involving inflammation such as asthma and other allergic disorders, COPD, acute rhinitis; reverse acute transplant rejection and acute exacerbations of selected autoimmune disorders, graft-versus-host disease in bone-marrow transplantation; autoimmune disorders such as rheumatoid and other arthritis; skin conditions such as systemic lupus erythematosus, systemic dermatomyositis, psoriasis; inflammatory bowel disease, inflammatory ophthalmic diseases, autoimmune hematologic disorders, and acute exacerbations of multiple sclerosis; kidney, liver, heart, and other organ transplantation; Behçet's acute ocular syndrome, endogenous uveitis, atopic dermatitis, and nephrotic syndrome; Hodgkin's disease and non-Hodgkin's lymphoma, multiple myeloma and chronic lymphocytic leukemia (CLL); autoimmune hemolytic anemia and thrombocytopenia associated with CLL; leukemia and malignant lymphoma.

Preferably the compounds of general formula (I') may be administered for the prevention and/or treatment of respiratory diseases such as from mild to acute severe conditions of asthma and COPD.

Other features of the invention will become apparent in the course of the following descriptions of exemplary embodiments which are given for illustration of the invention and are not intended to be limiting thereof.

EXAMPLES

Example 1

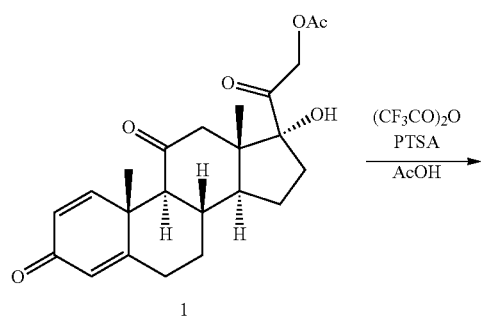

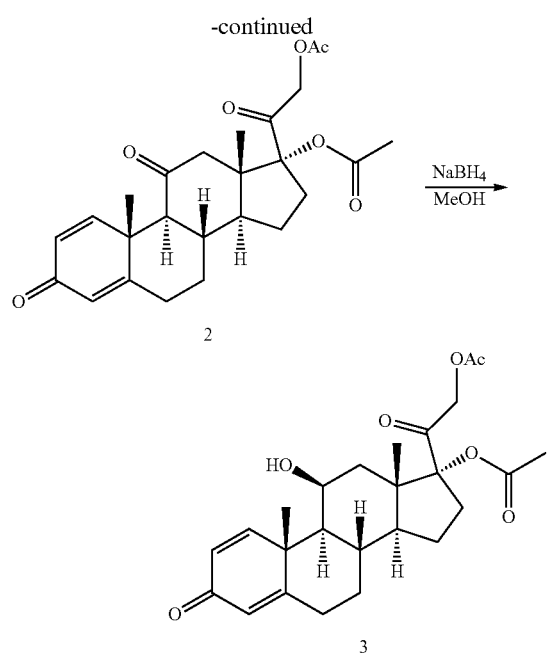

Preparation of acetic acid (8S,9S,10R,13S,14S,17R)-17-(2-acetoxy-acetyl)-10,13-dimethyl-3,11-dioxo-6,7,8,9,10,11,12,13,14,15,16,17-dodecahydro-3H-cyclopenta[α]phenanthren-17-yl ester (intermediate 2)

To a suspension of acetic acid 2-((8S,9S,10R,13S,14S,17R)-17-hydroxy-10,13-dimethyl-3,11-dioxo-6,7,8,9,10,11,12,13,14,15,16,17-dodecahydro-3H-cyclopenta[a]phenanthren-17-yl)-2-oxo-ethyl ester (intermediate 1) (2 g, 4.99 mmol) and PTSA (200 mg, 1.051 mmol) in acetic acid (5 ml), at 0° C., trifluoroacetic anhydride (5 ml, 35.4 mmol) is slowly added over 10 minutes. After stirring at 0° C. for 20 minutes, the reaction mixture is stirred at RT for 3 hours.

The reaction mixture is poured in ice/water (130 ml), and the resulting mixture is extracted with DCM (2×100 ml) and AcOEt (2×100 ml). The combined organic extracts are dried over anhydrous Na2SO4 and concentrated. The crude material is purified by flash chromatography on silica gel, in gradient elution from DCM to DCM/AcOEt 50:50 to give the title compound (2.22 g, quantitative yield).

LC-MS (ESI POS): 443.2 (MH+)

Preparation of acetic acid (8S,9S,10R,11S,13S,14S,17R)-17-(2-acetoxy-acetyl)-11-hydroxy-10,13-dimethyl-3-oxo-6,7,8,9,10,11,12,13,14,15,16,17-dodecahydro-3H-cyclopenta[a]phenanthren-17-yl ester (intermediate 3)

To an ice cooled solution of intermediate 2 (2.22 g, 5.0 mmol) in tetrahydrofuran (15 ml) and MeOH (15 ml), sodium borohydride (221 mg, 5.84 mmol) is added in portions over a period of 2.5 hours. The reaction mixture is poured in 1 N HCl and ice (150 ml). The formed precipitate is extracted with AcOEt (3×100 ml), and the combined organic layers are dried over anhydrous Na2SO4 and concentrated. The crude material is crystallized from Ethyl acetate/petroleum ether. The residue from mother liquor is purified by flash chromatography on silica gel, in gradient elution from DCM to DCM/AcOEt 40:60 affording a second crop. The combined crops give the title the compound (1.85 g, 83% total yield).

$^1$H NMR (300 MHz, CHLOROFORM-d) δ ppm 7.28 (d, 1H), 6.30 (dd, 1H), 6.05 (t, 1H), 4.92 (d, 1H), 4.69 (d, 1H), 4.48-4.58 (m, 1H), 2.75-2.91 (m, 1H), 2.61 (m, 1H), 2.37 (ddd, 1H), 2.18-2.21 (m, 3H), 2.09-2.28 (m, 3H), 2.07 (s, 3H), 1.74-1.98 (m, 3H), 1.51-1.70 (m, 1H), 1.48 (s, 3H), 1.26-1.39 (m, 2H), 1.11-1.19 (m, 1H), 1.05 (s, 3H)

LC-MS (ESI POS): 445.2 (MH+)

Example 2

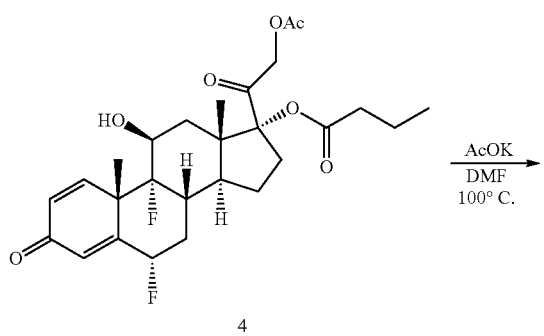

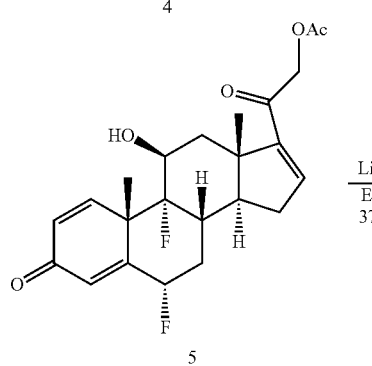

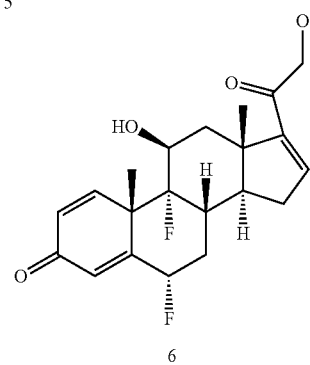

Preparation of Acetic acid 2-((6S,8S,9R,10S,11S, 13S,14S)-6,9-difluoro-11-hydroxy-10,13-dimethyl-3-oxo-6,7,8,9,10,11,12,13,14,15-decahydro-3H-cyclopenta[a]phenanthren-17-yl)-2-oxo-ethyl ester (intermediate 5)

To a solution of butyric acid (6S,8S,9R,10S,11S,13S,14S,17R)-17-(2-acetoxyacetyl)-6,9-difluoro-11-hydroxy-10,13-dimethyl-3-oxo-7,8,9,10,11,12,13,14,15,16,17-dodecahydro-3H-cyclopenta[a]phenanthren-17-yl ester (2.48 g, 4.88 mmol) in anhydrous DMF (60 ml), under nitrogen atmosphere, potassium acetate (3.83 g, 39.0 mmol) is added and the reaction mixture is stirred at 100° C. for 1.5 hours. The reaction mixture is cooled at RT and then poured into ice and brine (200 ml), and the aqueous layer is extracted with AcOEt (3×150 ml). The combined organic extracts are washed with water and brine, dried over Na$_2$SO$_4$ and concentrated to afford 2.55 g of crude title compound which is used in the next step without further purification.

$^1$H NMR (300 MHz, DMSO-d$_6$): δ ppm 7.29 (dd, 1H), 6.99 (dd, 1H), 6.29 (dd, 1H), 5.98-6.15 (m, 1H), 5.68 (dddd, 1H), 5.56 (dd, 1H), 5.10 (d, 1H), 4.92 (d, 1H), 3.98-4.23 (m, 1H), 2.56-2.83 (m, 1H), 2.26-2.44 (m, 3H), 2.14-2.26 (m, 1H), 2.09 (s, 3H), 1.71-1.87 (m, 1H), 1.55-1.65 (m, 2H), 1.53 (s, 3H), 1.15 (s, 3H)

LC-MS (ESI POS): 421.2 (MH+)

Preparation of (6S,8S,9R,10S,11S,13S,14S)-6,9-Difluoro-11-hydroxy-17-(2-hydroxy-acetyl)-10,13-dimethyl-6,7,8,9,10,11,12,13,14,15-decahydro cyclopenta[a]phenanthren-3-one (intermediate 6)

To a solution of intermediate 5 (2.55 g, 6.06 mmol) in ethanol (100 ml), *Candida Antarctica* Lipase (2 U/mg) (510 mg, 6.06 mmol) is added, and the reaction mixture is stirred at 37° C. overnight. The reaction mixture is filtered, washing with methanol, and the residue is purified by flash chromatography on silica gel, in gradient elution from DCM/AcOEt 90:10 to DCM/AcOEt 50:50, to afford 1.62 g of title compound (70.6% yield).

$^1$H NMR (300 MHz, DMSO-d$_6$): ppm 7.29 (dd, 1H), 6.87 (dd, 1H), 6.29 (dd, 1H), 6.09-6.17 (m, 1H), 5.67 (dddd, 1H), 5.53 (dd, 1H), 4.77 (t, 1H), 4.44 (dd, 1H), 4.26 (dd, 1H), 4.04-4.15 (m, 1H), 2.56-2.79 (m, 1H), 2.39 (dd, 1H), 2.25-2.35 (m, 2H), 2.09-2.25 (m, 1H), 1.76 (td, 1H), 1.55-1.66 (m, 2H), 1.53 (s, 3H), 1.17 (s, 3H)

LC-MS (ESI POS): 379.2 (MH+)

Intermediate 7 in Table 1 is prepared as previously described for intermediate 5 starting from intermediate 3.

TABLE 1

| Intermediate | Structure | Yield | Analytical |
|---|---|---|---|
| 7 | 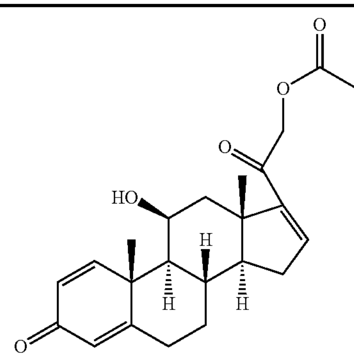 | 50% | $^1$H NMR (300 MHz, CHLOROFORM-d) δ ppm 7.32 (d, 1 H), 6.74 (dd, 1 H), 6.29 (dd, 1 H), 6.03 (t, 1 H), 5.02 (d, 1 H), 4.88 (d, 1 H), 4.36-4.51 (m, 1 H), 2.55-2.73 (m, 1 H), 2.21-2.54 (m, 5 H), 2.19 (s, 3 H), 2.05-2.18 (m, 1 H), 1.66 (dd, 1 H), 1.51 (s, 3 H), 1.28 (s, 3 H), 1.04-1.44 (m, 4 H) LC-MS (ESI POS): 385.45 (MH+) |

Example 3

1,3-dipolar Cycloaddition Method A

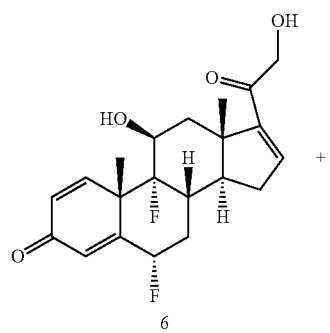

placed in a closed vessel and heated at 140° C. for 1 hour. The solvent is removed under vacuum, and the residue is purified by silica gel cartridge eluting with DCM to DCM:AcOEt 6:4 leading to the title compound (52 mg, 0.102 mmol, 54.9% yield).

$^1$H NMR (300 MHz, CHLOROFORM-d): δ ppm 7.04-7.35 (m, 6H), 6.29 (dd, 1H), 6.12 (s, 1H), 5.48-5.82 (m, 1H), 5.39 (dd, 1H), 4.82 (t, 1H), 4.24 (dd, 1H), 4.10-4.17 (m, 1H), 4.12 (dd, 1H), 3.44 (s, 2H), 3.02-3.22 (m, 1H), 2.80-2.96 (m, 1H), 2.54-2.62 (m, 1H), 2.38 (d, 1H), 2.25-2.32 (m, 1H), 1.94-2.10 (m, 2H), 1.78-1.93 (m, 1H), 1.51-1.77 (m, 4H), 1.49 (s, 3H), 1.29-1.41 (m, 1H), 0.86 (s, 3H)

LC-MS (ESI POS): 512.14 (MH+)

$[α]_D^{20}$=+50.8 c=0.3, MeOH)

Compound 9 listed in Table 2, is prepared as previously described for intermediate 8.

TABLE 2

| Compound | Structure | Yield | Analytical |
|---|---|---|---|
| 9 | 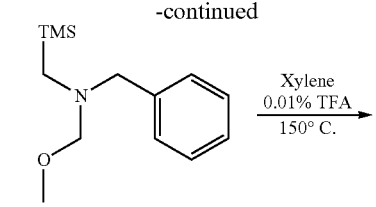 | 40% | $^1$H NMR (300 MHz, DMSO-d$_6$) δ ppm 7.14-7.37 (m, 5 H), 6.29 (dd, 1 H), 6.12 (s, 1 H), 5.48-5.79 (m, 1 H), 5.40 (dd, 1 H), 4.83 (t, 1 H), 4.24 (dd, 1 H), 4.11-4.14 (m, 1 H), 4.12 (dd, 1 H), 3.43 (s, 2 H), 3.07-3.22 (m, 1 H), 2.79-2.94 (m, 1 H), 2.55-2.67 (m, 1 H), 2.17-2.44 (m, 3 H), 1.92-2.09 (m, 2 H), 1.84 (d, 1 H), 1.52-1.75 (m, 3 H), 1.49 (s, 3 H), 1.27-1.42 (m, 1 H), 0.86 (s, 3 H) LC-MS (ESI POS): 546.04 (MH+) $[α]_D^{20}$ = +83.5 (CHCl$_3$, c 0.23) |

-continued

Preparation of (4aS,4bR,5S,6aS,6bS,9aR,10aS,10bS, 12S)-8-Benzyl-4b,12-difluoro-5-hydroxy-6b-(2-hydroxy-acetyl)-4a,6a-dimethyl-4b,5,6,6a,6b,7,8,9, 9a,10,10a,10b,11,12-tetradecahydro-4aH-8-aza-pentaleno[2,1-a]phenanthren-2-one (compound 8)

A mixture of intermediate 6 (95 mg, 0.185 mmol), N-benzyl-1-methoxy-N-((trimethylsilyl)methyl)methanamine (500 mg) and then Xylene (5 ml) containing 0.01% of TFA is

1,3-dipolar Cycloaddition Method B

Preparation of Acetic acid 2-((4aR,4bS,5S,6aS,6bS, 9aR,10aS,10bS)-8-benzyl-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl)-2-oxo-ethyl ester (compound 10)

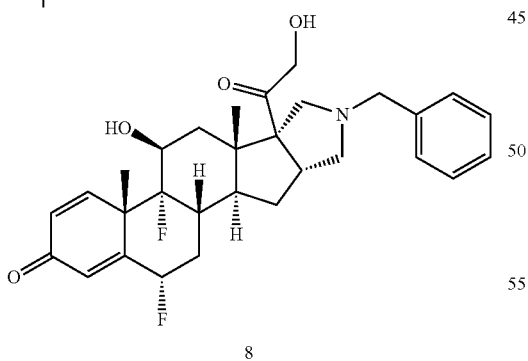

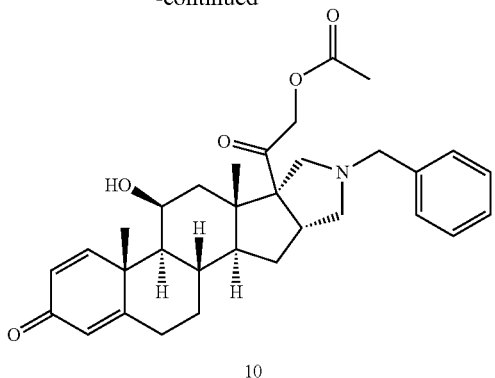

10

A solution of (intermediate 7) (200 mg, 0.520 mmol) and TFA (5 μl, 0.065 mmol) in Dioxane (15 ml) is prepared (Solution A). A solution of N-benzyl-1-methoxy-N-((trimethylsilyl)methyl)methanamine (618 mg, 2.60 mmol) in Dioxane (15 ml) is prepared (Solution B). The two solutions are reacted in the Flow reaction System setting each flow at 0.25 ml/min at 100° C. in the 10 ml reactor (Residence time: 20 min). The solvent is removed under vacuum and then the residue is first triturated twice with AcOEt and petroleum ether and then it is purified by silica gel chromatography (DCM:AcOEt 85:15) to give the title compound (255 mg, 0.493 mmol, 95% yield).

LC-MS (ESI POS): 518.2 (MH+)

Compounds listed in Table 3 are prepared as previously described for compound 10, reacting intermediate 5 or 6 with the suitable azomethine ylide precursor.

TABLE 3

| Compound | Structure | Yield | Analytical |
|---|---|---|---|
| 11 | 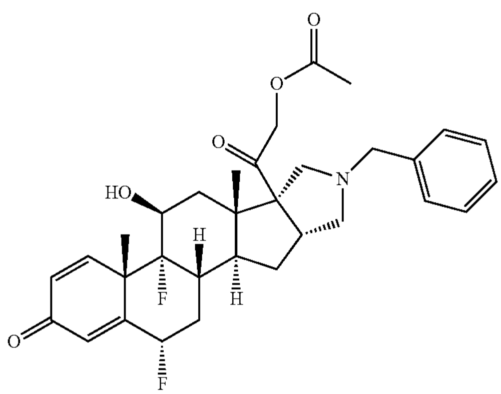 | 82% | $^1$H NMR (300 MHz, DMSO-d$_6$) δ ppm 6.79-7.68 (m, 6 H), 6.29 (dd, 1 H), 6.13 (s, 1 H), 5.48-5.82 (m, 1 H), 5.36-5.46 (m, 1 H), 4.95 (d, 1 H), 4.79 (d, 1 H), 4.01-4.24 (m, 1 H), 3.47 (s, 1 H), 3.03-3.21 (m, 1 H), 2.83-2.98 (m, 1 H), 2.54-2.61 (m, 1 H), 2.24-2.46 (m, 4 H), 2.11 (s, 3 H), 1.94-2.10 (m, 2 H), 1.85 (d, 1 H), 1.52-1.74 (m, 3 H), 1.49 (s, 3 H), 1.28-1.43 (m, 1 H), 0.92 (s, 3 H)<br>LC-MS (ESI POS): 554.2 (MH+) |
| 12 | 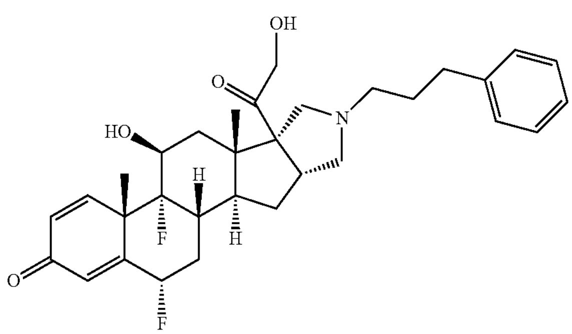 | 17% | $^1$H NMR (300 MHz, DMSO-d$_6$) δ ppm 7.06-7.32 (m, 6 H), 6.29 (dd, 1 H), 6.10 (s, 1 H), 5.49-5.81 (m, 1 H), 5.40 (dd, 1 H), 4.82 (t, 1 H), 4.29 (dd, 1 H), 4.16-4.22 (m, 1 H), 4.13 (dd, 1 H), 3.02-3.19 (m, 1 H), 2.74-2.83 (m, 1 H), 2.54-2.61 (m, 2 H), 2.40-2.48 (m, 2 H), 2.13-2.30 (m, 4 H), 1.93-2.08 (m, 2 H), 1.83-1.92 (m, 1 H), 1.73-1.83 (m, 1 H), 1.56-1.71 (m, 3 H), 1.49-1.55 (m, 1 H), 1.49 (s, 3 H), 1.35 (dd, 1 H), 0.87 (s, 3 H)<br>LC-MS (ESI POS): 540.44 (MH+)<br>[α]$_D^{20}$ = +37.64 (c 0.33, CHCl$_3$) |
| 13 | 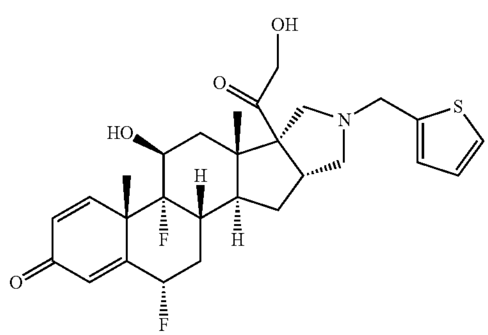 | 40% | $^1$H NMR (300 MHz, DMSO-d$_6$) δ ppm 7.38 (dd, 1 H), 7.25 (dd, 1 H), 6.92 (dd, 1 H), 6.88 (dd, 1 H), 6.29 (dd, 1 H), 6.12 (s, 1 H), 5.49-5.78 (m, 1 H), 5.40 (dd, 1 H), 4.83 (t, 1 H), 4.25 (dd, 1 H), 4.13-4.18 (m, 1 H), 4.11 (dd, 1 H), 3.65 (s, 1 H), 3.02-3.21 (m, 1 H), 2.85 (t, 1 H), 2.54-2.62 (m, 1 H), 2.19-2.41 (m, 3 H), 2.14 (dd, 1 H), 1.95-2.08 (m, 1 H), 1.84 (d, 1 H), 1.54-1.78 (m, 4 H), 1.49 (s, 3 H), 1.36 (dd, 1 H), 0.86 (s, 3 H))<br>LC-MS (ESI POS): 518.48 (MH+)<br>[α]$_D^{20}$ = +79.35 (C = 0.7 CHCl$_3$) |

TABLE 3-continued

| Compound | Structure | Yield | Analytical |
|---|---|---|---|
| 14 | 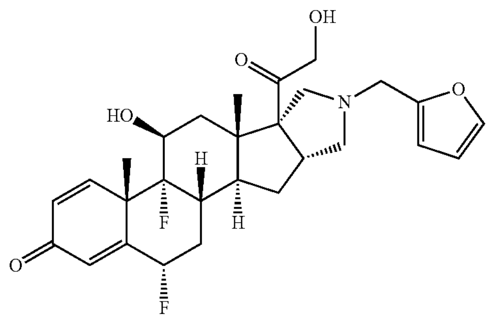 | 44% | ¹H NMR (300 MHz, DMSO-d₆) δ ppm 7.52 (dd, 1 H), 7.25 (dd, 1 H), 6.36 (dd, 1 H), 6.29 (dd, 1 H), 6.17 (d, 1 H), 6.11 (s, 1 H), 5.48-5.74 (m, 1 H), 5.41 (dd, 1 H), 4.83 (t, 1 H), 4.26 (dd, 1 H), 4.15-4.18 (m, 1 H), 4.10 (dd, 1 H), 3.48 (d, 1 H), 3.42 (d, 1 H), 3.04-3.16 (m, 1 H), 2.91 (t, 1 H), 2.63 (d, 1 H), 2.38 (d, 1 H), 2.19-2.31 (m, 2 H), 1.78-2.06 (m, 3 H), 1.52-1.78 (m, 3 H), 1.48 (s, 3 H), 1.32 (dd, 1 H), 0.86 (s, 3 H) <br> LC-MS (ESI POS): 502.42 (MH+) <br> $[\alpha]_D^{20} = +60.0$ (c = 1 CHCl₃) |
| 15 | 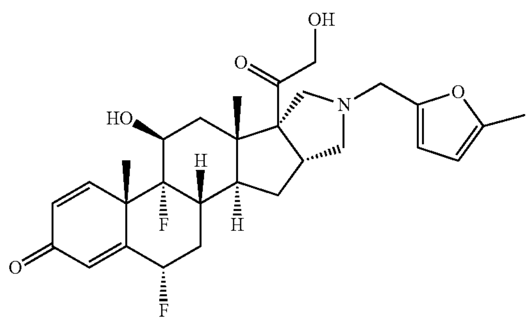 | 20% | ¹H NMR (300 MHz, DMSO-d₆) δ ppm 7.25 (dd, 1 H), 6.29 (dd, 1 H), 6.11 (s, 1 H), 6.02 (d, 1 H), 5.89-5.97 (m, 1 H), 5.50-5.77 (m, 1 H), 5.40 (dd, 1 H), 4.83 (t, 1 H), 4.27 (dd, 1 H), 4.14-4.20 (m, 1 H), 4.11 (dd, 1 H), 3.42 (d, 1 H), 3.34 (d, 1 H), 3.05-3.20 (m, 1 H), 2.92 (t, 1 H), 2.65 (d, 1 H), 2.53-2.60 (m, 1 H), 2.36 (d, 1 H), 2.20-2.27 (m, 1 H), 2.19 (s, 3 H), 1.80-2.05 (m, 3 H), 1.52-1.79 (m, 3 H), 1.48 (s, 3 H), 1.32 (dd, 1 H), 0.86 (s, 3 H) <br> LC-MS (ESI POS): 516.07 (MH+) <br> $[\alpha]_D^{20} = +75.81$ (c 0.43, CHCl₃) |
| 16 | 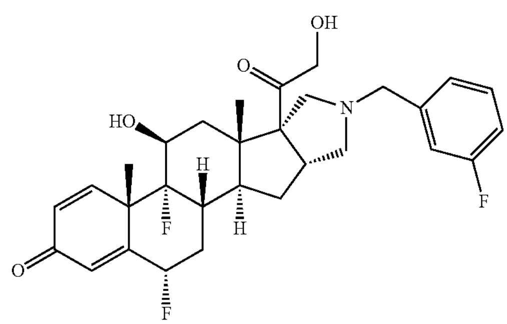 | 14% | ¹H NMR (300 MHz, DMSO-d₆) δ ppm 7.20-7.39 (m, 2 H) 6.95-7.11 (m, 3 H) 6.29 (dd, J = 10.1, 1.9 Hz, 1 H) 6.12 (s, 1 H) 5.64-5.80 (m, 1 H) 5.38 (br. s., 1 H) 4.85 (br. s., 1 H) 4.25 (d, 1 H) 4.11-4.18 (m, 1 H) 4.09 (d, 1 H) 3.47 (s, 2 H) 3.07-3.22 (m, 1 H) 2.87 (t, J = 8.5 Hz, 1 H) 2.53-2.67 (m, 1 H) 2.43-2.46 (m, 1 H) 2.36-2.44 (m, 1 H) 2.16-2.35 (m, 1 H) 1.92-2.11 (m, 2 H) 1.78-1.89 (m, 1 H) 1.54-1.77 (m, 3 H) 1.50 (s, 3 H) 1.35 (dd, 1 H) 0.87 (s, 3 H) <br> LC-MS (ESI POS): 530.08 (MH+) <br> $[\alpha]_D^{20} = +63.5$ (c: 0.27, CHCl₃) |
| 17 | 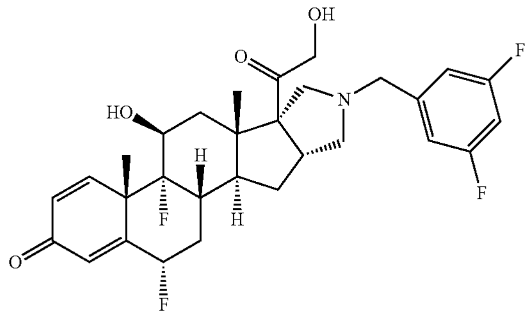 | 19% | ¹H NMR (300 MHz, DMSO-d₆) δ ppm 7.25 (dd, 1 H), 6.99-7.12 (m, 1 H), 6.81-6.98 (m, 2 H), 6.29 (dd, 1 H), 6.12 (s, 1 H), 5.49-5.74 (m, 1 H), 5.41 (dd, 1 H), 4.86 (t, 1 H), 4.26 (dd, 1 H), 4.13-4.19 (m, 1 H), 4.13 (dd, 1 H), 3.51 (d, 1 H), 3.45 (d, 1 H), 3.08-3.23 (m, 1 H), 2.87 (t, 1 H), 2.55-2.62 (m, 1 H), 2.39-2.45 (m, 1 H), 2.23-2.34 (m, 1 H), 1.94-2.10 (m, 2 H), 1.80-1.89 (m, 1 H), 1.52-1.78 (m, 4 H), 1.49 (s, 3 H), 1.31-1.41 (m, 1 H), 0.87 (s, 3 H) <br> LC-MS (ESI POS): 548.24 (MH+) <br> $[\alpha]_D^{20} = +63.2$ (c: 0.28, CHCl₃) |

Example 4

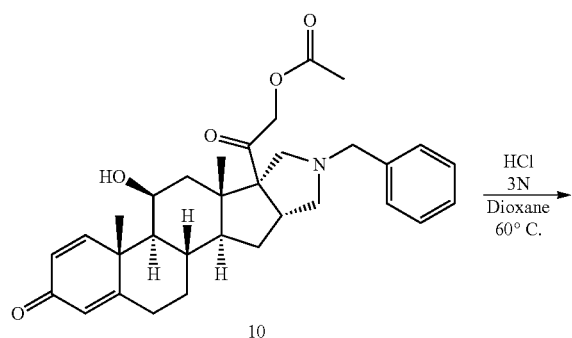
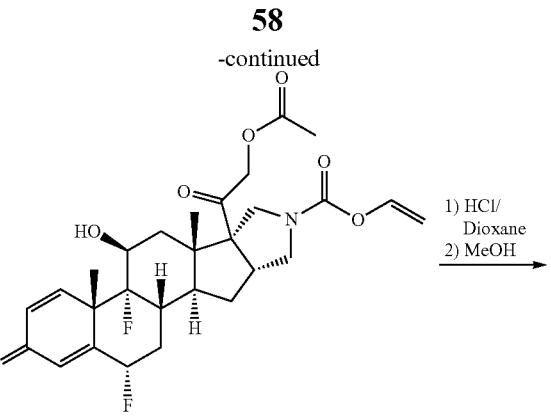

Preparation of (4aR,4bS,5S,6aS,6bS,9aR,10aS, 10bS)-8-Benzyl-5-hydroxy-6b-(2-hydroxy-acetyl)-4a,6a-dimethyl-4b,5,6,6a,6b,7,8,9,9a,10,10a,10b,11, 12-tetradecahydro-4aH-8-aza-pentaleno[2,1-a] phenanthren-2-one (compound 18)

Compound 10 (130 mg, 0.251 mmol) is dissolved in Dioxane (3 ml) and HCl 3 N (1 ml) and the reaction mixture is warmed at 60° C. for 2 hours. The reaction mixture is poured in NaHCO$_3$ and extracted with AcOEt. The organic phase is washed with brine, dried over Na$_2$SO$_4$ and evaporated the residue is purified by silica gel cartridge giving the title compound (20 mg, 0.042 mmol, 16.74% yield).

$^1$H NMR (300 MHz, DMSO-d$_6$) δ ppm 7.10-7.39 (m, 6H), 6.16 (dd, 1H), 5.93 (s, 1H), 4.77 (t, 1H), 4.66 (d, 1H), 4.16-4.29 (m, 2H), 4.10 (dd, 1H), 3.47 (d, 1H), 3.37 (d, 1H), 3.04-3.19 (m, 1H), 2.91 (t, 1H), 2.57 (d, 1H), 2.36 (d, 1H), 1.95-2.08 (m, 2H), 1.77-1.95 (m, 2H), 1.43-1.61 (m, 3H), 1.38 (s, 3H), 1.30-1.37 (m, 1H), 0.95-1.15 (m, 2H), 0.86 (s, 3H)

LC-MS (ESI POS): 476.34 (MH+)

[α]$_D^{20}$=+84.8 (c=0.57, MeOH)

Example 5

Preparation of (4aS,4bR,5S,6aS,6bS,9aR,10aS,10bS, 12S)-6b-(2-Acetoxy-acetyl)-4b,12-difluoro-5-hydroxy-4a,6a-dimethyl-2-oxo-2,4b,5,6,6a,6b,7,9,9a, 10,10a,10b,11,12-tetradecahydro-4aH-8-aza-pentaleno[2,1-a]phenanthrene-8-carboxylic acid vinyl ester (compound 19)

Compound 11 (1.95 g, 3.52 mmol) and NaHCO$_3$ (0.592 g, 7.04 mmol) are dissolved in acetonitrile (30 ml) and then vinyl chloroformate (0.599 ml, 7.04 mmol) is added. The reaction mixture is warmed at 50° C. for 2 hours. The solution is partitioned between AcOEt and brine. The organic phase is separated while the aqueous solution is extracted with AcOEt. The combined organic phases are dried over Na$_2$SO$_4$ and then evaporated to give a residue that is purified by silica gel column chromatography, eluting with Petroleum Ether AcOEt 6:4 to 4:6 leading to pure title compound (1.1 g, 2.062 mmol, 58.5% yield).

LC-MS (ESI POS): 554.2 (MH+)

Preparation of Acetic acid 2-((4aS,4bR,5S,6aS,6bS, 9aR,10aS,10bS,12S)-4b,12-difluoro-5-hydroxy-4a, 6a-dimethyl-2-oxo-2,4b,5,6,6a,7,8,9,9a,10,10a,10b, 11,12-tetradecahydro-4aH-8-aza-pentaleno[2,1-a] phenanthren-6b-yl)-2-oxo-ethyl ester hydrochloride (compound 20)

Compound 19 (1.0 g, 1.874 mmol) is dissolved in dioxane (3 ml) and then HCl 2.0 M in Dioxane (5 ml, 1.874 mmol) is added. The solution is stirred at RT for 2 hours and then the solvent is evaporated and the residue is dried under vacuum for 1 hour. The solid is then dissolved in methanol and warmed at 40° C. for 1 hour. Methanol is evaporated and the residue is triturated with diethyl ether to give the title compound (0.93 g, 1.860 mmol, 99% yield).

LC-MS (ESI POS): 464.0 (MH+)

Compounds listed in Table 4 are prepared as previously described for compounds 19 and 20.

$^1$H NMR (300 MHz, DMSO-d6) δ ppm 7.80-7.96 (m, 2H), 7.36-7.66 (m, 3H), 7.26 (dd, 2H), 6.29 (dd, 2H), 6.13 (s, 2H), 5.47-5.82 (m, 2H), 5.42 (br. s., 1H), 4.71-4.90 (m, 1H), 4.01-4.44 (m, 3H), 3.71-4.01 (m, 2H), 3.03-3.21 (m, 1H), 2.84-3.03 (m, 1H), 2.58-2.69 (m, 1H), 2.10-2.26 (m, 2H), 1.91-

TABLE 4

| Compound | Structure | Yield | Analytical |
|---|---|---|---|
| 21 | 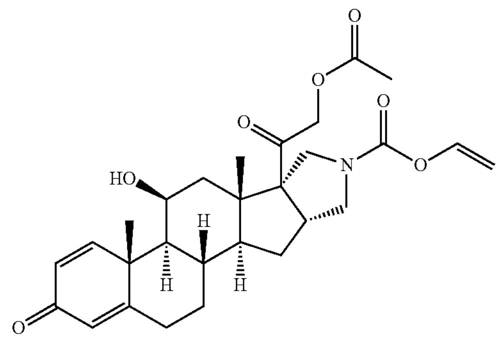 | 70% | LC-MS (ESI POS): 498.1 (MH+) |
| 22 | 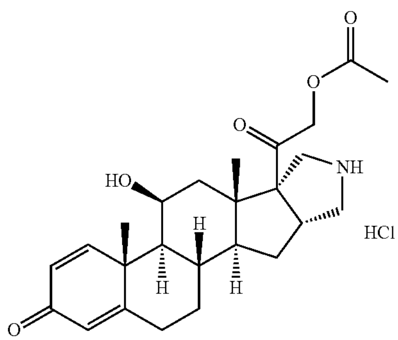 | 99% | LC-MS (ESI POS): 428.1 (MH+) |

Alkylation Method A

Preparation of Acetic acid 2-[(4aS,4bR,5S,6aS,6bS, 9aR,10aS,10bS,12S)-4b,12-difluoro-5-hydroxy-4a, 6a-dimethyl-2-oxo-8-(2-oxo-2-phenyl-ethyl)-2,4b,5, 6,6a,7,8,9,9a,10,10a,10b,11,12-tetradecahydro-4aH-8-aza-pentaleno[2,1-a]phenanthren-6b-yl]-2-oxo-ethyl ester (compound 23)

Compound 20 (50.2 mg, 0.252 mmol) and $K_2CO_3$ (26.8 mg, 0.194 mmol) are dissolved in acetonitrile (2 ml) and the reaction mixture is heated at 60° C. for 6 hours. The reaction mixture is partitioned between brine and AcOEt. The organic phase is separated, dried over $Na_2SO_4$ and then evaporated. The residue is purified by silica gel cartridge to give the title compound (60 mg, 0.103 mmol, 53.1% yield).

LC-MS (ESI POS): 582.2 (MH+)

Preparation of (4aS,4bR,5S,6aS,6bS,9aR,10aS,10bS, 12S)-4b,12-Difluoro-5-hydroxy-6b-(2-hydroxy-acetyl)-4a,6a-dimethyl-8-(2-oxo-2-phenyl-ethyl)-4b, 5,6,6a,6b,7,8,9,9a,10,10a,10b,11,12-tetradecahydro-4aH-8-aza-pentaleno[2,1-a]phenanthren-2-one (compound 24)

Compound 23 is hydrolyzed as described in Example 4 for the preparation of compound 18 obtaining the title compound in 66.5% yield.

2.06 (m, 1H), 1.73-1.91 (m, 2H), 1.48 (s, 3H), 1.36-1.46 (m, 1H), 0.87 (br. s., 3H)

LC-MS (ESI POS): 540.39 (MH+)

$[α]_D^{20}$=+47.4 (c=0.5 MeOH)

Alkylation Method B

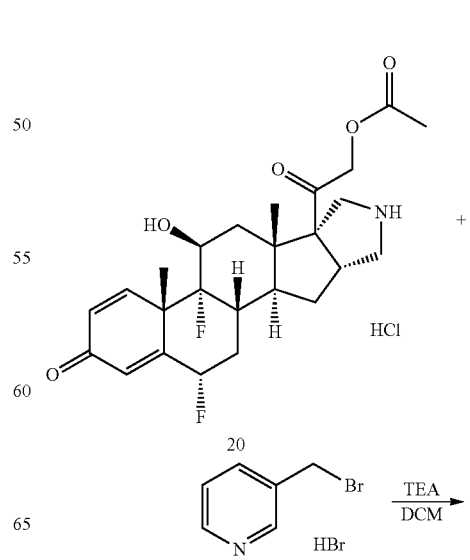

Preparation of Acetic acid 2-((4aS,4bR,5S,6aS,6bS,9aR,10aS,10bS,12S)-4b,12-difluoro-5-hydroxy-4a,6a-dimethyl-2-oxo-8-pyridin-3-ylmethyl-2,4b,5,6,6a,7,8,9,9a,10,10a,10b,11,12-tetradecahydro-4aH-8-aza-pentaleno[2,1-a]phenanthren-6b-yl)-2-oxo-ethyl ester (compound 25)

A mixture of Compound 20 (120 mg, 0.240 mmol), 3-(bromomethyl)pyridine hydrobromide (77 mg, 0.304 mmol) and TEA (134 µl, 0.960 mmol) in DCM (8 ml) is stirred at RT overnight. The mixture is diluted with DCM and treated with 5% NaHCO₃. The organic phase is then washed with brine, dried over Na₂SO₄ and filtered. The solvent is evaporated to give the title compound (130 mg, 0.24 mmol, quant. yield).
LC-MS (ESI POS): 555.3 (MH+)

Compounds listed in Table 5 are prepared as described for compound 25, by reacting compound 20 with the suitable commercially available halides.

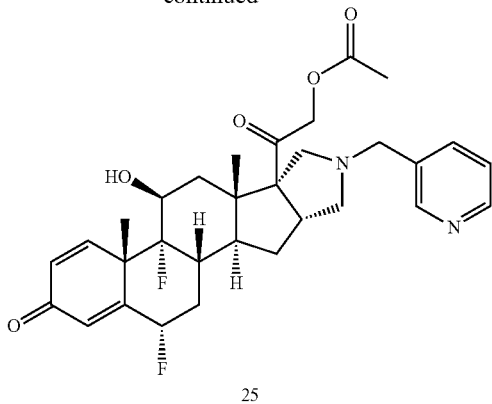

25

TABLE 5

| Compound | Structure | Yield | Analytical |
|---|---|---|---|
| 26 | 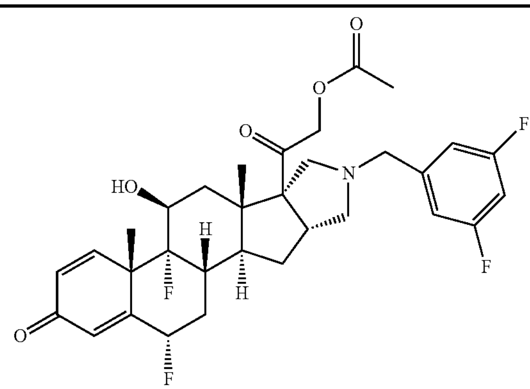 | 69% | LC-MS (ESI-POS): 590.0 MH+ |
| 27 | 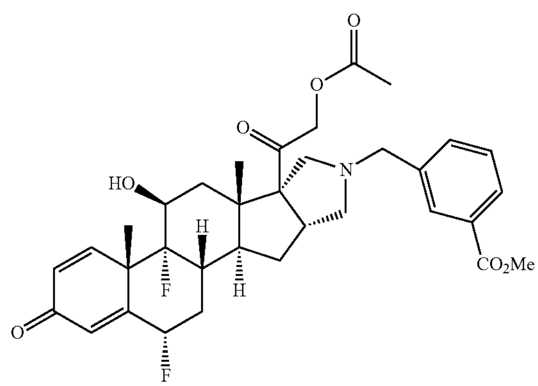 | 82% | LC-MS (ESI-POS): 612.4 MH+ |
| 28 | 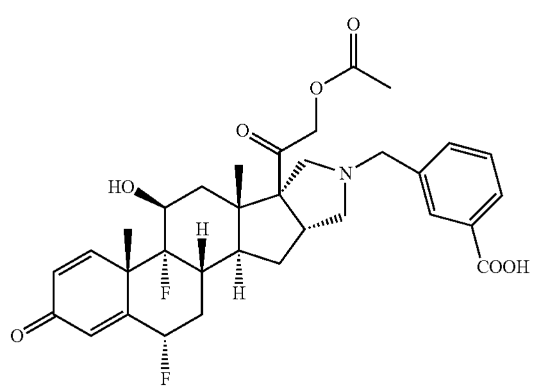 | 66% | LC-MS (ESI-POS): 598.5 MH+ |

Compounds listed in Table 6 are prepared through the procedure previously described for compound 24 or compound 25.

TABLE 6

| Compound | Structure | Yield | Analytical |
|---|---|---|---|
| 29 | 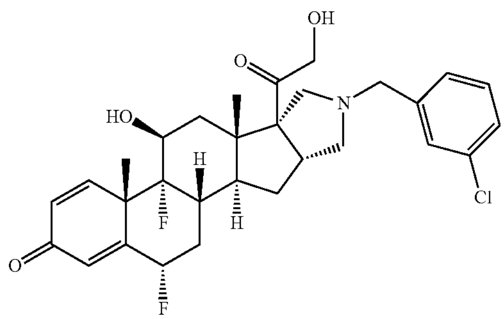 | 69% | $^1$H NMR (300 MHz, DMSO-d$_6$) δ ppm 7.21-7.38 (m, 4 H), 7.17 (dt, 1 H), 6.29 (dd, 1 H), 6.12 (s, 1 H), 5.50-5.85 (m, 1 H), 5.40 (dd, 1 H), 4.85 (t, 1 H), 4.25 (dd, 1 H), 4.13-4.18 (m, 1 H), 4.12 (dd, 1 H), 3.49 (d, 1 H), 3.43 (d, 1 H), 3.08-3.22 (m, 1 H), 2.85 (t, 1 H), 2.54-2.61 (m, 1 H), 2.42-2.48 (m, 1 H), 2.42 (d, 1 H), 2.21-2.33 (m, 1 H), 1.93-2.13 (m, 2 H), 1.79-1.90 (m, 1 H), 1.51-1.77 (m, 3 H), 1.49 (s, 3 H), 1.35 (dd, 1 H), 0.87 (s, 3 H) LC-MS (ESI POS): 546.31 (MH+) $[α]_D^{20}$ = +68.8 (c = 0.5 CHCl$_3$) |
| 30 | 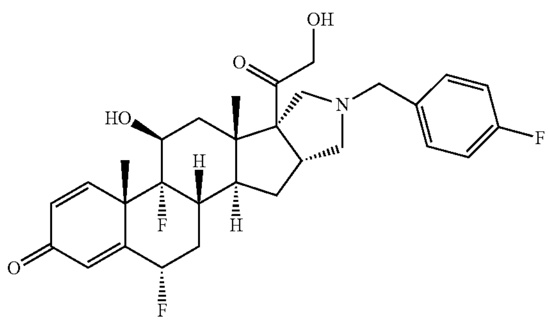 | 57% | $^1$H NMR (300 MHz, DMSO-d$_6$) δ ppm 7.17-7.34 (m, 3 H), 6.98-7.17 (m, 2 H), 6.29 (dd, 1 H), 6.12 (s, 1 H), 5.49-5.74 (m, 1 H), 5.40 (dd, 1 H), 4.82 (t, 1 H), 4.24 (dd, 1 H), 4.11-4.17 (m, 1 H), 4.12 (dd, 1 H), 3.42 (s, 2 H), 3.05-3.23 (m, 1 H), 2.86 (t, 1 H), 2.54-2.61 (m, 2 H), 2.36 (d, 1 H), 2.20-2.31 (m, 1 H), 1.91-2.10 (m, 2 H), 1.79-1.89 (m, 1 H), 1.52-1.75 (m, 3 H), 1.50 (s, 3 H), 1.34 (dd, 1 H), 0.86 (s, 3 H) LC-MS (ESI POS): 530.34 (MH+) $[α]_D^{20}$ = +79.7 (c: 0.66; CHCl$_3$) |
| 31 | 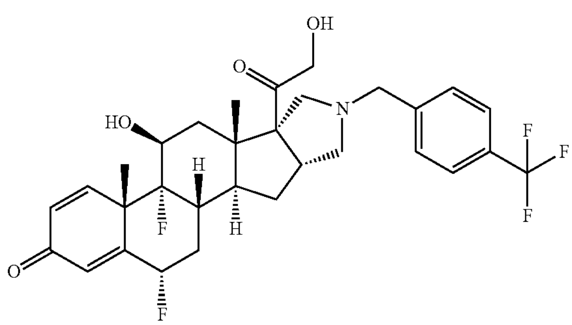 | 41% | $^1$H NMR (300 MHz, DMSO-d$_6$) δ ppm 7.55-7.74 (m, 2 H), 7.36-7.53 (m, 2 H), 7.26 (dd, 1 H), 6.29 (dd, 1 H), 6.13 (s, 1 H), 5.51-5.78 (m, 1 H), 5.40 (dd, 1 H), 4.84 (t, 1 H), 4.26 (dd, 1 H), 4.12-4.19 (m, 1 H), 4.13 (dd, 1 H), 3.54 (s, 2 H), 3.04-3.24 (m, 1 H), 2.89 (t, 1 H), 2.58 (d, 2 H), 2.41 (d, 1 H), 2.19-2.33 (m, 1 H), 1.93-2.13 (m, 2 H), 1.79-1.91 (m, 1 H), 1.51-1.76 (m, 3 H), 1.49 (s, 3 H), 1.35 (dd, 1 H), 0.87 (s, 3 H) LC-MS (ESI POS): 580.36 (MH+) $[α]_D^{20}$ = +72.5 (c = 0.45, MeOH) |
| 32 | 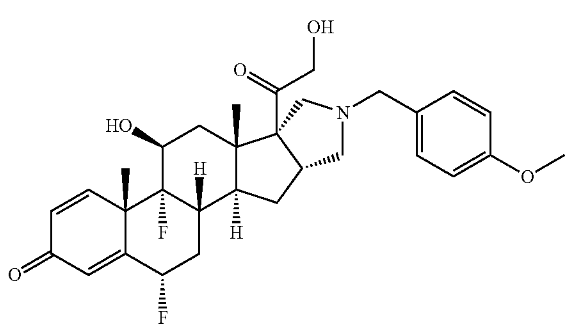 | 35% | $^1$H NMR (300 MHz, DMSO-d$_6$) δ ppm 7.26 (dd, 1 H), 7.12 (m, 2 H), 6.84 (m, 2 H), 6.29 (dd, 1 H), 6.12 (s, 1 H), 5.49-5.74 (m, 1 H), 5.40 (br. s., 1 H), 4.81 (br. s., 1 H), 4.01-4.33 (m, 3 H), 3.72 (s, 3 H), 3.36 (br. s., 2 H), 3.05-3.18 (m, 1 H), 2.79-2.96 (m, 1 H), 2.57-2.64 (m, 1 H), 2.21-2.40 (m, 3 H), 1.92-2.10 (m, 2 H), 1.77-1.91 (m, 1 H), 1.54-1.76 (m, 3 H), 1.49 (s, 3 H), 1.28-1.41 (m, 1 H), 0.86 (s, 3 H) LC-MS (ESI POS): 542.31 (MH+) $[α]_D^{20}$ = +84.5 (c = 0.34, MeOH) |

TABLE 6-continued

| Compound | Structure | Yield | Analytical |
|---|---|---|---|
| 33 | 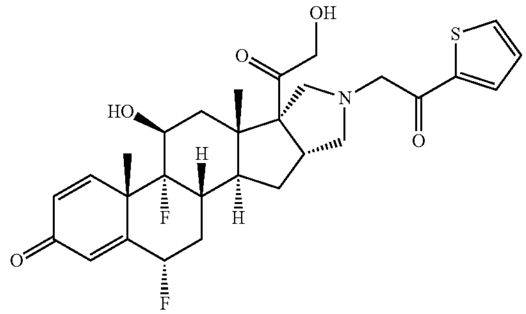 | 55% | ¹H NMR (300 MHz, DMSO-d₆) δ ppm 7.90-7.95 (m, 2 H), 7.26 (dd, 1 H), 7.15 (t, 1 H), 6.29 (dd, 1 H), 6.12 (s, 1 H), 5.48-5.73 (m, 1 H), 5.40 (dd, 1 H), 4.83 (t, 1 H), 4.31 (dd, 1 H), 4.12-4.20 (m, 1 H), 4.13 (dd, 1 H), 3.71 (s, 2 H), 3.08-3.22 (m, 1 H), 2.95 (t, 1 H), 2.70 (d, 1 H), 2.59 (d, 1 H), 2.32-2.45 (m, 1 H), 1.95-2.31 (m, 3 H), 1.52-1.91 (m, 4 H), 1.49 (s, 3 H), 1.27-1.39 (m, 1 H), 0.87 (s, 3 H)<br>LC-MS (ESI POS): 546.38 (MH+)<br>$[\alpha]_D^{20}$ = +46.31 (c = 0.39, MeOH) |
| 34 | 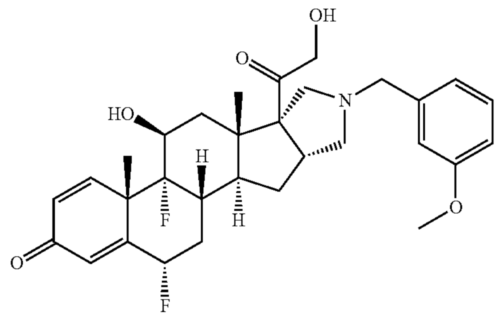 | 58% | ¹H NMR (300 MHz, DMSO-d₆) δ ppm 7.25 (dd, 1 H), 7.18 (t, 1 H), 6.71-6.85 (m, 3 H), 6.29 (dd, 1 H), 6.12 (s, 1 H), 5.49-5.79 (m, 1 H), 5.40 (dd, 1 H), 4.83 (t, 1 H), 4.24 (dd, 1 H), 4.10-4.15 (m, 1 H), 4.12 (dd, 1 H), 3.68 (s, 3 H), 3.42 (s, 2 H), 3.02-3.22 (m, 1 H), 2.85 (t, 1 H), 2.48 (d, 1 H), 2.40 (d, 1 H), 2.23-2.32 (m, 1 H), 2.04-2.12 (m, 1 H), 2.00-2.05 (m, 1 H), 1.83 (d, 1 H), 1.53-1.76 (m, 4 H), 1.49 (s, 3 H), 1.36 (dd, 1 H), 0.87 (s, 3 H)<br>LC-MS (ESI POS): 542.44 (MH+)<br>$[\alpha]_D^{20}$ = +64.26 (c = 0.31, MeOH) |
| 35 | 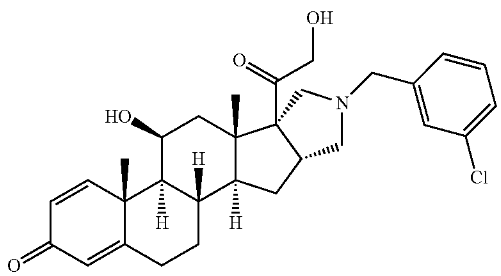 | 70% | ¹H NMR (300 MHz, DMSO-d₆) δ ppm 7.22-7.39 (m, 4 H), 7.16 (dt, 1 H), 6.16 (dd, 1 H), 5.93 (s, 1 H), 4.79 (t, 1 H), 4.66 (d, 1 H), 4.23-4.32 (m, 1 H), 4.21 (dd, 1 H), 4.09 (dd, 1 H), 3.44 (s, 2 H), 3.01-3.20 (m, 1 H), 2.87 (t, 1 H), 2.55 (d, 1 H), 2.43 (d, 1 H), 2.28-2.36 (m, 1 H), 1.77-2.08 (m, 4 H), 1.43-1.66 (m, 3 H), 1.38 (s, 3 H), 1.23-1.37 (m, 3 H), 0.97-1.18 (m, 1 H), 0.86 (s, 3 H)<br>LC-MS (ESI POS): 510.32 (MH+)<br>$[\alpha]_D^{20}$ = +71.80 (c = 0.5 MeOH) |
| 36 | 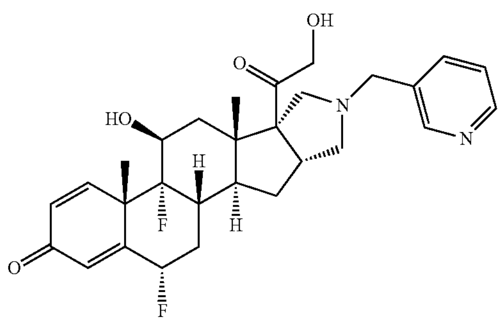 | | ¹H NMR (300 MHz, DMSO-d₆) δ ppm 8.32-8.51 (m, 2 H), 7.59 (dt, 1 H), 7.31 (ddd, 1 H), 7.25 (dd, 1 H), 6.29 (dd, 1 H), 6.13 (s, 1 H), 5.48-5.79 (m, 1 H), 5.40 (dd, 1 H), 4.83 (t, 1 H), 4.24 (dd, 1 H), 4.14-4.18 (m, 1 H), 4.12 (dd, 1 H), 3.48 (s, 2 H), 3.10-3.22 (m, 1 H), 2.87 (t, 1 H), 2.55-2.62 (m, 1 H), 2.41 (d, 1 H), 2.21-2.34 (m, 1 H), 1.95-2.12 (m, 2 H), 1.84 (d, 1 H), 1.52-1.75 (m, 4 H), 1.49 (s, 3 H), 1.35 (dd, 1 H), 0.87 (s, 3 H)<br>LC-MS (ESI POS): 513.2 (MH+)<br>$[\alpha]_D^{20}$ = +64.40 (c = 0.3, MeOH) |
| 37 | 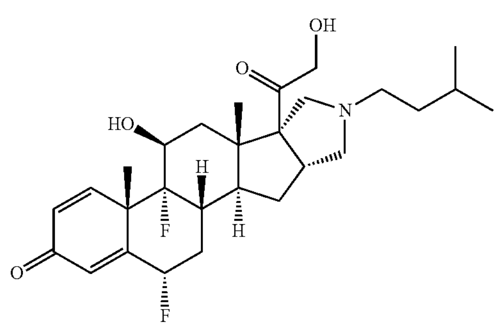 | 65% | ¹H NMR (300 MHz, DMSO-d6) δ ppm 7.26 (d, 1 H), 6.29 (dd, 1 H), 6.11 (s, 1 H), 5.47-5.83 (m, 1 H), 5.34-5.45 (m, 1 H), 4.68-4.91 (m, 1 H), 4.03-4.43 (m, 3 H), 3.06-3.18 (m, 1 H), 2.77-2.89 (m, 1 H), 2.12-2.45 (m, 8 H), 1.71-2.05 (m, 3 H), 1.58 (s, 2 H), 1.49 (s, 3 H), 1.32 (m, 3 H), 0.86 (s, 3 H), 0.82 (d, 6 H)<br>LC-MS (ESI POS): 491.28 (MH+)<br>$[\alpha]_D^{20}$ = +50.48 (c = 0.5, MeOH) |

TABLE 6-continued

| Compound | Structure | Yield | Analytical |
|---|---|---|---|
| 38 | 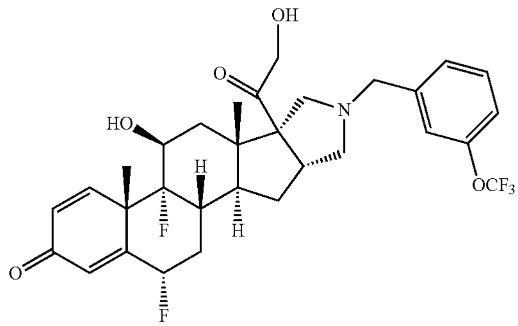 | 31% | ¹H NMR (300 MHz, DMSO-d6) ppm 7.33-7.50 (m, 1 H), 7.11-7.30 (m, 4 H), 6.29 (dd, 1 H), 6.12 (s, 1 H), 5.49-5.77 (m, 1 H), 5.39 (dd, 1 H), 4.83 (t, 1 H), 4.23 (dd, 1 H), 4.14-4.18 (m, 1 H), 4.11 (dd, 1 H), 3.54 (d, 1 H), 3.49 (d, 1 H), 3.08-3.22 (m, 1 H), 2.78 (t, 1 H), 2.55-2.62 (m, 2 H), 2.45 (d, 1 H), 2.23-2.33 (m, 1 H), 1.98-2.19 (m, 2 H), 1.53-1.90 (m, 4 H), 1.49 (s, 3 H), 1.28-1.41 (m, 1 H), 0.87 (s, 3 H) LC-MS (ESI POS): 596.29 MH+ $[\alpha]_D^{20}$ = +48.5 (c = 3.1, MeOH) |
| 39 | 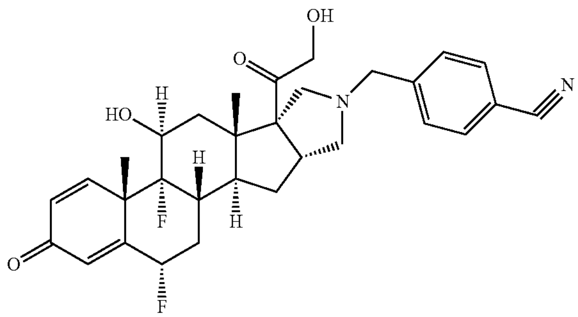 | 41% | ¹H NMR (300 MHz, DMSO-d6) ppm 7.67-7.83 (m, 2 H), 7.36-7.50 (m, 2 H), 7.25 (d, 1 H), 6.29 (dd, 1 H), 6.13 (s, 1 H), 5.50-5.76 (m, 1 H), 5.40 (d, 1 H), 4.83 (t, 1 H), 4.26 (dd, 1 H), 4.03-4.19 (m, 2 H), 3.54 (s, 2 H), 3.10-3.22 (m, 1 H), 2.88 (t, 1 H), 2.54-2.66 (m, 2 H), 2.41 (d, 1 H), 2.19-2.33 (m, 1 H), 1.93-2.12 (m, 2 H), 1.78-1.88 (m, 1 H), 1.52-1.76 (m, 3 H), 1.49 (s, 3 H), 1.35 (dd, 1 H), 0.87 (s, 3 H) LC-MS (ESI POS): 537.06 MH+ $[\alpha]_D^{25}$ = +69.77 (c 0.26, MeOH) |
| 40 | 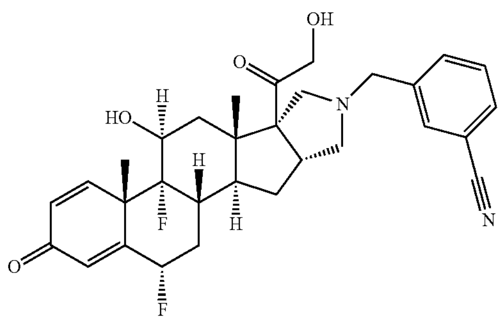 | 37% | ¹H NMR (300 MHz, DMSO-d6) ppm 7.69 (dt, 1 H), 7.63 (s, 1 H), 7.56 (dt, 1 H), 7.50 (t, 1 H), 7.25 (dd, 1 H), 6.29 (dd, 1 H), 6.12 (s, 1 H), 5.50-5.79 (m, 1 H), 5.40 (dd, 1 H), 4.83 (t, 1 H), 4.25 (dd, 1 H), 4.06-4.18 (m, 2 H), 3.54 (d, 1 H), 3.48 (d, 1 H), 3.09-3.21 (m, 1 H), 2.88 (t, 1 H), 2.57 (d, 1 H), 2.41-2.46 (m, 1 H), 2.40 (d, 1 H), 1.94-2.10 (m, 2 H), 1.84 (d, 1 H), 1.52-1.75 (m, 4 H), 1.49 (s, 3 H), 1.35 (dd, 1 H), 0.87 (s, 3 H) LC-MS (ESI POS): 537.34 MH+ $[\alpha]_D^{25}$ +67.70 (MeOH, c 0.33) |

Example 7

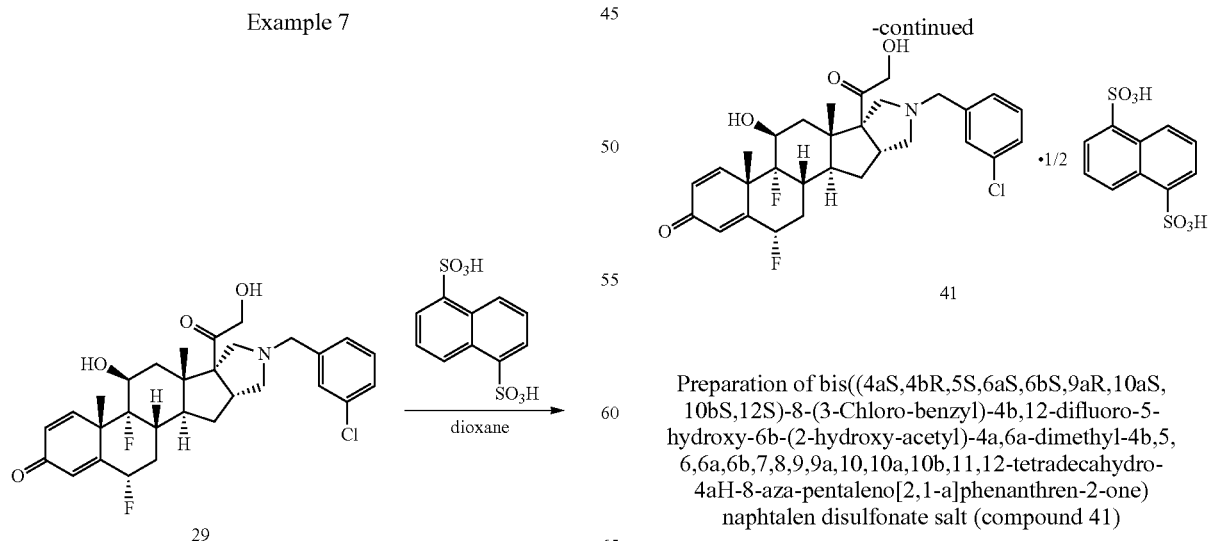

Preparation of bis((4aS,4bR,5S,6aS,6bS,9aR,10aS,10bS,12S)-8-(3-Chloro-benzyl)-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one) naphtalen disulfonate salt (compound 41)

To a solution of compound 29 (120 mg, 0.220 mmol) in dioxane (2.5 mL), a solution of naphthalene-1,5-disulfonic acid (40.8 mg, 0.110 mmol) in dioxane (2.5 mL) is added. The reaction mixture is stirred for 30 minutes, then it is concentrated to about 1 mL of volume. Water (about 6 mL) is added and a solid precipitates. After stirring for a while, the suspension is filtered and the title compound (92 mg, 0.110 mmol, 50% yield) is recovered by filtration.

$^1$H NMR (300 MHz, DMSO-d6) d ppm 9.73 (br. s., 1H) 7.38-7.67 (m, 4H) 7.27 (d, 1H) 6.32 (dd, 1H) 6.14 (s, 1H) 5.51-5.82 (m, 1H) 5.46-5.65 (m, 1H) 4.28-4.62 (m, 3H) 4.09-4.28 (m, 2H) 3.72-3.97 (m, 1H) 3.43-3.70 (m, 1H) 3.17-3.28 (m, 1H) 3.09 (t, 1H) 2.73-2.98 (m, 1H) 2.53-2.62 (m, 1H) 2.22-2.41 (m, 1H) 1.95-2.16 (m, 1H) 1.59-1.88 (m, 4H) 1.50 (s, 3H) 1.37-1.54 (m, 1H) 0.88 (s, 3H)

1,5 naphtalen disulfonate ion: $^1$H NMR (300 MHz, DMSO-d6) d ppm 8.88 (dd, 1H) 7.93 (dd, 1H) 7.40 (dd, 1H)

LC-MS (ESI POS): 546.23 MH+

$[\alpha]_D^{25}$+12.5 (c 0.5 MeOH)

Example 8

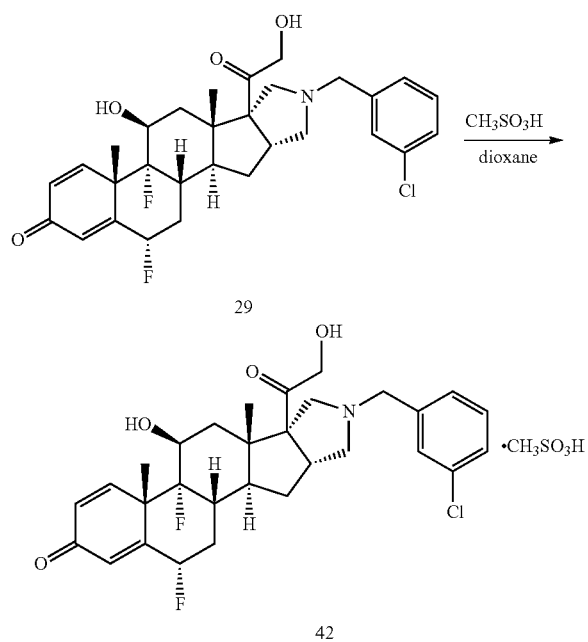

Preparation of (4aS,4bR,5S,6aS,6bS,9aR,10aS,10bS, 12S)-8-(3-Chloro-benzyl)-4b,12-difluoro-5-hydroxy-6b-(2-hydroxy-acetyl)-4a,6a-dimethyl-4b,5,6,6a,6b, 7,8,9,9a,10,10a,10b,11,12-tetradecahydro-4aH-8-aza-pentaleno[2,1-a]phenanthren-2-one methane sulfonate (compound 42)

Compound 29 (120 mg, 0.220 mmol) is dissolved in Dioxane (1 ml) and then a solution of methansulfonic acid (14.27 µl, 0.220 mmol) in dioxane (100 µL) is added under stirring. A precipitated forms. The stirring is continued for 1 hour and then the solid is collected by filtration obtaining the title compound (115 mg, 0.179 mmol, 81% yield).

$^1$H NMR (300 MHz, DMSO-d6) d ppm 7.35-7.76 (m, 4H), 7.15-7.34 (m, 1H), 6.32 (dd, 1H), 6.15 (s, 1H), 5.58-5.81 (m, 1H), 5.56 (br. s., 1H), 3.60-4.56 (m, 7H), 2.97-3.17 (m, 1H), 2.79-2.94 (m, 1H), 2.33-2.44 (m, 1H), 1.98-2.24 (m, 3H), 1.59-1.90 (m, 5H), 1.50 (s, 3H), 1.39-1.48 (m, 1H), 0.88 (s, 3H)

Methansulfonate ion: $^1$H NMR (300 MHz, DMSO-d6) d ppm 2.31 (s, 3H)

LC-MS (ESI POS): 546.20 MH+

$[\alpha]_D^{25}$+17.2 (c 0.4 MeOH)

Example 9'

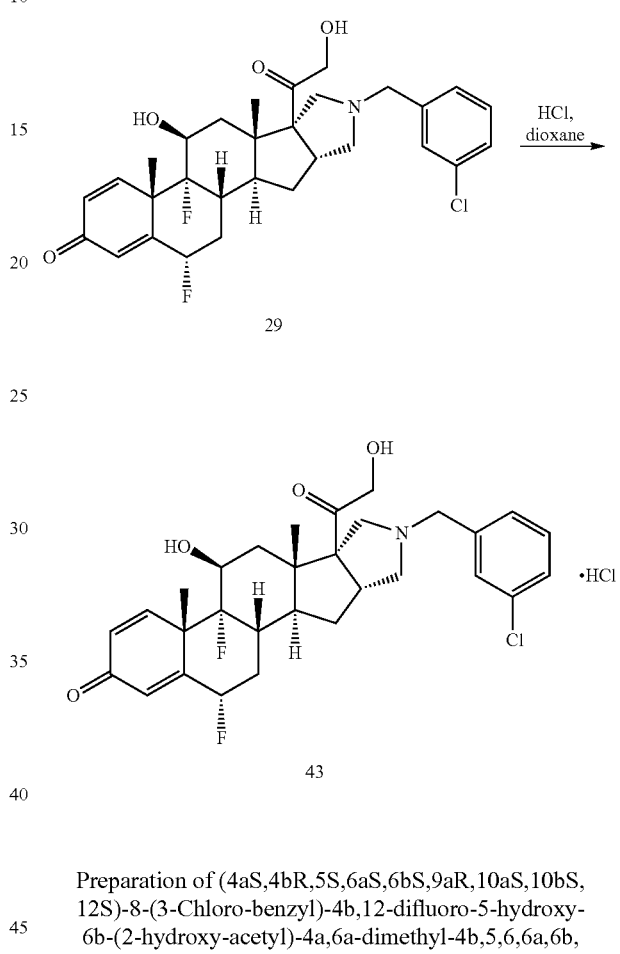

Preparation of (4aS,4bR,5S,6aS,6bS,9aR,10aS,10bS, 12S)-8-(3-Chloro-benzyl)-4b,12-difluoro-5-hydroxy-6b-(2-hydroxy-acetyl)-4a,6a-dimethyl-4b,5,6,6a,6b, 7,8,9,9a,10,10a,10b,11,12-tetradecahydro-4aH-8-aza-pentaleno[2,1-a]phenanthren-2-one hydrochloride (compound 43)

Hydrochloric acid 4M in dioxane (156 µl, 0.623 mmol) is added to a clear solution of compound 29 (68 mg, 0.125 mmol) in dioxane (8 ml). A solid immediately precipitates. The mixture is stirred for 15 minutes, then the solid is filtered. The amount of recovered product is very low, so the mother liquor is evaporated and the crude material is triturated with AcOEt to give the title compound (53 mg, 0.091 mmol, 73% yield).

$^1$H NMR (300 MHz, DMSO-d6) d ppm 10.23 (br. s., 1H), 7.05-7.83 (m, 5H), 6.32 (dd, 1H), 6.14 (s, 1H), 5.58-5.65 (m, 1H), 5.42-5.83 (m, 1H), 4.11-4.57 (m, 5H), 3.75-3.90 (m, 1H), 3.42-3.69 (m, 2H), 2.99-3.17 (m, 1H), 2.78-2.92 (m, 1H), 1.92-2.42 (m, 4H), 1.56-1.86 (m, 3H), 1.50 (s, 3H), 1.38-1.48 (m, 1H), 0.88 (s, 3H)

LC-MS (ESI POS): 546.23 MH+

$[\alpha]_D^{25}$+22.63 (c 0.35 MeOH)

Example 10

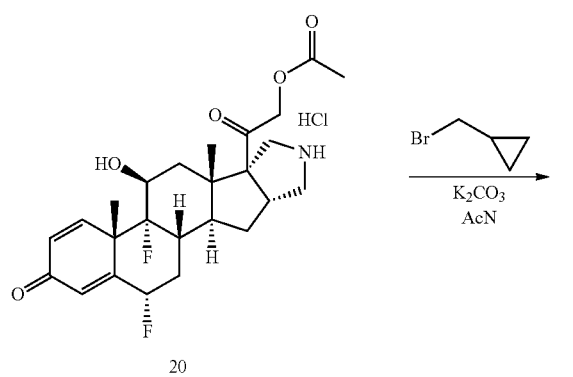

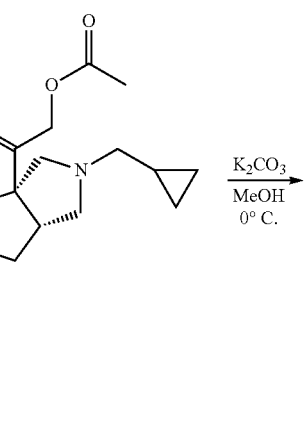

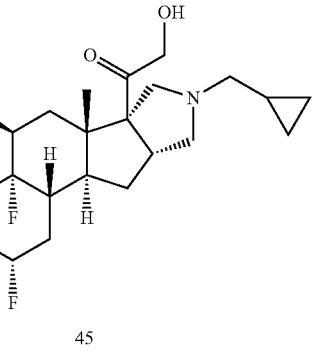

Preparation of Acetic acid 2-((4aS,4bR,5S,6aS,6bS, 9aR,10aS,10bS,12S)-8-cyclopropylmethyl-4b,12-difluoro-5-hydroxy-4a,6a-dimethyl-2-oxo-2,4b,5,6, 6a,7,8,9,9a,10,10a,10b,11,12-tetradecahydro-4aH-8-aza-pentaleno[2,1-a]phenanthren-6b-yl)-2-oxo-ethyl ester (compound 44)

Compound 44 is prepared from intermediate 20 by alkylation with bromomethyl-cyclopropane following Method A, as previously described in Example 6 for compound 23.

LC-MS (ESI POS): 518.3 MH+

Preparation of (4aS,4bR,5S,6aS,6bS,9aR,10aS,10bS, 12S)-8-Cyclopropylmethyl-4b,12-difluoro-5-hydroxy-6b-(2-hydroxy-acetyl)-4a,6a-dimethyl-4b,5,6, 6a,6b,7,8,9,9a,10,10a,10b,11,12-tetradecahydro-4aH-8-aza-pentaleno[2,1-a]phenanthren-2-one (45)

Compound 44 (154 mg, 0.298 mmol) is dissolved in MeOH (5 mL) and the mixture is degassed with N2 for 15 minutes. After cooling to 0° C., $K_2CO_3$ (20.56 mg, 0.149 mmol) is added and the mixture is stirred for 45 minutes. The reaction mixture is partitioned between water and AcOEt, the organic layer is separated, dried over $Na_2SO_4$ and concentrated. The crude material is purified by silica gel flash chromatography (eluent DCM/MeOH from 98/2 to 95/5+ TEA=1%), affording a solid that is further triturated in AcOEt and recovered by filtration to give the title compound (75 mg, 0.158 mmol, 53.0% yield).

$^1$H NMR (300 MHz, DMSO-d6) ppm 7.25 (dd, 1H), 6.29 (dd, 1H), 6.11 (s, 1H), 5.48-5.77 (m, 1H), 5.40 (d, 1H), 4.80 (t, 1H), 4.32 (dd, 1H), 4.12-4.15 (m, 1H), 4.14 (dd, 1H), 3.08-3.19 (m, 1H), 2.99 (t, 1H), 2.69 (d, 1H), 2.54-2.63 (m, 1H), 2.39-2.47 (m, 0H), 2.32 (d, 1H), 2.20-2.27 (m, 1H), 2.15 (dd, 1H), 2.05 (dd, 1H), 1.82-2.00 (m, 3H), 1.69-1.79 (m, 1H), 1.52-1.68 (m, 2H), 1.49 (s, 3H), 1.40-1.46 (m, 0H), 1.32 (dd, 1H), 0.87 (s, 3H), 0.64-0.82 (m, 1H), 0.29-0.49 (m, 2H), −0.08-0.14 (m, 2H)

LC-MS (ESI POS): 476.25 MH+

$[\alpha]_D^{25}$ +72.4 (c 0.5 MeOH)

Compounds reported in Table 7 are prepared as described for compound 45, starting from compounds 27 and 28.

TABLE 7

| Compound | Structure | Yield | Analytical |
|---|---|---|---|
| 46 | HO, HO, F, H, F, N, CO2Me | 54% | $^1$H NMR (300 MHz, DMSO-d6) ppm 7.84 (s, 1 H), 7.81 (dt, 1 H), 7.46-7.52 (m, 1 H), 7.43 (t, 1 H), 7.26 (dd, 1 H), 6.29 (dd, 1 H), 6.13 (s, 1 H), 5.47-5.80 (m, 1 H), 5.39 (dd, 1 H), 4.83 (t, 1 H), 4.23 (dd, 1 H), 4.11-4.18 (m, 1 H), 4.11 (dd, 1 H), 3.80 (s, 3 H), 3.56 (d, 1 H), 3.48 (d, 1 H), 3.05-3.22 (m, 1 H), 2.78 (t, 1 H), 2.54-2.67 (m, 2 H), 2.37-2.46 (m, 1 H), 2.22-2.36 (m, 1 H), 1.97-2.18 (m, 2 H), 1.78-1.90 (m, 1 H), 1.54-1.78 (m, 3 H), 1.49 (s, 3 H), 1.37 (dd, 1 H), 0.87 (s, 3 H) LC-MS (ESI POS): 570.35 MH+ $[\alpha]_D^{25}$ +49.91 (c 0.23, MeOH) |

TABLE 7-continued

| Compound | Structure | Yield | Analytical |
|---|---|---|---|
| 47 | 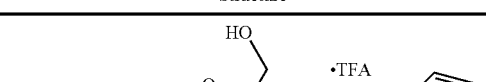 | 31% | $^1$H NMR (300 MHz, DMSO-d6 +Na$_2$CO$_3$) ppm 7.63-7.72 (m, 2 H), 7.26 (d, 1 H), 7.14 (t, 1 H), 7.06-7.10 (m, 1 H), 6.29 (dd, 1 H), 6.12 (s, 1 H), 5.43-5.83 (m, 1 H), 4.26 (d, 1 H), 4.11-4.15 (m, 1 H), 4.12 (d, 1 H), 3.40-3.51 (m, 2 H), 3.08-3.20 (m, 1 H), 2.87-3.02 (m, 1 H), 2.66 (d, 1 H), 2.32-2.47 (m, 2 H), 2.20-2.31 (m, 1 H), 1.77-2.08 (m, 3 H), 1.51-1.77 (m, 3 H), 1.49 (s, 3 H), 1.29-1.40 (m, 1 H), 0.86 (s, 3 H)<br>LC-MS (ESI POS): 556.39 MH+ |

Example 11

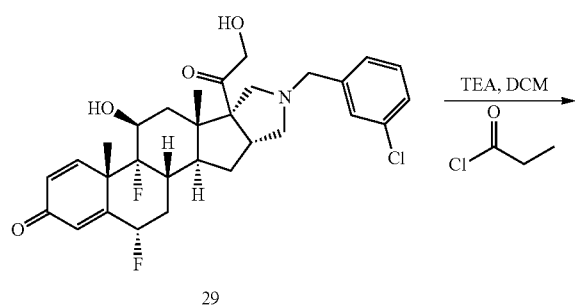

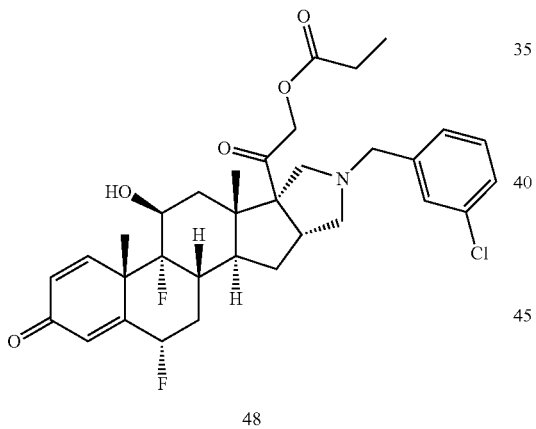

Preparation of Propionic acid 2-[(4aS,4bR,5S,6aS,6bS,9aR,10aS,10bS,12S)-8-(3-chloro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl]-2-oxo-ethyl ester (compound 48)

Compound 29 (100 mg, 0.183 mmol) is dissolved in dry DCM (4 ml) and propionyl chloride (31.8 µl, 0.366 mmol) and TEA (51.1 µl, 0.366 mmol) are added. The reaction mixture is stirred at RT for 2 hours. Further propionyl chloride (31.8 µA, 0.366 mmol) and TEA (51.1 µl, 0.366 mmol) are added, and the reaction mixture is stirred at RT for 16 hours. The reaction mixture is partitioned between brine and AcOEt. The organic phase is separated dried over Na$_2$SO$_4$ and evaporated to give a residue that is triturated with AcOEt and Petroleum Ether. The obtained product is eluted on a silica gel cartridge with AcOEt leading to title compound (50 mg, 45.4%).

$^1$H NMR (300 MHz, DMSO-d6) ppm 7.04-7.43 (m, 5H), 6.29 (dd, 1H), 6.12 (s, 1H), 5.48-5.79 (m, 1H), 5.41 (dd, 1H), 4.96 (d, 1H), 4.81 (d, 1H), 4.06-4.28 (m, 1H), 3.48 (s, 1H), 3.06-3.24 (m, 1H), 2.88 (t, 1H), 2.58 (d, 1H), 2.53-2.67 (m, 1H), 2.46 (d, 1H), 2.42 (q, 2H), 2.21-2.34 (m, 1H), 1.97-2.15 (m, 2H), 1.80-1.92 (m, 1H), 1.51-1.76 (m, 4H), 1.49 (s, 3H), 1.37 (dd, 1H), 1.08 (t, 3H), 0.93 (s, 3H).

LC-MS (ESI POS): 602.19 MH+

$[\alpha]_D^{25}$ +58.9 (c 0.3, MeOH)

Example 12

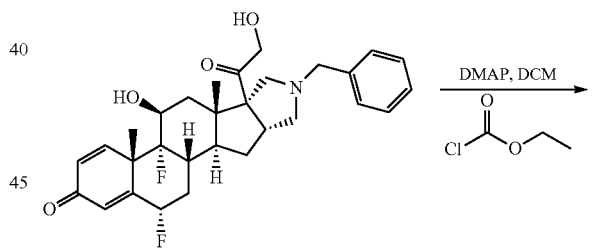

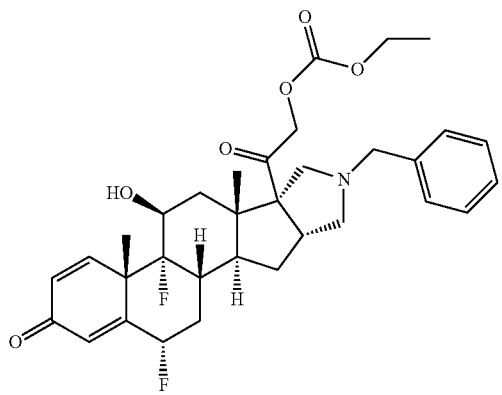

Preparation of Carbonic acid 2-((4aS,4bR,5S,6aS, 6bS,9aR,10aS,10bS,12S)-8-benzyl-4b,12-difluoro-5-hydroxy-4a,6a-dimethyl-2-oxo-2,4b,5,6,6a,7,8,9,9a, 10,10a,10b,11,12-tetradecahydro-4aH-8-aza-pentaleno[2,1-a]phenanthren-6b-yl)-2-oxo-ethyl ester ethyl ester (compound 49)

Compound 8 (144 mg, 0.281 mmol) is dissolved in dry DCM and cooled to 0° C., under nitrogen. N,N-dimethylpyridin-4-amine (34.4 mg, 0.281 mmol) and ethylchloroformate (30.5 mg, 0.281 mmol) are added and the mixture is stirred at 0° C. for 4 hours. The reaction mixture is partitioned between water and DCM. The organic layer is separated, dried and concentrated. The crude is purified on silica gel flash chromatography (eluent petroleum ether/AcOEt form 7/3 to 1/1). The obtained product is triturated in Et$_2$O and recovered by filtration to afford the title compound (72 mg, 0.123 mmol, 43.8% yield). $^1$H NMR (300 MHz, DMSO-d6) ppm 7.05-7.41 (m, 6H), 6.29 (dd, 1H), 6.13 (s, 1H), 5.48-5.79 (m, 1H), 5.38-5.44 (m, 1H), 5.00 (d, 1H), 4.82 (d, 1H), 4.16 (q, 2H), 4.09-4.15 (m, 1H), 3.47 (s, 2H), 3.06-3.21 (m, 1H), 2.92 (t, 1H), 2.56-2.62 (m, 1H), 2.57 (d, 1H), 2.40 (d, 1H), 2.20-2.35 (m, 1H), 1.92-2.13 (m, 2H), 1.84 (d, 1H), 1.51-1.75 (m, 3H), 1.49 (s, 3H), 1.37 (dd, 1H), 1.25 (t, 3H), 0.93 (s, 3H)

LC-MS (ESI POS): 584.5 MH+
$[\alpha]_D^{25}$+120.1 (c 0.6, CHCl$_3$)

Example 13

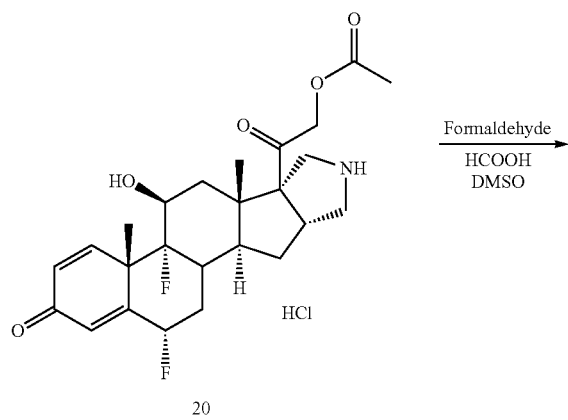

20

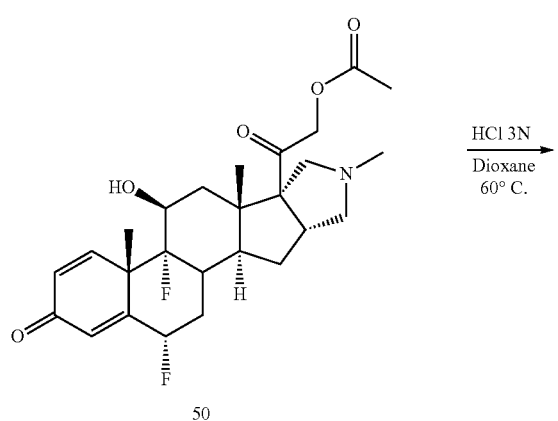

50

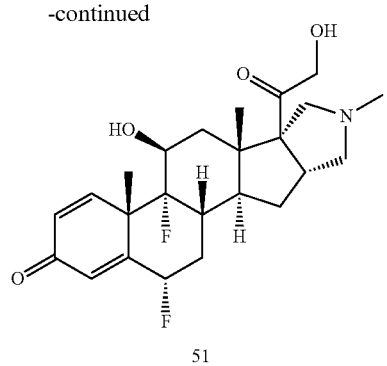

51

Preparation of Acetic acid 2-((4aS,4bR,5S,6aS,6bS, 9aR,10aS,10bS,12S)-4b,12-difluoro-5-hydroxy-4a, 6a,8-trimethyl-2-oxo-2,4b,5,6,6a,7,8,9,9a,10,10a, 10b,11,12-tetradecahydro-4aH-8-aza-pentaleno[2,1-a]phenanthren-6b-yl)-2-oxo-ethyl ester (compound 50)

In a closed vessel, Compound 20 (150 mg, 0.300 mmol) is dissolved in DMSO (1.5 ml) formic acid (0.046 ml, 1.200 mmol) and formaldehyde (0.089 ml, 1.200 mmol) are added, and the mixture is heated under microwave irradiation for 30 seconds at 120 W of power (the temperature reached 220° C.). LC-MS showed that the reaction is completed. The reaction mixture is diluted with AcOEt and, after addition of TEA (0.5 mL), washed with water. The organic layer is separated, dried over Na$_2$SO$_4$, filtered and concentrated. The crude is purified by silica gel flash chromatography (eluent DCM/MeOH 0 98/2) to yield the title compound (87 mg, 0.182 mmol, 60.7% yield).

LC-MS (ESI POS): 478.2 (MH+)

Preparation of (4aS,4bR,5S,6aS,6bS,9aR,10aS,10bS, 12S)-4b,12-Difluoro-5-hydroxy-6b-(2-hydroxy-acetyl)-4a,6a,8-trimethyl-4b,5,6,6a,6b,7,8,9,9a,10, 10a,10b,11,12-tetradecahydro-4aH-8-aza-pentaleno [2,1-a]phenanthren-2-one (compound 51)

Compound 50 (85 mg, 0.178 mmol) is suspended in a dioxane (2 ml)/water (2.000 ml) mixture. HCl (0.5 ml, 6.09 mmol) is added and the mixture is heated at 80° C. for 4 hours. The reaction mixture is concentrated to dryness under reduced pressure, redissolved in a acetate/water mixture and neutralized by the addition of NaHCO$_3$. The aqueous phase is washed with AcOEt several time and the it is freeze-dried. The solid is treated with EtOH/MeOH 9/1 mixture: the insoluble material removed by filtration while the mother liquors are concentrated to dryness and further triturated in a AcOEt/Et$_2$O mixture. The solid is recovered by filtration affording title compound in 45.2% yield.

$^1$H NMR (300 MHz, DMSO-d6) δ ppm 7.29 (d, 1H), 6.30 (dd, 1H), 6.13 (s, 1H), 5.48-5.87 (m, 2H), 3.60-4.60 (m, 5H), 2.86-3.04 (m, 1H), 2.74 (br. s., 3H), 1.91-2.23 (m, 4H), 1.57-1.87 (m, 6H), 1.49 (s, 3H), 1.34-1.46 (m, 1H), 0.88 (s, 3H)

LC-MS (ESI POS): 436.2 (MH+)
$[\alpha]_D^{20}$+51.73 (c=0.3 MeOH)

Intermediates listed in Table 8 are prepared as described in Example 13 for compound 50, by reacting compound 20 with the suitable commercially available ketones.

TABLE 8

| Compound | Structure | Yield | Analytical |
|---|---|---|---|
| 52 | 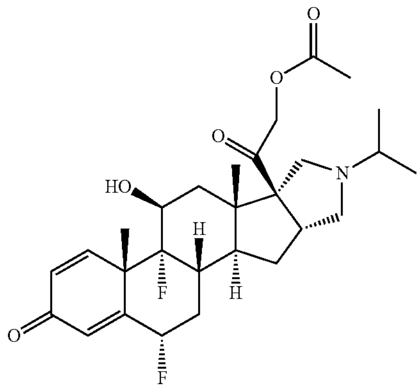 | 61% | LC-MS (ESI POS): 506.1 MH+ |
| 53 | 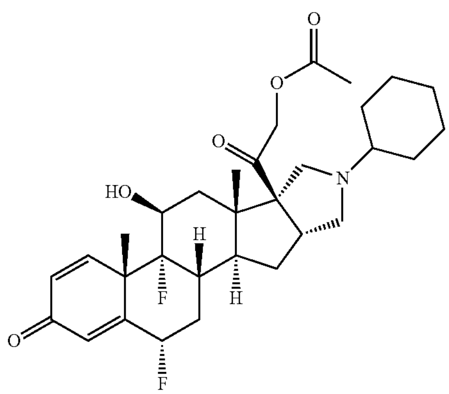 | 92% | LC-MS (ESI POS): 546.2 MH+ |

Compounds listed in Table 9 are prepared from the intermediates listed in Table 8 using the procedure reported in Example 10 for the preparation of compound 45.

TABLE 9

| Compound | Structure | Yield | Analytical |
|---|---|---|---|
| 54 | 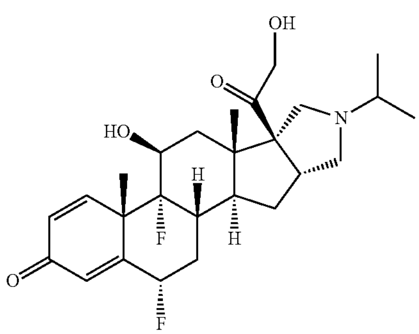 | 83% | $^1$H NMR (300 MHz, DMSO-d6) ppm 7.25 (dd, 1 H), 6.29 (dd, 1 H), 6.11 (s, 1 H), 5.48-5.79 (m, 1 H), 5.39 (dd, 1 H), 4.80 (t, 1 H), 4.29 (m, 1 H), 4.12-4.21 (m, 1 H), 4.12 (d, 1 H), 3.03-3.18 (m, 1 H), 2.95 (t, 1 H), 2.68 (d, 1 H), 2.39-2.47 (m, 1 H), 2.32 (d, 1 H), 2.21-2.28 (m, 1 H), 2.16 (spt, 1 H), 1.91-2.03 (m, 2 H), 1.81-1.91 (m, 1 H), 1.71-1.81 (m, 1 H), 1.51-1.70 (m, 2 H), 1.49 (s, 3 H), 1.31 (dd, 1 H), 0.93 (d, 6 H), 0.86 (s, 3 H) LC-MS (ESI POS): 464.24 MH+ $[\alpha]_D^{25}$ +64 (c = 0.5, MeOH) |

TABLE 9-continued

| Compound | Structure | Yield | Analytical |
|---|---|---|---|
| 55 | 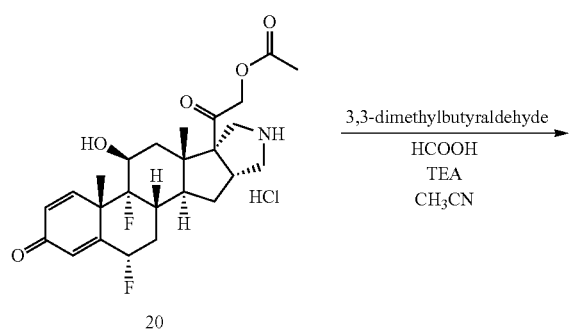 | 32% | $^1$H NMR (300 MHz, DMSO-d6) ppm 7.25 (dd, 1 H), 6.29 (dd, 1 H), 6.11 (s, 1 H), 5.47-5.79 (m, 1 H), 5.39 (dd, 1 H), 4.80 (t, 1 H), 4.26 (d, 1 H), 4.15-4.21 (m, 1 H), 4.11 (m, 1 H), 3.01-3.17 (m, 1 H), 2.85 (t, 1 H), 2.57 (d, 1 H), 2.53-2.58 (m, 1 H), 2.43 (d, 1 H), 2.18-2.32 (m, 1 H), 2.06 (dd, 1 H), 1.92-2.03 (m, 1 H), 1.72-1.92 (m, 3 H), 1.54-1.72 (m, 5 H), 1.48 (s, 3 H), 1.37-1.45 (m, 2 H), 1.25-1.36 (m, 1 H), 1.04-1.23 (m, 5 H), 0.86 (s, 3 H)<br>LC-MS (ESI POS): 504.14 MH+<br>$[\alpha]_D^{25}$ +63.6 (c 0.36, MeOH) |

Example 14

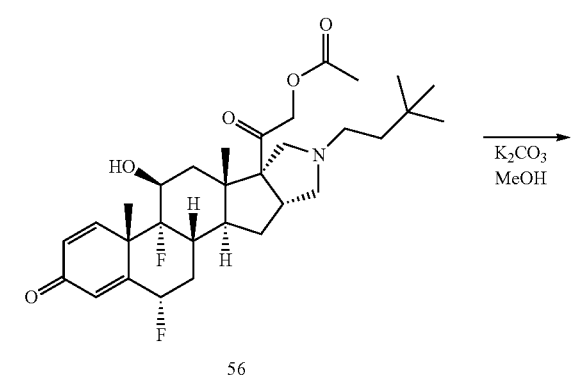

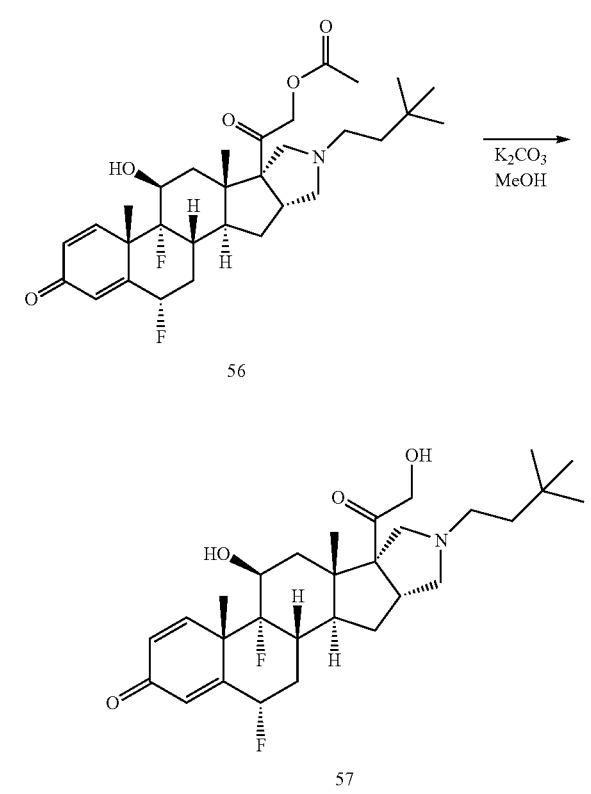

Preparation of Acetic acid 2-[(4aS,4bR,5S,6aS,6bS,9aR,10aS,10bS,12S)-8-(3,3-dimethyl-butyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthren-6b-yl]-2-oxo-ethyl ester (compound 56)

A solution of compound 20 (900 mg, 1.800 mmol), 3,3-dimethylbutyraldehyde (904 µl, 7.20 mmol), formic acid (552 µl, 14.40 mmol) and TEA (251 µl, 1.800 mmol) in acetonitrile (45 ml) is irradiated with microwaves (140° C., 15 minutes). The reaction is partitioned between AcOEt and NaHCO$_3$ solution. The organic layers are then washed with brine, dried over Na$_2$SO$_4$ and filtered. The solvent is evaporated to give a oil which is purified by silica gel chromatography (from DCM:MeOH 100:0 to 98.5:1.5) to give the title compound (721 mg, 1.316 mmol, 73.1% yield).

LC-MS (ESI POS): 548.2 MH+

Preparation of (4aS,4bR,5S,6aS,6bS,9aR,10aS,10bS,12S)-8-(3,3-Dimethyl-butyl)-4b,12-difluoro-5-hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one (compound 57)

The title compound is prepared from compound 56 following the procedure described in Example 10 for the synthesis of compound 45.

(95 mg, 0.188 mmol, 69% yield) as solid are obtained.

$^1$H NMR (300 MHz, DMSO-d6) ppm 7.26 (dd, 1H), 6.29 (dd, 1H), 6.11 (s, 1H), 5.49-5.81 (m, 1H), 5.40 (dd, 1H), 4.79 (t, 1H), 4.28 (d, 1H), 4.13-4.20 (m, 1H), 4.10 (d, 1H), 3.03-3.15 (m, 1H), 2.83 (t, 1H), 2.54-2.59 (m, 1H), 2.39-2.46 (m, 1H), 2.35 (d, 1H), 2.10-2.31 (m, 3H), 1.90-2.05 (m, 2H), 1.69-1.89 (m, 2H), 1.51-1.68 (m, 2H), 1.48 (s, 3H), 1.30-1.40 (m, 1H), 1.25 (t, 2H), 0.86 (s, 3H), 0.84 (s, 9H)

LC-MS (ESI POS): 506.26 MH+

$[\alpha]_D^{25}$ +51.70 (c=0.4, MeOH)

Intermediates listed in Table 10 are prepared as described for compound 56 starting from the suitable commercially available aldehydes or ketones. Intermediates 60 (4-benzyl-benzaldehyde) and 63 (4-(4-Hydroxy-phenylsulfanylmethyl)-benzaldehyde) are prepared according to the procedure described in WO2009/0690302, which is incorporated herein by reference in its entirety.

TABLE 10

| Compound | Structure | Yield | Analytical |
|---|---|---|---|
| 58 | 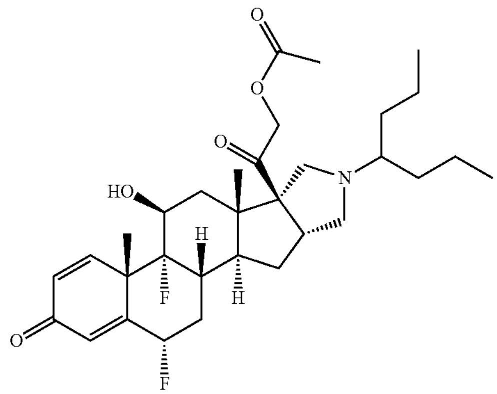 | 26% | LC-MS (ESI POS): 562.2 MH+ |
| 59 | 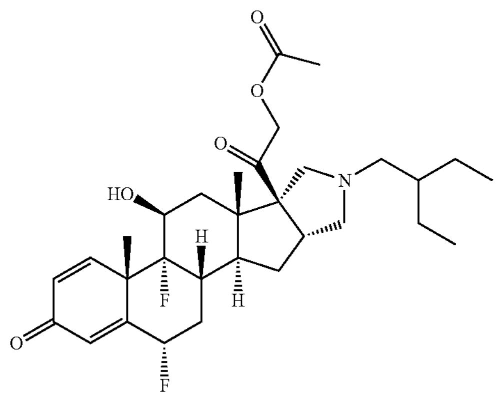 | 100% | LC-MS (ESI POS): 548.1 MH+ |
| 60 | 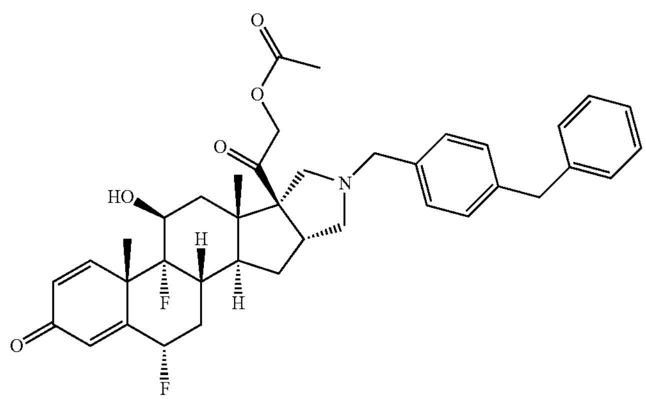 | 84% | LC-MS (ESI POS): 644.4 MH+ |
| 61 | 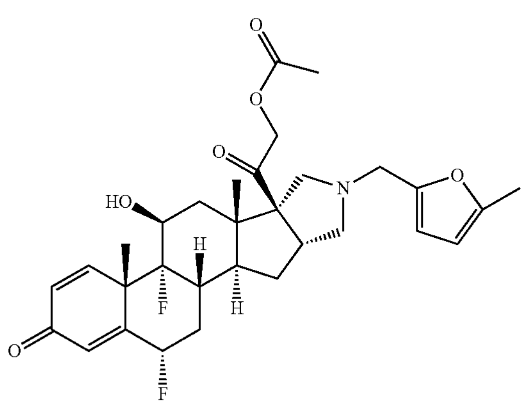 | 32% | LC-MS (ESI POS): 558.0 MH+ |

TABLE 10-continued

| Compound | Structure | Yield | Analytical |
|---|---|---|---|
| 62 | 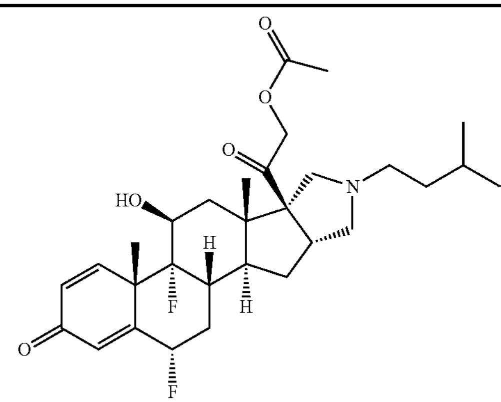 | 90% | LC-MS (ESI POS): 534.0 MH+ |
| 63 | 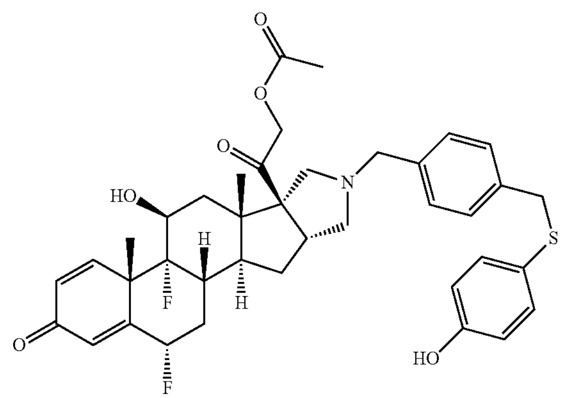 | 72% | LC-MS (ESI POS): (ESI POS): 692.3 MH+ |

The compounds listed in Table 11 are prepared from the intermediates in Table 10 as described in Example 14 for the preparation of compound 57.

TABLE 11

| Compound | Structure | Yield | Analytical |
|---|---|---|---|
| 64 | 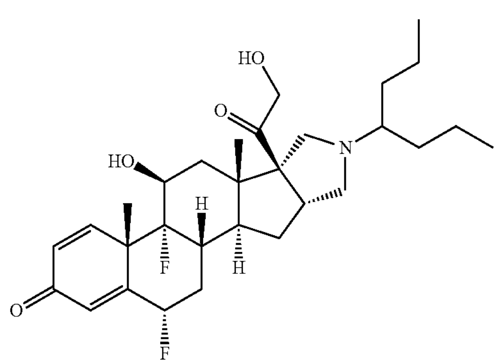 | 13% | $^1$H NMR (300 MHz, DMSO-d6) ppm 7.25 (dd, 1 H), 6.29 (dd, 1 H), 6.11 (s, 1 H), 5.47-5.81 (m, 1 H), 5.38 (dd, 1 H), 4.79 (t, 1 H), 4.26 (dd, 1 H), 4.15-4.19 (m, 1 H), 4.11 (dd, 1 H), 2.96-3.19 (m, 1 H), 2.77 (t, 1 H), 2.36-2.46 (m, 1 H), 2.09-2.31 (m, 3 H), 1.70-2.05 (m, 3 H), 1.53-1.70 (m, 1 H), 1.48 (s, 3 H), 1.05-1.44 (m, 12 H), 0.87 (s, 3 H), 0.77-0.85 (m, 6 H) LC-MS (ESI POS): 520.38 MH+ $[\alpha]_D^{25}$ +47.29 (c 0.28, MeOH) |

TABLE 11-continued

| Compound | Structure | Yield | Analytical |
|---|---|---|---|
| 65 | 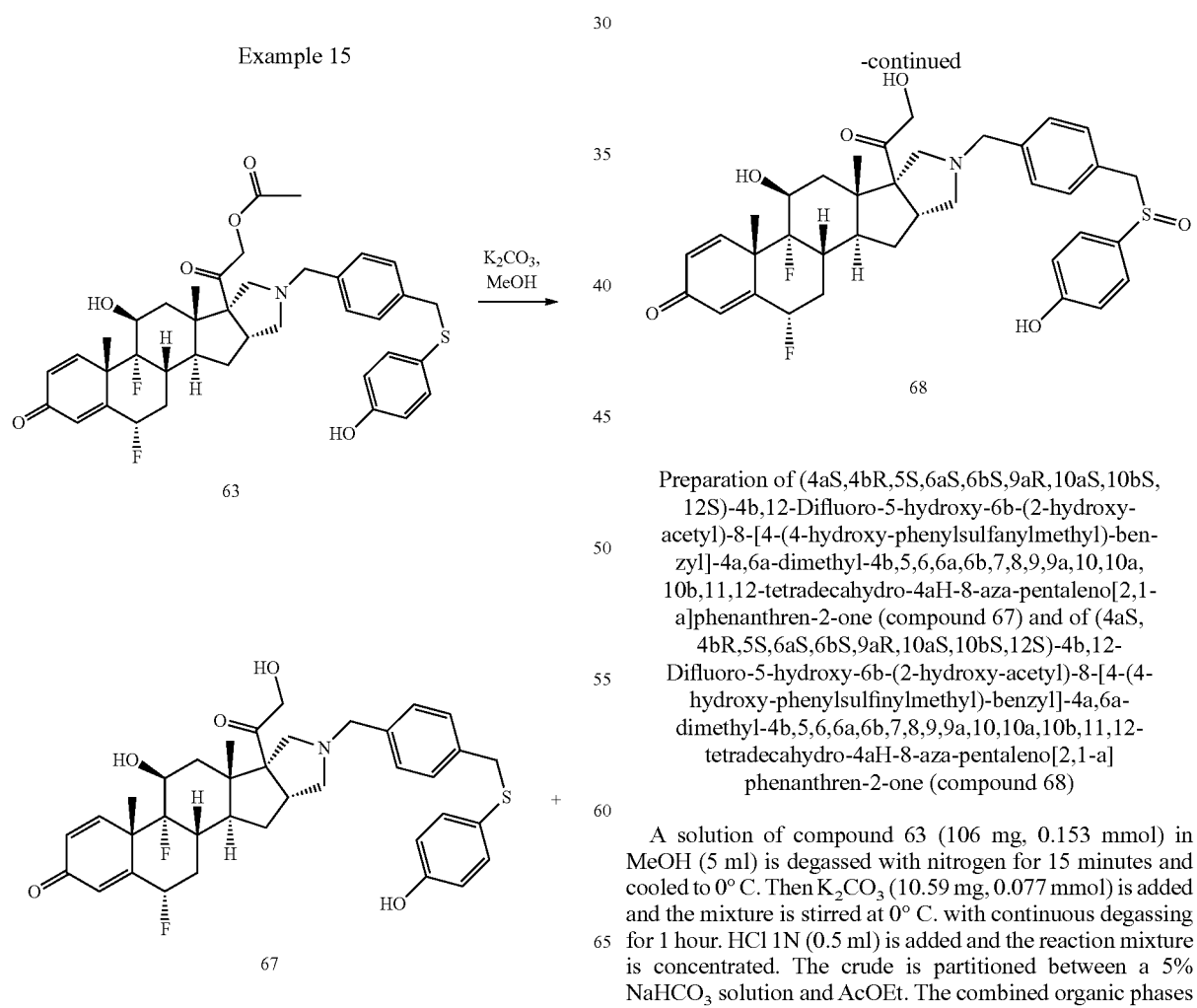 | 57% | $^1$H NMR (300 MHz, DMSO-d6) ppm 7.26 (dd, 1 H), 6.29 (dd, 1 H), 6.11 (s, 1 H), 5.47-5.79 (m, 1 H), 5.38 (dd, 1 H), 4.81 (t, 1 H), 4.26 (dd, 1 H), 4.14-4.20 (m, 1 H), 4.11 (dd, 1 H), 3.02-3.15 (m, 1 H), 2.66-2.72 (m, 1 H), 2.54-2.60 (m, 1 H), 2.48 (d, 1 H), 2.35 (d, 1 H), 2.19-2.30 (m, 1 H), 1.93-2.14 (m, 4 H), 1.72-1.93 (m, 2 H), 1.51-1.70 (m, 1 H), 1.48 (s, 3 H), 1.14-1.40 (m, 7 H), 0.87 (s, 3 H), 0.77 (t, 6 H) LC-MS (ESI POS): 506.22 MH+ [α]$_D^{25}$ +43.05 (c 0.21, MeOH) |
| 66 | 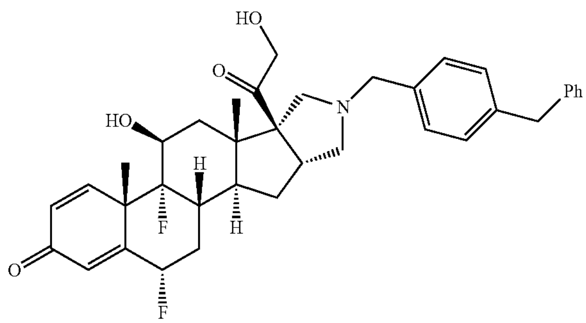 | 29% | $^1$H NMR (300 MHz, DMSO-d6) ppm 7.08-7.35 (m, 10 H) 6.29 (dd, 1 H) 6.12 (s, 1 H) 5.45-5.83 (m, 1 H) 5.39 (dd, 1 H) 4.81 (t, 1 H) 4.23 (dd, 1 H) 4.11-4.17 (m, 1 H) 4.11 (dd, 1 H) 3.89 (s, 2 H) 3.39 (s, 2 H) 3.04-3.21 (m, 1 H) 2.85 (t, 1 H) 2.54-2.61 (m, 1 H) 2.17-2.42 (m, 2 H) 1.92-2.09 (m, 2 H) 1.76-1.90 (m, 1 H) 1.52-1.76 (m, 3 H) 1.45-1.53 (m, 1 H) 1.48 (s, 3 H) 1.33 (dd, 1 H) 0.86 (s, 3 H) LC-MS (ESI POS): 602.37 MH+ [α]$_D^{25}$ +55.4 (c 0.75 MeOH) |

Example 15

Preparation of (4aS,4bR,5S,6aS,6bS,9aR,10aS,10bS, 12S)-4b,12-Difluoro-5-hydroxy-6b-(2-hydroxy-acetyl)-8-[4-(4-hydroxy-phenylsulfanylmethyl)-benzyl]-4a,6a-dimethyl-4b,5,6,6a,6b,7,8,9,9a,10,10a, 10b,11,12-tetradecahydro-4aH-8-aza-pentaleno[2,1-a]phenanthren-2-one (compound 67) and of (4aS, 4bR,5S,6aS,6bS,9aR,10aS,10bS,12S)-4b,12-Difluoro-5-hydroxy-6b-(2-hydroxy-acetyl)-8-[4-(4-hydroxy-phenylsulfinylmethyl)-benzyl]-4a,6a-dimethyl-4b,5,6,6a,6b,7,8,9,9a,10,10a,10b,11,12-tetradecahydro-4aH-8-aza-pentaleno[2,1-a] phenanthren-2-one (compound 68)

A solution of compound 63 (106 mg, 0.153 mmol) in MeOH (5 ml) is degassed with nitrogen for 15 minutes and cooled to 0° C. Then K$_2$CO$_3$ (10.59 mg, 0.077 mmol) is added and the mixture is stirred at 0° C. with continuous degassing for 1 hour. HCl 1N (0.5 ml) is added and the reaction mixture is concentrated. The crude is partitioned between a 5% NaHCO$_3$ solution and AcOEt. The combined organic phases are concentrated and purified by silica gel flash chromatography (eluent AcOEt/Petroleum ether 4/6). The obtained product is further purified by preparative HPLC (Acetonitrile/Water, no CF3COOH) to afford title compound 67 (17 mg, 17.08% yield) and 68 (7 mg, 6.86% yield).

Compound 67:

$^1$H NMR (300 MHz, DMSO-d6) ppm 9.52 (br. s., 1H), 7.26 (dd, 1H), 7.02-7.19 (m, 6H), 6.61-6.73 (m, 2H), 6.29 (dd, 1H), 6.13 (s, 1H), 5.48-5.81 (m, 1H), 5.40 (d, 1H), 4.83 (br. s., 1H), 4.17-4.29 (m, 1H), 4.02-4.21 (m, 2H), 4.00 (s, 2H), 3.39 (s, 2H), 3.06-3.22 (m, 1H), 2.77-2.91 (m, 1H), 2.55-2.68 (m, 2H), 2.35 (d, 1H), 2.16-2.30 (m, 1H), 1.93-2.10 (m, 2H), 1.84 (d, 1H), 1.50-1.77 (m, 3H), 1.49 (s, 3H), 1.34 (dd, 1H), 0.86 (s, 3H)

LC-MS (ESI POS): 650.41 MH+

$[\alpha]_D^{25}$+62.13 (C 0.16 MeOH)

Compound 68:

$^1$H NMR (300 MHz, DMSO-d6) ppm 10.01 (s, 1H), 7.27-7.36 (m, 2H), 7.26 (d, 1H), 7.07-7.16 (m, 2H), 6.94-7.06 (m, 2H), 6.77-6.93 (m, 2H), 6.30 (d, 1H), 6.13 (s, 1H), 5.50-5.79 (m, 1H), 5.41 (br. s., 1H), 4.84 (br. s., 1H), 3.88-4.51 (m, 5H), 3.41 (br. s., 2H), 3.05-3.22 (m, 1H), 2.79-2.97 (m, 1H), 2.56-2.69 (m, 2H), 2.32-2.42 (m, 1H), 2.22-2.32 (m, 1H), 1.92-2.11 (m, 2H), 1.54-1.92 (m, 4H), 1.49 (s, 3H), 1.28-1.42 (m, 1H), 0.87 (s, 3H)

LC-MS (ESI POS): 666.38 MH+

Example 16

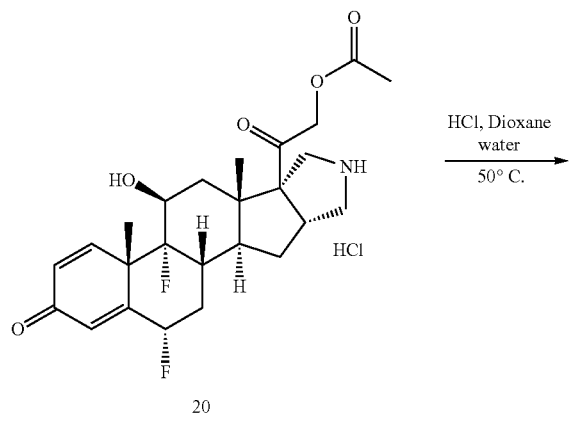

Preparation of (4aR,4bS,5S,6aS,6bS,9aR,10aS,10bS)-5-Hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one hydrochloride (compound 69)

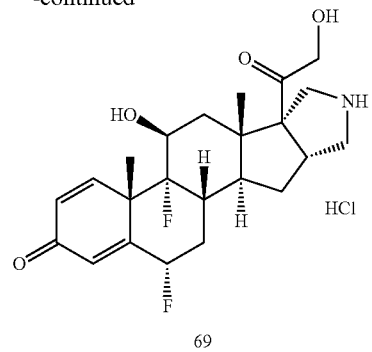

Method A.

A mixture of Compound 20 (130 mg, 0.260 mmol) and conc. HCl (1 mL, 32.9 mmol) in dioxane (4 ml) and water (4 ml) is stirred at 50° C. for 7.5 hours. The solvent is evaporated and the crude is triturated with EtOH to give the title compound (30 mg, 0.066 mmol, 25.2% yield).

$^1$H NMR (300 MHz, DMSO-d$_6$) δ ppm 9.08 (br. s., 2H), 7.28 (dd, 1H), 6.30 (dd, 1H), 6.12 (s, 1H), 5.57 (dd, 1H), 5.47-5.82 (m, 1H), 5.11 (br. s., 1H), 4.33-4.52 (m, 1H), 4.07-4.31 (m, 2H), 3.33-3.51 (m, 3H), 2.92-3.16 (m, 2H), 2.57-2.67 (m, 1H), 2.11-2.30 (m, 1H), 1.57-1.95 (m, 5H), 1.49 (s, 3H), 1.42-1.54 (m, 1H), 0.94 (s, 3H)

LC-MS (ESI POS): 421.97 (MH+)

$[\alpha]_D^{20}$=+64.8 (c 0.2, H$_2$O)

Method B.

In a closed vessel compound 20 (300 mg, 0.600 mmol) is dissolved in MeOH, HCl (0.045 ml, 0.180 mmol) in dioxane is added and the mixture is stirred at room temperature for 10 days, then further HCl (0.045 ml, 0.180 mmol) is added and the reaction mixture is stirred for further 2 days. The reaction mixture is concentrated to dryness affording the title compound (253 mg, 0.600 mmol, 100% yield).

LC-MS (ESI-POS): 421.97 (MH+)

Compound listed in Table 12 is prepared through the procedure previously described for compound 69 following (Method A).

TABLE 12

| Compound | Structure | Yield | Analytical |
|---|---|---|---|
| 70 | (steroid structure with OH, HO, HCl, N-benzyl) | 90% | $^1$H NMR (300 MHz, DMSO-d$_6$) δ ppm 10.47 (br. s., 1 H), 7.38-7.81 (m, 5 H), 7.30 (d, 1 H), 6.31 (dd, 1 H), 6.14 (s, 1 H), 5.40-5.82 (m, 2 H), 4.10-4.62 (m, 4 H), 3.15-3.88 (m, 8 H), 2.94-3.14 (m, 1 H), 2.68-2.93 (m, 1 H), 2.02-2.37 (m, 2 H), 1.56-1.88 (m, 3 H), 1.50 (s, 3 H), 0.89 (s, 3 H) LC-MS (ESI POS): 476.34 (MH+) |

Example 17

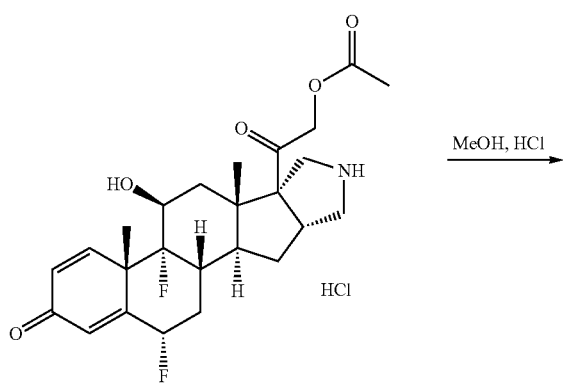

Preparation of (4aR,4bS,5S,6aS,6bS,9aR,10aS, 10bS)-5-Hydroxy-6b-(2-hydroxy-acetyl)-4a,6a-dimethyl-4b,5,6,6a,6b,7,8,9,9a,10,10a,10b,11,12-tetradecahydro-4aH-8-aza-pentaleno[2,1-a]phenanthren-2-one hydrochloride (compound 69)

Compound 69 is prepared from compound 20 as described in Example 16 following Method B.

Acetic acid 4-[(4aS,4bR,5S,6aS,6bS,9aR,10aS,10bS, 12S)-4b,12-difluoro-5-hydroxy-6b-(2-hydroxy-acetyl)-4a,6a-dimethyl-2-oxo-2,4b,5,6,6a,6b,7,9,9a, 10,10a,10b,11,12-tetradecahydro-4aH-8-aza-pentaleno[2,1-a]phenanthren-8-ylmethyl]-phenyl ester (compound 71)

In a nitrogen atmosphere compound 69 (275 mg, 0.6 mmol) is dissolved in dry acetonitrile (10 ml), DIPEA (0.210 ml, 1.200 mmol) and 4(chloromethyl)phenylacetate (0.092 ml, 0.600 mmol) are added and the mixture is stirred at RT overnight. The reaction mixture is partitioned between 5% NaHCO₃ solution and AcOEt. The organic phase is separated, dried over Na₂SO₄ and concentrated. The crude is purified by silica gel flash chromatography (eluent from DCM/AcOEt=7/3 to 1/1), then by preparative HPLC (neutral phase) to yield the title compound (38 mg, 0.067 mmol, 11% yield).

$^1$H NMR (300 MHz, DMSO-d6) ppm 7.13-7.32 (m, 3H), 6.89-7.11 (m, 2H), 6.29 (dd, 1H), 6.13 (s, 1H), 5.48-5.74 (m, 1H), 5.40 (br. s., 1H), 4.83 (t, 1H), 4.25 (dd, 1H), 4.10-4.14 (m, 1H), 4.13 (dd, 1H), 3.44 (s, 2H), 3.07-3.23 (m, 1H), 2.88 (t, 1H), 2.59-2.69 (m, 1H), 2.55 (d, 1H), 2.39 (d, 1H), 2.26-2.33 (m, 1H), 2.24 (s, 3H), 1.93-2.11 (m, 2H), 1.79-1.90 (m, 1H), 1.51-1.78 (m, 3H), 1.49 (s, 3H), 1.35 (dd, 1H), 0.87 (s, 3H)

LC-MS (ESI POS): 570.36 MH+

$[\alpha]_D^{25}$+64.4 (c 0.37, MeOH)

Example 18

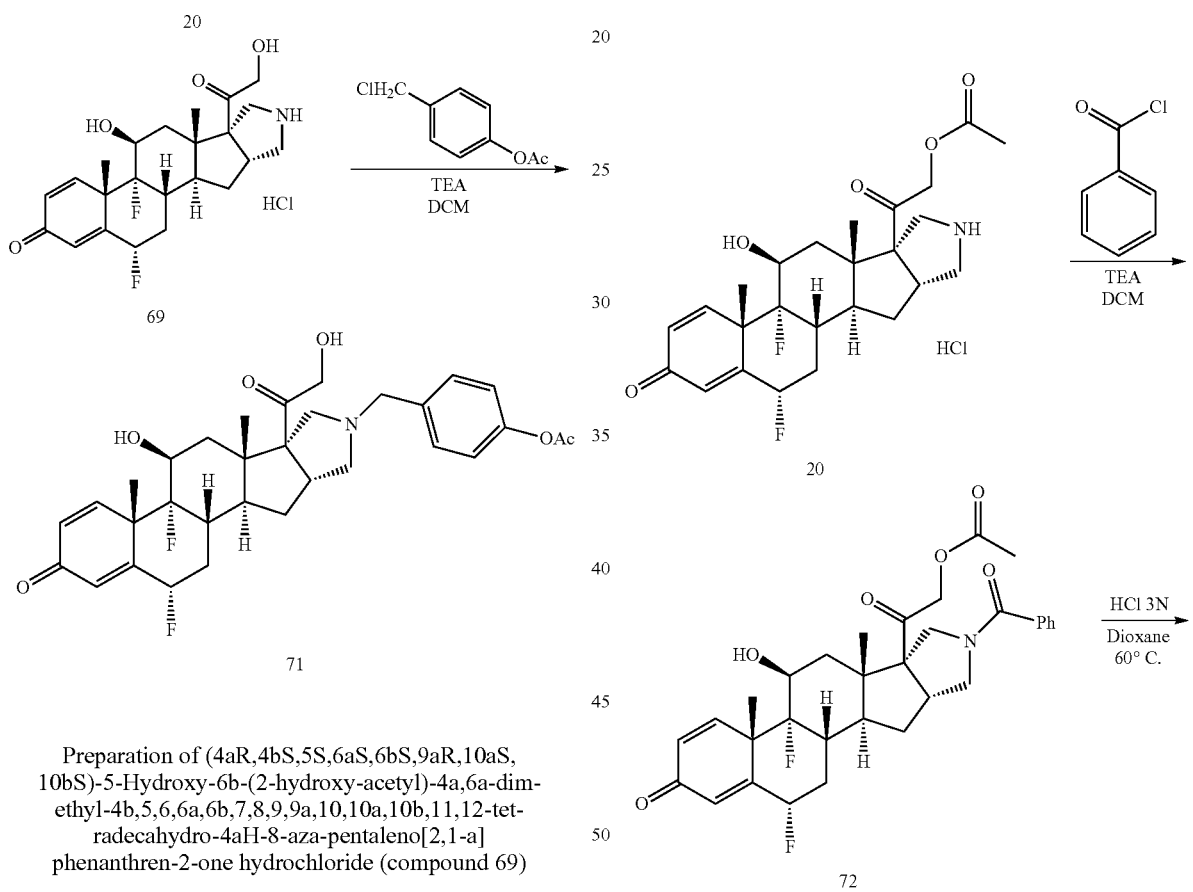

Preparation of Acetic acid 2-((4aS,4bR,5S,6aS,6bS, 9aR,10aS,10bS,12S)-8-benzoyl-4b,12-difluoro-5-hydroxy-4a,6a-dimethyl-2-oxo-2,4b,5,6,6a,7,8,9,9a, 10,10a,10b,11,12-tetradecahydro-4aH-8-aza-pentaleno[2,1-a]phenanthren-6b-yl)-2-oxo-ethyl ester (compound 72)

Compound 20 (110 mg, 0.237 mmol) is dissolved in dry DCM (3 ml) in a nitrogen atmosphere. TEA (0.099 ml, 0.712 mmol) and benzoyl chloride (0.041 ml, 0.356 mmol) are added and the mixture is stirred at RT for 1 hour. The reaction mixture is concentrated to dryness and the crude is purified by silica gel flash chromatography (DCM to DCM:MeOH=98: 2) yielding the title compound (107 mg, 0.189 mmol, 79% yield).

$^1$H NMR (300 MHz, DMSO-d$_6$ 353K) δ ppm 7.34-7.50 (m, 5H), 7.25 (dd, 1H), 6.28 (dd, 1H), 6.09-6.20 (m, 1H), 5.43-5.77 (m, 1H), 5.26 (br. s., 1H), 5.00 (d, 1H), 4.78 (d, 1H), 4.12-4.31 (m, 1H), 3.52-3.79 (m, 3H), 3.36-3.47 (m, 1H), 3.23-3.36 (m, 1H), 2.55-2.63 (m, 1H), 2.20-2.34 (m, 1H), 2.11 (s, 3H), 1.70-1.97 (m, 4H), 1.55-1.64 (m, 1H), 1.52 (s, 3H), 1.33-1.46 (m, 1H), 1.05 (s, 3H)

LC-MS (ESI POS): 568.3 (MH+)

Preparation of (4aS,4bR,5S,6aS,6bS,9aR,10aS,10bS, 12S)-8-Benzoyl-4b,12-difluoro-5-hydroxy-6b-(2-hydroxy-acetyl)-4a,6a-dimethyl-4b,5,6,6a,6b,7,8,9, 9a,10,10a,10b,11,12-tetradecahydro-4aH-8-aza-pentaleno[2,1-a]phenanthren-2-one (compound 73)

Compound 72 is hydrolyzed as described in Example 4 for the preparation of compound 18 obtaining the title compound in 53% yield.

$^1$H NMR (300 MHz, DMSO-d$_6$) δ ppm 7.33-7.59 (m, 5H), 7.26 (d, 1H), 6.30 (d, 1H), 6.12 (s, 1H), 5.49-5.75 (m, 1H), 5.46 (br. s., 1H), 4.89-5.07 (m, 1H), 3.98-4.58 (m, 3H), 3.35-3.95 (m, 4H), 2.54-2.62 (m, 1H), 2.15-2.26 (m, 1H), 1.67-2.05 (m, 5H), 1.52-1.65 (m, 1H), 1.49 (s, 3H), 1.17-1.38 (m, 1H), 0.95 (s, 3H)

LC-MS (ESI POS): 526.39 (MH+)

$[\alpha]_D^{20}$=+6.3 (c 0.35, MeOH)

Compounds listed in Table 13 are prepared through a two steps procedure as previously described for compound 73.

TABLE 13

| Compound | Structure | Yield | Analytical |
|---|---|---|---|
| 74 | 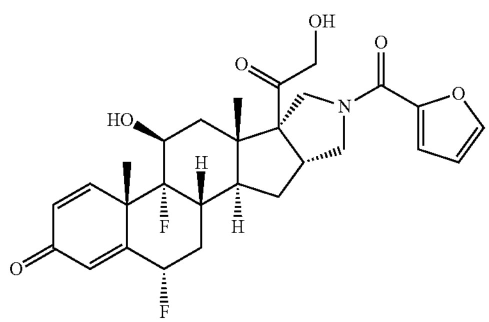 | 46% | $^1$H NMR (300 MHz, DMSO-d$_6$) δ ppm 7.83 (dd, 1 H), 7.26 (dd, 1 H), 7.04 (d, 1 H), 6.61 (dd, 1 H), 6.29 (dd, 1 H), 6.10 (s, 1 H), 5.50-5.75 (m, 1 H), 5.48 (dd, 1 H), 4.98 (t, 1 H), 4.45 (dd, 1 H), 4.07-4.28 (m, 2 H), 3.50-4.00 (m, 5 H), 2.56-2.63 (m, 1 H), 2.23 (dd, 1 H), 1.70-2.04 (m, 4 H), 1.52-1.58 (m, 1 H), 1.49 (s, 3 H), 1.43-1.48 (m, 1 H), 0.99 (s, 3 H) <br> LC-MS (ESI POS): 516.46 (MH+) <br> $[\alpha]_D^{20}$ = +12.5 (c = 0.5 CHCl$_3$) |
| 75 | 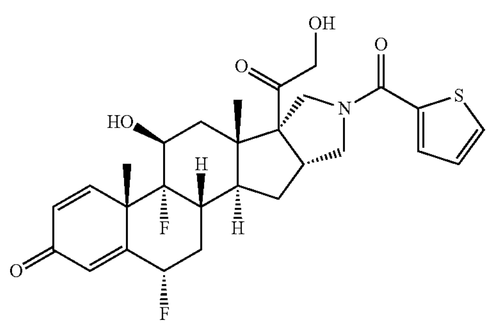 | 47% | $^1$H NMR (300 MHz, DMSO-d$_6$) δ ppm 7.75 (dd, 1 H), 7.54 (dd, 1 H), 7.26 (dd, 1 H), 7.13 (dd, 1 H), 6.29 (dd, 1 H), 6.10 (s, 1 H), 5.50-5.74 (m, 1 H), 5.48 (dd, 1 H), 4.99 (t, 1 H), 4.45 (dd, 1 H), 4.17-4.24 (m, 1 H), 4.14 (dd, 1 H), 3.90 (br. s., 1 H), 3.57-3.81 (m, 3 H), 3.33-3.44 (m, 1 H), 2.56-2.63 (m, 1 H), 2.11-2.27 (m, 1 H), 1.68-1.99 (m, 4 H), 1.51-1.59 (m, 1 H), 1.49 (s, 3 H), 1.40-1.48 (m, 1 H), 0.98 (s, 3 H) <br> LC-MS (ESI POS): 532.32 (MH+) <br> $[\alpha]_D^{20}$ = +10.37 (c = 0.38, DMSO) |
| 76 | 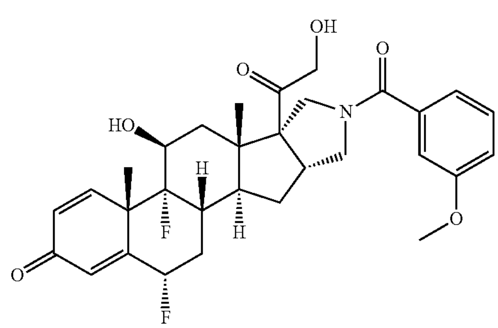 | 70% | $^1$H NMR (300 MHz, DMSO-d$_6$) δ ppm 7.18-7.41 (m, 2 H), 6.72-7.10 (m, 3 H), 6.30 (dd, 1 H), 6.12 (s, 1 H), 5.50-5.79 (m, 1 H), 5.47 (s, 1 H), 4.93-5.03 (m, 1 H), 4.40 (br. s., 1 H), 3.93-4.27 (m, 2 H), 3.74 (br. s., 3 H), 3.38-3.67 (m, 4 H), 2.55-2.63 (m, 1 H), 2.14-2.31 (m, 1 H), 1.66-2.05 (m, 4 H), 1.52-1.66 (m, 2 H), 1.48 (s, 3 H), 1.16-1.41 (m, 1 H), 0.95 (s, 3 H) <br> LC-MS (ESI POS): 556.42 (MH+) <br> $[\alpha]_D^{20}$ = +11.67 (c = 0.3, MeOH) |

TABLE 13-continued

| Compound | Structure | Yield | Analytical |
|---|---|---|---|
| 77 | 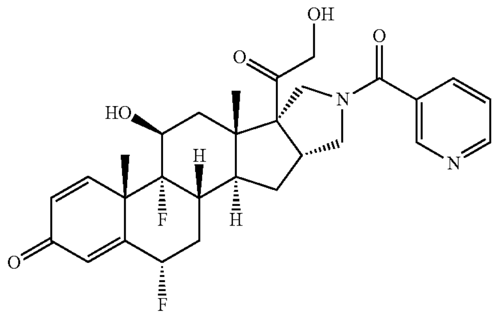 | 50% | $^1$H NMR (300 MHz, DMSO-d$_6$) δ ppm 8.63 (dd, 1 H), 8.61 (br. s., 1 H), 7.83 (br. s., 1 H), 7.45 (dd, 1 H), 7.19-7.31 (m, 1 H), 6.30 (d, 1 H), 6.12 (s, 1 H), 5.50-5.80 (m, 1 H), 5.27-5.50 (m, 1 H), 4.85-5.13 (m, 1 H), 3.98-4.59 (m, 3 H), 3.42-3.88 (m, 4 H), 2.54-2.61 (m, 1 H), 2.11-2.32 (m, 1 H), 1.65-2.01 (m, 5 H), 1.54-1.64 (m, 1 H), 1.49 (s, 3 H), 1.28-1.42 (m, 1 H), 0.96 (s, 3 H) LC-MS (ESI POS): 527.40 (MH+) [α]$_D^{20}$ = +12.96 (c = 0.5 MeOH) |
| 78 | 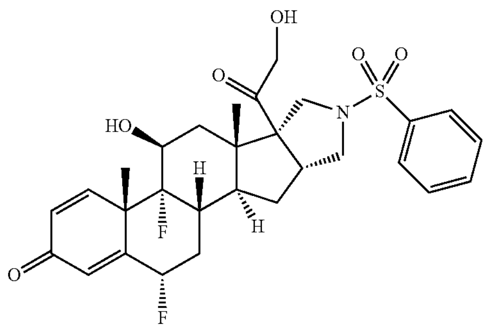 | 64% | $^1$H NMR (300 MHz, DMSO-d$_6$) δ ppm 7.66-7.79 (m, 3 H), 7.54-7.66 (m, 2 H), 7.23 (dd, 1 H), 6.29 (dd, 1 H), 6.11 (s, 1 H), 5.46-5.72 (m, 1 H), 5.43 (dd, 1 H), 5.02 (t, 1 H), 4.30 (dd, 1 H), 4.09-4.19 (m, 1 H), 4.03 (dd, 1 H), 3.18-3.28 (m, 2 H), 3.12 (d, 1 H), 2.96 (d, 1 H), 2.77-2.87 (m, 1 H), 2.30-2.47 (m, 1 H), 2.07-2.22 (m, 1 H), 1.79-1.89 (m, 1 H), 1.60-1.76 (m, 2 H), 1.47-1.57 (m, 1 H), 1.45 (s, 3 H), 1.11-1.38 (m, 2 H), 0.87 (s, 3 H) LC-MS (ESI POS): 562.35 (MH+) [α]$_D^{20}$ = +39.68 (c = 1, MeOH) |
| 79 | 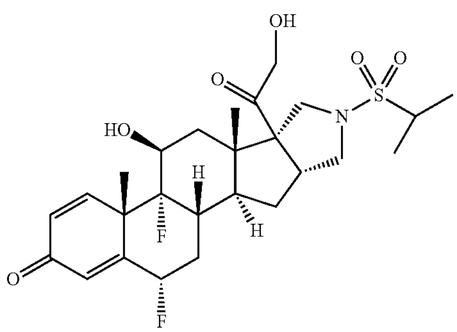 | 43% | $^1$H NMR (300 MHz, DMSO-d6) δ ppm 7.26 (dd, 1 H), 6.29 (dd, 1 H), 6.11 (s, 1 H), 5.49-5.79 (m, 1 H), 5.45 (dd, 1 H), 5.02 (t, 1 H), 4.37 (dd, 1 H), 4.16-4.23 (m, 1 H), 4.13 (dd, 1 H), 3.43 (m, 1 H), 3.30-3.37 (m, 4 H), 3.09 (dd, 1 H), 2.55-2.63 (m, 1 H), 2.15-2.33 (m, 1 H), 1.54-1.96 (m, 5 H), 1.49 (s, 3 H), 1.38-1.46 (m, 1 H), 1.17 (d, 3 H), 1.17 (d, 3 H), 0.93 (s, 3 H) LC-MS (ESI POS): 528.29 (MH+) [α]$_D^{20}$ = +44.29 (c 0.28, MeOH) |
| 80 | 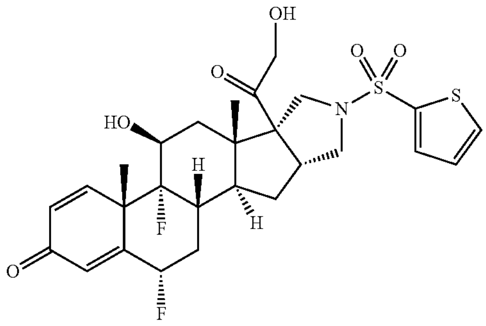 | 31% | $^1$H NMR (300 MHz, DMSO-d6) δ ppm 8.03 (dd, 1 H), 7.65 (dd, 1 H), 7.19-7.28 (m, 2 H), 6.29 (dd, 1 H), 6.11 (s, 1 H), 5.47-5.75 (m, 1 H), 5.45 (dd, 1 H), 5.05 (t, 1 H), 4.34 (dd, 1 H), 4.11-4.20 (m, 1 H), 4.06 (dd, 1 H), 3.30-3.37 (m, 1 H), 3.18 (d, 1 H), 3.02 (d, 1 H), 2.82-2.95 (m, 1 H), 2.33-2.47 (m, 1 H), 2.09-2.25 (m, 1 H), 1.85 (d, 1 H), 1.51-1.80 (m, 4 H), 1.46 (s, 3 H), 1.26-1.42 (m, 2 H), 0.89 (s, 3 H) LC-MS (ESI POS): 568.43 (MH+) [α]$_D^{20}$ = +28.09 (c 0.22, MeOH) |

TABLE 13-continued

| Compound | Structure | Yield | Analytical |
|---|---|---|---|
| 81 | 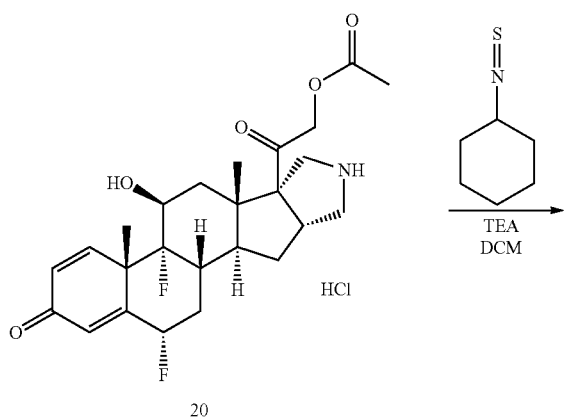 | 43% | ¹H NMR (300 MHz, DMSO-$d_6$) δ ppm 7.29-7.44 (m, 5 H), 7.26 (d, 1 H), 6.31 (dd, 1 H), 6.15 (s, 1 H), 5.51-5.82 (m, 1 H), 5.45 (dd, 1 H), 5.03 (t, 1 H), 4.46 (s, 2 H), 4.34 (dd, 1 H), 4.16-4.21 (m, 1 H), 4.10 (dd, 1 H), 3.35-3.42 (m, 2 H), 3.27 (d, 1 H), 3.13 (d, 1 H), 2.92 (dd, 1 H), 2.55-2.62 (m, 1 H), 2.18-2.30 (m, 1 H), 1.54-1.90 (m, 5 H), 1.49 (s, 3 H), 1.29-1.42 (m, 1 H), 0.91 (s, 3 H) LC-MS (ESI POS): 576.27 (MH+) |

Example 19

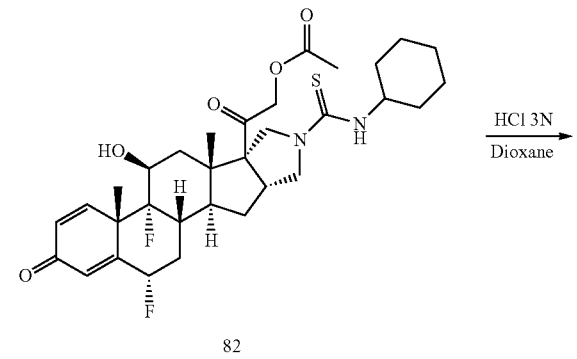

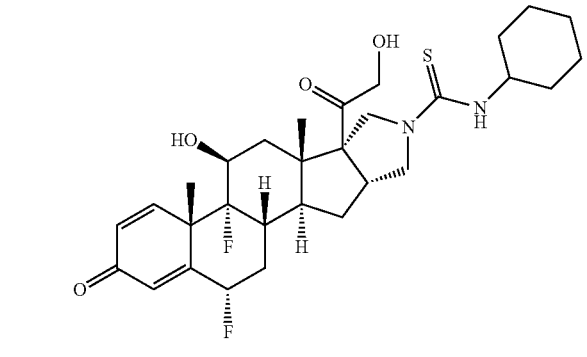

Preparation of Acetic acid 2-((4aS,4bR,5S,6aS,6bS, 9aR,10aS,10bS,12S)-8-cyclohexylthiocarbamoyl-4b, 12-difluoro-5-hydroxy-4a,6a-dimethyl-2-oxo-2,4b,5, 6,6a,7,8,9,9a,10,10a,10b,11,12-tetradecahydro-4aH-8-aza-pentaleno[2,1-a]phenanthren-6b-yl)-2-oxo-ethyl ester (compound 82)

20 (150 mg, 0.300 mmol) is suspended in dry DCM (4 ml) and TEA (167 µl, 1.200 mmol) is added followed by isothiocyanatocyclohexane (85 mg, 0.600 mmol). The reaction mixture is stirred at RT for 4 hours then it is washed with brine, dried over $Na_2SO_4$ and evaporated to give a residue that is purified by silica gel cartridge Petroleum Ether/AcOEt 6:4 to AcOEt leading to the title compound (91 mg, 0.150 mmol, 50.2% yield).

LC-MS (ESI POS): 605.2 (MH+)

Preparation of (4aS,4bR,5S,6aS,6bS,9aR,10aS,10bS, 12S)-4b,12-Difluoro-5-hydroxy-6b-(2-hydroxy-acetyl)-4a,6a-dimethyl-2-oxo-2,4b,5,6,6a,6b,7,9,9a, 10,10a,10b,11,12-tetradecahydro-4aH-8-aza-pentaleno[2,1-a]phenanthrene-8-carbothioic acid cyclohexylamide (compound 83)

Compound 82 is hydrolyzed as described in Example 4 for the preparation of compound 18 obtaining the title compound in 80% yield.

¹H NMR (300 MHz, DMSO-$d_6$) δ ppm 7.26 (dd, 1H), 6.84 (d, 1H), 6.29 (dd, 1H), 6.11 (s, 1H), 5.50-5.79 (m, 1H), 5.46 (dd, 1H), 5.00 (t, 1H), 4.42 (dd, 1H), 4.16-4.24 (m, 1H), 4.10 (dd, 1H), 3.98-4.06 (m, 1H), 3.61-3.79 (m, 2H), 3.46-3.59 (m, 2H), 2.38-2.47 (m, 1H), 2.17-2.25 (m, 1H), 1.51-1.97 (m, 10H), 1.49 (s, 4H), 1.00-1.31 (m, 6H), 0.97 (s, 3H)

LC-MS (ESI POS): 563.45 (MH+)

$[\alpha]_D^{20}$+30.06 (c=0.64 MeOH)

Compounds listed in Table 14 are prepared through a two steps procedure as previously described for compound 83.

TABLE 14

| Compound | Structure | Yield | Analytical |
|---|---|---|---|
| 84 | 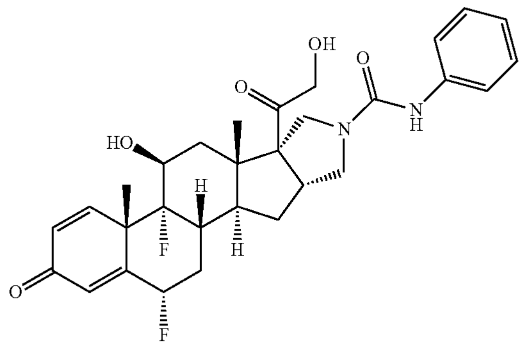 | 21% | $^1$H NMR (300 MHz, DMSO-d$_6$) δ ppm 8.16 (s, 1 H) 7.40-7.48 (m, 2 H) 7.27 (dd, 1 H) 7.14-7.24 (m, 2 H) 6.91 (tt, 1 H) 6.30 (dd, 1 H) 6.06-6.14 (m, 1 H) 5.50-5.77 (m, 1 H) 5.46 (dd, 1 H) 4.97 (t, 1 H) 4.44 (dd, 1 H) 4.06-4.24 (m, 2 H) 3.57-3.68 (m, 1 H) 3.53 (d, 1 H) 3.45 (d, 1 H) 3.31-3.38 (m, 2 H) 2.16-2.27 (m, 1 H) 1.71-2.00 (m, 4 H) 1.50 (s, 3 H) 1.35-1.64 (m, 3 H) 0.98 (s, 3 H) LC-MS (ESI POS): 541.1 (MH+) $[\alpha]_D^{20} = +13.8$ (c 0.25, CHCl$_3$) |
| 85 | 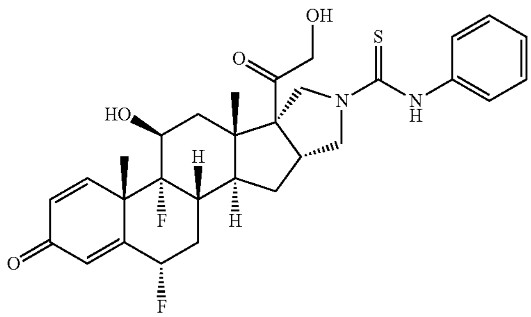 | 38% | $^1$H NMR (300 MHz, DMSO-d$_6$) δ ppm 8.92 (s, 1 H), 7.20-7.39 (m, 5 H), 6.95-7.16 (m, 1 H), 6.30 (dd, 1 H), 6.12 (s, 1 H), 5.52-5.74 (m, 1 H), 5.48 (dd, 1 H), 5.03 (t, 1 H), 4.47 (dd, 1 H), 4.18-4.26 (m, 1 H), 4.16 (dd, 1 H), 3.61-3.96 (m, 4 H), 3.34-3.49 (m, 1 H), 2.54-2.61 (m, 1 H), 2.18-2.33 (m, 1 H), 1.72-2.02 (m, 4 H), 1.51-1.69 (m, 2 H), 1.50 (s, 3 H), 1.00 (s, 3 H) LC-MS (ESI POS): 557.01 (MH+) $[\alpha]_D^{20} = +19.7$ (c 0.14 MeOH) |

Example 20

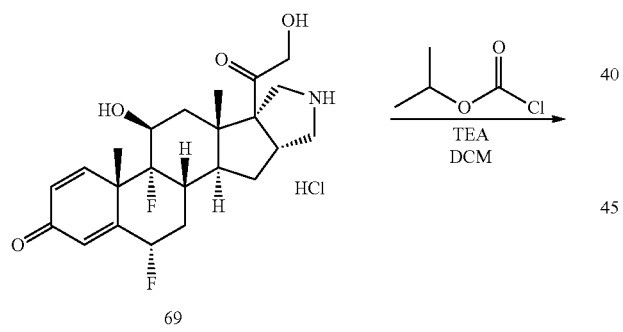

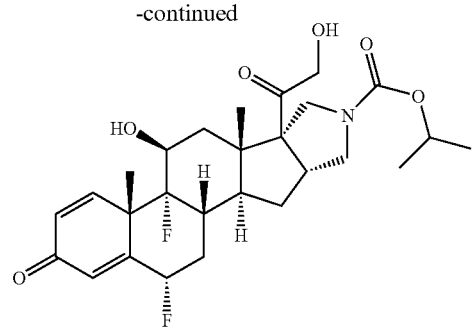

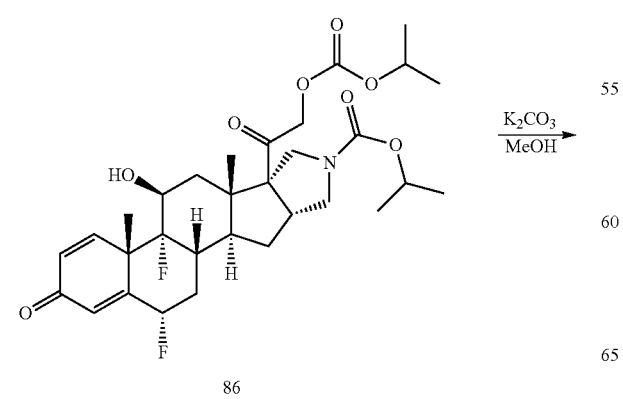

Preparation of (4aS,4bR,5S,6aS,6bS,9aR,10aS,10bS,12S)-4b,12-Difluoro-5-hydroxy-6b-(2-isopropoxy-carbonyloxy-acetyl)-4a,6a-dimethyl-2-oxo-2,4b,5,6,6a,6b,7,9,9a,10,10a,10b,11,12-tetradecahydro-4aH-8-aza-pentaleno[2,1-a]phenanthrene-8-carboxylic acid isopropyl ester (compound 86)

A mixture of Compound 69 (191 mg, 0.453 mmol), TEA (0.063 ml, 0.453 mmol) and isopropyl chloroformate (0.453 ml, 0.453 mmol) in DCM (10 ml) is stirred at RT for 20 minutes. The mixture is evaporated and the crude title compound obtained (269 mg, 0.453 mmol) is used in the next step without any further purification.

LC-MS (ESI POS): 594.07 (MH+)

Preparation of (4aS,4bR,5S,6aS,6bS,9aR,10aS,10bS, 12S)-4b,12-Difluoro-5-hydroxy-6b-(2-hydroxy-acetyl)-4a,6a-dimethyl-2-oxo-2,4b,5,6,6a,6b,7,9,9a, 10,10a,10b,11,12-tetradecahydro-4aH-8-aza-pentaleno[2,1-a]phenanthrene-8-carboxylic acid isopropyl ester (compound 87)

A solution of Compound 86 (269 mg, 0.453 mmol) in MeOH (10 ml) is degassed bubbling nitrogen at RT for 20 minutes and K$_2$CO$_3$ (15.65 mg, 0.113 mmol) is added. After 20 minutes 1N HCl is added to pH=3. The mixture is partitioned between AcOEt and brine. The organic phase is separated, washed with brine, dried over Na$_2$SO$_4$ and concentrated to give a oil that is purified by silica gel chromatography (DCM:MeOH 98:2) to give the title compound (24 mg, 0.047 mmol, 10.44% yield).

$^1$H NMR (300 MHz, DMSO-d$_6$) δ ppm 7.26 (dd, 1H), 6.29 (dd, 1H), 6.10 (s, 1H), 5.49-5.80 (m, 1H), 5.45 (dd, 1H), 4.97 (t, 1H), 4.70 (spt, 1H), 4.40 (dd, 1H), 4.15-4.22 (m, 1H), 4.10 (dd, 1H), 3.33-3.56 (m, 3H), 3.12-3.27 (m, 2H), 2.56-2.62 (m, 1H), 2.14-2.25 (m, 1H), 1.63-1.96 (m, 4H), 1.49 (s, 3H), 1.34-1.46 (m, 2H), 1.14 (d, 3H), 1.13 (d, 3H), 0.95 (s, 3H)

LC-MS (ESI POS): 508.09 (MH+)

[α]$_D^{20}$=+29.64 (c 0.22, MeOH)

Example 21

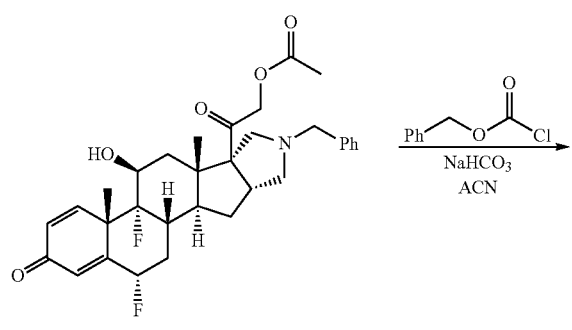

11

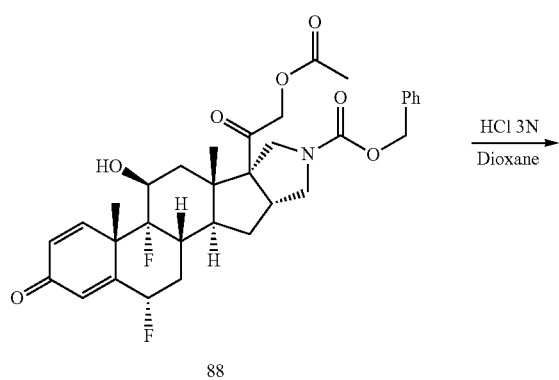

88

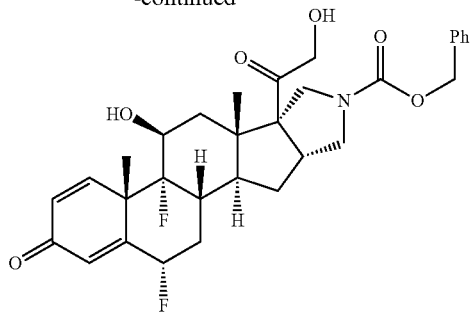

89

Preparation of (4aS,4bR,5S,6aS,6bS,9aR,10aS,10bS, 12S)-6b-(2-Acetoxy-acetyl)-4b,12-difluoro-5-hydroxy-4a,6a-dimethyl-2-oxo-2,4b,5,6,6a,6b,7,9,9a, 10,10a,10b,11,12-tetradecahydro-4aH-8-aza-pentaleno[2,1-a]phenanthrene-8-carboxylic acid benzyl ester (compound 88)

A mixture of compound 11 (86 mg, 0.155 mmol), benzyl chloroformate (44 μl, 0.311 mmol) and NaHCO$_3$ (26.1 mg, 0.311 mmol) in Acetonitrile (10 ml) is stirred at 50° C. for 2 hours. The mixture is partitioned between AcOEt and water, then the organic phase is separated and the aqueous phase is extracted with AcOEt. The combined organic layers are washed with brine, dried over Na$_2$SO$_4$ and filtered. The solvent is evaporated to give a colorless oil that is purified by silica gel chromatography (DCM:AcOEt 80:20) to give the title compound (72 mg, 0.120 mmol, 78% yield).

LC-MS (ESI POS): 598.4 (MH+)

Preparation of (4aS,4bR,5S,6aS,6bS,9aR,10aS,10bS, 12S)-4b,12-Difluoro-5-hydroxy-6b-(2-hydroxy-acetyl)-4a,6a-dimethyl-2-oxo-2,4b,5,6,6a,6b,7,9,9a, 10,10a,10b,11,12-tetradecahydro-4aH-8-aza-pentaleno[2,1-a]phenanthrene-8-carboxylic acid benzyl ester (compound 89)

Compound 88 is hydrolyzed as described in Example 4 for the preparation of compound 18 obtaining the title compound in 42% yield.

$^1$H NMR (300 MHz, DMSO-d$_6$) δ ppm 7.17-7.36 (m, 6H), 6.29 (dd, 1H), 6.12 (s, 1H), 5.50-5.79 (m, 1H), 5.45 (d, 1H), 5.03 (br. s., 2H), 4.96 (t, 1H), 4.41 (dd, 1H), 4.17-4.24 (m, 1H), 4.11 (dd, 1H), 3.45-3.59 (m, 1H), 3.38-3.45 (m, 3H), 2.14-2.30 (m, 1H), 1.67-1.95 (m, 5H), 1.48 (s, 3H), 1.36-1.46 (m, 3H), 0.96 (s, 3H)

LC-MS (ESI POS): 556.38 (MH+)

[α]$_D^{20}$=+17.15 (c 0.33, MeOH)

Example 22

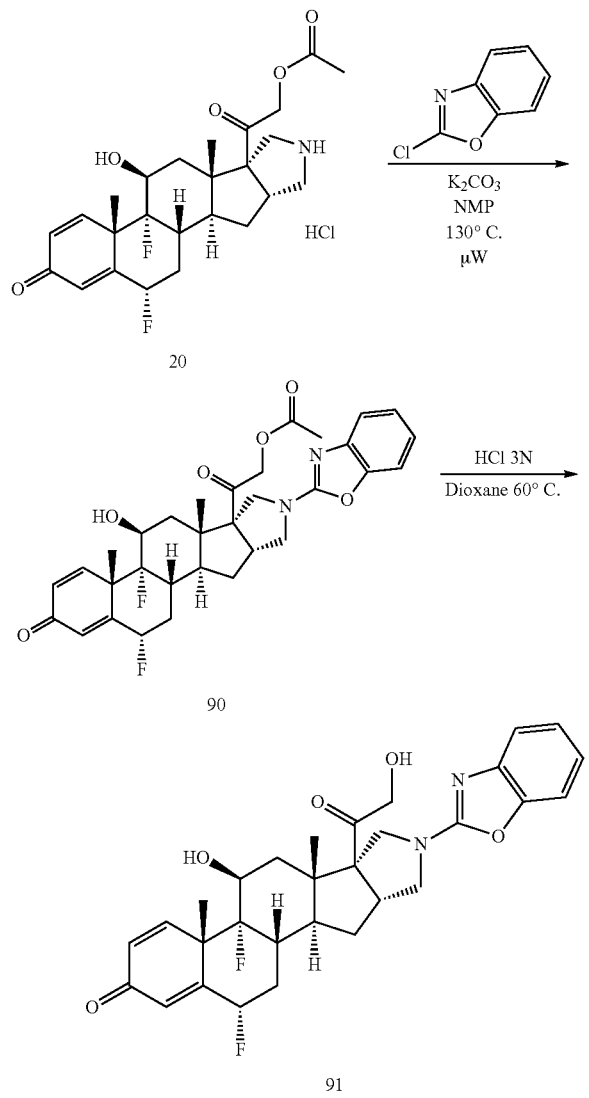

Preparation of Acetic acid 2-((4aS,4bR,5S,6aS,6bS, 9aR,10aS,10bS,12S)-8-benzooxazol-2-yl-4b,12-difluoro-5-hydroxy-4a,6a-dimethyl-2-oxo-2,4b,5,6, 6a,7,8,9,9a,10,10a,10b,11,12-tetradecahydro-4aH-8-aza-pentaleno[2,1-a]phenanthren-6b-yl)-2-oxo-ethyl ester (compound 90)

Compound 20 (150 mg, 0.300 mmol), 2-chlorobenzo[d] oxazole (92 mg, 0.600 mmol) and $K_2CO_3$ (83 mg, 0.600 mmol) are placed in microwave vessel with DMF (2 ml) and the reaction mixture is heated at 130° C. for 1 hour by microwaves. The mixture is partitioned between AcOEt and brine. The organic phase is separated, dried over $Na_2SO_4$ and evaporated to give a residue that is purified by silica gel cartridge (Petroleum Ether/AcOEt 8:2 to AcOEt) giving a solid that, after trituration with petroleum ether, gave the title compound (160 mg, 0.276 mmol, 92% yield).

LC-MS (ESI POS): 581.1 (MH+)

Preparation of (4aS,4bR,5S,6aS,6bS,9aR,10aS,10bS, 12S)-8-Benzooxazol-2-yl-4b,12-difluoro-5-hydroxy-6b-(2-hydroxy-acetyl)-4a,6a-dimethyl-4b,5,6,6a,6b, 7,8,9,9a,10,10a,10b,11,12-tetradecahydro-4aH-8-aza-pentaleno[2,1-a]phenanthren-2-one (compound 91)

Compound 90 is hydrolyzed as described in Example 4 for the preparation of compound 18 obtaining the title compound in 59% yield.

$^1$H NMR (300 MHz, DMSO-$d_6$) δ ppm 7.37 (d, 1H), 7.23-7.30 (m, 2H), 7.13 (td, 1H), 7.00 (td, 1H), 6.29 (dd, 1H), 6.08 (s, 1H), 5.51-5.78 (m, 1H), 5.39-5.59 (m, 1H), 4.99 (t, 1H), 4.48 (dd, 1H), 4.19-4.24 (m, 1H), 4.17 (dd, 1H), 3.75-3.85 (m, 1H), 3.70 (d, 1H), 3.59 (d, 1H), 3.37-3.53 (m, 2H), 2.55-2.62 (m, 1H), 2.15-2.26 (m, 1H), 1.73-2.06 (m, 4H), 1.52-1.62 (m, 2H), 1.50 (s, 3H), 1.01 (s, 3H)

LC-MS (ESI POS): 539.38 (MH+)

$[α]_{437}^{20}$=+19.87 (c=0.3, MeOH)

Compound listed in Table 15 is prepared through a two steps procedure as previously described for compound 91.

TABLE 15

| Compound | Structure | Yield | Analytical |
|---|---|---|---|
| 92 | (structure shown) | 75% | $^1$H NMR (300 MHz, DMSO-$d_6$) δ ppm 8.32 (d, 2H), 7.26 (dd, 1H), 6.62 (t, 1H), 6.29 (dd, 1H), 6.09 (s, 1H), 5.50-5.80 (m, 1H), 5.47 (dd, 1H), 4.94 (t, 1H), 4.44 (dd, 1H), 4.19-4.25 (m, 1H), 4.13 (dd, 1H), 3.60-3.75 (m, 2H), 3.45-3.58 (m, 2H), 3.34-3.42 (m, 1H), 2.58-2.67 (m, 1H), 2.16-2.33 (m, 1H), 1.74-2.03 (m, 4H), 1.50 (s, 3H), 1.40-1.49 (m, 2H), 1.01 (s, 3H) LC-MS (ESI POS): 500.38 (MH+) $[α]_{436}^{20}$ = −4.33 (c = 0.3, MeOH, 436 nm) |

Example 23

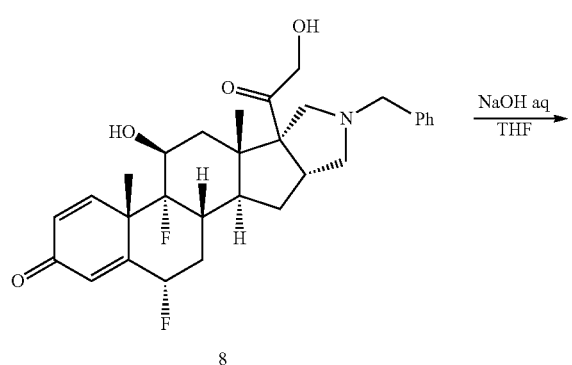

8

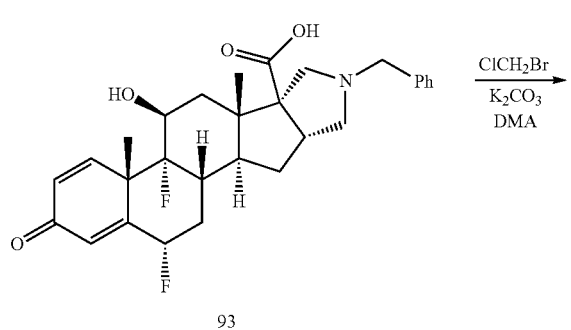

93

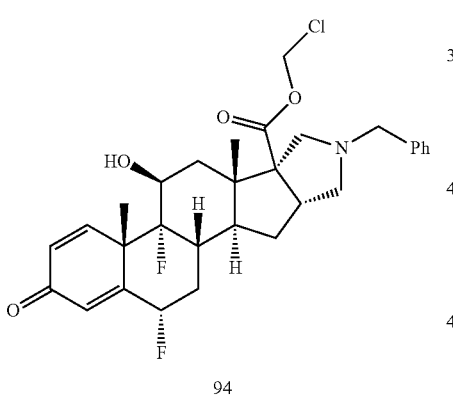

94

Preparation of (4aS,4bR,5S,6aS,6bS,9aR,10aS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid (compound 93)

A mixture of compound 8 (460 mg, 0.899 mmol) and NaOH 6N (1350 μl, 11.10 mmol) in THF (20 ml) and water (10 ml) is stirred at RT for 3 days. Water is added and the organic solvent is evaporated. The basic aqueous solution (pH 12) is washed with AcOEt. The aqueous phase is then treated with HCl 6N until pH 6 when a solid precipitated. The solid is recovered by filtration and the aqueous phase is extracted with AcOEt, washed with brine, dried over $Na_2SO_4$ and then evaporated. The two fractions of obtained solid are combined and triturated with AcOEt (containing 2% MeOH) to give the title compound (150 mg, 0.301 mmol, 33.5% yield).

$^1$H NMR (300 MHz, DMSO-d6) δ ppm 6.81-7.43 (m, 6H), 6.29 (dd, 1H), 6.13 (s, 1H), 5.47-5.82 (m, 1H), 5.24-5.47 (m, 1H), 3.96-4.25 (m, 1H), 3.47 (d, 1H), 3.42 (d, 1H), 2.94-3.10 (m, 1H), 2.81-2.92 (m, 1H), 2.64 (d, 1H), 2.36 (d, 1H), 2.21-2.32 (m, 2H), 1.92-2.11 (m, 2H), 1.77-1.85 (m, 1H), 1.54-1.69 (m, 3H), 1.50 (s, 3H), 1.31 (dd, 1H), 0.99 (s, 3H)

LC-MS (ESI POS): 498.1 (MH+)

$[α]_D^{20}$=+46.87 (c=0.3, DMSO)

Preparation of (4aS,4bR,5S,6aS,6bS,9aR,10aS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid chloromethyl ester (compound 94)

A mixture of Compound 93 (110 mg, 0.221 mmol), Potassium carbonate (61.1 mg, 0.442 mmol) and Bromochloromethane (71.9 μA 1.105 mmol) in DMA (3 ml) is stirred at RT under nitrogen overnight. The mixture is then diluted with AcOEt and washed with brine. The organic layer is then dried over $Na_2SO_4$ and evaporated to give the crude title compound.

LC-MS (ESI POS): 546.3 (MH+)

Intermediate reported in Table 16 is prepared as described for compound 93.

TABLE 16

| Compound | Structure | Yield | Analytical |
|---|---|---|---|
| 95 | 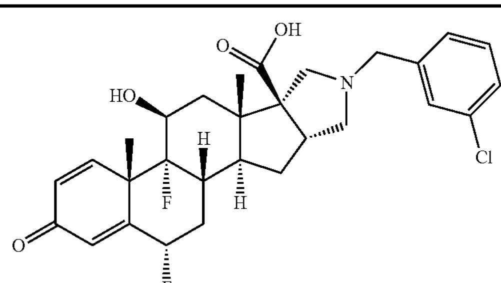 | 92% | $^1$H NMR (300 MHz, DMSO-d$_6$) ☐ ppm 12.14 (s, 1 H), 7.11-7.49 (m, 5 H), 6.29 (dd, 1 H), 6.12 (s, 1 H), 5.49-5.83 (m, 1 H), 5.40 (dd, 1 H), 4.00-4.29 (m, 1 H), 3.50 (d, 1 H), 3.43 (d, 1 H), 2.97-3.12 (m, 1 H), 2.88 (t, 1 H), 2.66 (d, 1 H), 2.56-2.61 (m, 1 H), 2.36 (d, 1 H), 2.22-2.33 (m, 1 H), 1.91-2.12 (m, 2 H), 1.76-1.87 (m, 1 H), 1.53-1.72 (m, 3 H), 1.49 (s, 3 H), 1.31 (dd, 1 H), 0.99 (s, 3 H) LC-MS (ESI POS): 532.2 MH+ |

Compounds listed in Table 17 are prepared as previously described for Compound 94, starting from intermediate 93 or intermediate 95 and using the suitable alkylhalide.

TABLE 17

| Compound | Structure | Yield | Analytical |
|---|---|---|---|
| 96 | 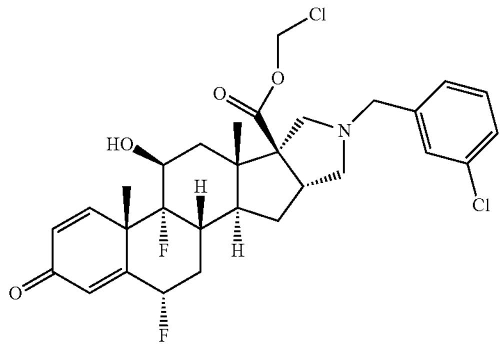 | 16% | $^1$H NMR (300 MHz, DMSO-d6) ppm 7.21-7.37 (m, 4 H), 7.18 (ddd, 1 H), 6.29 (dd, 1 H), 6.12 (s, 1 H), 5.91 (d, 1 H), 5.87 (d, 1 H), 5.54-5.77 (m, 1 H), 5.51 (d, 1 H), 4.04-4.21 (m, 1 H), 3.56 (d, 1 H), 3.40 (d, 1 H), 3.05-3.20 (m, 1 H), 2.96 (t, 1 H), 2.67 (d, 1 H), 2.53-2.62 (m, 1 H), 2.38 (d, 1 H), 2.22-2.34 (m, 1 H), 1.92-2.16 (m, 2 H), 1.79 (d, 1 H), 1.52-1.71 (m, 3 H), 1.49 (s, 3 H), 1.37 (dd, 1 H), 0.97 (s, 3 H) LC-MS (ESI POS): 580.19 MH+ $[\alpha]_D^{25}$ +83.04 (MeOH, c 0.27) |
| 97 | 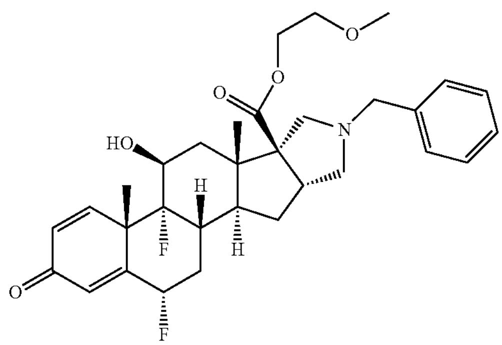 | 40% | $^1$H NMR (300 MHz, DMSO-d6) ppm 7.10-7.37 (m, 6 H), 6.29 (dd, 1 H), 6.12 (s, 1 H), 5.50-5.79 (m, 1 H), 5.44 (dd, 1 H), 4.13-4.19 (m, 2 H), 4.08-4.13 (m, 1 H), 3.48-3.57 (m, 2 H), 3.38-3.48 (m, 2 H), 3.24 (s, 3 H), 3.02-3.18 (m, 1 H), 2.87 (t, 1 H), 2.64 (d, 1 H), 2.54-2.61 (m, 1 H), 2.38 (d, 1 H), 2.22-2.33 (m, 1 H), 2.07 (dd, 1 H), 1.91-2.04 (m, 1 H), 1.80 (d, 1 H), 1.51-1.71 (m, 3 H), 1.49 (s, 3 H), 1.34 (dd, 1 H), 0.93 (s, 3 H) LC-MS (ESI POS): 556.18 MH+ $[\alpha]_D^{25}$ +90.4 (c 0.4, MeOH) |
| 98 | 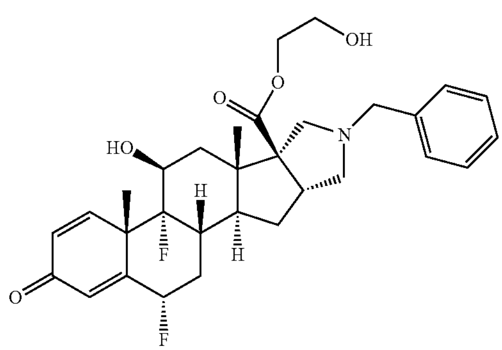 | 33% | $^1$H NMR (300 MHz, DMSO-d6) ppm 7.00-7.38 (m, 6 H), 6.29 (dd, 1 H), 6.13 (s, 1 H), 5.50-5.80 (m, 1 H), 5.40 (dd, 1 H), 4.71 (t, 1 H), 4.09-4.21 (m, 1 H), 4.04 (t, 2 H), 3.57 (qd, 2 H), 3.45 (s, 2 H), 3.01-3.19 (m, 1 H), 2.85 (t, 1 H), 2.64 (d, 1 H), 2.55-2.61 (m, 1 H), 2.41 (d, 1 H), 2.21-2.35 (m, 1 H), 2.05-2.17 (m, 1 H), 1.94-2.05 (m, 1 H), 1.83 (d, 1 H), 1.53-1.75 (m, 3 H), 1.49 (s, 3 H), 1.33 (dd, 1 H), 0.94 (s, 3 H) LC-MS (ESI POS): 542.25 MH+ $[\alpha]_D^{25}$ +79.75 (MeOH, c 0.24) |

Example 24

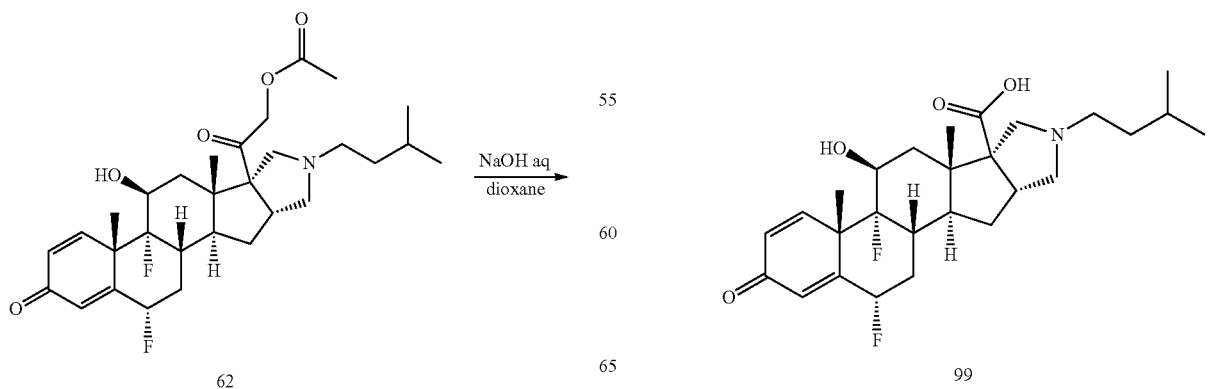

Preparation of (4aS,4bR,5S,6aS,6bS,9aR,10aS,10bS, 12S)-4b,12-Difluoro-5-hydroxy-4a,6a-dimethyl-8-(3-methyl-butyl)-2-oxo-2,4b,5,6,6a,7,8,9,9a,10,10a, 10b,11,12-tetradecahydro-4aH-8-aza-pentaleno[2,1-a]phenanthrene-6b-carboxylic acid (Compound 99)

Compound 62 (597 mg, 1.119 mmol) is dissolved in dioxane (20 ml), NaOH (2.237 ml, 4.47 mmol) is added and the mixture is stirred at open air for 2 days. The reaction mixture is diluted with water and the pH adjusted to 5-6 by adding HCl 1N solution. Dioxane is evaporated and a solid precipitates upon concentration. The solid is recovered by filtration and dried in vacuo to yield the title compound (146 mg, 0.306 mmol, 27.3% yield).

LC-MS (ESI POS): 478.2 MH+

Intermediates listed in Table 18 are prepared as described in Example 24 for compound 99.

TABLE 18

| Compound | Structure | Yield | Analytical |
|---|---|---|---|
| 100 | 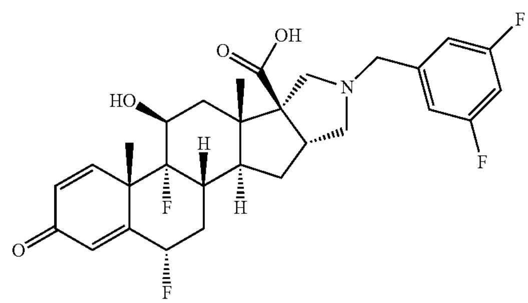 | 92% | LC-MS (ESI POS): 534.0 MH+ |
| 101 | 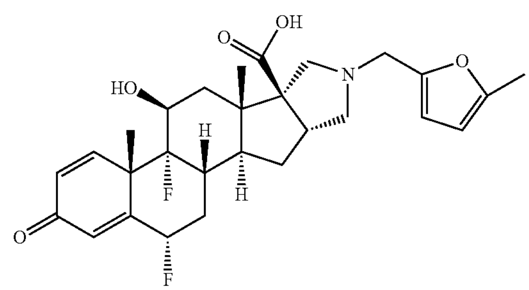 | 68% | LC-MS (ESI POS): 502.0 MH+ |
| 102 | 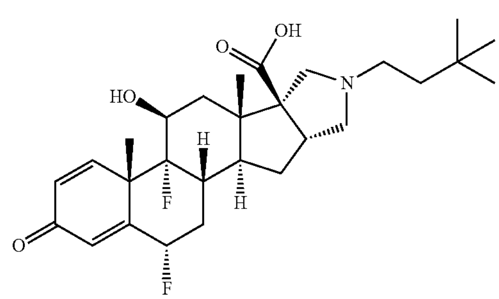 | 85% | LC-MS (ESI POS): 405.9 MH+ |
| 103 | 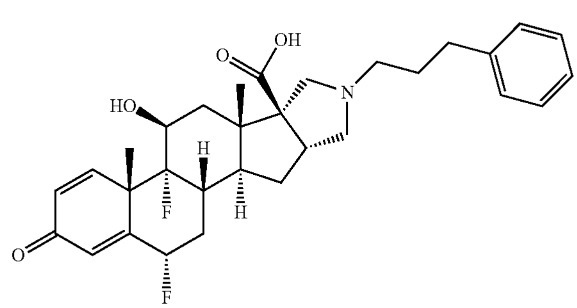 | 92%* | LC-MS (ESI POS): 526.0 MH+ |

TABLE 18-continued

| Compound | Structure | Yield | Analytical |
|---|---|---|---|
| 93 | 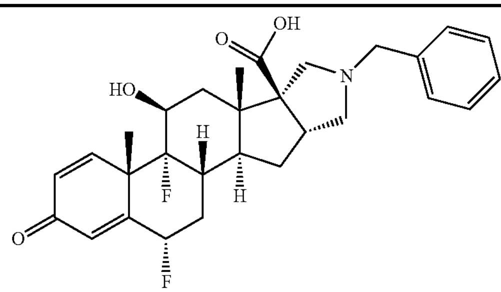 | 84% | LC-MS (ESI POS): 497.2 MH+ |
| 95 | 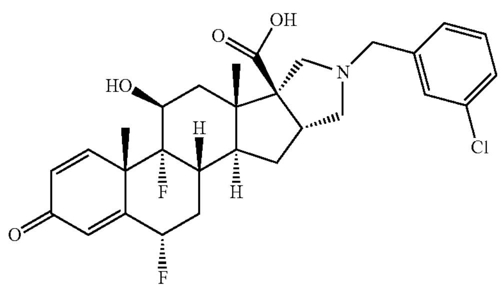 | 96% | LC-MS (ESI POS): 532.3 MH+ |

*THF is used instead of Dioxane

Example 25

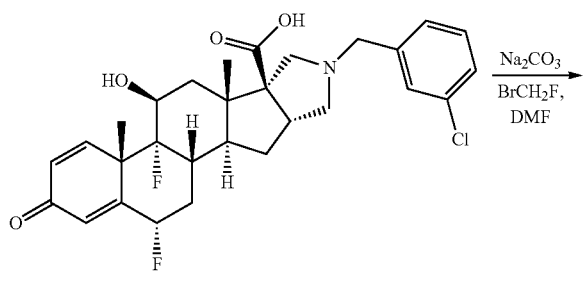

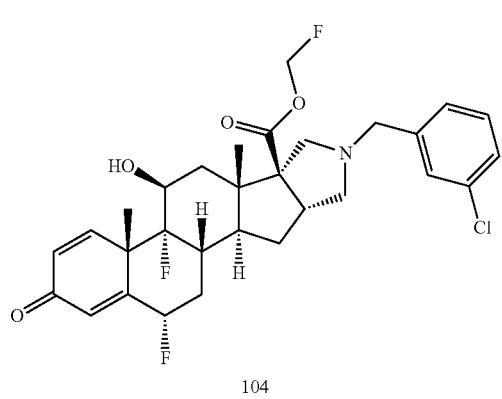

Preparation of (4aS,4bR,5S,6aS,6bS,9aR,10aS,10bS, 12S)-8-(3-Chloro-benzyl)-4b,12-difluoro-5-hydroxy-4a,6a-dimethyl-2-oxo-2,4b,5,6,6a,7,8,9,9a,10,10a, 10b,11,12-tetradecahydro-4aH-8-aza-pentaleno[2,1-a]phenanthrene-6b-carboxylic acid fluoromethyl ester (compound 104)

$Na_2CO_3$ (189 mg, 1.786 mmol) is added to a stirred solution of Compound 95 (190 mg, 0.357 mmol) in anhydrous N,N-dimethylformamide (3 ml) and after stirring at RT for 15 minutes the mixture is cooled to −20° C. under nitrogen. Bromofluoromethane (0.446 ml, 0.893 mmol) is added and the reaction stirred at −20° C. for 1 hour, then the reaction mixture is allowed to warm to RT overnight. The reaction is partitioned between water and ethyl acetate. The organic layer is dried over anhydrous $Na_2SO_4$, filtered and evaporated in vacuo. The crude product is purified on a silica gel cartridge (Hexane:AcOEt from 7/3 to 1/1), then it is triturated in $H_2O$, recovered by filtration and dried, to give the title compound (94 mg, 0.167 mmol, 46.7% yield).

$^1$H NMR (300 MHz, DMSO-d6) ppm 7.21-7.36 (m, 4H), 7.18 (dt, 1H), 6.30 (dd, 1H), 6.12 (s, 1H), 5.79 (dd, 1H), 5.79 (dd, 1H), 5.52-5.74 (m, 1H), 5.50 (dd, 1H), 4.08-4.22 (m, 1H), 3.53 (d, 1H), 3.46 (d, 1H), 3.07-3.20 (m, 1H), 2.93 (t, 1H), 2.70 (d, 1H), 2.54-2.62 (m, 1H), 2.43 (d, 1H), 2.21-2.35 (m, 1H), 2.10 (dd, 1H), 1.97-2.06 (m, 1H), 1.82 (d, 1H), 1.52-1.75 (m, 3H), 1.49 (s, 3H), 1.37 (dd, 1H), 0.97 (s, 3H)

LC-MS (ESI POS): 564.29 MH+

$[\alpha]_D^{25}$+78.6 (c 0.4, MeOH)

Compounds listed in Table 19 are prepared according to the previously described procedure for the preparation of compound 104, starting from intermediate 99 and from the intermediates listed in Table 18.

TABLE 19

| Compound | Structure | Yield | Analytical |
|---|---|---|---|
| 105 | 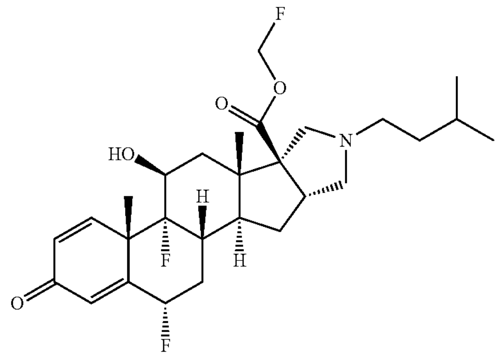 | 52% | ¹H NMR (300 MHz, DMSO-d6) ppm 7.26 (dd, 1 H), 6.29 (dd, 1 H), 6.11 (s, 1 H), 5.78 (dd, 1 H), 5.79 (dd, 1 H), 5.51-5.72 (m, 1 H), 5.49 (dd, 1 H), 4.06-4.29 (m, 1 H), 3.01-3.15 (m, 1 H), 2.86 (dd, 1 H), 2.66 (d, 1 H), 2.54-2.61 (m, 1 H), 2.42 (d, 1 H), 2.14-2.34 (m, 3 H), 2.02 (dd, 1 H), 1.89-1.99 (m, 1 H), 1.85 (d, 1 H), 1.52-1.79 (m, 4 H), 1.49 (s, 3 H), 1.33 (dd, 1 H), 1.24 (q, 2 H), 0.97 (s, 3 H), 0.82 (d, 6 H)<br>LC-MS (ESI POS): 510.35 MH+<br>$[\alpha]_D^{25}$ +63.2 (c 0.5, MeOH) |
| 106 | 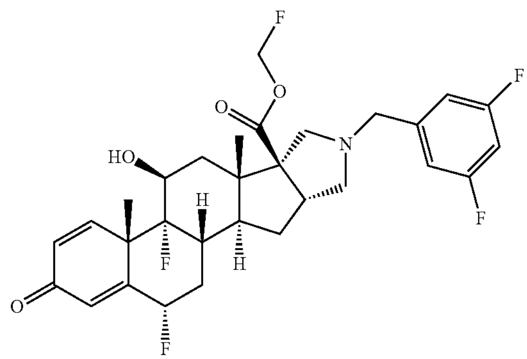 | 81% | ¹H NMR (300 MHz, DMSO-d6) ppm 7.26 (d, 1 H), 7.04 (tt, 1 H), 6.77-6.96 (m, 2 H), 6.30 (dd, 1 H), 6.13 (s, 1 H), 5.79 (d, 2 H), 5.53-5.80 (m, 1 H), 5.50 (d, 1 H), 4.15 (d, 1 H), 3.56 (d, 1 H), 3.47 (d, 1 H), 3.03-3.23 (m, 1 H), 2.95 (t, 1 H), 2.71 (d, 1 H), 2.55-2.64 (m, 1 H), 2.44 (d, 1 H), 2.20-2.36 (m, 1 H), 2.12 (dd, 1 H), 1.92-2.07 (m, 1 H), 1.76-1.89 (m, 1 H), 1.59-1.76 (m, 2 H), 1.50 (s, 3 H), 1.55 (m, 1 H), 1.38 (dd, 1 H), 0.97 (s, 3 H)<br>LC-MS (ESI POS): 566.28 MH+<br>$[\alpha]_D^{25}$ +69.3 (c 0.5, MeOH) |
| 107 | 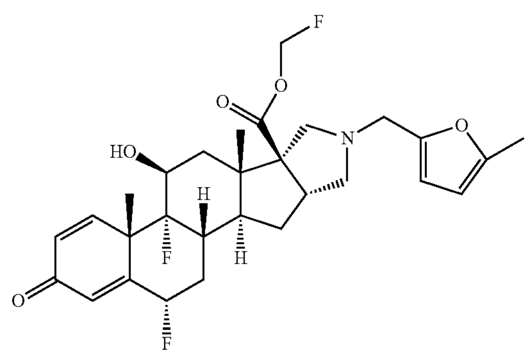 | 96% | ¹H NMR (300 MHz, DMSO-d6) ppm 7.26 (dd, 1 H), 6.30 (dd, 1 H), 6.12 (s, 1 H), 6.03 (d, 1 H), 5.94 (dd, 1 H), 5.78 (dd, 1 H), 5.79 (dd, 1 H), 5.51-5.76 (m, 1 H), 5.50 (dd, 1 H), 4.09-4.22 (m, 1 H), 3.45 (d, 1 H), 3.36 (d, 1 H), 3.04-3.16 (m, 1 H), 2.96 (t, 1 H), 2.80 (d, 1 H), 2.55-2.67 (m, 1 H), 2.42 (d, 1 H), 2.21-2.32 (m, 1 H), 2.18 (s, 3 H), 2.02 (dd, 1 H), 1.89-1.98 (m, 1 H), 1.78-1.88 (m, 1 H), 1.51-1.74 (m, 3 H), 1.49 (s, 3 H), 1.34 (dd, 1 H), 0.96 (s, 3 H)<br>LC-MS (ESI POS): 534.28 MH+<br>$[\alpha]_D^{25}$ +60.93 (c 0.108, CHCl3) |
| 108 | 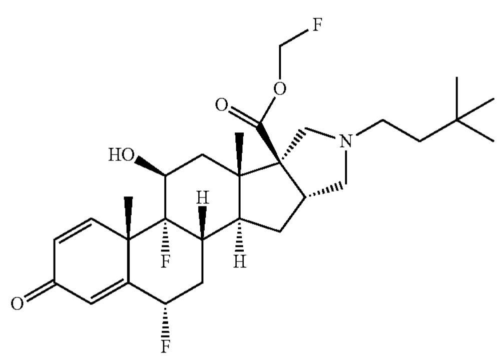 | 34% | ¹H NMR (300 MHz, DMSO-d6) ppm 7.25 (dd, 1 H), 6.29 (dd, 1 H), 6.11 (s, 1 H), 5.64-5.95 (m, 2 H), 5.51-5.72 (m, 1 H), 5.49 (dd, 1 H), 4.03-4.34 (m, 1 H), 3.00-3.15 (m, 1 H), 2.88 (t, 1 H), 2.68 (d, 1 H), 2.53-2.58 (m, 1 H), 2.41 (d, 1 H), 2.11-2.32 (m, 3 H), 1.89-2.06 (m, 2 H), 1.79-1.89 (m, 1 H), 1.51-1.79 (m, 2 H), 1.49 (s, 3 H), 1.33 (dd, 1 H), 1.20-1.29 (m, 3 H), 0.96 (s, 3 H), 0.84 (s, 9 H)<br>LC-MS (ESI POS): 524.32 MH+<br>$[\alpha]_D^{25}$ +47.67 (c 0.3, MeOH) |

Example 26

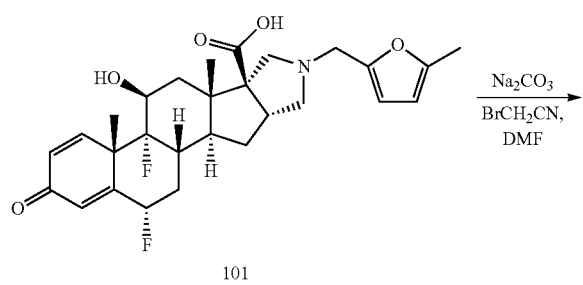

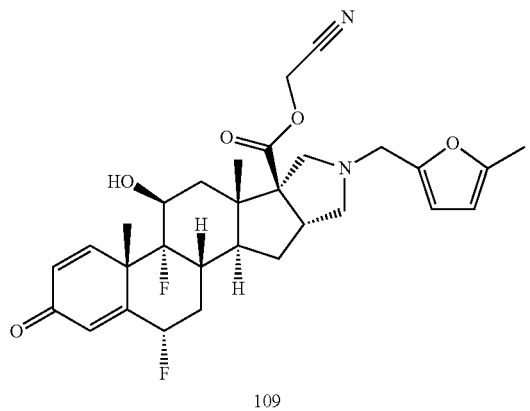

Preparation of (4aS,4bR,5S,6aS,6bS,9aR,10aS,10bS,12S)-4b,12-Difluoro-5-hydroxy-4a,6a-dimethyl-8-(5-methyl-furan-2-ylmethyl)-2-oxo-2,4b,5,6,6a,7,8,9,9a,10,10a,10b,11,12-tetradecahydro-4aH-8-aza-pentaleno[2,1-a]phenanthrene-6b-carboxylic acid cyanomethyl ester (compound 109)

To a solution of compound 101 (110 mg, 0.219 mmol) in dry DMF (4 ml), Na₂CO₃ (46.5 mg, 0.439 mmol) is added and the suspension stirred at RT for 20 minutes, after which time bromoacetonitrile (0.015 ml, 0.219 mmol) is added. HPLC-MS after 2 hours and 30 minutes indicates that the reaction is almost complete (about 6% of starting material is present). Another addition of Na₂CO₃ (4.65 mg, 0.044 mmol) is done, followed by addition of Bromoacetonitrile (1.528 µl, 0.022 mmol). After stirring 1 hour, the conversion is complete. The reaction mixture is diluted with AcOEt and washed with brine. The aqueous layer is extracted with AcOEt twice, then washed with brine again. The organic layer is dried over Na₂SO₄ and evaporated. Crude material is purified via chromatographic column on silica gel (DCM, DCM/AcOEt 5/1, DCM/AcOEt 2/1), affording the title compound (82 mg, 0.152 mmol, 69%).

$^1$H NMR (300 MHz, DMSO-d6) ppm 7.26 (dd, 1H), 6.30 (dd, 1H), 6.11 (s, 1H), 6.03 (d, 1H), 5.94 (dq, 1H), 5.54-5.77 (m, 1H), 5.53 (dd, 1H), 5.01 (s, 2H), 4.06-4.25 (m, 1H), 3.44 (d, 1H), 3.37 (d, 1H), 3.03-3.17 (m, 1H), 2.96 (t, 1H), 2.77 (d, 1H), 2.55-2.67 (m, 1H), 2.39 (d, 1H), 2.22-2.33 (m, 1H), 2.18 (d, 3H), 2.01 (dd, 1H), 1.86-1.98 (m, 1H), 1.79 (d, 1H), 1.51-1.72 (m, 3H), 1.49 (s, 3H), 1.34 (dd, 1H), 0.95 (s, 3H)

LC-MS (ESI POS): 541.27 MH+

$[\alpha]_D^{25}$ +94.39 (c 0.103, CHCl3)

Compound reported in Table 20 is prepared as described for compound 109 in Example 26.

TABLE 20

| Compound | Structure | Yield | Analytical |
|---|---|---|---|
| 110 | 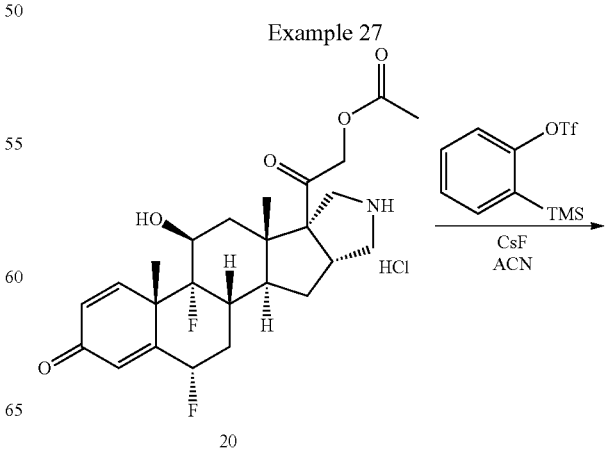 | 22% | $^1$H NMR (300 MHz, DMSO-d6) d ppm 7.26 (dd, 1 H), 6.29 (dd, 1 H), 6.11 (s, 1 H), 5.54-5.80 (m, 1 H), 5.52 (dd, 1 H), 5.00 (s, 2 H), 4.07-4.26 (m, 1 H), 2.97-3.14 (m, 1 H), 2.88 (t, 1 H), 2.65 (d, 1 H), 2.54-2.60 (m, 1 H), 2.39 (d, 1 H), 2.14-2.32 (m, 2 H), 2.00 (dd, 1 H), 1.87-1.97 (m, 1 H), 1.51-1.86 (m, 4 H), 1.49 (s, 3 H), 1.15-1.40 (m, 4 H), 0.96 (s, 3 H), 0.84 (s, 9 H) LC-MS (ESI POS): 531.32 MH+ $[\alpha]_D^{25}$ +59.83 (c 0.23, CHCl3) |

Example 27

2H), 3.01-3.09 (m, 1H), 2.35-2.46 (m, 1H), 2.15-2.26 (m, 2H), 1.71-2.00 (m, 4H), 1.50 (s, 3H), 1.41-1.48 (m, 2H), 1.00 (s, 3H)

LC-MS (ESI POS): 498.2 (MH+)

Example 28

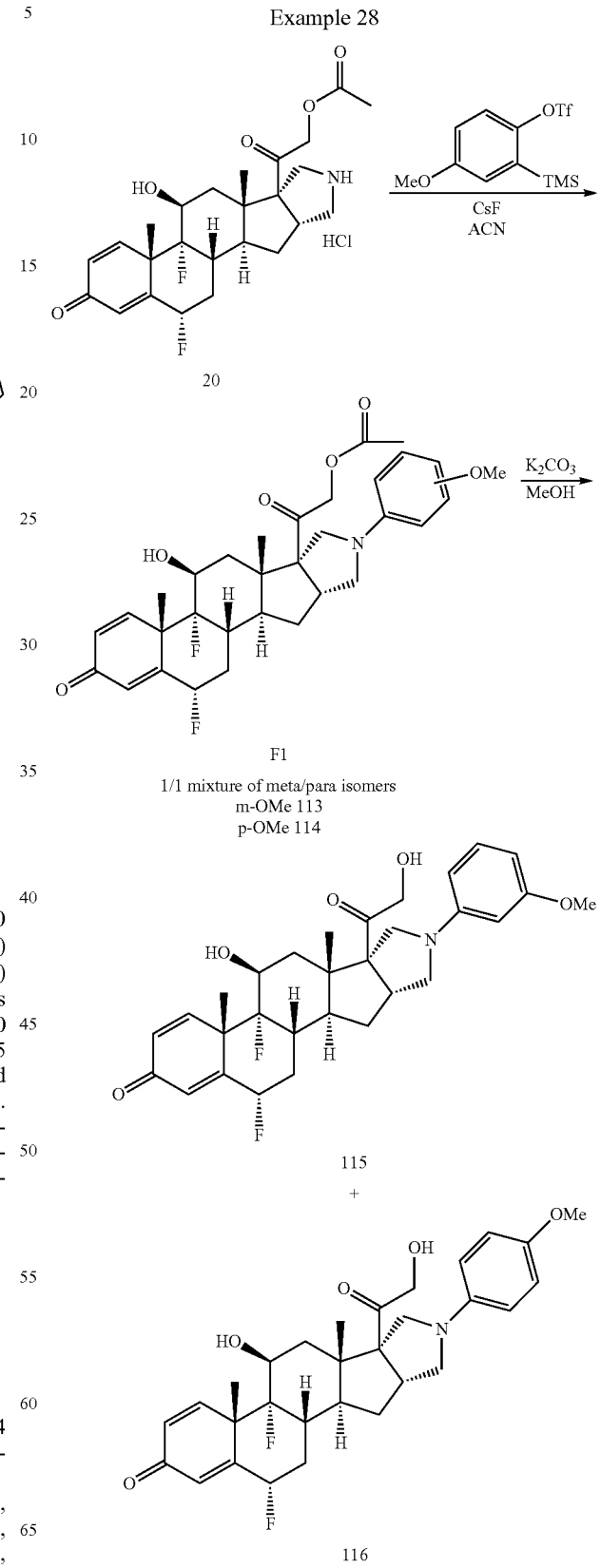

F1
1/1 mixture of meta/para isomers
m-OMe 113
p-OMe 114

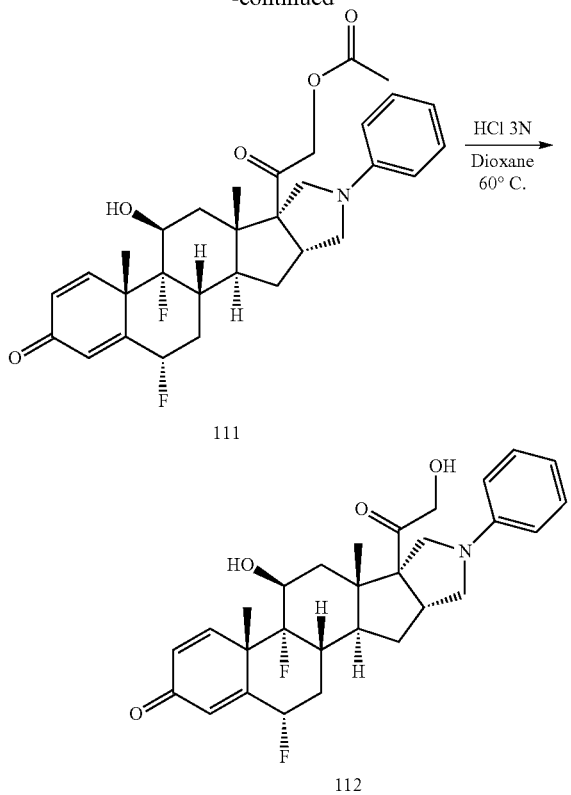

Preparation of Acetic acid 2-((4aS,4bR,5S,6aS,6bS, 9aR,10aS,10bS,12S)-4b,12-difluoro-5-hydroxy-4a, 6a-dimethyl-2-oxo-8-phenyl-2,4b,5,6,6a,7,8,9,9a,10, 10a,10b,11,12-tetradecahydro-4aH-8-aza-pentaleno [2,1-a]phenanthren-6b-yl)-2-oxo-ethyl ester (compound 111)

In a nitrogen atmosphere compound 20 (150 mg, 0.300 mmol) is suspended in Acetonitrile (4 ml). 2-(trimethylsilyl) phenyl trifluoromethanesulfonate (0.146 ml, 0.600 mmol) and CsF (182 mg, 1.200 mmol) are added and the mixture is stirred for 45 minutes at RT. Additional CsF (137 mg, 0.900 mmol) (not dried) is added and the mixture is stirred for 5 hours then it is poured in water. Acetonitrile is evaporated and the reaction mixture is partitioned between water and AcOEt. The organic layer is separated dried over $Na_2SO_4$ and concentrated. The crude is purified by silica gel flash chromatography (eluent DCM/MeOH 98/2) affording the title compound (49 mg, 0.091 mmol, 30.3% yield).

LC-MS (ESI POS): 540.2 (MH+)

Preparation of (4aS,4bR,5S,6aS,6bS,9aR,10aS,10bS, 12S)-4b,12-Difluoro-5-hydroxy-6b-(2-hydroxyacetyl)-4a,6a-dimethyl-8-phenyl-4b,5,6,6a,6b,7,8,9, 9a,10,10a,10b,11,12-tetradecahydro-4aH-8-azapentaleno[2,1-a]phenanthren-2-one (compound 112)

Compound 111 is hydrolyzed as described in Example 4 for the preparation of compound 18 obtaining the title compound, after preparative HPLC, in 5% yield.

$^1$H NMR (300 MHz, DMSO-$d_6$) δ ppm 7.27 (dd, 1H), 7.07-7.21 (m, 2H), 6.57-6.74 (m, 3H), 6.29 (dd, 1H), 6.08 (s, 1H), 5.50-5.84 (m, 1H), 5.39-5.47 (m, 1H), 4.45 (d, 1H), 4.17-4.25 (m, 1H), 4.13 (d, 1H), 3.44-3.54 (m, 2H), 3.26 (s, Preparation of Acetic acid 2-[(4aS,4bR,5S,6aS,6bS,
9aR,10aS,10bS,12S)-4b,12-difluoro-5-hydroxy-8-(3-
methoxy-phenyl)-4a,6a-dimethyl-2-oxo-2,4b,5,6,6a,
7,8,9,9a,10,10a,10b,11,12-tetradecahydro-4aH-8-
aza-pentaleno[2,1-a]phenanthren-6b-yl]-2-oxo-ethyl
ester (compound 113) and of Acetic acid 2-[(4aS,
4bR,5S,6aS,6bS,9aR,10aS,10bS,12S)-4b,12-dif-
luoro-5-hydroxy-8-(4-methoxy-phenyl)-4a,6a-dim-
ethyl-2-oxo-2,4b,5,6,6a,7,8,9,9a,10,10a,10b,11,12-
tetradecahydro-4aH-8-aza-pentaleno[2,1-a]
phenanthren-6b-yl]-2-oxo-ethyl ester (compound
114)

Compound 20 (320 mg, 0.640 mmol) is suspended in acetonitrile (12 ml), cesium fluoride (292 mg, 1.920 mmol) and 4-methoxy-2-(trimethylsilyl)phenyl trifluoromethanesulfonate (210 mg, 0.640 mmol) are added and the mixture is stirred at RT for 48 hours. LC-MS shows that the reaction is not complete and the formation of a 1/1 mixture of regioisomers is detected. Pyridine (0.052 ml, 0.640 mmol) is added and the reaction mixture is stirred for 24 hours. Although the reaction is not complete, mixture is partitioned between water and AcOEt, the organic layer is separated, dried and concentrated. The crude is purified by silica gel flash chromatography (eluent DCM-MeOH=99/1) to yield a mixture title compounds 113 and 114 (124 mg, 0.218 mmol, 34.0% yield).
LC-MS (ESI POS): 570.2 MH+

Preparation of (4aS,4bR,5S,6aS,6bS,9aR,10aS,10bS,
12S)-4b,12-Difluoro-5-hydroxy-6b-(2-hydroxy-
acetyl)-8-(3-methoxy-phenyl)-4a,6a-dimethyl-4b,5,
6,6a,6b,7,8,9,9a,10,10a,10b,11,12-tetradecahydro-
4aH-8-aza-pentaleno[2,1-a]phenanthren-2-one
(compound 115) and of (4aS,4bR,5S,6aS,6bS,9aR,
10aS,10bS,12S)-4b,12-Difluoro-5-hydroxy-6b-(2-
hydroxy-acetyl)-8-(4-methoxy-phenyl)-4a,6a-dim-
ethyl-4b,5,6,6a,6b,7,8,9,9a,10,10a,10b,11,12-
tetradecahydro-4aH-8-aza-pentaleno[2,1-a]
phenanthren-2-one (compound 116)

Mixture of compounds 113 and 114 is hydrolyzed as described in Example 10 for the preparation of compound 45. Compounds 115 and 116 are isolated by purification of the crude via preparative HPLC obtaining the title compounds 115 (58 mg, 30%) and 116 (65 mg, 33%).
Compound 115:

$^1$H NMR (300 MHz, DMSO-d6) ppm 7.26 (dd, 1H), 7.03 (t, 1H), 6.29 (dd, 1H), 6.20-6.28 (m, 2H), 6.16 (t, 1H), 6.08 (s, 1H), 5.48-5.80 (m, 1H), 5.44 (dd, 1H), 4.90 (br. s., 1H), 4.45 (d, 1H), 4.17-4.23 (m, 1H), 4.12 (d, 1H), 3.69 (s, 3H), 3.44-3.52 (m, 1H), 3.32-3.43 (m, 1H), 3.25 (s, 2H), 3.05 (dd, 1H), 2.55-2.69 (m, 1H), 2.34-2.46 (m, 0H), 2.17-2.32 (m, 1H), 1.73-2.02 (m, 4H), 1.50 (s, 3H), 1.41-1.49 (m, 2H), 0.99 (s, 3H)
LC-MS (ESI POS): 528.26 MH+
$[\alpha]_D^{25}$+11.47 (c 0.75, MeOH, 546 nm)
Compound 116:
$^1$H NMR (300 MHz, DMSO-d6) ppm 7.26 (dd, 1H), 6.72-6.85 (m, 2H), 6.54-6.72 (m, 2H), 6.29 (dd, 1H), 6.08 (s, 1H), 5.49-5.75 (m, 1H), 5.44 (br. s., 1H), 4.43 (d, 1H), 4.17-4.24 (m, 1H), 4.13 (d, 1H), 3.65 (s, 3H), 3.40-3.50 (m, 1H), 3.30-3.40 (m, 1H), 3.18 (s, 2H), 2.91 (dd, 1H), 2.55-2.62 (m, 1H), 2.34-2.46 (m, 1H), 2.18-2.34 (m, 1H), 1.63-1.98 (m, 3H), 1.49 (s, 3H), 1.35-1.48 (m, 2H), 0.97 (s, 3H)
LC-MS (ESI POS): 528.23 MH+
$[\alpha]_D^{25}$+15.16 (c 1.0, MeOH, 546 nm)
Compound reported in Table 21 is prepared as previously described for compounds 115 and 116.

TABLE 21

| Compound | Structure | Yield | Analytical |
|---|---|---|---|
| 117 | mixture of meta and para isomers about 1:1 | 51% | $^1$H NMR (300 MHz, DMSO-d6) δ ppm 7.26 (dd, 2 H), 6.38-7.11 (m, 4 H), 6.29 (dd, 1 H), 6.08 (s, 1 H), 5.48-5.77 (m, 1 H), 5.39-5.48 (m, 1 H), 4.90 (t, 1 H), 4.36-4.51 (m, 1 H), 4.02-4.26 (m, 2 H), 3.35-3.52 (m, 2 H), 3.17-3.25 (m, 1 H), 2.94-3.08 (m, 1 H), 2.54-2.61 (m, 1 H), 2.22-2.33 (m, 1 H), 2.16 and 2.21 (s, 3 H), 1.71-2.03 (m, 4 H), 1.50 (s, 3 H), 1.40-1.49 (m, 2 H), 0.98 and 0.99 (s, 3 H). LC-MS (ESI POS): 512.18 MH+ |

Example 29

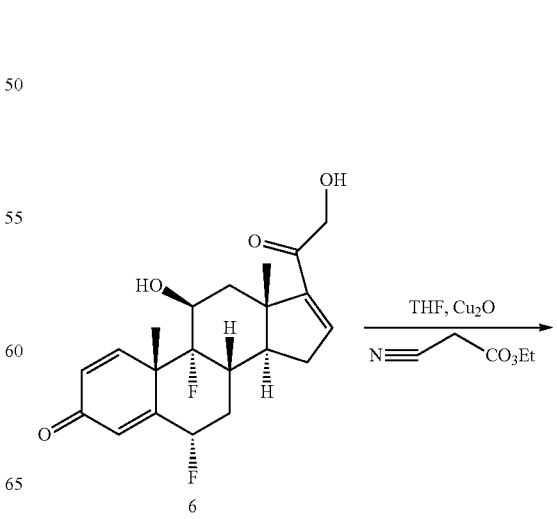

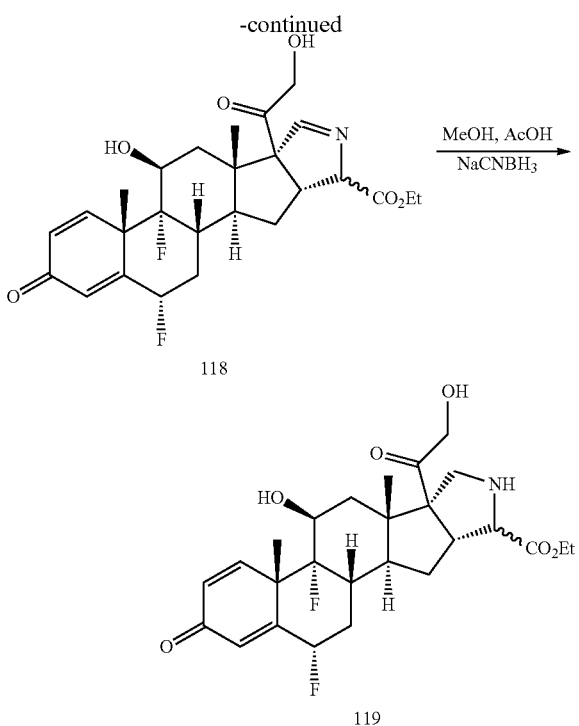

118

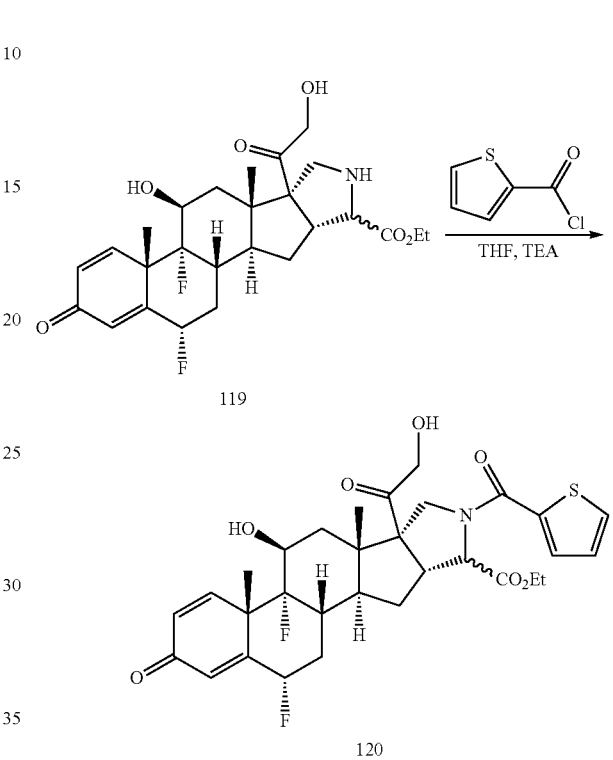

Preparation of (4aS,4bR,5S,6aS,6bS,9aR,10aS,10bS,
12S)-4b,12-Difluoro-5-hydroxy-6b-(2-hydroxy-
acetyl)-4a,6a-dimethyl-2-oxo-2,4a,4b,5,6,6a,6b,9,9a,
10,10a,10b,11,12-tetradecahydro-8-aza-pentaleno[2,
1-a]phenanthrene-9-carboxylic acid ethyl ester
(intermediate 118)

To a mixture of intermediate 6 (563 mg; 1.49 mmol) and a catalytic amount of $Cu_2O$, in anhydrous THF (16 ml), ethyl isocyanate (326 µl; 2.98 mmol) is added and the mixture is stirred at 60° C. for 1 hour. The reaction mixture is filtered through a celite pad, washing with methanol and the solvent is evaporated. The residue is purified by silica gel flash chromatography in gradient elution from DCM to DCM/AcOEt 60:40, to afford of title compound (629 mg, 86% yield).
LC-MS (ESI POS): 492.3 (MH+)

Preparation of ((4aS,4bR,5S,6aS,6bS,9aR,10aS,
10bS,12S)-4b,12-Difluoro-5-hydroxy-6b-(2-hy-
droxy-acetyl)-4a,6a-dimethyl-2-oxo-2,4a,4b,5,6,6a,
6b,7,8,9,9a,10,10a,10b,11,12-hexadecahydro-8-aza-
pentaleno[2,1-a]phenanthrene-9-carboxylic acid
ethyl ester (compound 119)

To a solution of intermediate 118 (629 mg; 1.28 mmol) in methanol (13 ml; 0.1 M), $NaCNBH_3$ (169 mg; 2.56 mmol) is added at 0° C.; pH is adjusted to 5 by addition of acetic acid. The reaction mixture is stirred at 0° C. for 2 hours and at RT for 5 hours, then it is poured into brine (50 ml), and pH is adjusted to 7 by addition of a saturated solution of $NaHCO_3$. The aqueous phase is extracted with AcOEt (3×60 ml) and the combined organic layers are concentrated. The crude material is purified by silica gel flash chromatography in gradient elution from DCM to DCM/MeOH 88:12, to afford pure title compound (335 mg, 53% yield mixture of stereoisomers).
$^1$H NMR (300 MHz, DMSO-$d_6$) δ ppm 9.52 (br. s., 1H) 7.27-7.36 (m, 1H) 6.18 (dd, 1H) 5.94 (s, 1H) 4.78 (br. s., 1H) 4.45-4.61 (m, 1H) 4.35-4.45 (m, 1H) 4.16-4.35 (m, 4H) 4.01-4.16 (m, 2H) 3.52-3.92 (m, 2H) 3.37-3.50 (m, 1H) 3.16-3.6 (m, 1H) 2.29-2.39 (m, 1H) 1.43-2.12 (m, 7H) 1.37 (s, 3H) 1.27 (t, 3H) 1.01-1.13 (m, 2H) 0.81-1.00 (m, 3H)
LC-MS (ESI POS): 458.15 (MH+)

Example 30

Preparation of (4aS,4bR,5S,6aS,6bS,9aR,10aS,10bS,
12S)-4b,12-Difluoro-5-hydroxy-6b-(2-hydroxy-
acetyl)-4a,6a-dimethyl-2-oxo-2,4a,4b,5,6,6a,6b,7,8,
9,9a,10,10a,10b,11,12-hexadecahydro-8-aza-N-(2-
thienoyl)-pentaleno[2,1-a]phenanthrene-9-carboxylic
acid ethyl ester (compound 120)

Under an inert atmosphere, Compound 119 (600 mg; 1.217 mmol) is dissolved in dry THF (15 ml) and 2-thienoyl chloride (195 µl; 1.825 mmol; d=1.37 g/ml) is added. The formed suspension is cooled to 0° C., triethylamine (169 µA; 1.217 mmol) is added and the reaction mixture is stirred at 0° C. for 15 minutes. The reaction mixture is poured into brine (35 ml) and the aqueous phase is extracted with AcOEt (3×60 ml). The combined organic extracts are dried and concentrated. The crude material is purified by silica gel flash chromatography in DCM/MeOH 98:2, to afford the title compound (560 mg 76% yield; mixture of diastereoisomer).
$^1$H NMR (300 MHz, Chloroform-d) δ ppm 7.52 (dd, 1H), 7.44 (br. s., 1H), 6.98-7.21 (m, 2H), 6.23-6.56 (m, 2H), 5.14-5.54 (m, 1H), 4.74 (s, 1H), 4.42-4.47 (m, 1H), 4.45 (d, 1H), 4.05-4.34 (m, 4H), 3.92 (d, 1H), 3.61 (d, 1H), 2.34-2.60 m, 1H), 2.20-2.34 (m, 2H), 1.89-2.20 (m, 3H), 1.61-1.89 (m, 3H), 1.53 (s, 3H), 1.28 (t, 3H), 1.05 (s, 3H)
LC-MS (ESI POS): 604.15 (MH+)
Compounds listed in Table 22 are prepared through the procedure previously described for compound 120.

TABLE 22

| Compound | Structure | Yield | Analytical |
|---|---|---|---|
| 121 | 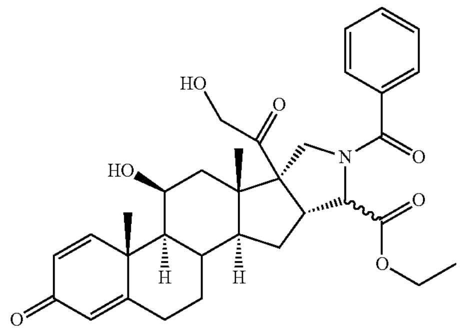 | 35% | $^1$H NMR (300 MHz, CHLOROFORM-d) δ ppm 7.29-7.56 (m, 5 H), 7.24 (d, 1 H), 6.33 (dd, 1 H), 6.09 (s, 1 H), 4.52 (br. s., 1 H), 4.41 (d, 2 H), 3.95-4.27 (m, 4 H), 3.69 (d, 1 H), 3.57 (d, 1 H), 2.50-2.71 (m, 1 H), 2.29-2.48 (m, 1 H), 1.92-2.23 (m, 3 H), 1.70-1.90 (m, 2 H), 1.50-1.67 (m, 1 H), 1.46 (s, 3 H), 1.08-1.40 (m, 6 H), 1.04 (s, 3 H) LC-MS (ESI POS): 562.22 (MH+) |
| 122 | 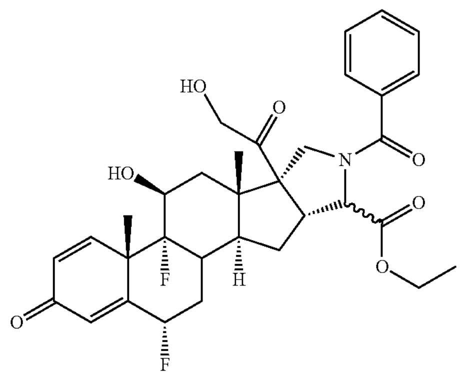 | 30% | $^1$H NMR (300 MHz, CHLOROFORM-d) δ ppm 7.30-7.55 (m, 3 H), 7.08 (d, 1 H), 6.50 (s, 1 H), 6.42 (dd, 1 H), 5.14-5.81 (m, 1 H), 4.03-4.68 (m, 6 H), 3.67-3.83 (m, 1 H), 3.53-3.66 (m, 1 H), 1.64-2.56 (m, 11 H), 1.54 (s, 3 H), 1.13-1.43 (m, 3 H), 1.3 (s, 3 H) LC-MS (ESI POS): 598.02 (MH+) |
| 123 | 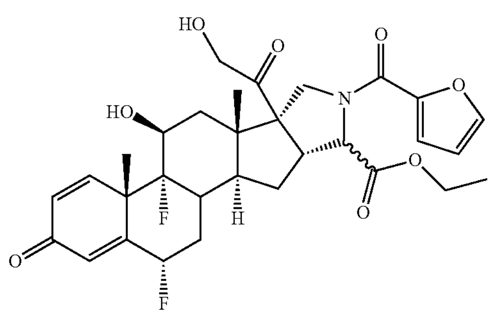 | 91% | $^1$H NMR (300 MHz, DMSO-d$_6$ 353K) δ ppm 7.75 (dd, 1 H), 7.25 (dd, 1 H), 7.05 (dd, 1 H), 6.59 (dd, 1 H), 6.27 (dd, 1 H), 6.12 (s, 1 H), 5.58 (dddd, 1 H), 5.25 (dd, 1 H), 4.76 (t, 1 H), 4.74 (s, 1 H), 4.21-4.32 (m, 2 H), 4.03-4.18 (m, 4 H), 3.85 (d, 1 H), .54 (d, 1 H), 2.53-2.64 (m, 1 H), 2.12-2.33 (m, 1 H), 1.95-2.12 (m, 2 H), 1.85 (m, 3 H), 1.55-1.71 (m, 1 H), 1.51 (s, 3 H), 1.20 (t, 3 H), 0.99 (s, 3 H) LC-MS (ESI POS): 588.19 (MH+) |
| 124 | 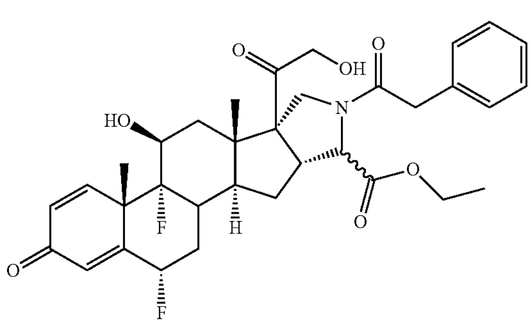 | 51% | $^1$H NMR (300 MHz, DMSO-d6 353K) δ ppm 6.88-7.36 (m, 6 H), 6.28 (dd, 1 H), 6.17 (d, 1 H), 5.58 (dddd, 1 H), 5.21 (d, 1 H), 4.69 (t, 1 H), 4.38-4.53 (m, 1 H), 4.25 (dd, 1 H), 4.15-4.25 (m, 1 H), 3.95-4.13 (m, 3 H), 3.78-3.89 (m, 1 H), 3.29-3.70 (m, 4 H), 2.35-2.47 (m, 1 H), 2.13-2.29 (m, 1 H), 1.60-2.04 (m, 4 H), 1.50 (s, 3 H), 1.34-1.48 (m, 2 H), 1.19 (t, 3 H), 0.94 (s, 3 H) LC-MS (ESI POS): 612.14 (MH+) |

TABLE 22-continued

| Compound | Structure | Yield | Analytical |
|---|---|---|---|
| 125 | 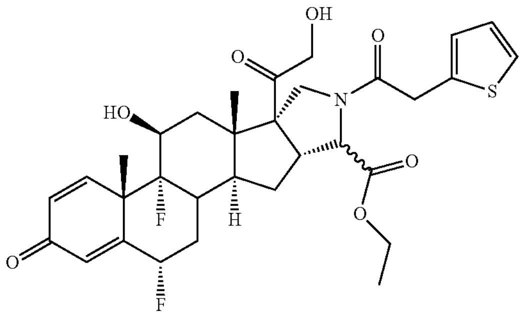 | 46% | ¹H NMR (300 MHz, DMSO-d6) δ ppm 7.14-7.39 (m, 2 H), 6.71-7.03 (m, 2 H), 6.22-6.41 (m, 1 H), 6.12 (s, 1 H), 5.49-5.80 (m, 1 H), 5.46 (d, 1 H), 5.10 (t, 1 H), 4.23-4.43 (m, 1 H), 4.12-4.24 (m, 1 H), 3.72-4.12 (m, 7 H), 3.32-3.68 (m, 2 H), 2.8-2.46 (m, 1 H), 2.06-2.28 (m, 1 H), 1.71-2.02 (m, 4 H), 1.51-1.66 (m, 2 H), 1.48 (s, 3 H), 1.16 (t, 3 H), 0.90 (s, 3 H) LC-MS (ESI POS): 618.09 (MH+) |

Example 31

Preparation of (4aS,4bR,5S,6aS,6bS,9aR,10aS,10bS,12S)-4b,12-Difluoro-8-furan-2-ylmethyl-5-hydroxy-6b-(2-hydroxy-acetyl)-4a,6a-dimethyl-2-oxo-2,4a,4b,5,6,6a,6b,7,8,9,9a,10,10a,10b,11,12-hexadecahydro-8-aza-pentaleno[2,1-a]phenanthrene-9-carboxylic acid ethyl ester (compound 126)

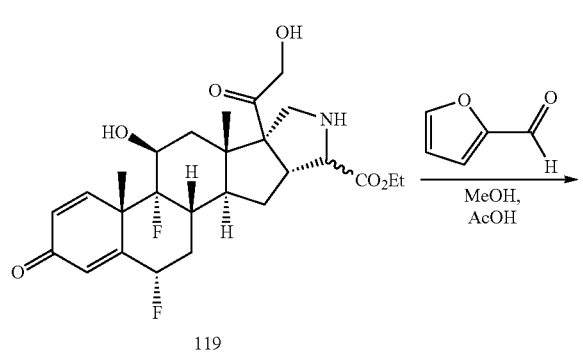

To a solution of Compound 119 (80 mg; 0.162 mmol) and 2-furaldehyde (14 µl; 0.162 mmol; d=1.158 g/ml) in methanol (2 ml) under nitrogen atmosphere, NaCNBH₃ (12 mg; 0.195 mmol) is added. After 1 hour stirring at RT, acetic acid (10 µl; 0.174 mmol; d=1.05 g/ml) is added and the reaction mixture is stirred for further 2 hours at RT. The reaction mixture is poured into brine (20 ml) and the aqueous phase is extracted with AcOEt (3×30 ml). The combined organic extracts are dried over Na₂SO₄ and concentrated. The residue is purified by preparative HPLC to afford 13 mg of title compound (14% yield; mixture of diastereoisomers).

¹H NMR (300 MHz, Chloroform-d) δ ppm 7.37 (dd, 1H), 7.11 (dd, 1H), 6.43-6.49 (m, 1H), 6.39 (dd, 1H), 6.33 (dd, 1H), 6.19 (d, 1H), 5.39-5.60 (m, 1H), 5.31 (ddd, 1H), 4.49 (d, 1H), 4.35-4.40 (m, 1H), 4.37 (d, 1H), 4.17-4.31 (m, 2H), 3.85 (d, 1H), 3.70 (d, 1H), 3.26 (t, 1H), 3.18 (d, 1H), 2.88 (d, 1H), 2.64 (d, 1H), 2.23-2.55 (m, 2H), 1.59-2.12 (m, 5H), 1.53 (s, 3H), 1.33 (t, 3H), 0.97 (s, 3H)

LC-MS (ESI POS): 574.31 (MH+)

Compounds listed in Table 23 are prepared through the procedure previously described for compound 126.

TABLE 23

| Compound | Structure | Yield | Analytical |
|---|---|---|---|
| 127 | 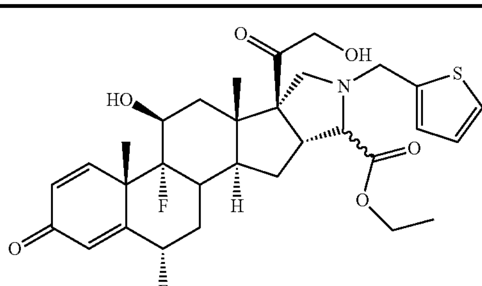 | 53% | ¹H NMR (300 MHz, DMSO-d₆) δ ppm 7.39 (dd, 1 H), 7.24 (dd, 1 H), 6.77-6.97 (m, 2 H), 6.29 (dd, 1 H), 6.12 (s, 1 H), 5.49-5.79 (m, 1 H), 5.42 (d, 1 H), 4.83 (t, 1 H), 4.10 (q, 2 H), 4.02-4.32 (m, 3 H), 3.92 (d, 1 H), 3.65 (d, 1 H), 3.22 (dd, 1 H), 2.8-3.00 (m, 2 H), 2.55-2.64 (m, 1 H), 2.46 (d, 1 H), 2.16-2.35 (m, 1 H), 1.87-2.13 (m, 1 H), 1.51-1.87 (m, 5 H), 1.48 (s, 3 H), 1.21 (t, 3 H), 0.85 (s, 3 H) LC-MS (ESI POS): 90.14 (MH+) |

TABLE 23-continued

| Compound | Structure | Yield | Analytical |
|---|---|---|---|
| 128 | 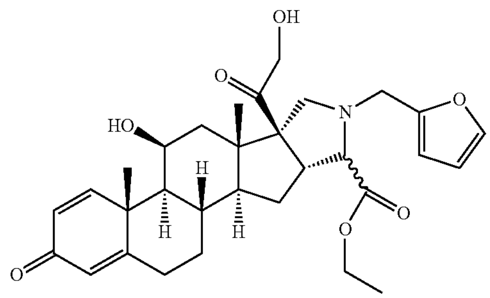 | 24% | $^1$H NMR (300 MHz, DMSO-d$_6$) δ ppm 7.44-7.64 (m, 1 H), 7.30 (d, 1 H), 6.29-6.44 (m, 1 H), 6.10-6.25 (m, 2 H), 5.93 (s, 1 H), 4.79 (t, 1 H), 4.69 (d, 1 H), 4.29 (dd, 1 H), 4.20-4.26 (m, 1 H), 4.17 (dd, 1 H), 3.94-4.12 (m, 2 H), 3.63 (d, 1 H), 3.43 (d, 1 H), 3.12 (t, 1 H), 2.94 (d, 1 H), 2.65 (d, 1 H), 2.44 (d, 1 H), 2.22-2.37 (m, 1 H), 1.93-2.12 (m, 2 H), 1.77-1.93 (m, 1 H), 1.57-1.77 (m, 1 H), 1.37 (s, 3 H), 1.33-1.57 (m, 2 H), 1.16-1.34 (m, 4 H), 0.89-1.16 (m, 3 H), 0.84 (s, 3 H)<br>LC-MS (ESI POS): 538.42 (MH+) |
| 129 | 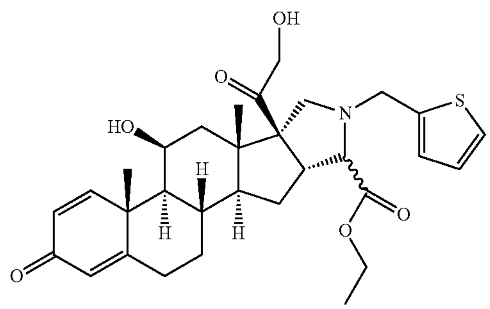 | 40% | $^1$H NMR (300 MHz, DMSO-d6) δ ppm 7.39 (dd, 1 H), 7.30 (d, 1 H), 6.92 (dd, 1 H), 6.85 (d, 1 H), 6.16 (dd, 1 H), 5.93 (s, 1 H), 4.79 (t, 1 H), 4.68 (d, 1 H), 4.09-4.33 (m, 3 H), 4.09 (q, 2 H), 3.89 (d, 1 H), 3.58 (d, 1 H), 3.10-3.24 (m, 1 H), 2.90 (d, 1 H), 2.82 (d, 1 H), 2.53-2.60 (m, 1 H), 2.41-2.48 (m, 1 H), 2.22-2.39 (m, 1 H), 1.91-2.12 (m, 2 H), 1.76-1.91 (m, 1 H), 1.39-1.74 (m, 5 H), 1.37 (s, 3 H), 1.20 (t, 3 H), 0.89-1.14 (m, 1 H), 0.83 (s, 3 H)<br>LC-MS (ESI POS): 554.38 (MH+) |
| 130 | 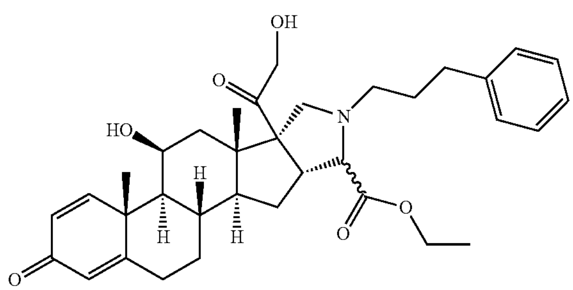 | 52% | $^1$H NMR (300 MHz, DMSO-d6) δ ppm 7.32 (d, 1 H), 7.20-7.29 (m, 1 H), 7.06-7.20 (m, 2 H), 6.15 (dd, 1 H), 5.91 (s, 1 H), 4.35 (d, 1 H), 4.29-4.35 (m, 1 H), 4.23 (d, 1 H), 4.15 (m, 1 H), 3.22-3.33 (m, 1 H), 2.53-2.78 (m, 7 H), 2.28-2.39 (m, 2 H), 1.99-2.16 (m, 3 H), 1.94 (dd, 1 H), 1.50-1.80 (m, 8 H), 1.42 (s, 3 H), 1.22 (t, 3 H), 1.01-1.18 (m, 2 H), 0.91 (s, 3 H)<br>LC-MS (ESI POS): 576.34 (MH+) |
| 131 | 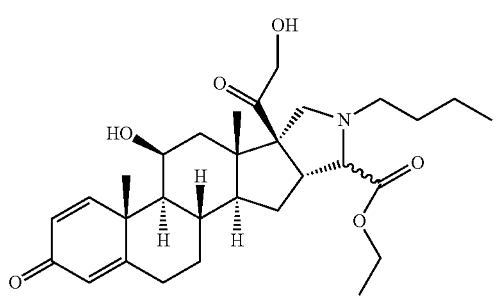 | 7% | $^1$H NMR (300 MHz, CHLOROFORM-d) δ ppm 7.25 (d, 1 H), 6.29 (dd, 1 H), 5.81-6.11 (m, 1 H), 4.52 (d, 1 H), 4.43-4.53 (m, 1 H), 4.37 (d, 1 H), 4.23 (q, 2 H), 2.91-3.35 (m, 2 H), 2.48-2.79 (m, 2 H), 2.24-2.45 (m, 2 H), 2.04-2.23 (m, 3 H), 1.98 (dd, 1 H), 1.50-1.87 (m, 6 H), 1.32 (t, 3 H), 1.28 (s, 3 H), 1.17-1.41 (m, 3 H), 1.06-1.17 (m, 2 H), 0.99 (s, 3 H), 0.87 (t, 3 H)<br>LC-MS (ESI POS): 514.42 (MH+) |

Example 32

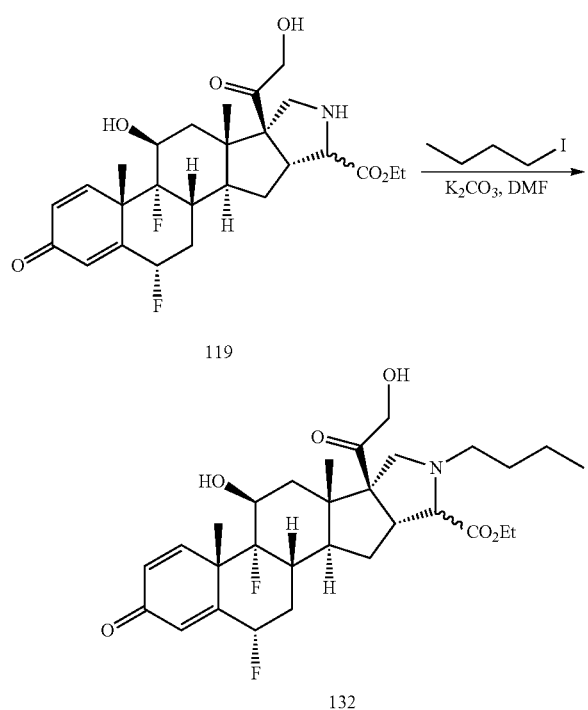

Preparation of (4aS,4bR,5S,6aS,6bS,9aR,10aS,10bS,12S)-8-Butyl-4b,12-difluoro-5-hydroxy-6b-(2-hydroxy-acetyl)-4a,6a-dimethyl-2-oxo-2,4a,4b,5,6,6a,6b,7,8,9,9a,10,10a,10b,11,12-hexadecahydro-8-azapentaleno[2,1-a]phenanthrene-9-carboxylic acid ethyl ester (compound 132)

Compound 119 (100 mg; 0.20 mmol) is dissolved in dry DMF (2 ml); butyl iodide (91 µl; 0.8 mmol; d=1.617 g/ml) and $K_2CO_3$ (41 mg; 0.3 mmol) are added. The reaction mixture is stirred under microwave heating at 100° C. for 20 minutes. The reaction mixture is partitioned between AcOEt and brine; the organic layer is washed with water, dried over $Na_2SO_4$ and concentrated. The crude is purified by preparative HPLC to give the title compound (88 mg, 80% yield; mixture of diastereoisomers).

$^1$H NMR (300 MHz, DMSO-d6+$Na_2CO_3$) δ ppm 7.25 (dd, 1H), 6.28 (dd, 1H), 6.11 (s, 1H), 5.48-5.79 (m, 1H), 5.44 (br. s., 1H), 4.80 (br. s., 1H), 4.35 (d, 1H), 4.24 (d, 1H), 4.10-4.20 (m, 1H), 4.10 (q, 2H), 3.14 (dd, 1H), 3.07 (d, 1H), 2.70 (d, 1H), 2.37-2.47 (m, 1H), 2.24 (d, 2H), 2.05-2.19 (m, 1H), 1.53-2.06 (m, 6H), 1.49 (s, 3H), 1.21 (t, 3H), 1.27 (br. s., 5H), 0.86 (s, 3H), 0.81 (t, 3H)

LC-MS (ESI POS): 550.12 (MH+)

When a substituted alkylbromide is used as alkylating agent in place of a substitute alkyliodide, 0.5 eq of KI are used in the reaction mixture.

Compounds listed in Table 24 are prepared through a two steps procedure as previously described for compound 132.

TABLE 24

| Compound | Structure | Yield | Analytical |
|---|---|---|---|
| 133 | 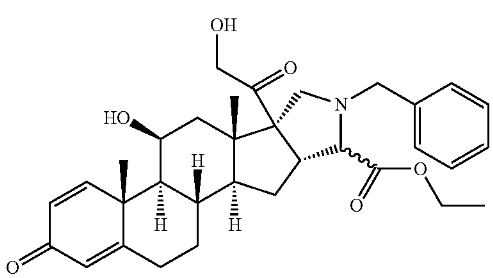 | 18% | $^1$H NMR (300 MHz, DMSO-d$_6$) δ ppm 7.04-7.45 (m, 6 H), 6.16 (dd, 1 H), 5.93 (s, 1 H), 4.14-4.28 (m, 1 H), 4.11-4.24 (m, 2 H), 4.06 (q, 2 H), 3.74 (d, 1 H), 3.21 (d, 1 H), 3.07-3.21 (m, 1 H), 2.79 (d, 1 H), 2.70-2.77 (m, 1 H), 2.51-2.60 (m, 1 H), .35 (d, 1 H), 2.22-2.36 (m, 1 H), 1.89-2.12 (m, 2 H), 1.74-1.87 (m, 1 H), 1.38-1.72 (m, 5 H), 1.37 (s, 3 H), 1.18 (t, 3 H), 1.05-1.29 (m, 2 H), 0.99 (dd, 1 H), 0.83 (s, 3 H) LC-MS (ESI POS): 548.18 (MH+) |
| 134 | 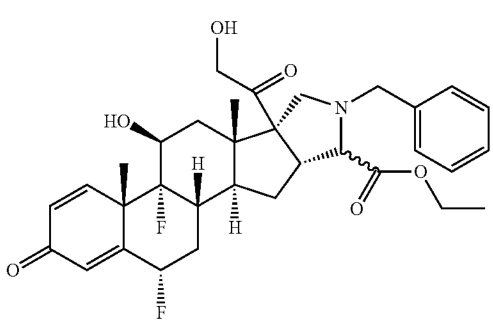 | 15% | $^1$H NMR (300 MHz, DMSO-d$_6$ + $Na_2CO_3$) δ ppm 7.17-7.31 (m, 6 H), 6.28 (dd, 1 H), 6.12 (s, 1 H), 5.43-5.84 (m, 1 H), 4.22 (s, 2 H), 4.06-4.17 (m, 1 H), 4.07 (q, 2 H), 3.75 (d, 1 H), 2.96-3.25 (m, 2 H), 2.88 (d, 1 H), 2.84 (d, 1 H), 2.18-2.38 (m, 2 H) 1.86-2.18 (m, 1 H), 1.50-1.83 (m, 5 H), 1.48 (s, 3 H), 1.20-1.32 (m, 1 H), 1.19 (t, 3 H), 0.84 (s, 3 H) LC-MS (ESI POS): 584.21 (MH+) |

TABLE 24-continued

| Compound | Structure | Yield | Analytical |
|---|---|---|---|
| 135 | 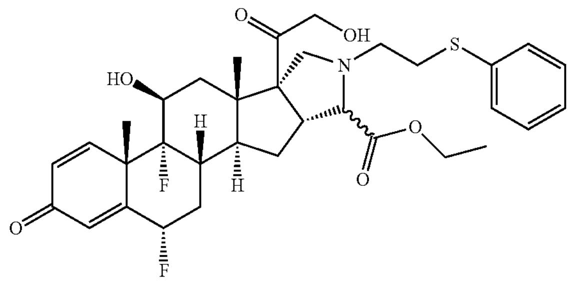 | 29% | $^1$H NMR (300 MHz, DMSO-$d_6$) δ ppm 6.99-7.45 (m, 6 H), 6.29 (dd, 1 H), 6.12 (s, 1 H), 5.48-5.82 (m, 1 H), 5.42 (d, 1 H), 4.83 (t, 1 H), 4.39 (dd, 1 H), 4.20 (dd, 1 H), 4.10-4.19 (m, 1 H), 4.07 (q, 2 H), 3.17-3.24 (m, 1 H), 3.17 (d, 1 H), 2.92-3.10 (m, 4 H), 2.89 (d, 1 H), 2.74-2.84 (m, 1 H), 2.41 (d, 1 H), 2.17-2.28 (m, 1 H), 1.52-2.10 (m, 6 H), 1.49 (s, 3 H), 1.16 (t, 3 H), 0.85 (s, 3 H)<br>LC-MS (ESI POS): 630.12 (MH+) |
| 136 | 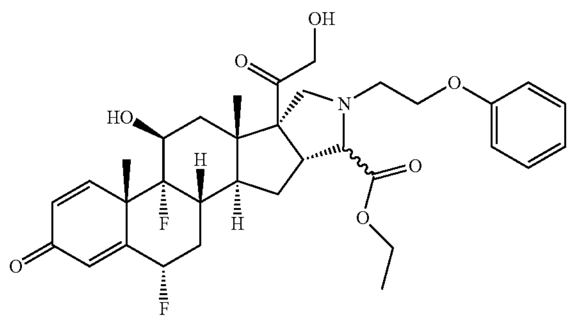 | 21% | $^1$H NMR (300 MHz, DMSO-$d_6$) δ ppm 7.12-7.33 (m, 3 H), 6.75-6.97 (m, 3 H), 6.29 (dd, 1 H), 6.12 (s, 1 H), 5.49-5.81 (m, 1 H), 5.42 (dd, 1 H), 4.81 (t, 1 H), 4.36 (dd, 1 H), 4.21 (dd, 1 H), 4.10-4.18 (m, 1 H), 4.02 (qd, 2 H), 3.91-4.00 (m, 2 H), 3.0-3.24 (m, 2 H), 2.94 (s, 1 H), 2.84 (ddd, 1 H), 2.55-2.76 (m, 2 H), 2.16-2.38 (m, 1 H), 1.99 (d, 1 H), 1.52-1.91 (m, 6 H), 1.49 (s, 3 H), 1.17 (t, 3 H), 0.85 (s, 3 H)<br>LC-MS (ESI POS): 614.14 (MH+) |
| 137 | 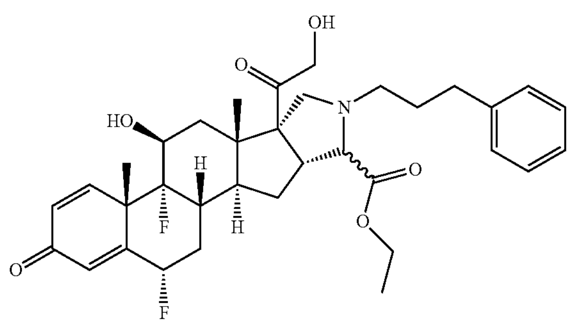 | 74% | $^1$H NMR (300 MHz, DMSO-$d_6$) δ ppm 7.09-7.31 (m, 6 H), 6.29 (dd, 1 H), 6.11 (s, 1 H), 5.47-5.80 (m, 1 H), 5.42 (dd, 1 H), 4.83 (t, 1 H), 4.37 (dd, 1 H), 4.26 (dd, 1 H), 4.10-4.20 (m, 1 H), 4.08 (q, 2 H), 3.12-3.23 (m, 1 H), 3.09 (d, 1 H), 2.77 (d, 1 H), 2.53-2.71 (m, 1 H), 2.38-2.48 (m, 1 H), 1.65-2.38 (m, 10 H), 1.57 (br. s., 3 H), 1.49 (s, 3 H), 1.17 (t, 3 H), 0.87 (s, 3 H)<br>LC-MS (ESI POS): 612.16 (MH+) |

Example 33

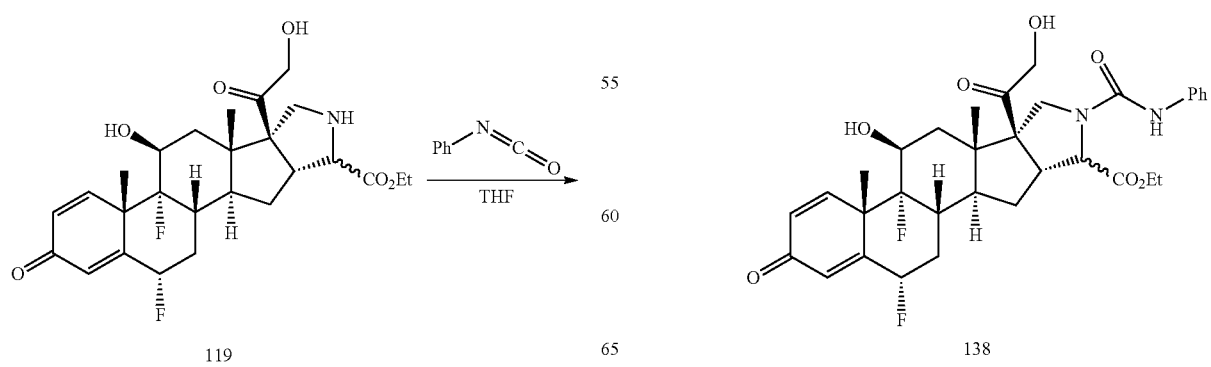

Preparation of (4aS,4bR,5S,6aS,6bS,9aR,10aS,10bS,12S)-4b,12-Difluoro-5-hydroxy-6b-(2-hydroxy-acetyl)-4a,6a-dimethyl-2-oxo-8-phenylcarbamoyl-2,4a,4b,5,6,6a,6b,7,8,9,9a,10,10a,10b,11,12-hexadecahydro-8-aza-pentaleno[2,1-a]phenanthrene-9-carboxylic acid ethyl ester (compound 138)

To a solution of Compound 119 (70 mg; 0.142 mmol) in dry THF (4 ml), phenyl isocyanate (17 µl; 0.156 mmol; d=1.096 g/ml) is added and the reaction mixture is stirred at RT for 2 hours. The reaction mixture is poured into brine (20 ml) and the aqueous phase is extracted with AcOEt (3×35 ml). The combined organic extracts are dried over anhydrous sodium sulphate and concentrated. The residue is purified by preparative HPLC to afford the title compound (30 mg 34% yield).

$^1$H NMR (300 MHz, DMSO-d6): ppm 8.37 (s, 1H), 7.34-7.58 (m, 2H), 7.13-7.34 (m, 3H), 6.82-7.04 (m, 1H), 6.30 (dd, 1H), 6.10 (s, 1H), 5.51-5.79 (m, 1H), 5.44-5.51 (m, 1H), 5.13 (t, 1H), 4.36 (s, 1H), 4.33 (dd, 1H), 3.95-4.22 (m, 3H), 3.80 (d, 1H), 3.56-3.73 (m, 1H), 3.34-3.45 (m, 1H), 2.55-2.70 (m, 1H), 2.17-2.35 (m, 1H), 1.72-2.05 (m, 4H), 1.50 (s, 3H), 1.28-1.71 (m, 5H), 1.20 (t, 3H), 0.93 (s, 3H)

LC-MS (ESI POS):613.43 (MH+)

Compounds listed in Table 25 are prepared through the procedure previously described for compound 138.

Example 34

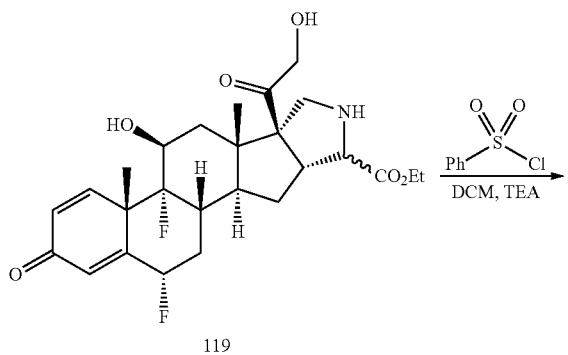

TABLE 25

| Compound | Structure | Yield | Analytical |
|---|---|---|---|
| 139 | 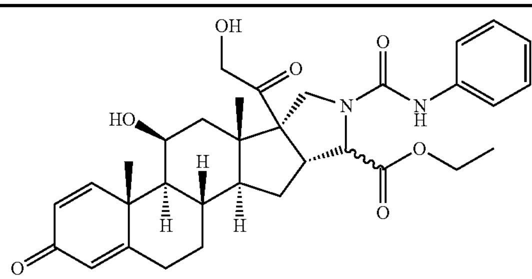 | 30% | $^1$H NMR (300 MHz, DMSO-d$_6$) δ ppm 8.24 (s, 1 H), 7.43 (d, J = 7.63 Hz, 2 H), 7.32 (d, J = 10.27 Hz, 1 H), 7.13-7.27 (m, 2 H), 6.93 (t, J = 7.34 Hz, 1 H), 6.17 (dd, J = 10.12, 1.91 Hz, 1 H), 5.91 (s, 1 H), 4.72 (br. s., 1 H), 4.24-4.40 (m, 3 H), 3.93-4.18 (m, 3 H), 3.84 (d, J = 11.44 Hz, 1 H), 3.59 (d, J = 11.44 Hz, 1 H), 3.35 (d, J = 10.56 Hz, 1 H), 2.54-2.61 (m, 1 H), 2.25-2.39 (m, 1 H), 1.82-2.07 (m, 4 H), 1.72-1.80 (m, 1 H), 1.52-1.68 (m, 1 H), 1.40-1.50 (m, 1 H), 1.39 (s, 3 H), 1.19 (t, J = 7.19 Hz, 3 H), 0.99-1.15 (m, 2 H), 0.92 (s, 3 H)<br>LC-MS (ESI POS):577.33 (MH+) |
| 140 | 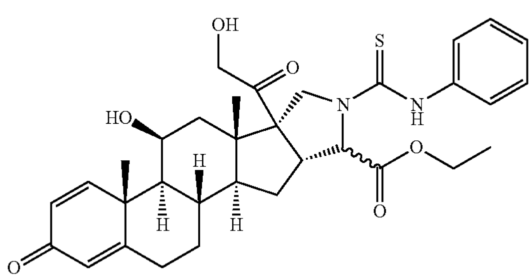 | 47% | $^1$H NMR (300 MHz, DMSO-d$_6$) δ ppm 9.08 (s, 1 H), 7.20-7.51 (m, 5 H), 6.97-7.20 (m, 1 H), 6.17 (dd, J = 10.12, 1.91 Hz, 1 H), 5.93 (s, 1 H), 4.89 (s, 1 H), 4.74 (br. s., 1 H), 4.23-4.42 (m, 2 H), 3.93-4.23 (m, 4 H), 3.79 (d, J = 12.91 Hz, 1 H), 3.39 (d, = 9.10 Hz, 1 H), 2.55-2.67 (m, 1 H), 2.21-2.40 (m, 1 H), 1.86-2.15 (m, 3 H), 1.65-1.86 (m, 2 H), 1.57 (br. s., 1 H), 1.39-1.52 (m, 1 H), 1.39 (s, 3 H), 1.19 (t, J = 7.19 Hz, 3 H), 1.02-1.15 (m, 2 H), 0.93 (s, 3 H).<br>LC-MS (ESI POS):593.19 (MH+) |
| 141 | 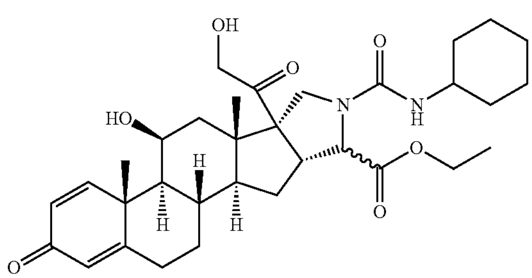 | 46% | $^1$H NMR (300 MHz, DMSO-d$_6$) δ ppm 7.31 (d, 1 H), 6.17 (dd, 1 H), 5.93-5.98 (m, 1 H), 5.92 (s, 1 H), 4.71 (br. s., 1 H), 4.18-4.37 (m, 2 H), 4.11 (s, 1 H), 3.84-4.09 (m, 4 H), 3.55-3.63 (m, 1 H), 3.18-3.44 (m, 3 H), 2.54-2.62 (m, 1 H), 2.22-2.3 (m, 1 H), 1.90-2.04 (m, 2 H), 1.60-1.89 (m, 6 H), 1.46-1.58 (m, 2 H), 1.38 (s, 3 H), 1.27 (d, 2 H), 1.16 (t, 3 H), 0.95-1.20 (m, 6 H), 0.89 (s, 3 H)<br>LC-MS (ESI POS):583.32 (MH+) |

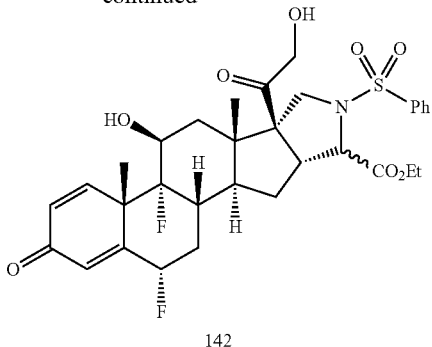

142

Preparation of (4aS,4bR,5S,6aS,6bS,9aR,10aS,10bS,12S)-8-Benzenesulfonyl-4b,12-difluoro-5-hydroxy-6b-(2-hydroxy-acetyl)-4a,6a-dimethyl-2-oxo-2,4a,4b,5,6,6a,6b,7,8,9,9a,10,10a,10b,11,12-hexadecahydro-8-aza-pentaleno[2,1-a]phenanthrene-9-carboxylic acid ethyl ester (compound 142)

To a solution of Compound 119 (80 mg; 0.162 mmol) in dry DCM (5 ml), triethylamine (25 µl; 0.178 mmol; d=0.726 g/ml) and phenylsulfonyl chloride (21 µl; 0.162 mmol; d=1.377 g/ml) are added. After 6 hrs stirring at RT, under nitrogen atmosphere, further triethylamine (7 µl; 0.049 mmol; d=0.726 g/ml) and phenylsulfonyl chloride (6 µl; 0.049 mmol; d=1.377 g/ml) are added and the reaction mixture is stirred for further 30 minutes. The reaction mixture is diluted with DCM (40 ml) and the organic layer is washed with 1 N HCl, water and brine, dried and concentrated. The residue is purified by preparative HPLC to afford the title compound (31 mg, 30% yield).

$^1$H NMR (300 MHz, Chloroform-d): δ ppm 7.70-7.92 (m, 2H), 7.56-7.64 (m, 1H), 7.45-7.56 (m, 2H), 7.04 (dd, 1H), 6.45-6.52 (m, 1H), 6.40 (dd, 1H), 5.31 (dddd, 1H), 4.35-4.41 (m, 1H), 4.39 (d, 1H), 4.18 (d, 1H), 4.15 (dq, 2H), 4.10 (d, 1H), 3.70 (d, 1H), 3.48 (d, 1H), 3.43 (dt, 1H), 2.17-2.48 (m, 1H), 1.78-2.10 (m, 3H), 1.48 (s, 3H), 1.43-1.77 (m, 3H), 1.29-1.40 (m, 1H), 1.27 (t, 3H), 0.95 (s, 3H)

LC-MS (ESI POS):634.24 (MH+)

Compounds listed in Table 26 are prepared the procedure previously described for compound 142.

TABLE 26

| Compound | Structure | Yield | Analytical |
|---|---|---|---|
| 143 | 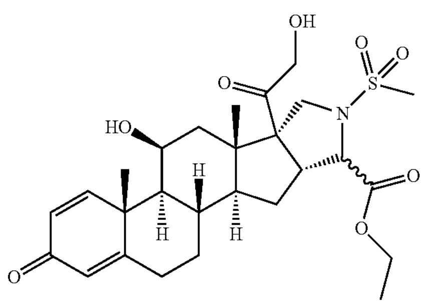 | 37% | $^1$H NMR (300 MHz, DMSO-$d_6$) pm 7.31 (d, 1 H), 6.17 (dd, 1 H), 5.93 (s, 1 H), 5.06 (t, 1 H), 4.70 (d, 1 H), 4.32 (dd, 1 H), 4.22-4.29 (m, 1 H), 3.88-4.17 (m, 4 H), 3.51 (s, 2 H), 3.32-3.44 (m, 1 H), 3.00 (s, 3 H), 2.54-2.66 (m, 1 H), 2.18-2.39 (m, 1 H), 1.76-2.06 (m, 4 H), 1.57-1.74 (m, 1 H), 1.38 (s, 3 H), 1.32-1.55 (m, 1 H), 1.20 (t, 3 H), 1.03-1.29 (m, 3 H), 0.89 (s, 3 H) LC-MS (ESI POS): 536.19 (MH+) |
| 144 | 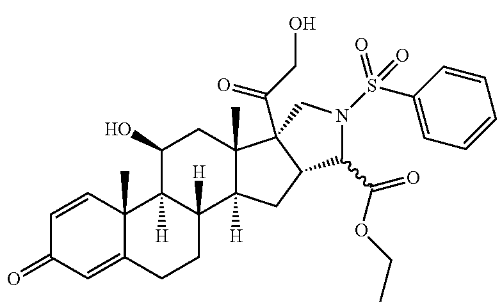 | 45% | $^1$H NMR (300 MHz, DMSO-$d_6$) ppm 7.71-7.98 (m, 2 H), 7.38-7.71 (m, 3 H), 7.26 (d, 1 H), 6.18 (dd, 1 H), 5.98 (s, 1 H), 5.09 (t, 1 H), 4.67 (d, 1 H), 4.12-4.38 (m, 3 H), 3.79-4.12 (m, 3 H), 3.50 (d, 1 H), 3.32-3.40 (m, 2 H), 2.34-2.47 (m, 1 H), .13-2.33 (m, 1 H), 1.65-1.90 (m, 3 H), 1.42-1.60 (m, 1 H), 1.30 (s, 3 H), 1.20-1.39 (m, 3 H), 1.16 (t, 3 H), 0.81 (s, 3 H), 0.46-0.63 (m, 1 H), 0.15-0.48 (m, 1 H) LC-MS (ESI POS): 598.24 (MH+) |

Example 35

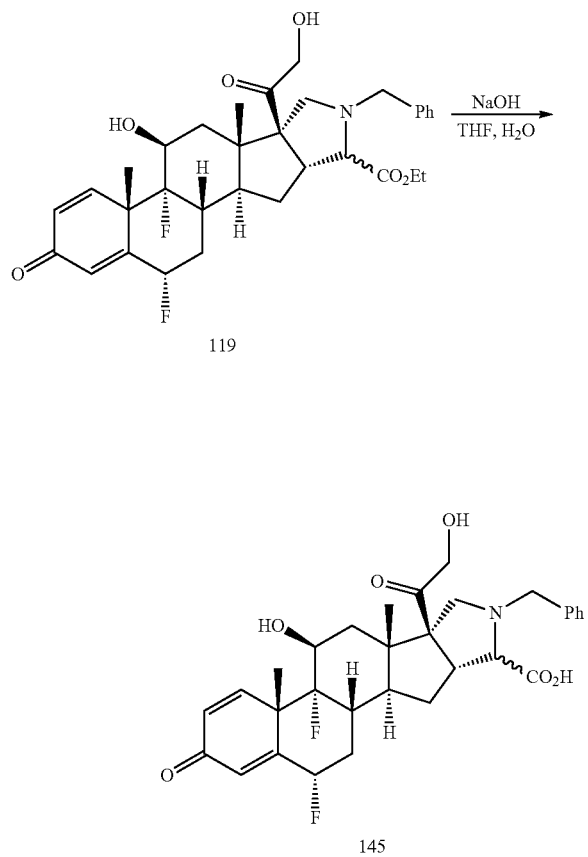

Preparation of 4aS,4bR,5S,6aS,6bS,9aR,10aS,10bS, 12S)-8-Benzyl-4b,12-difluoro-5-hydroxy-6b-(2-hydroxy-acetyl)-4a,6a-dimethyl-2-oxo-2,4a,4b,5,6, 6a,6b,7,8,9,9a,10,10a,10b,11,12-hexadecahydro-8-aza-pentaleno[2,1-a]phenanthrene-9-carboxylic acid (compound 145)

To a solution of compound 119 (66 mg; 0.113 mmol) in dry THF (3 ml) and water (1 ml) 1 N NaOH (400 µl) is added and the reaction mixture is stirred at RT overnight. The reaction mixture is poured into 1 N HCl (10 ml) and brine (10 ml), and the aqueous phase is extracted with AcOEt (3×40 ml). The combined organic extracts are dried and concentrated. Crude is purified by preparative HPLC, to afford title compound (15% yield).

$^1$H NMR (300 MHz, MeOD) δ ppm 6.89-7.63 (m, 6H), 6.15-6.49 (m, 2H), 5.33-5.74 (m, 1H), 4.49 (d, 1H), 4.35 (d, 1H), 4.17-4.29 (m, 1H), 4.11 (d, 1H), 3.42 (d, 1H), 3.09 (d, 1H), 2.84-2.92 (m, 1H), 2.52-2.75 (m, 1H), 2.48 (d, 1H), 2.28-2.43 (m, 1H), 1.60-2.09 (m, 7H), 1.31 (s, 3H), 0.99 (s, 3H)

LC-MS (ESI POS): 556.27 (MH+)

Example 36

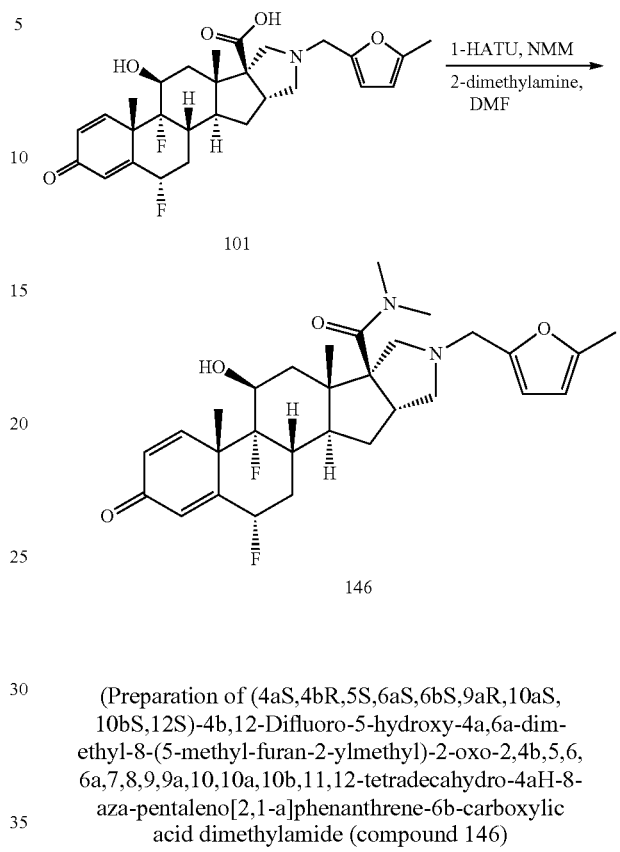

(Preparation of (4aS,4bR,5S,6aS,6bS,9aR,10aS, 10bS,12S)-4b,12-Difluoro-5-hydroxy-4a,6a-dimethyl-8-(5-methyl-furan-2-ylmethyl)-2-oxo-2,4b,5,6, 6a,7,8,9,9a,10,10a,10b,11,12-tetradecahydro-4aH-8-aza-pentaleno[2,1-a]phenanthrene-6b-carboxylic acid dimethylamide (compound 146)

To a solution of compound 101 (165.9 mg, 0.331 mmol) in dry DMF (6.615 ml), kept under nitrogen, HATU (138 mg, 0.364 mmol) is added, followed by N-methylmorpholine (0.036 ml, 0.331 mmol). The reaction is heated at 65° C. for 1 hour, then the mixture is allowed to cool down at RT and dimethylamine (2M solution in THF), (1.654 ml, 3.31 mmol) is added, the reaction is sealed and let stir overnight. The conversion is complete. The mixture is diluted with AcOEt, then poured onto brine and the aqueous layer is extracted with AcOEt twice. Combined organic extracts are washed with brine, dried over Na$_2$SO$_4$ and evaporated to dryness. The crude material is purified via chromatographic column over silica gel (AcOEt): the recovered product (160 mg) is triturated with water and filtered, affording the title compound (80 mg, 0.151 mmol, 46% yield).

$^1$H NMR (300 MHz, DMSO-d6) ppm 7.26 (dd, 1H), 6.29 (dd, 1H), 6.12 (s, 1H), 6.01 (d, 1H), 5.95 (dq, 1H), 5.47-5.81 (m, 1H), 5.39 (dd, 1H), 4.08-4.32 (m, 1H), 3.48-3.65 (m, 1H), 3.45 (d, 1H), 3.39 (d, 1H), 3.04 (d, 1H), 2.85 (s, 6H), 2.55-2.68 (m, 1H), 2.36-2.47 (m, 2H), 2.20-2.33 (m, 2H), 2.18 (s, 3H), 1.99-2.13 (m, 1H), 1.87-1.99 (m, 1H), 1.76 (d, 1H), 1.52-1.68 (m, 1H), 1.48 (s, 3H), 1.37-1.47 (m, 1H), 1.27 (dd, 1H), 0.92 (s, 3H)

LC-MS (ESI POS): 529.34 MH+

$[\alpha]_D^{25}$+38.33 (c 0.3, MeOH)

The compounds listed in Table 27 are prepared as described in Example 36 for compound 146. Compounds 93, 95, 100 and 102 are reacted with the suitable commercially available amines.

TABLE 27

| Compound | Structure | Yield | Analytical |
|---|---|---|---|
| 147 | 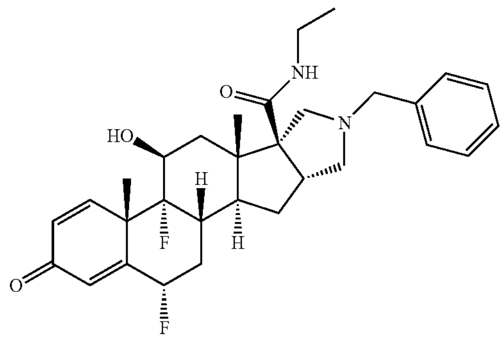 | 9% | ¹H NMR (300 MHz, DMSO-d6) ppm 7.07-7.43 (m, 7 H) 6.29 (dd, 1 H) 6.12 (s, 1 H) 5.47-5.82 (m, 1 H) 5.33-5.41 (m, 1 H) 4.02-4.19 (m, 1 H) 3.43 (s, 2 H) 3.00-3.22 (m, 3 H) 2.78 (t, 1 H) 2.53-2.56 (m, 1 H) 2.34-2.45 (m, 1 H) 2.24-2.33 (m, 2 H) 2.12 (dd, 1 H) 1.93-2.07 (m, 1 H) 1.72-1.87 (m, 1 H) 1.53-1.69 (m, 2 H) 1.49 (s, 4 H) 1.21-1.38 (m, 1 H) 0.96-1.07 (m, 3 H) 0.90 (s, 3 H)<br>LC-MS (ESI POS): 525.25 MH+<br>$[\alpha]_D^{25}$ + 82.5 (c 0.19, MeOH) |
| 148 | 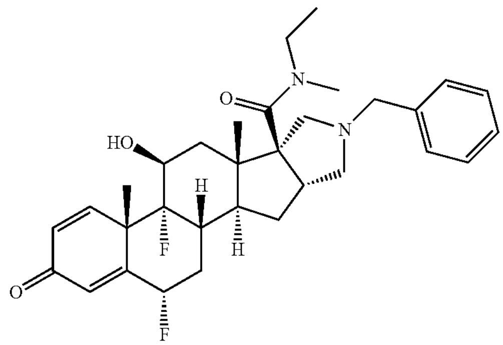 | 27% | ¹H NMR (300 MHz, DMSO-d6) ppm 6.99-7.44 (m, 6 H) 6.30 (dd, 1 H) 6.14 (s, 1 H) 5.50-5.83 (m, 1 H) 5.40 (d, 1 H) 4.10-4.26 (m, 1 H) 3.51-3.64 (m, 1 H) 3.51 (d, 1 H) 3.44 (d, 1 H) 3.30-3.39 (m, 2 H) 3.08-3.19 (m, 1 H) 2.95-3.09 (m, 1 H) 2.78 (s, 3 H) 2.04-2.46 (m, 5 H) 1.84-1.98 (m, 1 H) 1.51-1.78 (m, 3 H) 1.49 (s, 3 H) 1.24-1.39 (m, 1 H) 1.02 (t, 3 H) 0.93 (s, 3 H)<br>LC-MS (ESI POS): 539.31 MH+<br>$[\alpha]_D^{25}$ + 35.58 (c 0.19, MeOH) |
| 149 | 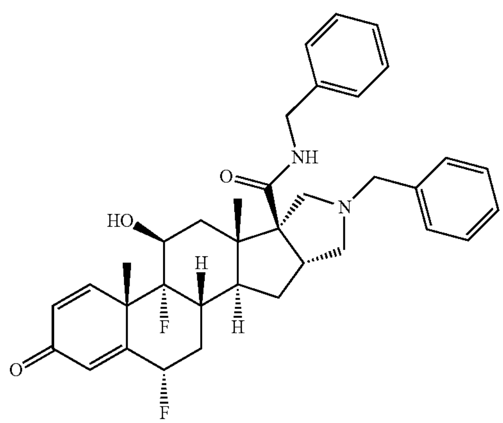 | 30% | ¹H NMR (300 MHz, DMSO-d6) ppm 7.89 (t, 1 H) 7.07-7.42 (m, 11 H) 6.29 (dd, 1 H) 6.13 (s, 1 H) 5.49-5.80 (m, 1 H) 5.40 (dd, 1 H) 4.33 (dd, 1 H) 4.22 (dd, 1 H) 4.07-4.16 (m, 1 H) 3.48 (d, 1 H) 3.42 (d, 1 H) 3.14-3.24 (m, 1 H) 2.91 (t, 1 H) 2.68-2.76 (m, 1 H) 2.55-2.62 (m, 1 H) 2.37 (d, 1 H) 2.19-2.34 (m, 1 H) 1.94-2.10 (m, 2 H) 1.86 (d, 1 H) 1.52-1.72 (m, 3 H) 1.49 (s, 3 H) 1.27-1.39 (m, 1 H) 0.91 (s, 3 H)<br>LC-MS (ESI POS): 587.26 MH+<br>$[\alpha]_D^{25}$ + 91.47 (c 0.34, MeOH) |
| 150 | 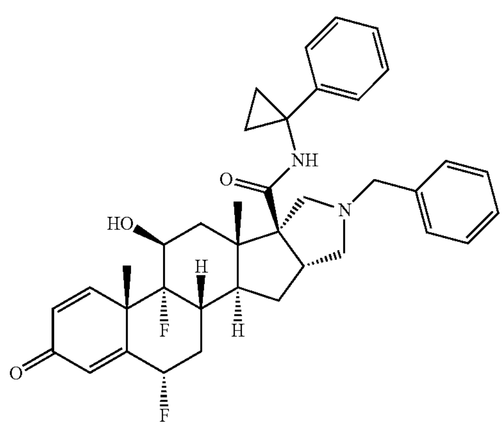 | 41% | ¹H NMR (300 MHz, DMSO-d6) ppm 8.02 (s, 1 H) 7.04-7.47 (m, 11 H) 6.29 (dd, 1 H) 6.13 (s, 1 H) 5.45-5.86 (m, 1 H) 5.29-5.43 (m, 1 H) 4.05-4.21 (m, 1 H) 3.56 (d, 1 H) 3.38 (d, 1 H) 3.19-3.26 (m, 1 H) 3.03 (t, 1 H) 2.88 (d, 1 H) 2.55-2.61 (m, 1 H) 2.13-2.38 (m, 2 H) 1.88-2.12 (m, 2 H) 1.75-1.88 (m, 1 H) 1.49 (s, 3 H) 1.42-1.72 (m, 3 H) 1.25-1.40 (m, 1 H) 1.08-1.20 (m, 4 H) 0.85 (s, 3 H)<br>LC-MS (ESI POS): 613.27 MH+<br>$[\alpha]_D^{25}$ +83.2 (c 0.45 MeOH) |

TABLE 27-continued

| Compound | Structure | Yield | Analytical |
|---|---|---|---|
| 151 | 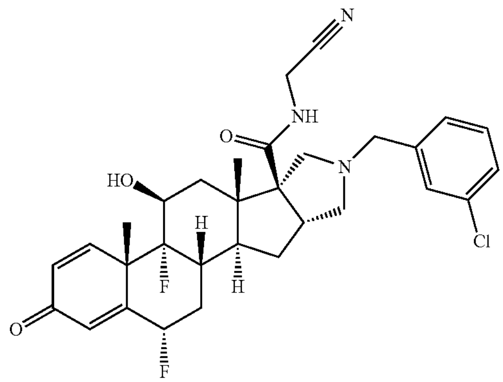 | 43% | $^1$H NMR (300 MHz, DMSO-d6) ppm 8.06 (t, 1 H), 7.13-7.40 (m, 5 H), 6.29 (dd, 1 H), 6.12 (s, 1 H), 5.51-5.81 (m, 1 H), 5.46 (dd, 1 H), 4.10-4.20 (m, 1 H), 4.07 (d, 2 H), 3.49 (d, 1 H), 3.43 (d, 1 H), 3.08-3.24 (m, 1 H), 2.86 (t, 1 H), 2.55-2.68 (m, 2 H), 2.38 (d, 1 H), 2.20-2.34 (m, 1 H), 2.10 (dd, 1 H), 1.94-2.06 (m, 1 H), 1.74-1.86 (m, 1 H), 1.51-1.71 (m, 3 H), 1.49 (s, 3 H), 1.34 (dd, 1 H), 0.91 (s, 3 H)<br>LC-MS (ESI POS): 570.39 MH+<br>$[a]_D^{25}$ + 79.2 (c 0.2, MeOH) |
| 152 | 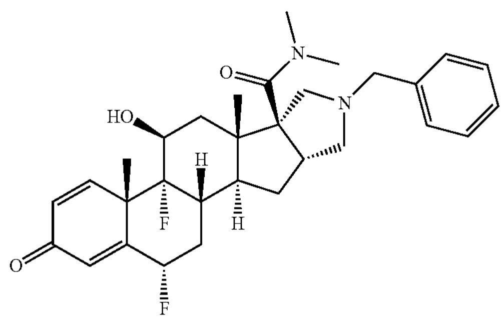 | 35% | $^1$H NMR (300 MHz, DMSO-d6) ppm 6.91-7.42 (m, 6 H), 6.30 (dd, 1 H), 6.14 (s, 1 H), 5.48-5.79 (m, 1 H), 5.32-5.48 (m, 1 H), 4.08-4.31 (m, 1 H), 3.38-3.63 (m, 3 H), 2.98-3.15 (m, 1 H), 2.82 (s, 6 H), 2.05-2.47 (m, 5 H), 1.83-1.98 (m, 1 H), 1.54-1.83 (m, 4 H), 1.49 (s, 3 H), 1.22-1.39 (m, 1 H), 0.93 (s, 3 H)<br>LC-MS (ESI POS): 525.41 MH+<br>$[a]_D^{25}$ + 13.1 (c 0.27, DMSO) |
| 153 | 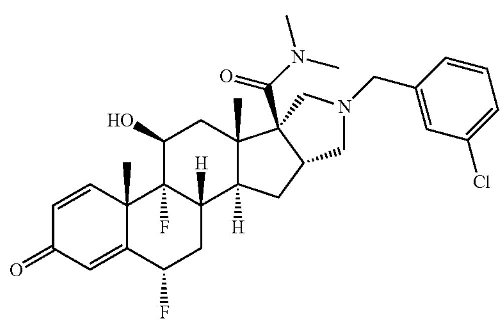 | 43% | $^1$H NMR (300 MHz, DMSO-d6) ppm 7.11-7.38 (m, 5 H), 6.29 (dd, 1 H), 6.13 (s, 1 H), 5.46-5.82 (m, 1 H), 5.39 (dd, 1 H), 4.09-4.24 (m, 1 H), 3.42-3.61 (m, 2 H), 3.01-3.20 (m, 2 H), 2.83 (s, 6 H), 2.30-2.43 (m, 2 H), 2.10-2.23 (m, 3 H), 1.86-2.03 (m, 2 H), 1.52-1.80 (m, 3 H), 1.49 (s, 3 H), 1.26-1.37 (m, 1 H), 0.93 (s, 3 H)<br>LC-MS (ESI POS): 559.35 MH+<br>$[a]_D^{25}$ + 32.25 (c 0.24, CHCl3) |
| 154 | 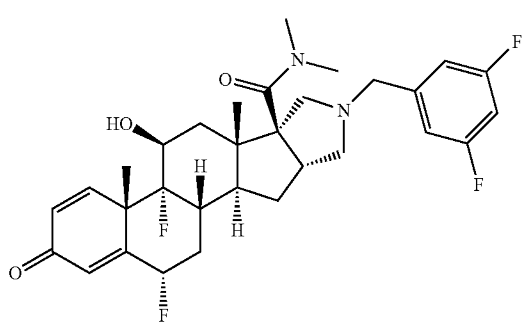 | 47% | $^1$H NMR (300 MHz, DMSO-d6) ppm 7.26 (dd, 1 H), 7.03 (tt, 1 H), 6.86-6.98 (m, 2 H), 6.29 (dd, 1 H), 6.14 (s, 1 H), 5.51-5.83 (m, 1 H), 5.40 (dd, 1 H), 4.09-4.32 (m, 1 H), 3.54-3.61 (m, 1 H), 3.55 (d, 1 H), 3.49 (d, 1 H), 3.02-3.16 (m, 1 H), 2.82 (s, 6 H), 2.24-2.47 (m, 3 H), 2.06-2.24 (m, 3 H), 1.86-2.01 (m, 1 H), 1.51-1.82 (m, 3 H), 1.49 (s, 3 H), 1.25-1.38 (m, 1 H), 0.93 (s, 3 H)<br>LC-MS (ESI POS): 561.37 MH+<br>$[a]_D^{25}$ + 26.2 (c 0.20, CHCl3) |

TABLE 27-continued

| Compound | Structure | Yield | Analytical |
|---|---|---|---|
| 155 | 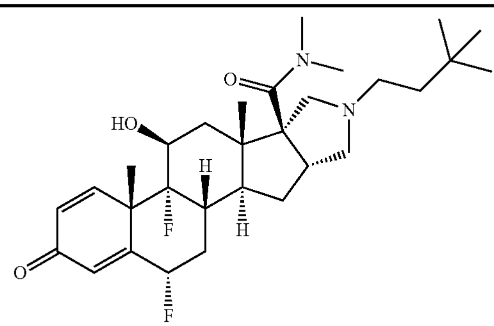 | 15% | ¹H NMR (300 MHz, DMSO-d6) ppm 7.25 (dd, 1 H), 6.29 (dd, 1 H), 6.10 (s, 1 H), 5.46-5.77 (m, 1 H), 5.38 (dd, 1 H), 4.10-4.27 (m, 1 H), 3.42-3.57 (m, 1 H), 3.00-3.21 (m, 1 H), 2.84 (s, 3 H), 2.55-2.70 (m, 3 H), 2.14-2.32 (m, 4 H), 1.89-2.14 (m, 4 H), 1.76 (d, 1 H), 1.52-1.69 (m, 1 H), 1.48 (s, 3 H), 1.15-1.45 (m, 5 H), 0.91 (s, 3 H), 0.86 (s, 9 H) LC-MS (ESI POS): 519.37 MH+ |
| 156 | 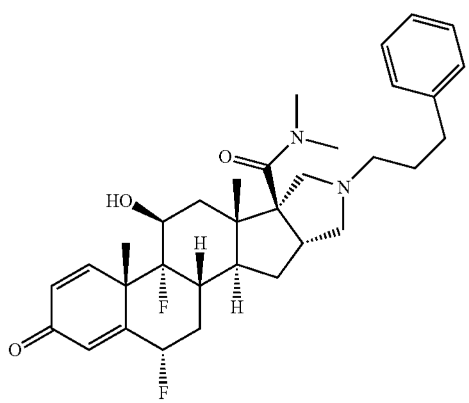 | 38% | ¹H NMR (300 MHz, DMSO-d6) d ppm 7.08-7.30 (m, 6 H), 6.29 (dd, 1 H), 6.09 (s, 1 H), 5.46-5.79 (m, 1 H), 5.39 (dd, 1 H), 3.98-4.36 (m, 1 H), 3.50 (dd, 1 H), 3.13 (d, 1 H), 2.84 (s, 6 H), 2.53-2.62 (m, 1 H), 2.57 (t, 2 H), 2.09-2.42 (m, 5 H), 1.88-2.09 (m, 3 H), 1.58-1.85 (m, 4 H), 1.48 (s, 3 H), 1.42-1.55 (m, 1 H), 1.24-1.41 (m, 1 H), 0.93 (s, 3 H) LC-MS (ESI POS): 553.17 MH+ $[\alpha]_D^{25}$ +38.08 (c 0.24, CHCl3) |

Example 37

Preparation of (4aS,4bR,5S,6aS,6bS,9aR,10aS,10bS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carboxylic acid methyl ester trifluoroacetate (compound 157)

Compound 93 (161 mg, 0.403 mmol) is dissolved in dimethyl carbonate (5 mL, 59.37 mmol), DBU (0.06 mL, 0.403 mmol) is added and the mixture is heated at 90° C. for 3 days. The formation of the product is detected by LC-MS. The reaction mixture is concentrated to dryness and purified by preparative HPLC to yield 45 mg of compound as TFA salt, which is further purified on a silica gel cartridge (eluent DCM/MeOH 98/2) affording the title compound, as TFA salt, (39 mg, 0.062 mmol, 15% yield).

¹H NMR (300 MHz, DMSO-d6+Na₂CO₃) ppm 7.13-7.35 (m, 6H) 6.29 (dd, 1H) 6.09-6.15 (m, 1H) 5.45-5.83 (m, 1H) 4.14 (d, 1H) 3.61 (s, 3H) 3.45 (s, 2H) 3.04-3.15 (m, 1H) 2.87 (t, 1H) 2.62 (d, 1H) 2.42-2.48 (m, 1H) 2.38 (d, 1H) 2.22-2.34 (m, 1H) 1.91-2.14 (m, 2H) 1.55-1.85 (m, 3H) 1.43-1.53 (m, 1H) 1.49 (s, 3H) 1.34 (dd, 1H) 0.91 (s, 3H)

LC-MS (ESI POS): 512.18 MH+

$[\alpha]_D^{25}$ +32.08 (c 0.49, MeOH)

Example 38

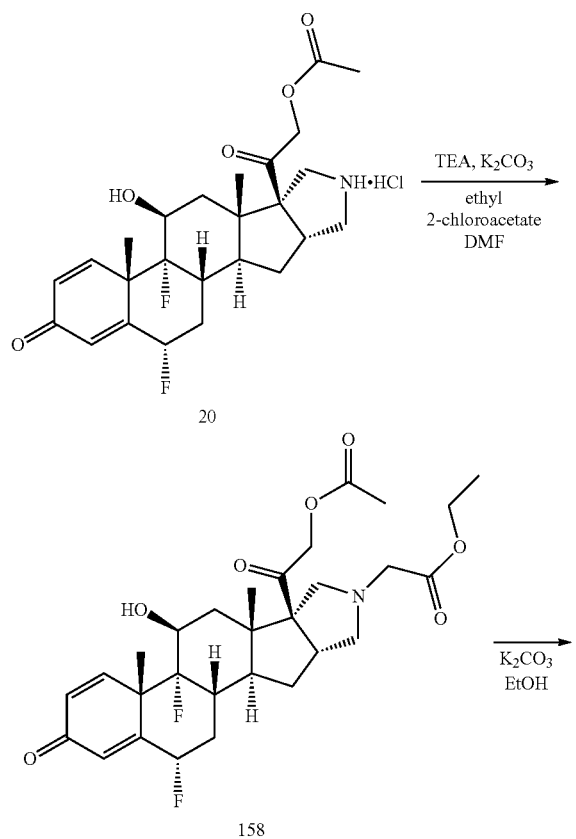

Preparation of [(4aS,4bR,5S,6aS,6bS,9aR,10aS,10bS,12S)-6b-(2-Acetoxy-acetyl)-4b,12-difluoro-5-hydroxy-4a,6a-dimethyl-2-oxo-2,4b,5,6,6a,6b,7,9,9a,10,10a,10b,11,12-tetradecahydro-4aH-8-azapentaleno[2,1-a]phenanthren-8-yl]-acetic acid ethyl ester (compound 158)

Compound 20 (160 mg, 0.320 mmol) is dissolved in DMF (5 ml), TEA (0.045 ml, 0.320 mmol), K₂CO₃ (44.2 mg, 0.320 mmol) and ethyl 2-chloroacetate (0.068 ml, 0.640 mmol) are added and the mixture is stirred at 60° C. for 2 hours. The reaction mixture is diluted with EtOAc and washed with water. The organic phase is separated and the aqueous phase is extracted with AcOEt. The combined organic layers are dried over Na₂SO₄ and concentrated. The crude is purified by silica gel flash chromatography (eluent from DCM:MeOH=99/1 to 99/2) affording the title compound (75 mg, 0.136 mmol, 43% yield).

LC-MS (ESI-POS): 550.2 MH+

Preparation of [(4aS,4bR,5S,6aS,6bS,9aR,10aS,10bS,12S)-4b,12-Difluoro-5-hydroxy-6b-(2-hydroxy-acetyl)-4a,6a-dimethyl-2-oxo-2,4b,5,6,6a,6b,7,9,9a,10,10a,10b,11,12-tetradecahydro-4aH-8-azapentaleno[2,1-a]phenanthren-8-yl]-acetic acid ethyl ester (compound 159)

A solution of compound 158 (75 mg, 0.136 mmol) in ethanol (5 ml) is degassed with nitrogen for 15 minutes and cooled to 0° C. Then K₂CO₃ (9.43 mg, 0.068 mmol) is added and the mixture is stirred at 0° C. with continuous degassing for 1 hour. The reaction mixture is partitioned between water and AcOEt. The combined organic phases are concentrated and crude is purified by silica gel flash chromatography (eluent DCM/EtOH=99/1 to 95/5) to yield the title compound (31 mg, 0.061 mmol, 45% yield).

¹H NMR (300 MHz, DMSO-d6) ppm 7.26 (dd, 1H), 6.29 (dd, 1H), 6.11 (s, 1H), 5.49-5.79 (m, 1H), 5.41 (d, 1H), 4.81 (t, 1H), 4.33 (dd, 1H), 4.10-4.21 (m, 1H), 4.13 (dd, 1H), 4.04 (q, 2H), 3.21 (d, 1H), 3.13-3.17 (m, 1H), 3.14 (d, 1H), 2.99 (t, 1H), 2.74 (d, 1H), 2.56-2.67 (m, 1H), 2.37-2.47 (m, 1H), 2.18-2.31 (m, 1H), 2.10 (dd, 1H), 1.91-2.06 (m, 1H), 1.81-1.91 (m, 1H), 1.52-1.80 (m, 2H), 1.49 (s, 3H), 1.40-1.48 (m, 1H), 1.33 (dd, 1H), 1.15 (t, 3H), 0.86 (s, 3H)

LC-MS (ESI POS): 508.31 MH+

$[\alpha]_D^{25}$+60.3 (c 0.35, CHCl₃)

Example 39

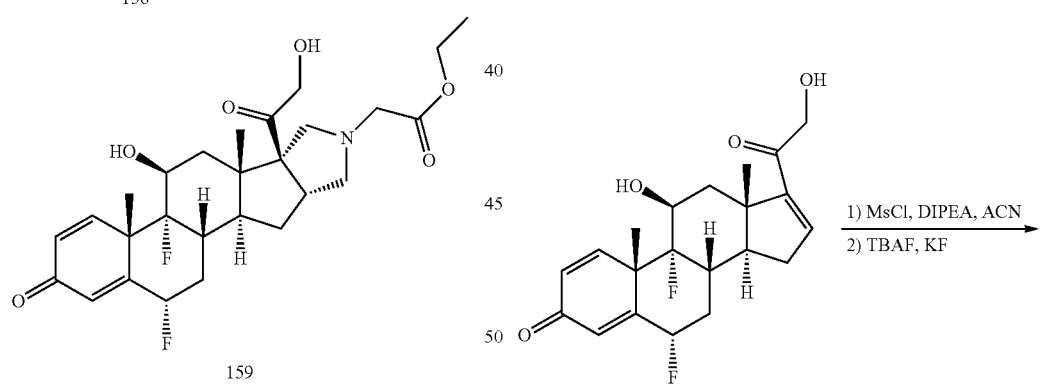

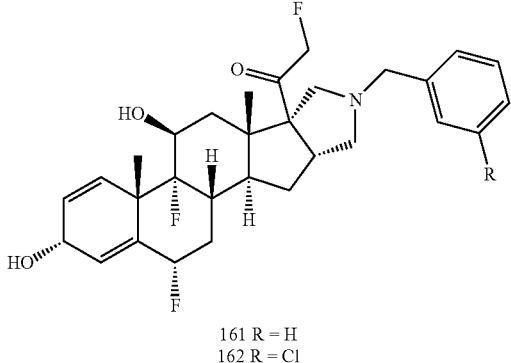

161 R = H
162 R = Cl

Preparation of (6S,8S,9R,10S,11S,13S,14S)-6,9-difluoro-17-(2-fluoroacetyl)-11-hydroxy-10,13-dimethyl-6,7,8,9,10,11,12,13,14,15-decahydro-3H-cyclopenta[α]phenanthren-3-one (compound 160)

In a nitrogen atmosphere, compound 6 (100 mg, 0.264 mmol) is dissolved in acetonitrile (4 ml), Mesyl-Cl (32 μl, 0.411 mmol) and DIPEA (78 μl, 0.447 mmol) are added and the mixture is stirred at RT for 30 minutes. Potassium fluoride (154 mg, 2.64 mmol) is added and the mixture is stirred for 1 hour at 60° C. (complete conversion into chloride occurred). TBAF 1M in THF (529 μl, 0.529 mmol) is added and the mixture is stirred at 60° C. for 4 hours. The reaction mixture is partitioned between water and AcOEt, the organic layer is separated, dried over $Na_2SO_4$ and concentrated. The crude material is purified by silica gel flash chromatography (eluent DCM/AcOEt=1:1) to yield title compound (62 mg, 61.7% yield).

LC-MS (ESI POS): 381.0 (MH+)

Preparation of (4aS,4bR,5S,6aS,6bS,9aR,10aS,10bS,12S)-8-Benzyl-4b,12-difluoro-6b-(2-fluoro-acetyl)-5-hydroxy-4a,6a-dimethyl-4b,5,6,6a,6b,7,8,9,9a,10,10a,10b,11,12-tetradecahydro-4aH-8-aza-pentaleno[2,1-a]phenanthren-2-one (compound 161)

In a closed vessel, to a mixture of compound 160 (125 mg, 0.329 mmol) and N-benzyl-1-methoxy-N-((trimethylsilyl)methyl)methanamine (0.318 ml, 1.314 mmol) in 1,4-dioxane (5 ml), 1 drop of TFA (cat) is added and the mixture is stirred at 100° C. for 1 hour. The reaction mixture is concentrated and purified by silica gel flash chromatography (eluent DCM/AcOEt 7/3) and then by preparative HPLC to afford the title compound (45 mg, 26.7% yield).

$^1$H NMR (300 MHz, DMSO-d6) ppm 7.11-7.47 (m, 6H), 6.29 (dd, 1H), 6.12 (s, 1H), 5.49-5.77 (m, 1H), 5.40 (dd, 1H), 5.26 (dd, 1H), 5.11 (dd, 1H), 4.05-4.22 (m, 1H), 3.49 (d, 1H), 3.44 (d, 1H), 3.03-3.19 (m, 1H), 2.92 (t, 1H), 2.53-2.61 (m, 2H), 2.38 (d, 1H), 2.20-2.33 (m, 1H), 1.93-2.10 (m, 2H), 1.84 (d, 1H), 1.51-1.77 (m, 3H), 1.49 (s, 3H), 1.37 (dd, 1H), 0.91 (s, 3H)

LC-MS (ESI POS): 514.39 MH+
$[α]_D^{25}$+84.2 (c 0.36 CHCl3)

Preparation of (4aS,4bR,5S,6aS,6bS,9aR,10aS,10bS,12S)-8-(3-Chloro-benzyl)-4b,12-difluoro-6b-(2-fluoro-acetyl)-5-hydroxy-4a,6a-dimethyl-4b,5,6,6a,6b,7,8,9,9a,10,10a,10b,11,12-tetradecahydro-4aH-8-aza-pentaleno[2,1-a]phenanthren-2-one (compound 162)

A solution of intermediate 160 (225 mg, 0.591 mmol) and TFA (5 μl, 0.065 mmol) in dioxane (12 ml) is prepared (Solution A). A solution of N-(3-chlorobenzyl)-1-methoxy-N-((trimethylsilyl)methyl)methanamine (1126 mg, 4.14 mmol) in Dioxane (12 ml) is prepared (Solution B). The two solutions are reacted in the Flow reaction System setting each flow at 0.2 ml/min at 100° C. in the 10 ml reactor (Residence time: 25 min). The solvent is evaporated and the residue is triturated in hexane. The solvent is decanted and the obtained crude is purified by preparative HPLC first, then by silica gel flash chromatography (eluent: DCM/AcOEt 9/1). Trituration with petroleum ether gives the title compound (45 mg, 15.8% yield).

$^1$H NMR (300 MHz, DMSO-d6) ppm 7.22-7.42 (m, 4H), 7.18 (dt, 1H), 6.29 (dd, 1H), 6.12 (s, 1H), 5.48-5.81 (m, 1H), 5.40 (d, 1H), 5.27 (dd, 1H), 5.11 (dd, 1H), 3.97-4.25 (m, 1H), 3.51 (d, 1H), 3.45 (d, 1H), 3.01-3.21 (m, 1H), 2.90 (t, 1H), 2.57-2.67 (m, 1H), 2.58 (d, 1H), 2.41 (d, 1H), 2.17-2.34 (m, 1H), 1.91-2.15 (m, 2H), 1.77-1.90 (m, 1H), 1.51-1.78 (m, 3H), 1.49 (s, 3H), 1.37 (dd, 1H), 0.91 (s, 3H)

LC-MS (ESI POS): 548.31 MH+
$[α]_D^{25}$+72.72 (c 0.25, CHCl3)

Example 40

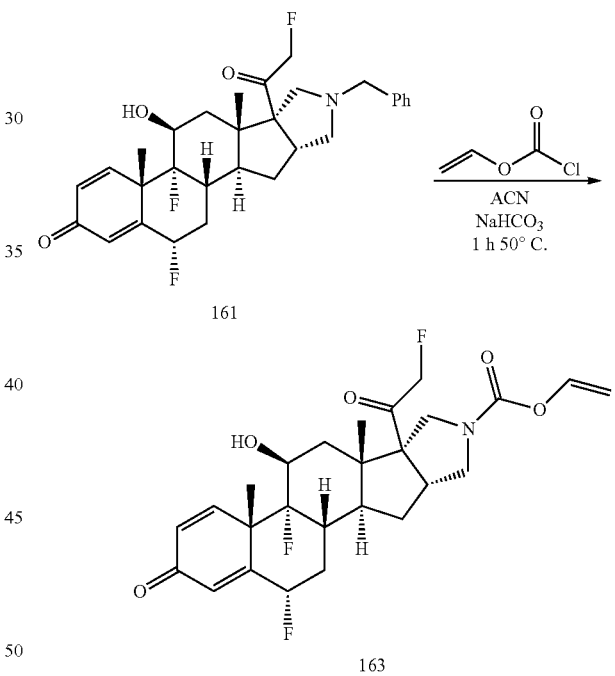

Preparation of (4aS,4bR,5S,6aS,6bS,9aR,10aS,10bS,12S)-4b,12-Difluoro-6b-(2-fluoro-acetyl)-5-hydroxy-4a,6a-dimethyl-2-oxo-2,4b,5,6,6a,6b,7,9,9a,10,10a,10b,11,12-tetradecahydro-4aH-8-aza-pentaleno[2,1-a]phenanthrene-8-carboxylic acid vinyl ester (compound 163) METHOD A Compound 161 (614 mg, 1.196 mmol) and $NaHCO_3$ (100 mg, 1.196 mmol) are dissolved in acetonitrile (12 ml) and then vinyl chloroformate (0.204 ml, 2.391 mmol) is added. The reaction mixture is warmed at 50° C. for 1 hour. The solution is partitioned between AcOEt and water. The organic phase is separated and the aqueous solution is extracted with AcOEt. The combined organic phases are dried over $Na_2SO_4$ and then evaporated to give a residue that is purified by silica gel column chromatography (eluent AcOEt:petroleum ether 2/8 to 8/2) leading to the pure title compound (411 mg, 0.833 mmol, 69.7% yield).

LC-MS (ESI POS): 494.0 MH+

Example 41

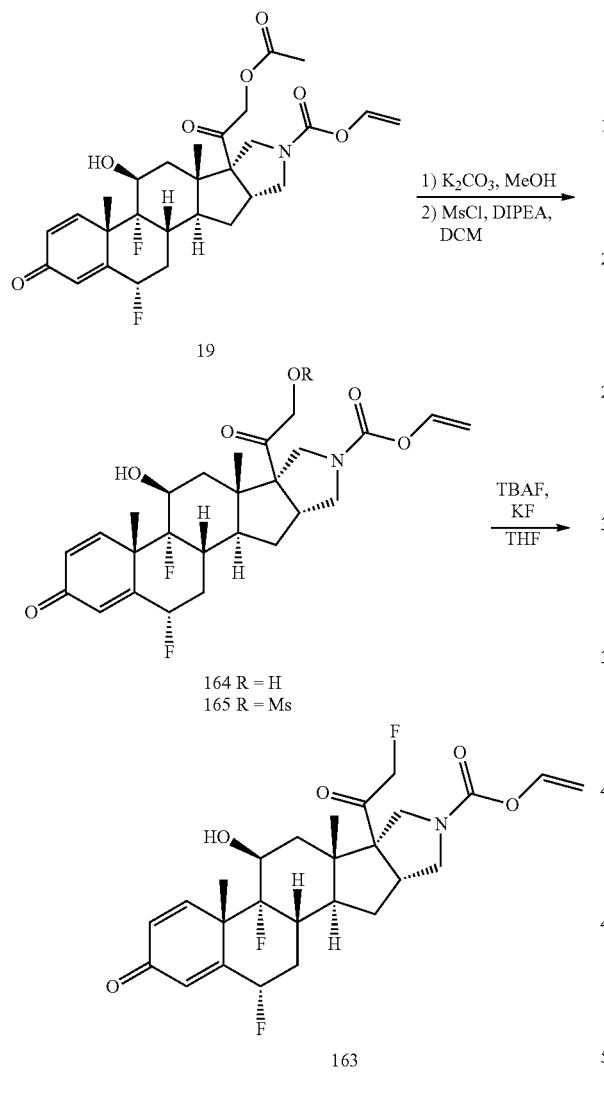

Preparation of (4aS,4bR,5S,6aS,6bS,9aR,10aS,10bS, 12S)-4b,12-Difluoro-5-hydroxy-6b-(2-hydroxy-acetyl)-4a,6a-dimethyl-2-oxo-2,4b,5,6,6a,6b,7,9,9a, 10,10a,10b,11,12-tetradecahydro-4aH-8-aza-pentaleno[2,1-a]phenanthrene-8-carboxylic acid vinyl ester (164)

A solution of compound 19 (1.175 g, 2.202 mmol) in MeOH is degassed with nitrogen at 0° C. for 15 minutes, then $K_2CO_3$ (0.152 g, 1.101 mmol) is added and the mixture is stirred at 0° C. for 1 hour, then the mixture is partitioned between AcOEt and water. The aqueous phase is extracted with AcOEt and the combined organic layers are washed with brine, dried over $Na_2SO_4$ and filtered. The solvent is evaporated to give a solid which is triturated with petroleum ether to give the title compound (1.08 g, 100%).

LC-MS (ESI POS): 492.2 (MH+)

Preparation of (4aS,4bR,5S,6aS,6bS,9aR,10aS,10bS, 12S)-4b,12-Difluoro-5-hydroxy-6b-(2-methanesulfo-nyloxy-acetyl)-4a,6a-dimethyl-2-oxo-2,4b,5,6,6a,6b, 7,9,9a,10,10a,10b,11,12-tetradecahydro-4aH-8-aza-pentaleno[2,1-a]phenanthrene-8-carboxylic acid vinyl ester (165)

A mixture of 164 (840 mg, 1.709 mmol), methansulfonyl chloride (160 μA, 2.051 mmol) and DIPEA (448 μl, 2.56 mmol) in DCM is stirred at RT under nitrogen overnight. The solution is partitioned between DCM and water, then the aqueous phase is extracted with DCM. The combined organic phases are washed with brine, dried over $Na_2SO_4$ and filtered. The solvent is evaporated to give the title compound (774 mg, 80% yield).

LC-MS (ESI POS): 570.0 (MH+)

Preparation of (4aS,4bR,5S,6aS,6bS,9aR,10aS,10bS, 12S)-4b,12-Difluoro-6b-(2-fluoro-acetyl)-5-hy-droxy-4a,6a-dimethyl-2-oxo-2,4b,5,6,6a,6b,7,9,9a, 10,10a,10b,11,12-tetradecahydro-4aH-8-aza-pentaleno[2,1-a]phenanthrene-8-carboxylic acid vinyl ester (compound 163) METHOD B A mixture of 165 (774 mg, 1.359 mmol), TBAF 1M in THF (2038 μl, 2.038 mmol) and potassium fluoride (79 mg, 1.359 mmol) in dry THF (25 ml) is stirred under nitrogen at r.t. for 2 hours, then at reflux for 1 hour 30 minutes. The mixture is partitioned between AcOEt and water, then the aqueous phase is extracted with AcOEt; the combined organic layers are washed with brine, dried over $Na_2SO_4$ and filtered. The solvent is evaporated to give an orange oil which is purified by silica gel chromatography (eluent: DCM/MeOH 98/2) to give the title compound (185 mg, 27.6% yield).

LC-MS (ESI POS): 494.1 (MH+)

Example 42

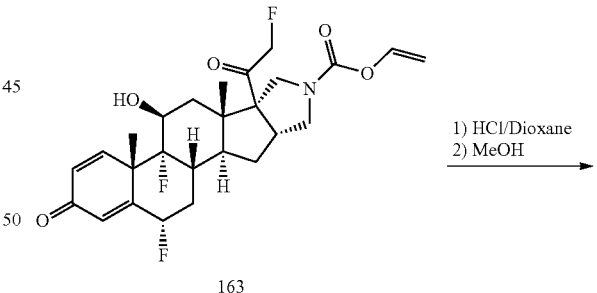

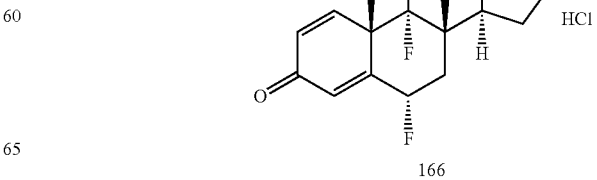

Preparation of (4aS,4bR,5S,6aS,6bS,9aR,10aS,10bS, 12S)-4b,12-Difluoro-6b-(2-fluoro-acetyl)-5-hydroxy-4a,6a-dimethyl-4b,5,6,6a,6b,7,8,9,9a,10,10a, 10b,11,12-tetradecahydro-4aH-8-aza-pentaleno[2,1-a]phenanthren-2-one hydrochloride (compound 166)

Compound 163 (294 mg, 0.596 mmol) is dissolved in DCM (20 ml) and then HCl 4.0 M in dioxane (2.98 ml, 11.91 mmol) is added. The solution is stirred at RT for 5 hours and then the solvent is evaporated and the residue is dried under vacuum for 16 hours. The solid is then dissolved in methanol (30 ml) and warmed at 45° C. for 20 minutes. Methanol is evaporated to give the title compound (274 mg, 0.596 mmol, 100% yield).

LC-MS (ESI POS): 424.0 (MH+)

Example 43

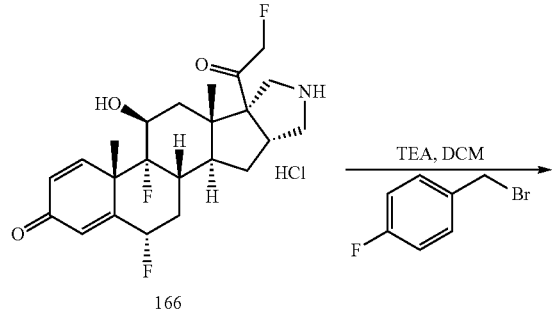

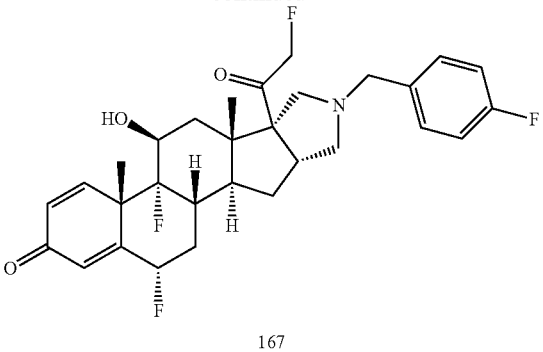

167

Preparation of (4aS,4bR,5S,6aS,6bS,9aR,10aS,10bS, 12S)-4b,12-Difluoro-6b-(2-fluoro-acetyl)-8-(4-fluoro-benzyl)-5-hydroxy-4a,6a-dimethyl-4b,5,6,6a, 6b,7,8,9,9a,10,10a,10b,11,12-tetradecahydro-4aH-8-aza-pentaleno[2,1-a]phenanthren-2-one (compound 167)

A mixture of compound 166 (145 mg, 0.315 mmol), 4-fluorobenzylbromide (0.059 ml, 0.473 mmol) and TEA (0.132 ml, 0.946 mmol) in DCM (10 ml) is stirred at RT overnight. The mixture is diluted with DCM and treated with 5% $NaHCO_3$. The organic phase is then washed with brine, dried over $Na_2SO_4$ and filtered. The solvent is evaporated and the crude is purified by silica gel flash chromatography (eluent DCM(AcOEt 7/3 to 1/1) to yield a solid that is triturated in $Et_2O$. Title compound (54 mg, 32.2% yield) is recovered by filtration.

$^1$H NMR (300 MHz, DMSO-d6) ppm 7.19-7.35 (m, 3H), 7.02-7.18 (m, 2H), 6.29 (dd, 1H), 6.12 (s, 1H), 5.49-5.79 (m, 1H), 5.39 (d, 1H), 5.27 (dd, 1H), 5.10 (dd, 1H), 4.07-4.23 (m, 1H), 3.47 (d, 1H), 3.42 (d, 1H), 3.04-3.17 (m, 1H), 2.91 (t, 1H), 2.54-2.65 (m, 2H), 2.36 (d, 1H), 2.19-2.33 (m, 1H), 1.90-2.08 (m, 2H), 1.84 (d, 1H), 1.51-1.73 (m, 3H), 1.49 (s, 3H), 1.36 (dd, 1H), 0.91 (s, 3H)

LC-MS (ESI POS): 532.31 MH+

$[\alpha]_D^{25}$ +62.6 (c 0.4, MeOH)

Compound listed in Table 28 is prepared using the procedure previously described for compound 167 starting from the suitable commercially available benzylbromide.

TABLE 28

| Compound | Structure | Yield | Analytical |
|---|---|---|---|
| 168 | 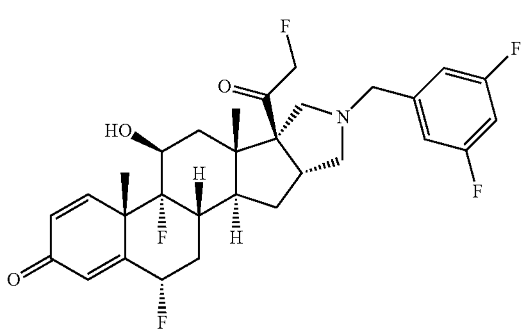 | 31% | $^1$H NMR (300 MHz, DMSO-d6) ppm 7.26 (d, 1 H), 7.05 (tt, 1 H), 6.83-6.99 (m, 2 H), 6.29 (dd, 1 H), 6.12 (s, 1 H), 5.51-5.81 (m, 1 H), 5.29 (dd, 1 H), 5.12 (dd, 1 H), 4.07-4.25 (m, 1 H), 3.54 (d, 1 H), 3.46 (d, 1 H), 3.05-3.19 (m, 1 H), 2.92 (t, 1 H), 2.58 (d, 1 H), 2.55-2.67 (m, 1 H), 2.43 (d, 1 H), 2.23-2.34 (m, 1 H), 1.94-2.12 (m, 2 H), 1.84 (d, 1 H), 1.51-1.76 (m, 4 H), 1.49 (s, 3 H), 1.32-1.43 (m, 1 H), 0.92 (s, 3 H) LC-MS (ESI POS): 550.41 MH+ $[a]_D^{25}$ + 68.2 (c 0.25, MeOH) |

Example 44

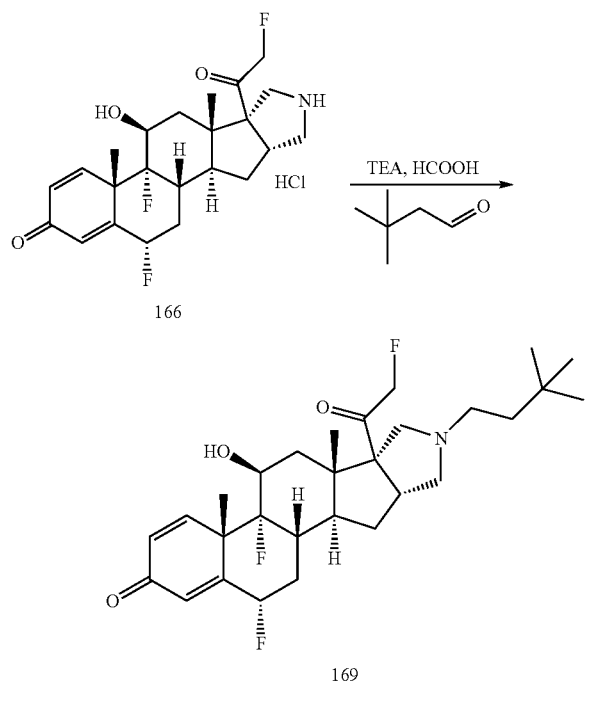

Preparation of (4aS,4bR,5S,6aS,6bS,9aR,10aS,10bS,12S)-8-(3,3-Dimethyl-butyl)-4b,12-difluoro-6b-(2-fluoro-acetyl)-5-hydroxy-4a,6a-dimethyl-4b,5,6,6a,6b,7,8,9,9a,10,10a,10b,11,12-tetradecahydro-4aH-8-aza-pentaleno[2,1-a]phenanthren-2-one (compound 169)

In a closed vessel, compound 166 (180 mg, 0.391 mmol), 3,3-dimethylbutanal (0.196 ml, 1.565 mmol) and TEA (0.055 ml, 0.391 mmol) are dissolved in acetonitrile (4 ml). Formic acid (0.120 ml, 3.13 mmol) is added and the mixture is heated under microwave irradiation for 15 minutes at 140° C. LC-MS shows that the reaction is complete. The reaction mixture is diluted with AcOEt and the organic phase is washed with a saturated solution of NaHCO$_3$ and with brine. The organic layer is dried over Na$_2$SO$_4$ and filtered. The solvent is evaporated to give an orange oil which is purified by preparative HPLC (acetonitrile/water, neutral phase) to yield the title compound (55 mg, 0.108 mmol, 27.7% yield).

$^1$H NMR (300 MHz, DMSO-d6) ppm 7.26 (dd, 1H), 6.29 (dd, 1H), 6.11 (s, 1H), 5.48-5.78 (m, 1H), 5.39 (dd, 1H), 5.31 (dd, 1H), 5.07 (dd, 1H), 4.05-4.24 (m, 1H), 2.99-3.13 (m, 1H), 2.87-2.97 (m, 1H), 2.59 (d, 1H), 2.54-2.59 (m, 1H), 2.33 (d, 1H), 2.14-2.30 (m, 3H), 1.86-2.06 (m, 2H), 1.52-1.86 (m, 4H), 1.49 (s, 3H), 1.34 (dd, 1H), 1.26 (t, 2H), 0.90 (s, 3H), 0.84 (s, 9H)

LC-MS (ESI POS): 508.46 MH+

$[\alpha]_D^{25}$ +64.3 (c 0.24, MeOH)

Compounds listed in Table 29 are prepared using the procedure previously described for compound 169 starting from the suitable commercially available aldehydes. For compound 173, 4-((4-hydroxyphenylthio)methyl)benzaldehyde is prepared as described in WO2009/069032 A2, which is incorporated herein by reference in its entirety.

TABLE 29

| Compound | Structure | Yield | Analytical |
|---|---|---|---|
| 170 | 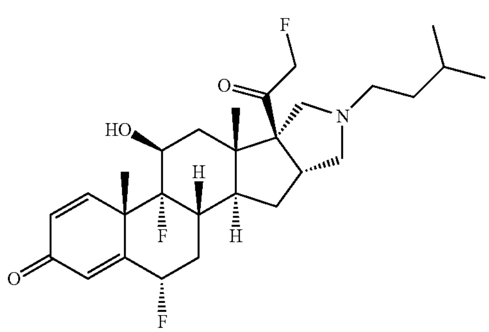 | 33% | $^1$H NMR (300 MHz, DMSO-d6) ppm 7.25 (m, 1 H), 6.29 (dd, 1 H), 6.11 (s, 1 H), 5.45-5.81 (m, 1 H), 5.38-5.43 (m, 1 H), 5.34 (dd, 1 H), 5.07 (dd, 1 H), 4.12-4.19 (m, 1 H), 2.99-3.14 (m, 1 H), 2.82-2.96 (m, 1 H), 2.57 (d, 2 H), 2.33 (d, 1 H), 2.16-2.30 (m, 3 H), 1.81-2.01 (m, 3 H), 1.51-1.81 (m, 3 H), 1.49 (s, 3 H), 1.40-1.46 (m, 1 H), 1.18-1.40 (m, 3 H), 0.91 (s, 3 H), 0.82 (d, 6 H) LC-MS (ESI POS): 494.34 MH+ $[a]_D^{25}$ + 61.7 (c 0.5, MeOH) |
| 171 | 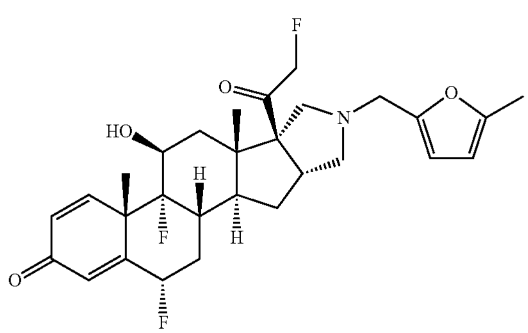 | 22% | $^1$H NMR (300 MHz, DMSO-d6) ppm 7.26 (dd, 1 H), 6.29 (dd, 1 H), 6.11 (d, 1 H), 6.03 (d, 1 H), 5.95 (dq, 1 H), 5.50-5.76 (m, 1 H), 5.40-5.44 (m, 0 H), 5.29 (dd, 1 H), 5.08 (dd, 1 H), 4.08-4.20 (m, 1 H), 3.45 (d, 1 H), 3.36 (d, 1 H), 3.03-3.17 (m, 1 H), 2.96 (t, 1 H), 2.67 (d, 1 H), 2.54-2.64 (m, 1 H), 2.37 (d, 1 H), 2.22-2.31 (m, 1 H), 2.19 (s, 3 H), 1.79-2.01 (m, 4 H), 1.51-1.78 (m, 3 H), 1.49 (s, 3 H), 1.34 (dd, 1 H), 0.90 (s, 3 H) LC-MS (ESI POS): 518.4 MH+ $[a]_D^{25}$ + 57.0 (c 0.34, MeOH) |

TABLE 29-continued

| Compound | Structure | Yield | Analytical |
|---|---|---|---|
| 172 | 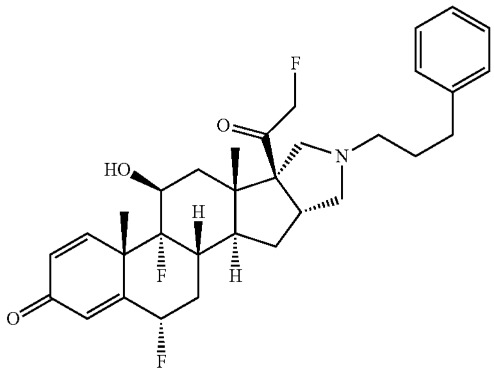 | 39% | ¹H NMR (300 MHz, DMSO-d6) ppm 7.08-7.33 (m, 6 H), 6.29 (dd, 1 H), 6.10 (s, 1 H), 5.47-5.77 (m, 1 H), 5.39 (dd, 1 H), 5.31 (dd, 1 H), 5.09 (dd, 1 H), 4.08-4.22 (m, 1 H), 2.99-3.17 (m, 1 H), 2.84 (t, 1 H), 2.55-2.66 (m, 4 H), 2.41 (d, 1 H), 2.11-2.33 (m, 3 H), 1.93-2.09 (m, 2 H), 1.53-1.93 (m, 6 H), 1.49 (s, 3 H), 1.36 (dd, 1 H), 0.92 (s, 3 H)<br>LC-MS (ESI POS): 542.31 MH+<br>$[a]_D^{25}$ + 47.4 (c 0.3, MeOH) |
| 173 | 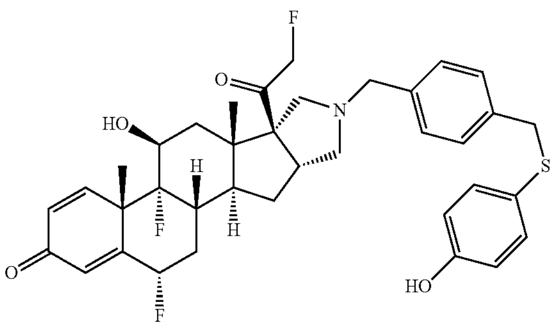 | 30% | ¹H NMR (300 MHz, DMSO-d6) ppm 9.51 (br. s., 1 H), 7.26 (d, 1 H), 7.01-7.20 (m, 6 H), 6.56-6.80 (m, 2 H), 6.29 (dd, 1 H), 6.13 (s, 1 H), 5.49-5.83 (m, 1 H), 5.40 (br. s., 1 H), 5.24 (dd, 1 H), 5.09 (dd, 1 H), 4.07-4.24 (m, 1 H), 4.00 (s, 2 H), 3.35-3.49 (m, 2 H), 3.01-3.17 (m, 1 H), 2.90 (t, 1 H), 2.55-2.67 (m, 2 H), 2.36 (d, 1 H), 2.19-2.32 (m, 1 H), 1.92-2.10 (m, 2 H), 1.84 (d, 1 H), 1.51-1.75 (m, 3 H), 1.49 (s, 3 H), 1.36 (dd, 1 H), 0.91 (s, 3 H)<br>LC-MS (ESI POS): 652.24 MH+<br>$[a]_D^{25}$ + 68.3 (c 0.8, MeOH) |
| 174 | 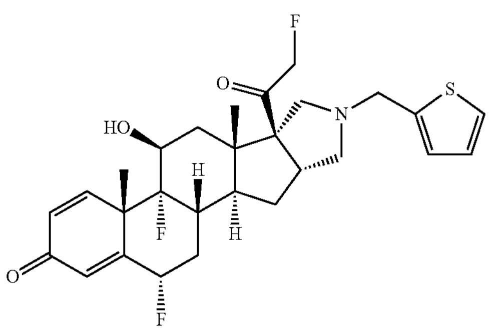 | 41% | ¹H NMR (300 MHz, DMSO-d6) ppm 7.39 (dd, 1 H), 7.26 (dd, 1 H), 6.92 (dd, 1 H), 6.89 (dd, 1 H), 6.29 (dd, 1 H), 6.12 (s, 1 H), 5.48-5.83 (m, 1 H), 5.38-5.45 (m, 1 H), 5.27 (dd, 1 H), 5.09 (dd, 1 H), 4.02-4.22 (m, 1 H), 3.68 (s, 2 H), 3.03-3.19 (m, 1 H), 2.92 (t, 1 H), 2.54-2.64 (m, 2 H), 2.39-2.47 (m, 1 H), 2.20-2.36 (m, 1 H), 2.14 (dd, 1 H), 1.92-2.06 (m, 1 H), 1.84 (d, 1 H), 1.51-1.76 (m, 3 H), 1.49 (s, 3 H), 1.38 (dd, 1 H), 0.91 (s, 3 H)<br>LC-MS (ESI POS): 520.23 MH+<br>$[a]_D^{25}$ + 77.1 (c 0.4, MeOH) |
| 175 | 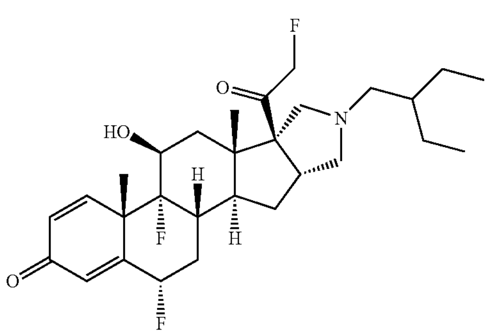 | 32% | ¹H NMR (300 MHz, DMSO-d₆) ☐ ppm 7.26 (dd, 1 H), 6.29 (dd, 1 H), 6.11 (s, 1 H), 5.47-5.78 (m, 1 H), 5.38-5.42 (m, 0 H), 5.29 (dd, 1 H), 5.07 (dd, 1 H), 4.03-4.25 (m, 1 H), 2.97-3.14 (m, 1 H), 2.79 (dd, 1 H), 2.54-2.60 (m, 1 H), 2.40-2.48 (m, 2 H), 2.18-2.33 (m, 1 H), 1.93-2.17 (m, 4 H), 1.83-1.92 (m, 1 H), 1.51-1.83 (m, 3 H), 1.49 (s, 3 H), 1.09-1.46 (m, 7 H), 0.91 (s, 3 H), 0.78 (t, 6 H)<br>LC-MS (ESI POS): 508.30 MH+<br>$[a]_D^{25}$ + 43.2 (c 0.22, MeOH) |

Example 45

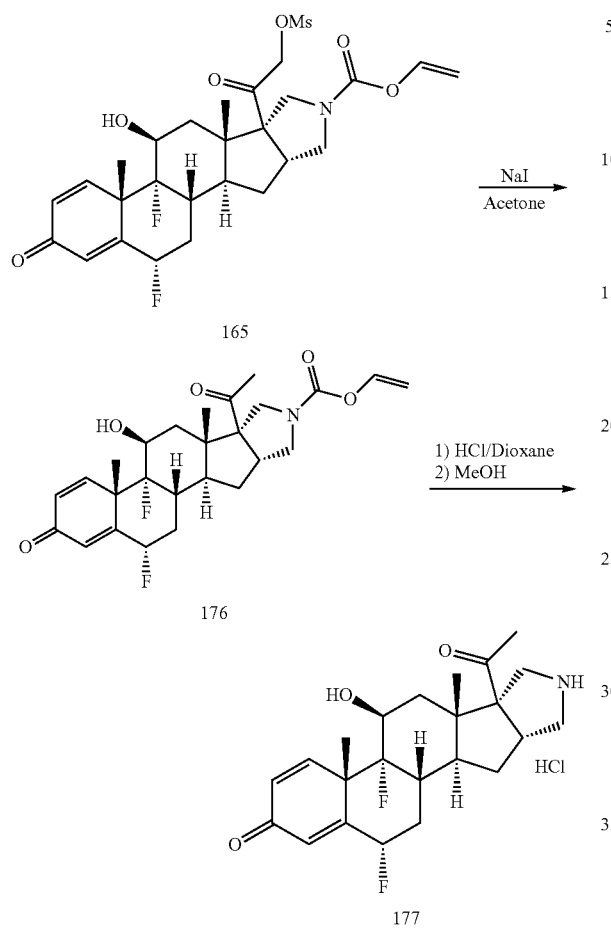

Preparation of (4aS,4bR,5S,6aS,6bS,9aR,10aS,10bS,12S)-6b-Acetyl-4b,12-difluoro-5-hydroxy-4a,6a-dimethyl-2-oxo-2,4b,5,6,6a,6b,7,9,9a,10,10a,10b,11,12-tetradecahydro-4aH-8-aza-pentaleno[2,1-a]phenanthrene-8-carboxylic acid vinyl ester (compound 176)

In a closed vessel, a mixture of compound 165 (592 mg, 1.039 mmol) and sodium iodide (2181 mg, 14.55 mmol) in acetone (25 ml) is heated under microwave irradiation for 3 hours at 110° C. The reaction mixture is partitioned between AcOEt and a 5% solution of $Na_2S_2O_5$. The organic phase is washed with brine, dried over $Na_2SO_4$ and filtered. The solvent is evaporated to give the title compound (495 mg, 100%).

LC-MS (ESI POS): 476.0 MH+

Preparation of (4aS,4bR,5S,6aS,6bS,9aR,10aS,10bS,12S)-6b-Acetyl-4b,12-difluoro-5-hydroxy-4a,6a-dimethyl-4b,5,6,6a,6b,7,8,9,9a,10,10a,10b,11,12-tetradecahydro-4aH-8-aza-pentaleno[2,1-a]phenanthren-2-one hydrochloride (compound 177)

A solution of compound 176 (495 mg, 1.041 mmol) and HCl 4M in dioxane (5205 µl, 20.82 mmol) in DCM (20 ml) is stirred at RT for 30 minutes. The solvent is evaporated and the crude is dried in vacuo for 16 hours. The crude is dissolved in MeOH (30 ml) and stirred at 45° C. for 30 minutes. The solvent is evaporated and the crude is triturated with AcOEt/Et2O (1/1 mixture) to afford the title compound (457 mg, 99%).

LC-MS (ESI POS): 406.0 MH+

Example 46

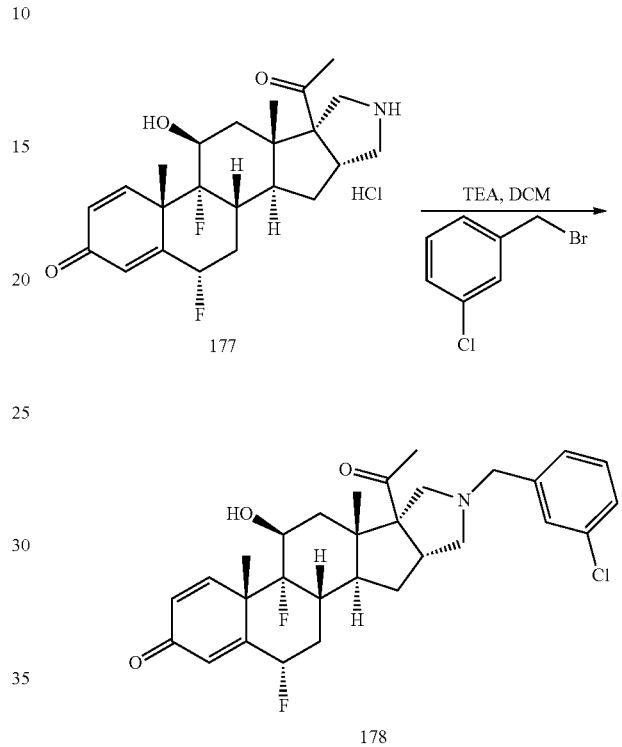

Preparation of (4aS,4bR,5S,6aS,6bS,9aR,10aS,10bS,12S)-6b-Acetyl-8-(3-chloro-benzyl)-4b,12-difluoro-5-hydroxy-4a,6a-dimethyl-4b,5,6,6a,6b,7,8,9,9a,10,10a,10b,11,12-tetradecahydro-4aH-8-aza-pentaleno[2,1-a]phenanthren-2-one (compound 178)

A mixture of compound 177 (143 mg, 0.324 mmol), 1-(bromomethyl)-3-chlorobenzene (55.1 µl, 0.421 mmol) and TEA (113 µl, 0.809 mmol) in DCM (10 ml) is stirred under nitrogen at RT overnight. The crude is purified by silica gel chromatography (eluent: AcOEt/petroleum ether 1/1) and by trituration with diisopropylether to afford (79 mg, 46.1% yield).

$^1$H NMR (300 MHz, DMSO-d6) ppm 7.11-7.43 (m, 5H), 6.30 (dd, 1H), 6.13 (s, 1H), 5.64-5.84 (m, 1H), 5.41 (dd, 1H), 4.17 (dd, 1H), 3.47 (s, 2H), 3.05-3.22 (m, 1H), 2.71-2.85 (m, 2H), 2.53-2.62 (m, 2H), 2.20-2.35 (m, 1H), 2.11 (d, 2H), 2.08 (s, 3H), 1.69-1.94 (m, 2H), 1.51-1.69 (m, 2H), 1.49 (s, 3H), 1.27-1.40 (m, 1H), 0.87 (s, 3H)

LC-MS (ESI POS): 530.25 MH+

$[\alpha]_D^{25}$+62.69 (c 0.26, MeOH)

Compound listed in Table 30 is prepared using the procedure previously described for compound 178 starting from the suitable commercially available benzylhalide.

TABLE 30

| Compound | Structure | Yield | Analytical |
|---|---|---|---|
| 179 | 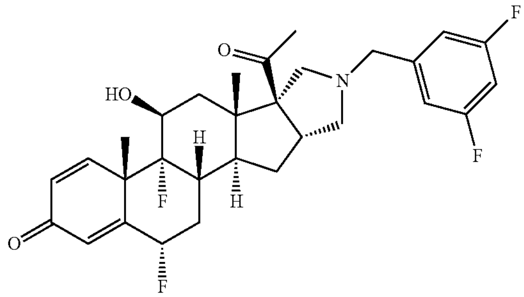 | 47% | ¹H NMR (300 MHz, DMSO-d6) ppm 7.26 (dd, 1 H), 7.04 (tt, 1 H), 6.79-6.98 (m, 2 H), 6.30 (dd, 1 H), 6.13 (s, 1 H), 5.49-5.80 (m, 1 H), 5.40 (dd, 1 H), 4.05-4.35 (m, 1 H), 3.49 (s, 2 H), 3.04-3.21 (m, 1 H), 2.69-2.88 (m, 1 H), 2.54-2.66 (m, 3 H), 2.21-2.36 (m, 1 H), 2.12 (dd, 1 H), 2.09 (s, 3 H), 2.00-2.07 (m, 1 H), 1.72-1.92 (m, 2 H), 1.51-1.68 (m, 2 H), 1.49 (s, 3 H), 1.27-1.39 (m, 1 H), 0.87 (s, 3 H)<br>LC-MS (ESI POS): 532.3 MH+<br>$[\alpha]_D^{25}$ + 69.7 (c 0.28, MeOH) |

Example 47

Preparation of (4aS,4bR,5S,6aS,6bS,9aR,10aS,10bS,12S)-6b-Acetyl-4b,12-difluoro-5-hydroxy-4a,6a-dimethyl-8-(5-methyl-furan-2-ylmethyl)-4b,5,6,6a,6b,7,8,9,9a,10,10a,10b,11,12-tetradecahydro-4aH-8-aza-pentaleno[2,1-a]phenanthren-2-one (compound 180)

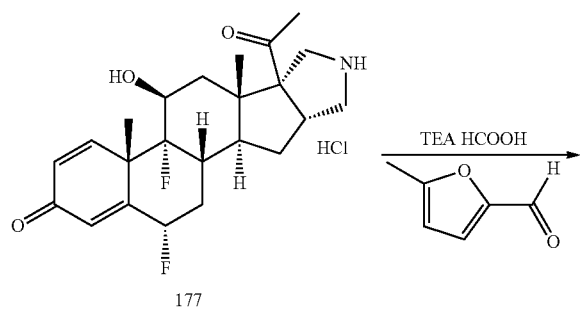

In a closed vessel, a mixture of compound 177 (306 mg, 0.692 mmol), 5-methylfurfural (344 µl, 3.46 mmol), TEA (97 µl, 0.692 mmol) and formic acid (266 µl, 6.92 mmol) in acetonitrile (15 ml) is heated under microwave irradiation for 15 minutes at 140° C. LC-MS shows that the reaction is complete. The solution is partitioned between AcOEt and a saturated solution of NaHCO₃, the aqueous phase is extracted with AcOEt and the combined organic layers are washed with brine, dried over Na₂SO₄ and filtered. The solvent is evaporated to give a oil which is purified by silica gel chromatography (eluent AcOEt/petroleum ether 1/1). Trituration with petroleum ether affords the title compound (236 mg, 0.472 mmol, 68.2% yield).

¹H NMR (300 MHz, DMSO-d6) ppm 7.26 (dd, 1H), 6.30 (dd, 1H), 6.12 (s, 1H), 6.02 (d, 1H), 5.94 (dq, 1H), 5.63 (m, 1H), 5.41 (dd, 1H), 4.09-4.24 (m, 1H), 3.43 (d, 1H), 3.33 (d, 1H), 3.02-3.20 (m, 1H), 2.81 (t, 1H), 2.64 (d, 1H), 2.39-2.47 (m, 2H), 2.20-2.34 (m, 1H), 2.19 (s, 3H), 2.09 (s, 3H), 1.93-2.06 (m, 2H), 1.74-1.93 (m, 2H), 1.49 (s, 3H), 1.39-1.65 (m, 2H), 1.30 (dd, 1H), 0.85 (s, 3H)

LC-MS (ESI POS): 500.32 MH+
$[\alpha]_D^{25}$+49.17 (c 2.4, MeOH)

Compounds listed in Table 31 are prepared using the procedure previously described for compound 180 starting from the suitable commercially available aldehydes.

TABLE 31

| Compound | Structure | Yield | Analytical |
|---|---|---|---|
| 181 | 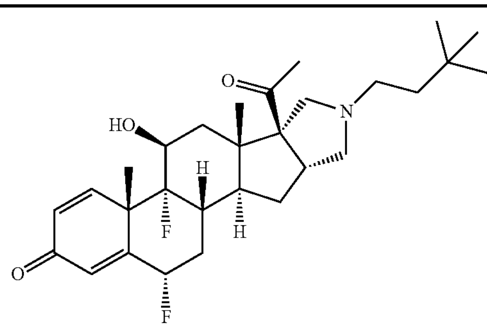 | 61% | ¹H NMR (300 MHz, DMSO-d6) ppm 7.26 (dd, 1 H), 6.29 (dd, 1 H), 6.11 (s, 1 H), 5.45-5.84 (m, 1 H), 5.40 (d, 1 H), 4.18 (dd, 1 H), 3.05-3.13 (m, 1 H), 2.67-2.75 (m, 1 H), 2.39-2.48 (m, 2 H), 2.16-2.30 (m, 3 H), 2.10 (s, 3 H), 1.94-2.14 (m, 2 H), 1.87 (br. s., 2 H), 1.49 (s, 3 H), 1.42-1.58 (m, 2 H), 1.21-1.34 (m, 4 H), 0.86 (br. s., 3 H), 0.84 (s, 9 H)<br>LC-MS (ESI POS): 490.38 MH+<br>$[\alpha]_D^{25}$ + 51.48 (c 0.31, MeOH) |

TABLE 31-continued

| Compound | Structure | Yield | Analytical |
|---|---|---|---|
| 182 | 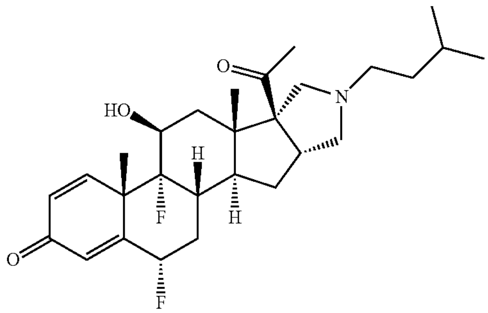 | 50% | ¹H NMR (300 MHz, DMSO-d6) ppm 7.27 (dd, 1 H), 6.29 (dd, 1 H), 6.1 (s, 1 H), 5.46-5.81 (m, 1 H), 5.40 (dd, 1 H), 4.02-4.30 (m, 1 H), 3.01-3.15 (m, 1 H), 2.65-2.73 (m, 1 H), 2.53-2.60 (m, 1 H), 2.43-2.47 (m, 2 H), 2.15-2.31 (m, 3 H), 2.10 (s, 3 H), 1.82-2.07 (m, 4 H), 1.51-1.67 (m, 2 H), 1.49 (s, 3 H), 1.39-1.47 (m, 1 H), 1.16-1.34 (m, 3 H), 0.86 (s, 3 H), 0.83 (d, 3 H), 0.82 (d, 3 H) LC-MS (ESI POS): 476.29 MH+ [a]$_D^{25}$ + 68.32 (c 0.25, MeOH) |
| 183 | 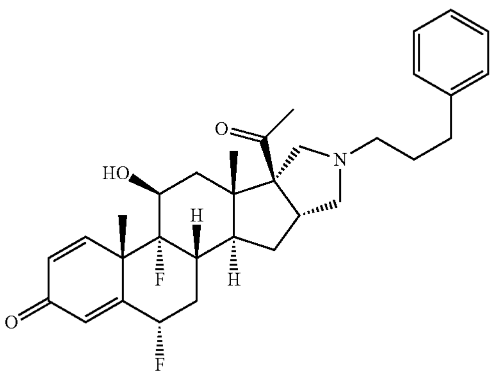 | 45% | ¹H NMR (300 MHz, DMSO-d6) ppm 7.19-7.31 (m, 3 H), 7.05-7.18 (m, 3 H), 6.29 (dd, 1 H), 6.10 (s, 1 H), 5.48-5.80 (m, 1 H), 5.41 (dd, 1 H), 3.98-4.31 (m, 1 H), 2.93-3.20 (m, 1 H), 2.64 (dd, 1 H), 2.53-2.59 (m, 4 H), 2.41 (d, 1 H), 2.13-2.35 (m, 3 H), 2.10 (s, 3 H), 1.96-2.09 (m, 2 H), 1.86-1.95 (m, 2 H), 1.52-1.72 (m, 3 H), 1.49 (s, 3 H), 1.39-1.48 (m, 1 H), 1.32 (dd, 1 H), 0.87 (s, 3 H) LC-MS (ESI POS): 524.33 MH+ [a]$_D^{25}$ + 59.4 (c 0.24, MeOH) |
| 184 | 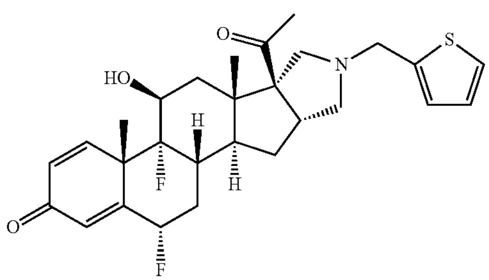 | 47% | ¹H NMR (300 MHz, DMSO-d6) ppm 7.38 (dd, 1 H), 7.27 (dd, 1 H), 6.92 (dd, 1 H), 6.88 (m, 1 H), 6.30 (dd, 1 H), 6.13 (s, 1 H), 5.46-5.82 (m, 1 H), 5.40 (d, 1 H), 4.01-4.32 (m, 1 H), 3.65 (s, 2 H), 3.03-3.22 (m, 1 H), 2.69-2.86 (m, 1 H), 2.54-2.63 (m, 2 H), 2.38-2.46 (m, 1 H), 2.25-2.35 (m, 1 H), 2.20 (dd, 1 H), 2.07 (s, 3 H), 1.99-2.06 (m, 1 H), 1.70-1.96 (m, 2 H), 1.51-1.67 (m, 2 H), 1.49 (s, 3 H), 1.34 (dd, 1 H), 0.86 (s, 3 H) LC-MS (ESI POS): 502.22 MH+ [a]$_D^{25}$ + 92.8 (c 0.25, MeOH) |

Example 48

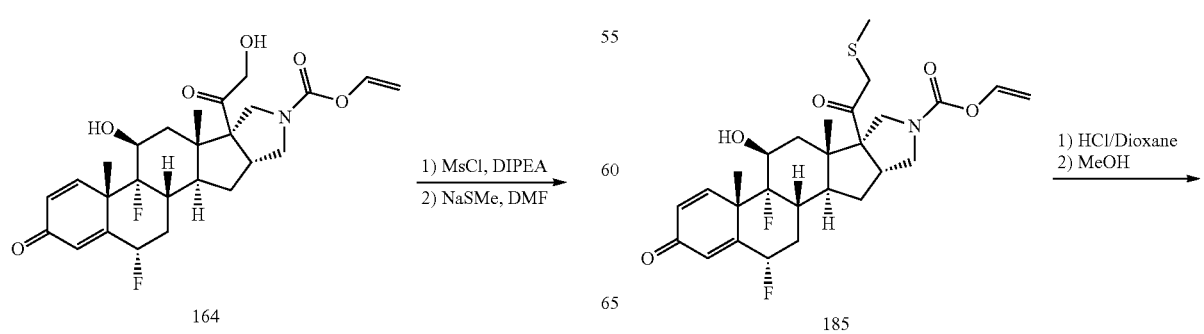

-continued

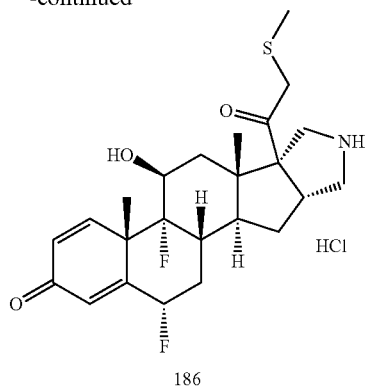

Preparation of (4aS,4bR,5S,6aS,6bS,9aR,10aS,10bS,12S)-4b,12-Difluoro-5-hydroxy-4a,6a-dimethyl-6b-(2-methylsulfanyl-acetyl)-2-oxo-2,4b,5,6,6a,6b,7,9,9a,10,10a,10b,11,12-tetradecahydro-4aH-8-aza-pentaleno[2,1-a]phenanthrene-8-carboxylic acid vinyl ester (compound 185)

A mixture of compound 164 (203 mg, 0.413 mmol), methansulfonyl chloride (38.6 µl, 0.496 mmol) and DIPEA (108 µl, 0.620 mmol) in dry DMF (3 ml) is stirred at RT under nitrogen for 1 hour. Further methansulfonyl chloride (16.09 µl, 0.207 mmol) and DIPEA (54.1 µl, 0.310 mmol) are added and the mixture is stirred at RT for 2 hours. Sodiumethanethiolate (87 mg, 1.239 mmol) is added and the mixture is stirred at RT for 16 hours. The reaction the mixture is partitioned between AcOEt and brine, then the aqueous phase is extracted with AcOEt and the combined organic layers are washed with brine, dried over $Na_2SO_4$ and filtered. The solvent is evaporated to give a oil which is purified by silica gel chromatography (eluent: AcOEt/petroleum ether 2/3) to afford the title compound (118 mg, 0.226 mmol, 54.8% yield).

LC-MS (ESI POS): 544.3 M+Na+

Preparation of (4aS,4bR,5S,6aS,6bS,9aR,10aS,10bS,12S)-4b,12-Difluoro-5-hydroxy-4a,6a-dimethyl-6b-(2-methylsulfanyl-acetyl)-4b,5,6,6a,6b,7,8,9,9a,10,10a,10b,11,12-tetradecahydro-4aH-8-aza-pentaleno[2,1-a]phenanthren-2-one hydrochloride (compound 186)

A mixture of compound 185 (122 mg, 0.234 mmol) and HCl 4M in Dioxane (2 ml, 8.00 mmol) in DCM (10 ml) is stirred at RT for 2 hours, then the solvent is evaporated and the crude is dried in vacuo for 16 hours. MeOH (15 ml) is added and the solution is stirred at 45° C. for 20 minutes. The solvent is evaporated to afford the title compound (106 mg, 93% yield).

LC-MS (ESI POS): 452.3 MH+

Example 49

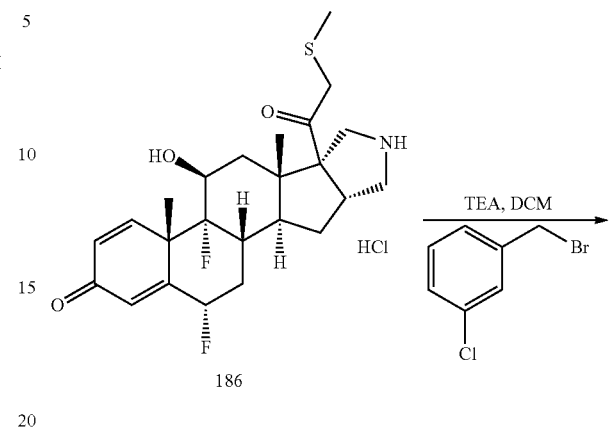

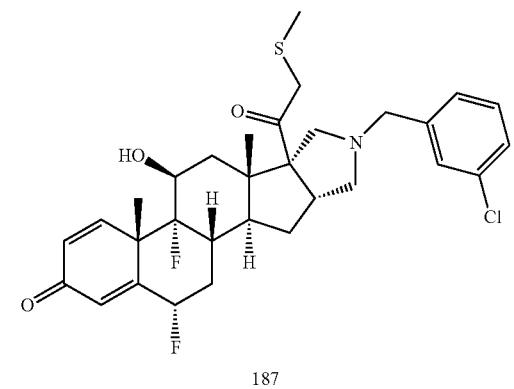

Preparation of (4aS,4bR,5S,6aS,6bS,9aR,10aS,10bS,12S)-8-(3-Chloro-benzyl)-4b,12-difluoro-5-hydroxy-4a,6a-dimethyl-6b-(2-methylsulfanyl-acetyl)-4b,5,6,6a,6b,7,8,9,9a,10,10a,10b,11,12-tetradecahydro-4aH-8-aza-pentaleno[2,1-a]phenanthren-2-one (compound 187)

A solution of compound 186 (103 mg, 0.211 mmol), 3-chorobenzylbromide (66.0 µl, 0.317 mmol) and TEA (88 µl, 0.633 mmol) in DCM (10 ml) is stirred under nitrogen at RT for 16 hours. The solution is diluted with DCM and washed with brine, dried over $Na_2SO_4$ and filtered. The solvent is evaporated and the crude is purified by silica gel chromatography (eluent: DCM/MeOH 99/1). Trituration with petroleum ether affords the title compound (36 mg, 29.6% yield).

$^1$H NMR (300 MHz, DMSO-d6) ppm 7.04-7.40 (m, 5H), 6.29 (dd, 1H), 6.12 (s, 1H), 5.45-5.80 (m, 1H), 5.39 (dd, 1H), 4.08-4.25 (m, 1H), 3.63 (d, 1H), 3.41-3.54 (m, 3H), 3.08-3.24 (m, 1H), 2.89 (t, 1H), 2.61 (d, 1H), 2.56-2.61 (m, 1H), 2.44 (d, 1H), 2.22-2.36 (m, 1H), 2.06-2.16 (m, 2H), 2.05 (s, 3H), 1.52-1.94 (m, 4H), 1.49 (s, 3H), 1.35 (dd, 1H), 0.90 (s, 3H)

LC-MS (ESI POS): 576.21 MH+

$[\alpha]_D^{25}$ +83.36 (c 0.28, MeOH)

Example 50

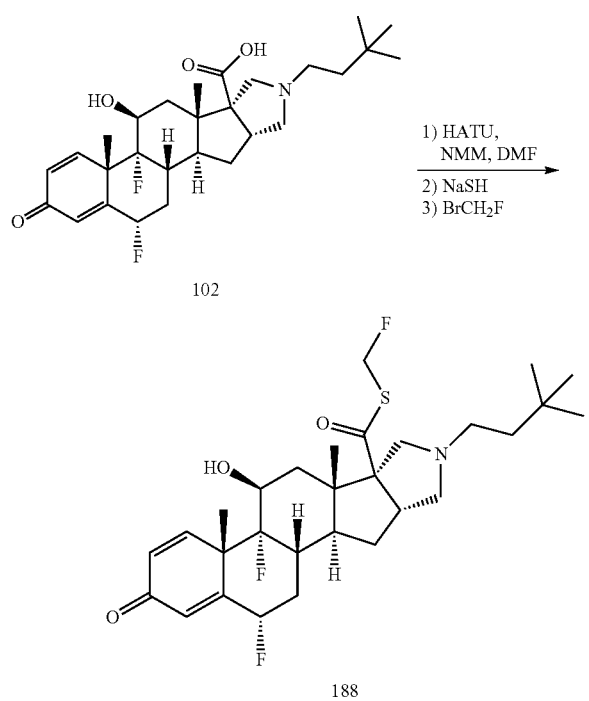

Preparation of (4aS,4bR,5S,6aS,6bS,9aR,10aS,10bS,12S)-8-(3,3-Dimethyl-butyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carbothioic acid S-fluoromethyl ester (compound 188)

A mixture of compound 102 (177 mg, 0.360 mmol), HATU (151 mg, 0.396 mmol) and N-methylmorpholine (0.044 ml, 0.396 mmol) in dry DMF (4 ml) is stirred at 60° C. under nitrogen for 40 minutes. After cooling to RT, anhydrous sodium hydrogensulfide (60.6 mg, 1.080 mmol) is added and the solution is stirred at RT for 1 hour. Bromofluoromethane (0.360 ml, 0.720 mmol, solution 2M in DMF) is added and the mixture is stirred at RT for 1 hour. The reaction mixture is partitioned between AcOEt and brine, the aqueous phase is extracted with AcOEt and the combined organic layers are dried over $Na_2SO_4$ and filtered. After evaporation of the solvent, the crude is purified by preparative HPLC (CH3CN/H2O, No CF3COOH) to afford the title compound (52 mg, 0.096 mmol, 26.8% yield).

$^1$H NMR (300 MHz, DMSO-d6) ppm 7.25 (dd, 1H), 6.30 (dd, 1H), 6.11 (s, 1H), 5.94 (dd, 1H), 5.89 (dd, 1H), 5.54-5.76 (m, 1H), 5.53 (dd, 1H), 4.06-4.25 (m, 1H), 3.11-3.24 (m, 1H), 2.97 (t, 1H), 2.83 (d, 1H), 2.55-2.62 (m, 1H), 2.38 (d, 1H), 2.19-2.31 (m, 3H), 1.88-2.06 (m, 3H), 1.53-1.82 (m, 2H), 1.49 (s, 3H), 1.31-1.47 (m, 2H), 1.20-1.30 (m, 2H), 0.95 (s, 3H), 0.84 (s, 9H).

LC-MS (ESI POS): 540.6 MH+
$[\alpha]_D^{25}$ +68.6 (c 0.34, MeOH)

Compounds listed in Table 32 are prepared using the procedure previously described for compound 188 starting from the suitable carboxylic acids 99,100,101 previously described.

TABLE 32

| Compound | Structure | Yield | Analytical |
|---|---|---|---|
| 189 | 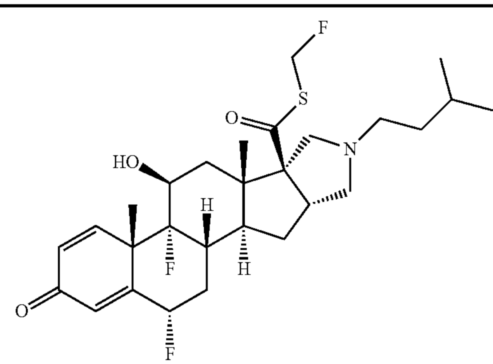 | 30% | $^1$H NMR (300 MHz, DMSO-d6) ppm 7.25 (dd, 1 H), 6.30 (dd, 1 H), 6.11 (s, 1 H), 5.94 (dd, 1 H), 5.89 (dd, 1 H), 5.53-5.77 (m, 1 H), 5.53 (dd, 1 H), 4.10-4.28 (m, 1 H), 3.13-3.25 (m, 1 H), 2.95 (t, 1 H), 2.82 (d, 1 H), 2.56-2.67 (m, 1 H), 2.38 (d, 1 H), 2.17-2.31 (m, 3 H), 1.88-2.09 (m, 3 H), 1.52-1.84 (m, 5 H), 1.49 (s, 3 H), 1.36 (dd, 1 H), 1.18-1.29 (m, 1 H), 0.95 (s, 3 H), 0.82 (d, 6 H) LC-MS (ESI POS): 526.39 MH+ $[a]_D^{25}$ + 59.17 (c 0.29, CHCl3) |
| 190 | 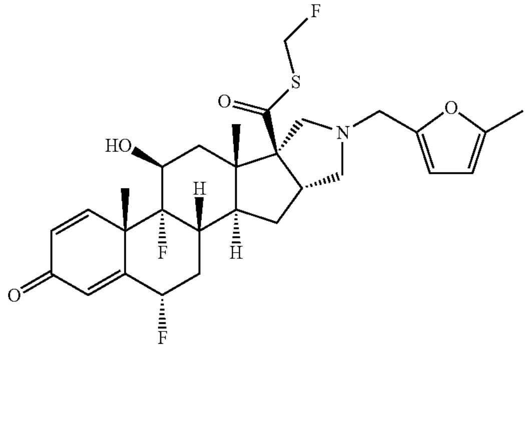 | 23% | $^1$H NMR (300 MHz, DMSO-d6) ppm 7.25 (dd, 1 H), 6.30 (dd, 1 H), 6.12 (s, 1 H), 6.04 (d, 1 H), 5.94 (dq, 1 H), 5.94 (dd, 1 H), 5.89 (dd, 1 H), 5.55-5.74 (m, 1 H), 5.53 (dd, 1 H), 4.07-4.26 (m, 1 H), 3.45 (d, 1 H), 3.38 (d, 1 H), 3.15-3.25 (m, 1 H), 3.02 (t, 1 H), 2.93 (d, 1 H), 2.56-2.68 (m, 1 H), 2.42 (d, 1 H), 2.21-2.33 (m, 1 H), 2.18 (d, 3 H), 1.89-2.06 (m, 3 H), 1.52-1.77 (m, 3 H), 1.49 (s, 3 H), 1.30-1.42 (m, 1 H), 0.94 (s, 3 H) LC-MS (ESI POS): 550.25 MH+ $[a]_D^{25}$ + 61.7 (c 0.45, MeOH) |

TABLE 32-continued

| Compound | Structure | Yield | Analytical |
|---|---|---|---|
| 191 | 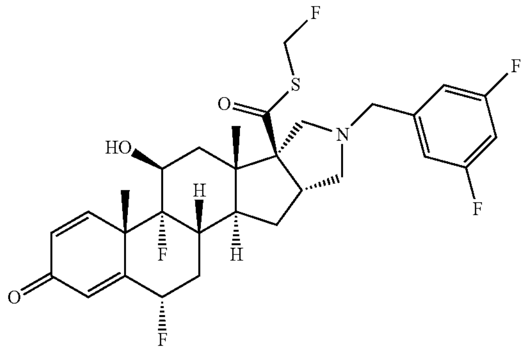 | 20% | ¹H NMR (300 MHz, DMSO-d6) ppm 7.25 (dd, 1 H), 7.05 (tt, 1 H), 6.83-6.98 (m, 2 H), 6.30 (dd, 1 H), 6.13 (s, 1 H), 5.96 (dd, 1 H), 5.91 (dd, 1 H), 5.54-5.78 (m, 1 H), 5.52 (dd, 1 H), 4.01-4.25 (m, 1 H), 3.59 (d, 1 H), 3.46 (d, 1 H), 3.20-3.26 (m, 1 H), 3.03 (t, 1 H), 2.83 (d, 1 H), 2.56-2.70 (m, 1 H), 2.43 (d, 1 H), 2.21-2.37 (m, 1 H), 1.89-2.13 (m, 3 H), 1.51-1.76 (m, 3 H), 1.49 (s, 3 H), 1.41 (dd, 1 H), 0.96 (s, 3 H) LC-MS (ESI POS): 582.4 MH+ $[\alpha]_D^{25}$ + 84.15 (c0.26,CHCl3) |

Example 51

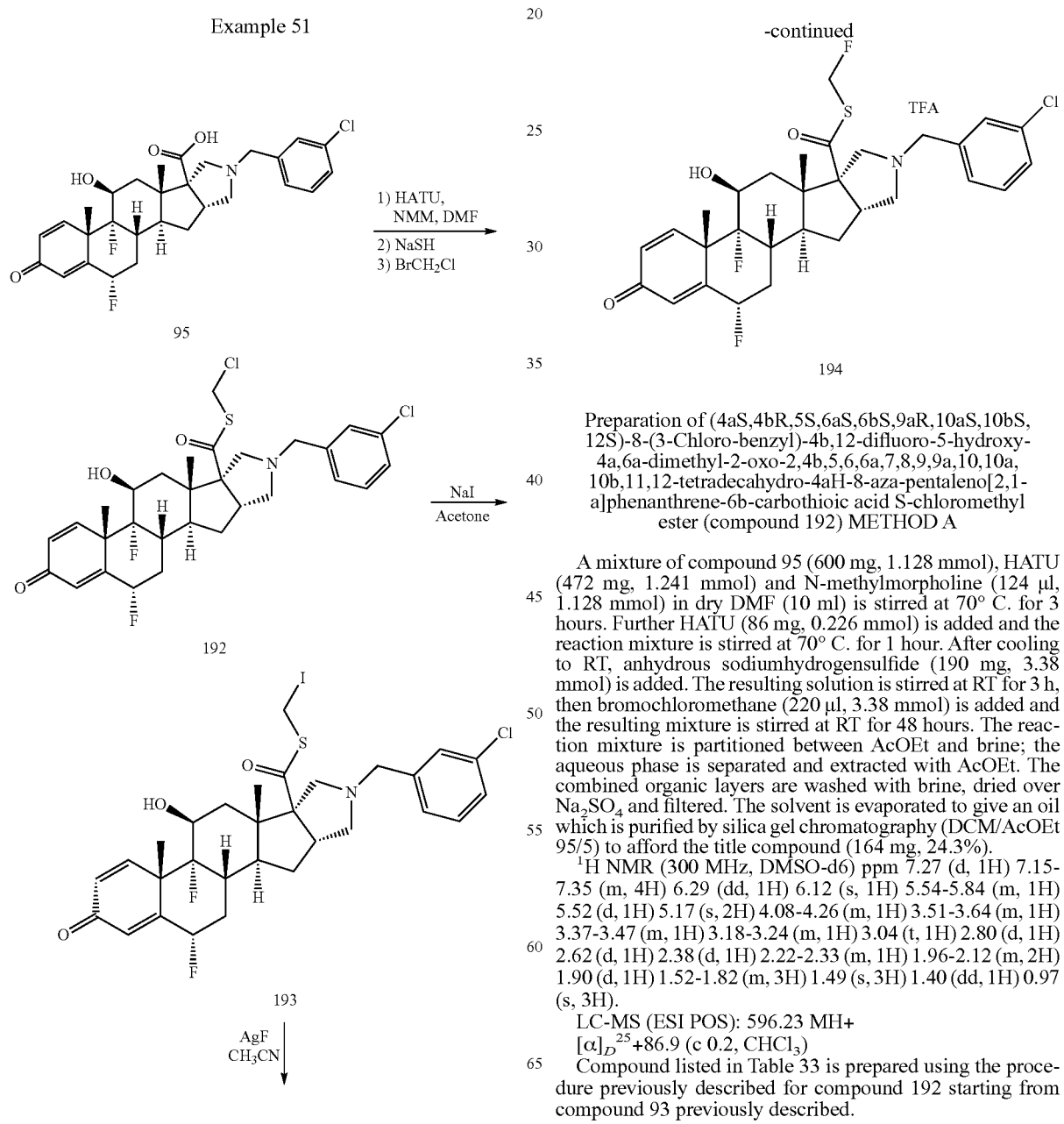

Preparation of (4aS,4bR,5S,6aS,6bS,9aR,10aS,10bS,12S)-8-(3-Chloro-benzyl)-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carbothioic acid S-chloromethyl ester (compound 192) METHOD A A mixture of compound 95 (600 mg, 1.128 mmol), HATU (472 mg, 1.241 mmol) and N-methylmorpholine (124 μl, 1.128 mmol) in dry DMF (10 ml) is stirred at 70° C. for 3 hours. Further HATU (86 mg, 0.226 mmol) is added and the reaction mixture is stirred at 70° C. for 1 hour. After cooling to RT, anhydrous sodiumhydrogensulfide (190 mg, 3.38 mmol) is added. The resulting solution is stirred at RT for 3 h, then bromochloromethane (220 μl, 3.38 mmol) is added and the resulting mixture is stirred at RT for 48 hours. The reaction mixture is partitioned between AcOEt and brine; the aqueous phase is separated and extracted with AcOEt. The combined organic layers are washed with brine, dried over Na₂SO₄ and filtered. The solvent is evaporated to give an oil which is purified by silica gel chromatography (DCM/AcOEt 95/5) to afford the title compound (164 mg, 24.3%).

¹H NMR (300 MHz, DMSO-d6) ppm 7.27 (d, 1H) 7.15-7.35 (m, 4H) 6.29 (dd, 1H) 6.12 (s, 1H) 5.54-5.84 (m, 1H) 5.52 (d, 1H) 5.17 (s, 2H) 4.08-4.26 (m, 1H) 3.51-3.64 (m, 1H) 3.37-3.47 (m, 1H) 3.18-3.24 (m, 1H) 3.04 (t, 1H) 2.80 (d, 1H) 2.62 (d, 1H) 2.38 (d, 1H) 2.22-2.33 (m, 1H) 1.96-2.12 (m, 2H) 1.90 (d, 1H) 1.52-1.82 (m, 3H) 1.49 (s, 3H) 1.40 (dd, 1H) 0.97 (s, 3H).

LC-MS (ESI POS): 596.23 MH+
$[\alpha]_D^{25}$+86.9 (c 0.2, CHCl₃)

Compound listed in Table 33 is prepared using the procedure previously described for compound 192 starting from compound 93 previously described.

TABLE 33

| Compound | Structure | Yield | Analytical |
|---|---|---|---|
| 195 | 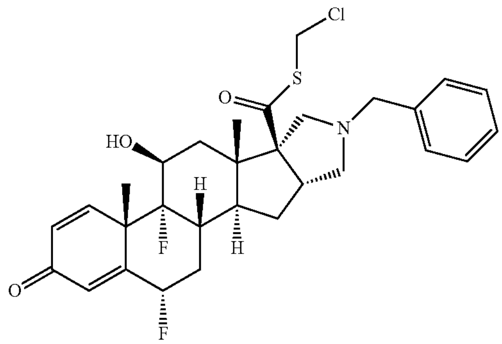 | 70% | LC-MS (ESI POS): 562.1 MH+ |

Preparation of (4aS,4bR,5S,6aS,6bS,9aR,10aS,10bS, 12S)-8-(3-Chloro-benzyl)-4b,12-difluoro-5-hydroxy-4a,6a-dimethyl-2-oxo-2,4b,5,6,6a,7,8,9,9a,10,10a, 10b,11,12-tetradecahydro-4aH-8-aza-pentaleno[2,1-a]phenanthrene-6b-carbothioic acid S-iodomethyl ester (compound 193)

A mixture of compound 192 (220 mg, 0.369 mmol) and sodium iodide (498 mg, 3.32 mmol) in acetone (20 ml) is stirred at reflux for 6 hours, at RT overnight, then at reflux for 8 hours, and at RT overnight. The reaction mixture is partitioned between AcOEt and a 5% solution of $Na_2S_2O_5$. The aqueous phase is extracted with AcOEt and the combined organic layers are washed with brine, dried over $Na_2SO_4$ and filtered. The solvent is evaporated affording the title compound (240 mg, 95% yield). The crude is not purified any further.

LC-MS (ESI POS): 596.23 MH+

Compound listed in Table 34 is prepared using the procedure previously described for compound 193 starting from compound 195 previously described.

Preparation of (4aS,4bR,5S,6aS,6bS,9aR,10aS,10bS, 12S)-8-(3-Chloro-benzyl)-4b,12-difluoro-5-hydroxy-4a,6a-dimethyl-2-oxo-2,4b,5,6,6a,7,8,9,9a,10,10a, 10b,11,12-tetradecahydro-4aH-8-aza-pentaleno[2,1-a]phenanthrene-6b-carbothioic acid S-fluoromethyl ester trifluoroacetate (compound 194)

A mixture of compound 193 (240 mg, 0.349 mmol) and AgF (89 mg, 0.698 mmol) in dry acetonitrile (15 ml) is stirred at RT in the dark under nitrogen for 1 hour and 30 minutes. The reaction mixture is decanted and the residual Ag salts are washed several times with dioxane. The organic layers are combined and the solvent is evaporated. The resulting crude is purified by preparative HPLC to give the title compound (20 mg, 0.029 mmol, 8.26% yield).

$^1$H NMR (300 MHz, DMSO-d6 Na2CO3) ppm 7.21-7.38 (m, 4H), 7.17 (dt, 1H), 6.29 (dd, 1H), 6.12 (s, 1H), 5.96 (dd, 1H), 5.90 (dd, 1H), 5.47-5.77 (m, 1H), 4.10-4.23 (m, 1H), 3.56 (d, 1H), 3.45 (d, 1H), 2.95-3.05 (m, 1H), 2.83 (d, 1H), 2.56-2.62 (m, 1H), 2.42 (d, 1H), 2.22-2.32 (m, 1H), 1.87-2.14 (m, 3H), 1.53-1.76 (m, 4H), 1.49 (s, 3H), 1.35-1.45 (m, 1H), 0.96 (s, 3H)

LC-MS (ESI POS): 580.27 MH+

TABLE 34

| Compound | Structure | Yield | Analytical |
|---|---|---|---|
| 196 | 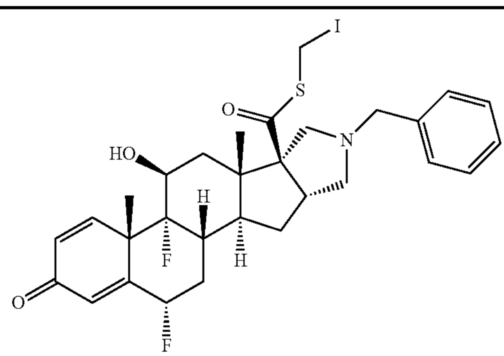 | 81 % | LC-MS (ESI POS): 654.2 MH+ |

Compound listed in Table 35 is prepared using the procedure previously described for compound 194 starting from compound 196 previously described. The reaction is quenched with HCl in dioxane before purification by preparative HPLC.

TABLE 35

| Compound | Structure | Yield | Analytical |
|---|---|---|---|
| 197 | 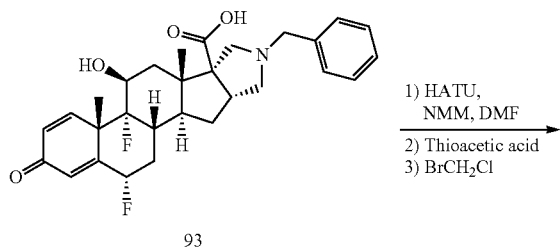 | 11% | $^1$H NMR (300 MHz, DMSO-d6) ppm 10.19 (br. s., 1 H) 7.32-7.62 (m, 5 H) 7.26 (d, 1 H) 6.32 (d, 1 H) 6.14 (s, 1 H) 5.96 (d, 2 H) 5.45-5.81 (m, 2 H) 4.27-4.66 (m, 2 H) 4.09-4.27 (m, 1 H) 3.53-4.01 (m, 3 H) 3.40-3.50 (m, 1 H) 2.78-3.12 (m, 1 H) 2.55-2.68 (m, 2 H) 2.23-2.40 (m, 1 H) 1.98-2.24 (m, 1 H) 1.92 (d, 1 H) 1.54-1.83 (m, 3 H) 1.50 (s, 3 H) 0.95 (s, 3 H) LC-MS (ESI POS): 546.3 MH+ |

Example 52

Preparation of (4aS,4bR,5S,6aS,6bS,9aR,10aS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carbothioic acid S-chloromethyl ester (compound 195) METHOD B A mixture of compound 93 (257 mg, 0.517 mmol), HATU (196 mg, 0.517 mmol) and N-methylmorpholine (56.8 μl, 0.517 mmol) in dry DMF (5 ml) is stirred at 70° C. under nitrogen for 1 hour. Further HATU (40 mg, 0.105 mmol) is added and the resulting mixture is stirred at 70° C. for 30 minutes. The solution is cooled to RT and it is poured into a solution of thioacetic acid (74.2 μl, 1.033 mmol) in dry DMF (2 ml). The resulting solution is stirred at RT under nitrogen for 2 hours. Potassium thioacetate (59.0 mg, 0.517 mmol) is added and the mixture is stirred at RT for 2 hours. NaHCO$_3$ (87 mg, 1.033 mmol) and bromochloromethane (101 μl, 1.550 mmol) are added. The resulting mixture is stirred at RT under nitrogen overnight. The reaction mixture is partitioned between AcOEt and brine; the aqueous phase is extracted with AcOEt and the combined organic layers are washed with brine, dried over Na$_2$SO$_4$ and filtered. The solvent is evaporated and the crude is purified by silica gel chromatography (AcOEt/petroleum ether 3/7) to give a solid which is further triturated with petroleum ether to afford the title compound (32 mg, 10.9%).

$^1$H NMR (300 MHz, DMSO-d6) ppm 7.08-7.47 (m, 6H) 6.29 (dd, 1H) 6.12 (s, 1H) 5.54-5.77 (m, 1H) 5.52 (d, 1H) 5.17 (s, 2H) 4.03-4.24 (m, 1H) 3.55 (d, 1H) 3.41 (d, 1H) 3.18-3.24 (m, 1H) 3.02 (t, 1H) 2.79 (d, 1H) 2.61-2.69 (m, 1H) 2.31-2.44 (m, 1H) 2.28 (s, 1H) 1.83-2.14 (m, 3H) 1.51-1.76 (m, 3H) 1.49 (s, 3H) 1.33-1.45 (m, 1H) 0.97 (s, 3H).

LC-MS (ESI POS): 562.18 MH+

$[\alpha]_D^{25}$ +94.48 (c 0.29, MeOH)

Example 53

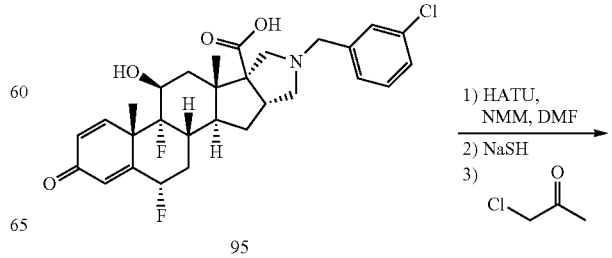

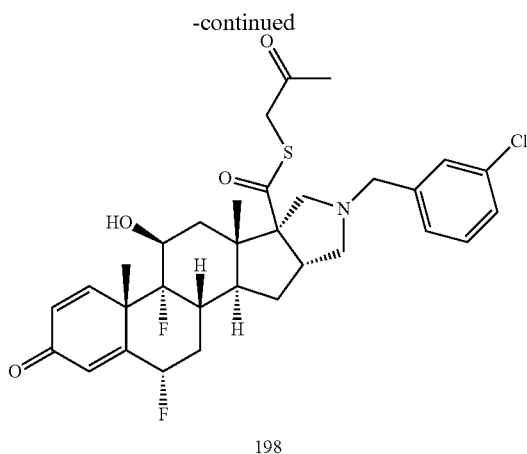

198

Preparation of (4aS,4bR,5S,6aS,6bS,9aR,10aS,10bS, 12S)-8-(3-Chloro-benzyl)-4b,12-difluoro-5-hydroxy-4a,6a-dimethyl-2-oxo-2,4b,5,6,6a,7,8,9,9a,10,10a, 10b,11,12-tetradecahydro-4aH-8-aza-pentaleno[2,1-a]phenanthrene-6b-carbothioic acid S-(2-oxo-propyl) ester (compound 198)

A mixture of compound 95 (200 mg, 0.376 mmol), HATU (172 mg, 0.451 mmol) and N-methylmorpholine (41.3 µl, 0.376 mmol) in dry DMF (4 ml) is stirred at 70° C. for 1 hour; after cooling to RT anhydrous sodiumhydrogensulfide (63.2 mg, 1.128 mmol) is added and the mixture is stirred at RT for 3 hours. Chloroacetone (60.0 µl, 0.752 mmol) is added and a solid precipitates immediately. The mixture is partitioned between AcOEt and brine. The aqueous phase is extracted with AcOEt and then the combined organic layers are washed with brine, dried over $Na_2SO_4$ and filtered. The solvent is evaporated to give a oil which is purified by silica gel chromatography (AcOEt/petroleum ether 2/3) and then triturated with AcOEt and petroleum ether (1/9 mixture) to afford the title compound (140 mg, 61.6% yield).

$^1$H NMR (300 MHz, DMSO-d6) ppm 7.01-7.42 (m, 5H), 6.29 (dd, 1H), 6.12 (s, 1H), 5.52-5.79 (m, 1H), 5.50 (dd, 1H), 4.09-4.22 (m, 1H), 3.85 (s, 2H), 3.56 (d, 1H), 3.42 (d, 1H), 3.13-3.24 (m, 1H), 2.98 (t, 1H), 2.80 (d, 1H), 2.55-2.67 (m, 1H), 2.42 (d, 1H), 2.23-2.34 (m, 1H), 2.20 (s, 3H), 1.85-2.13 (m, 3H), 1.53-1.77 (m, 3H), 1.49 (s, 3H), 1.38 (dd, 1H), 0.96 (s, 3H)

LC-MS (ESI POS): 604.27 MH+

$[\alpha]_D^{25}$+79.04 (c 0.23, MeOH)

Compounds listed in Table 36 are prepared by the procedure previously described for compound 198 starting from the proper carboxylic acid previously described (93, 95) and using the suitable commercially available alkylhalide as the alkylating agent (for 201 alkylation occurs in the presence of $NaHCO_3$).

TABLE 36

| Compound | Structure | Yield | Analytical |
|---|---|---|---|
| 199 | 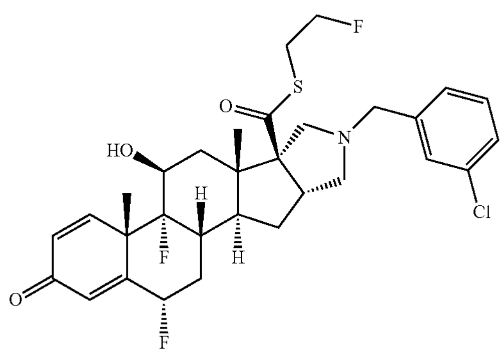 | 33% | $^1$H NMR (300 MHz, DMSO-d6) ppm 7.10-7.41 (m, 5 H), 6.29 (dd, 1 H), 6.12 (s, 1 H), 5.51-5.80 (m, 1 H), 5.49 (dd, 1 H), 4.50 (dt, 2 H), 4.07-4.25 (m, 1 H), 3.58 (d, 1 H), 3.41 (d, 1 H), 3.15-3.26 (m, 3 H), 3.00 (t, 1 H), 2.81 (d, 1 H), 2.55-2.69 (m, 1 H), 2.39 (d, 1 H), 2.20-2.34 (m, 1 H), 1.87-2.13 (m, 3 H), 1.60-1.79 (m, 2 H), 1.53-1.61 (m, 1 H), 1.49 (s, 3 H), 1.35-1.44 (m, 1 H), 0.95 (s, 3 H)<br>LC-MS (ESI POS): 594.25 MH+<br>$[\alpha]_D^{25}$ +93.57 (c 0.23, CHCl3) |
| 200 | 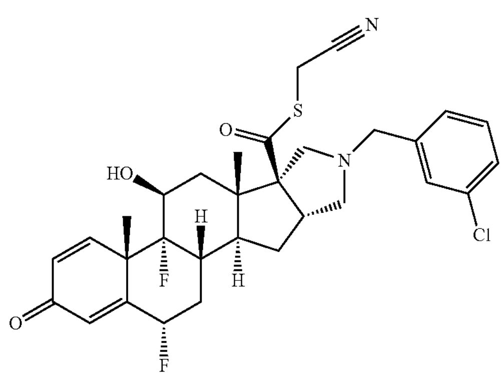 | 65% | $^1$H NMR (300 MHz, DMSO-d6) ppm 7.21-7.37 (m, 4 H), 7.16-7.22 (m, 1 H), 6.29 (dd, 1 H), 6.12 (s, 1 H), 5.54 (dd, 1 H), 5.50-5.78 (m, 1 H), 4.10-4.25 (m, 1 H), 4.03 (s, 2 H), 3.57 (d, 1 H), 3.44 (d, 1 H), 3.18-3.25 (m, 1 H), 3.04 (t, 1 H), 2.81 (d, 1 H), 2.56-2.68 (m, 1 H), 2.40 (d, 1 H), 2.21-2.34 (m, 1 H), 1.95-2.14 (m, 2 H), 1.90 (d, 1 H), 1.52-1.77 (m, 3 H), 1.49 (s, 3 H), 1.41 (dd, 1 H), 0.97 (s, 3 H)<br>LC-MS (ESI POS): 587.17 MH+<br>$[\alpha]_D^{25}$ + 63.05 (c 0.21, MeOH) |

TABLE 36-continued

| Compound | Structure | Yield | Analytical |
|---|---|---|---|
| 201 | 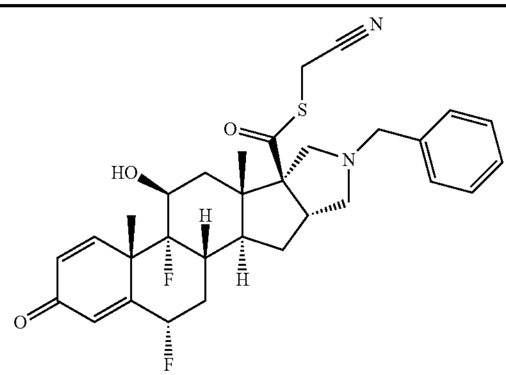 | 22% | $^1$H NMR (300 MHz, DMSO-d6) ppm 7.08-7.44 (m, 6 H) 6.29 (dd, 1 H) 6.13 (s, 1 H) 5.56-5.80 (m, 1 H) 5.53 (d, 1 H) 4.14 (d, 1 H) 4.02 (s, 2 H) 3.55 (d, 1 H) 3.42 (d, 1 H) 3.13-3.24 (m, 1 H) 3.05 (t, 1 H) 2.81 (d, 1 H) 2.60-2.67 (m, 1 H) 2.37 (d, 1 H) 2.24-2.32 (m, 1 H) 1.97-2.12 (m, 2 H) 1.90 (d, 1 H) 1.53-1.80 (m, 3 H) 1.49 (s, 3 H) 1.34-1.46 (m, 1 H) 0.97 (s, 3 H) LC-MS (ESI POS): 553.22 MH+ $[\alpha]_D^{25}$ + 101.0 (c 0.23, MeOH) |

Example 54

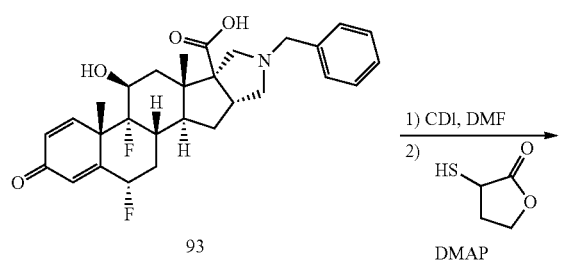

Preparation of (4aS,4bR,5S,6aS,6bS,9aR,10aS,10bS,12S)-8-Benzyl-4b,12-difluoro-5-hydroxy-4a,6a-dimethyl-2-oxo-2,4b,5,6,6a,7,8,9,9a,10,10a,10b,11,12-tetradecahydro-4aH-8-aza-pentaleno[2,1-a]phenanthrene-6b-carbothioic acid S-(2-oxo-tetrahydro-furan-3-yl) ester (compound 202)

A solution of compound 93 and 1,1-carbonyldiimidazole (74.3 mg, 0.458 mmol) in dry DMF (3 ml) is stirred under nitrogen at RT for 1 hour and at 65° C. for 1 hour 30 minutes. The mixture is cooled to RT and 4-dimethylaminopyridine (46.7 mg, 0.382 mmol) and a solution of 3-mercaptodihydrofuran-2(3H)-one (54.1 mg, 0.458 mmol) in dry DMF (1.2 ml) are added. The mixture is stirred at RT for 1 hour then at 70° C. for 48 hours. The mixture is diluted with AcOEt and washed with brine. The organic phase is dried over Na$_2$SO$_4$ and filtered. The solvent is evaporated to give a brown oil which is purified by silica gel chromatography (AcOEt/petroleum ether 45/55) to afford the title compound (30 mg, 0.050 mmol, 13.14% yield).

$^1$H NMR (300 MHz, DMSO-d6) ppm 7.10-7.39 (m, 6H), 6.29 (dd, 1H), 6.12 (s, 1H), 5.54-5.80 (m, 1H), 5.48-5.54 (m, 1H), 4.23-4.50 (m, 3H), 4.08-4.19 (m, 1H), 3.57 (d, 1H), 3.39 (d, 1H), 3.12-3.25 (m, 1H), 3.00 (t, 1H), 2.79 (d, 1H), 2.60-2.71 (m, 1H), 2.32-2.44 (m, 1H), 2.09-2.32 (m, 3H), 1.82-2.12 (m, 3H), 1.52-1.78 (m, 3H), 1.49 (s, 3H), 1.32-1.44 (m, 1H), 0.98 and 0.99 (s, 3H)

LC-MS (ESI POS): 598.27 MH+

Compound listed in Table 37 is prepared by the procedure previously described for compound 202 using the commercially available sodiumethanthiolate (DMAP is not used in this case).

TABLE 37

| Compound | Structure | Yield | Analytical |
|---|---|---|---|
| 203 | 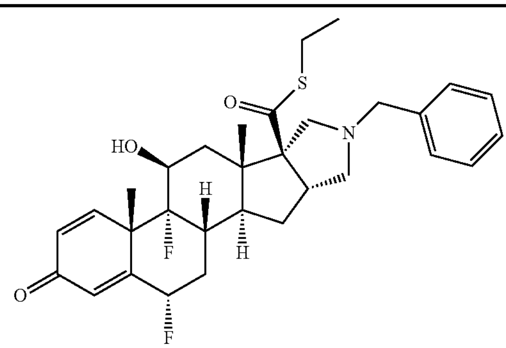 | 15% | $^1$H NMR (300 MHz, DMSO-d6) ppm 7.08-7.34 (m, 6 H), 6.29 (dd, 1 H), 6.12 (s, 1 H), 5.50-5.80 (m, 1 H), 5.47 (br. s., 1 H), 4.09-4.23 (m, 1 H), 3.52 (d, 1 H), 3.40 (d, 1 H), 3.16-3.25 (m, 1 H), 2.95 (t, 1 H), 2.85 (qd, 2 H), 2.77 (d, 1 H), 2.38 (d, 1 H), 2.21-2.33 (m, 1 H), 1.98-2.10 (m, 2 H), 1.95 (d, 1 H), 1.51-1.72 (m, 4 H), 1.49 (s, 3 H), 1.37 (dd, 1 H), 1.19 (t, 3 H), 0.94 (s, 3 H) LC-MS (ESI POS): 542.12 MH+ $[\alpha]_D^{25}$ + 93.8 (MeOH, c 0.3) |

Legend
*NMR
s = singlet
d = doublet
t = triplet
q = quartet
dd = doublet of doublets
m = multiplet
br = broad Pharmacological Activity of the Compounds of the Invention In Vivo Studies Example 55

Lipopolysaccharide (LPS)-Induced Lung Neutrophilia

The potency of the compounds described in the present invention was evaluated in vivo in an acute model of lung inflammation following a method described by A. Miller-Larsson and coworkers (*Am. J. Respir. Crit. Care Med.*, vol 162. pp, 1455-1461, 2000, which is incorporated herein by reference in its entirety) with minor modifications. The tests were performed on Sprague-Dawley male rats (200 g). Intratracheal instillation of LPS resulted in a statistically significant increase in neutrophil concentration in BALF, a hallmark of acute ongoing pulmonary inflammation.

For the dose of glucocorticoid producing a 75% inhibition (ED75 dose) assessment test, compounds (0.01-3 μmoles/Kg of body weight) were administered intratracheally as suspension (0.2% Tween 80 in NaCl 0.9%) 1 hour before LPS challenge. A dose-response curve of the inhibitory effect of the test compounds on LPS-induced lung neutrophilia was performed and the ED75 dose of glucocorticoid was taken as a measure of potency in this bioassay. The ED75 dose values for the most potent compounds described in this patent are comprised between 0.2 and 1.5 μmoles/Kg of body weight.

In Vitro Studies

Example 56

Glucocorticoid Receptor (GR) Translocation Assay Protocol

A quantitative measurement of GR nuclear translocation of the compounds of the present invention was performed according to *ASSAY Drug Devel. Technol.*, 4(3), 263-272, 2006, which is incorporated herein by reference in its entirety, through a novel cell-based GR-translocation assay in Enzyme Fragment Complementation (EFC) format developed by DiscoveRx (Fremont, Calif.). The DiscoveRx assay uses EFC of b-galactosidase (b-gal) as an indicator of GR-translocation in engineered CHO-K1 biosensor cells. The enzyme acceptor (EA) fragment of b-gal resides in the nucleus, as designed through the use of a proprietary set of sequence additions and modifications. The small peptide enzyme donor (ED) fragment of b-gal is fused directly to the C-terminus of GR, and is localized in the cytoplasm is the absence of receptor signaling. Upon binding to a GR ligand, the complex translocates to the nucleus, where intact enzyme activity is restored by complementation and b-gal activity is detected.

CHO-K1 cells stably expressing NLS-enzyme acceptor fragment (EA) of b-gal and GR-enzyme donor (ED) fragment of b-gal were maintained in F12 medium (Invitrogen, Carlsbad, Calif.) at 37° C. under a humidified atmosphere containing 5% $CO_2$ and 95% air. The medium contained 10% FBS, 2 mM L-glutamine, 50 U/ml penicillin 50 μg/ml streptomycin, and 250 μg/ml hygromycin and 500 μg/ml G418 (Invitrogen).

GR-translocation was measured using the PathHunter Detection Kit containing cell membrane permeabilizing reagent and beta-gal substrate (DiscoveRx, Fremont, Calif.). All compounds were screened using varying concentrations ranging from $10^{-11}$ to $10^{-6}$ M. The assay was performed in 48-wells (105 cells/well). Incubation with screened compounds was performed at 37° C. for two hours. Detection was made by adding the detection buffer from the kit supplied by DiscoveRx and incubating at RT for one hour. Luminescence was detected by using a CENTRO LB 960 microplate reader (Berthold Technologies). Statistical analysis and determinations of EC50s were performed by using Prism-version 3.0 Graphpad Software (San Diego, Calif.). The compounds assayed with the GR translocation assay displayed a EC50 comprised between 1 nM and 20 nM.

Example 57

Inhibition of LPS-Induced Nitric Oxide Production in RAW 264.7 Macrophages

An in vitro model based on macrophagic murine cell line RAW 264.7 was used for testing the anti-inflammatory effects of the corticosteroids of the present invention. During the inflammatory process, large amounts of nitric oxide (NO) are generated by the inducible isoforms of NO synthase (iNOS). Bacterial lipopolysaccharide (LPS) is commonly used in experimental settings to stimulate inflammatory responses in macrophages.

Cells were grown in a culture medium (RPMI supplemented with heat-inactivated 10% fetal calf serum, 2 mM glutamine, 100 U/ml penicillin and 0.1 mg/ml streptomycin) without phenol red. Cell stimulation was elicited by incubating cells for 24 hours with LPS to final concentrations ranging from 100 ng/ml. Treatments with the compounds of the invention were carried out by adding such compounds vehicled in DMSO (0.1% final concentration) to the final desired concentrations 15 minutes before LPS exposure. As an index of nitric oxide production, the concentration of nitrite was measured in the conditioned media by using the Griess colorimetric reaction (*J. Neuroimmunol.*, 150, 29-36, 2004, which is incorporated herein by reference in its entirety). Statistical analysis and determinations of IC50s were performed by using Prism-version 3.0 Graphpad Software (San Diego, Calif.). The IC50 values tested on the compounds of the invention are comprised between 0.2 and 20 nM.

Kinetic Characterisation: Lung Retention.

Lung retention was measured by means of two parameters: the $MRT_L$ (Mean Residence Time in the Lung), i.e. the residence of the compound in the lung, which is the time of the last measurable concentration of the compound in the rat lung after intratracheal administration of 1 µmol/kg, determined after lung homogenization, and the $C_{48}L/C_{0.5}L$ (%), i.e. the percentage of the amount of the compound in the lung 48 hours after intratracheal administration vs the amount the same compound in the lung 0.25 hours after administration. $MRT_L$ and $C_{48}L/C_{0.5}L$ (%) are two meaningful and predictive parameters of the duration of a drug's effect after single dose pulmonary administration. The compounds of the invention showed very slow lung elimination with $MRT_L$ higher than 20 hours and $C_{48}L/C_{0.5}L$ higher than 20%.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

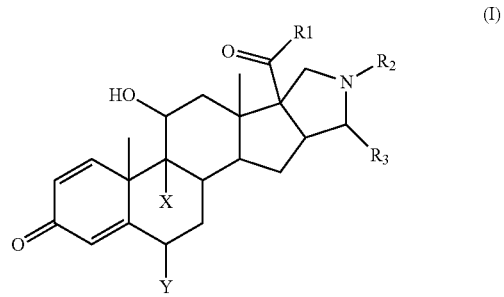

wherein:
$R_1$ is $(CH_2)_n$—V—$(CH_2)_{n'}$—Z—$R_4$, wherein:
  n and n' are independently 0, 1 or 2;
  V is absent or is selected from the group consisting of —O—, —S—, —OCOO, and NH;
  Z is a single bond or is selected from the group consisting of —S—, —O—, carbonyl, carboxyl, $(C_3-C_8)$ cycloalkyl, —$NR_5$—, and —$NR_5C(O)$—, wherein $R_5$ is H or is selected from the group consisting of $(C_1-C_6)$alkyl, $(C_3-C_8)$cycloalkyl, aryl, aryl$(C_1-C_6)$alkyl, aryl$(C_3-C_8)$cycloalkylene and heteroaryl, optionally substituted by CN;
$R_4$ is:
  —H, —OH, —CN, —SH, halogen,
  $(C_1-C_6)$alkyl, $(C_1-C_6)$alkylsulfonyl, $(C_1-C_6)$alkylcarboxyl, $(C_1-C_6)$alkylcarbonyl and $(C_3-C_8)$cycloalkyl, wherein one or more of the hydrogen atoms of the alkyl groups may be optionally substituted by one or more groups selected from oxo, —CN, —SH or halogen; or
  a mono-, bi- or tricyclic saturated, partially saturated or fully unsaturated ring, optionally substituted by one or more halogen atoms or oxo groups; and wherein when $R_4$ and $R_5$ are both $(C_1-C_6)$alkyl, they may form a 4-8 membered heterocycle together with the nitrogen atom to which they are bonded;
$R_2$ is $(CH_2)_m$—W—W'—$R_6$, wherein:
  m=0 or 1 to 6;
  W is a single bond or is selected from the group consisting of —S—, —O—, carbonyl, and thiocarbonyl;
  W' is absent, NH or arylene group;
  M is absent or is selected from the group consisting of $(C_1-C_6)$alkylsulfanyl, $(C_1-C_6)$alkylsulfonyl and $(C_1-C_6)$alkylsulfinyl;
$R_6$ is:
  H;
  $(C_1-C_6)$alkyl;
  a mono-, bi- or tricyclic saturated, partially unsaturated or fully unsaturated ring, having 3 to 10 ring atoms, and optionally containing at least one ring atom which is selected from the group consisting of N, NH, S, and O and wherein any of the above rings is optionally substituted by one or more groups selected from oxo, OH, CN, COOH, $(C_1-C_6)$ alkoxy, halo$(C_1-C_6)$alkoxy, aryl$(C_1-C_6)$alkyl, $(C_1-C_6)$alkyl, halo$(C_1-C_6)$alkyl, cyano, OCO$(C_1-C_6)$ alkyl and halogen;
  —$OR_7$
  —$OCOR_7$

—COR$_7$
—COOR$_8$
—CONR$_9$R$_{10}$
—CSNR$_9$R$_{10}$
—S(O)$_2$R$_{11}$ wherein R$_7$, R$_8$ and R$_{11}$ are independently selected from the group consisting of (C$_1$-C$_6$)alkyl, (C$_2$-C$_6$)alkenyl, (C$_3$-C$_8$)cycloalkyl, (C$_1$-C$_6$)alkylaryl, aryl(C$_1$-C$_6$)alkyl and a saturated, partially unsaturated or fully unsaturated optionally fused ring having 3 to 10 ring atoms and optionally containing at least one ring atom which is selected from the group consisting of N, NH, S, and O, which groups may be optionally substituted with one or more substituents selected from the group consisting of halogen, cyano, nitro, (C$_1$-C$_6$)alkyl, aryl, heteroaryl, hydroxy, amino and alkoxy; and wherein R$_9$ and R$_{10}$ are independently selected from the group consisting of H, (C$_1$-C$_6$)alkyl, (C$_3$-C$_8$)cycloalkyl, aryl (C$_1$-C$_6$)alkyl and a saturated, partially unsaturated or fully unsaturated optionally fused ring having 3 to 10 ring atoms and optionally containing at least one ring atom which is selected from the group consisting of N, NH, S and O, which groups may be optionally substituted with one or more substituents selected from the group consisting of halogen, cyano, nitro, (C$_1$-C$_6$) alkyl, and hydroxyl, and when R$_9$ and R$_{10}$ are both (C$_1$-C$_6$)alkyl, they may form a 4-8 membered heterocycle together with the nitrogen atom to which they are bonded;

R$_3$ is selected from the group consisting of:
H;
aryl;
C(O)OR$_{12}$ wherein R$_{12}$ is selected from the group consisting of H, (C$_1$-C$_6$)alkyl, (C$_3$-C$_8$)cycloalkyl, aryl and heteroaryl;
C(O)NR$_{13}$R$_{14}$ wherein R$_{13}$ and R$_{14}$ are independently selected from the group consisting of H, (C$_1$-C$_6$)alkyl, (C$_3$-C$_8$)cycloalkyl, aryl(C$_1$-C$_6$)alkyl and a saturated, partially unsaturated or fully unsaturated optionally fused ring having 3 to 10 ring atoms and optionally containing at least one ring atom selected from the group consisting of N, NH, S and O, which groups may be optionally substituted with one or more substituents selected from the group consisting of halogen, cyano, nitro, (C$_1$-C$_6$)alkyl, and hydroxy and when R$_{13}$ and R$_{14}$ are both (C$_1$-C$_6$)alkyl, they may form a 4-8 membered heterocycle together with the nitrogen atom to which they are bonded;

X and Y are independently selected from the group consisting of H and halogen;
or a pharmaceutically acceptable salt thereof.

2. A compound or pharmaceutically acceptable salt according to claim 1, represented by formula (I'),

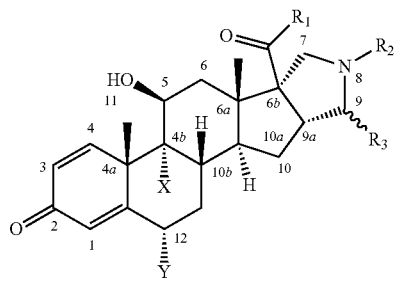

(I')

wherein the configuration of the carbon atom in position 5 is S, in position 6a is S, in position 6b is S, in position 9a is R, in position 10a is S, in position 10b is S, in position 4a is S when X is halogen or 4a is R when X is hydrogen, in position 4b is R when X is halogen or 4b is S when X is hydrogen and in position 12 is S when X is halogen, and wherein the symbol represents an unspecified bond, which indicates an asymmetric carbon atom in position 9, wherein the configuration may be R or S, and wherein the values of R$_1$, R$_2$, R$_3$, X and Y are as defined in claim 1.

3. A compound or pharmaceutically acceptable salt according to claim 1, wherein:
R$_1$ is (CH$_2$)$_n$—V—(CH$_2$)$_{n'}$—Z—R$_4$, wherein:
n and n' are independently 0, 1 or 2;
V is absent or is selected from the group consisting of —O—, —S—, —OCOO and —NH;
Z is a single bond or is selected from the group consisting of O, carbonyl, carboxyl, (C$_3$-C$_8$)cycloalkyl, —S— and —NR$_5$, wherein R$_5$ is selected from the group consisting of H, (C$_1$-C$_6$)alkyl, (C$_3$-C$_8$)cycloalkyl, aryl, aryl(C$_1$-C$_6$)alkyl, aryl(C$_3$-C$_8$)cycloalkyl and heteroaryl, optionally substituted by CN;
R$_4$ is selected from the group consisting of H, CN, OH, COR$_8$, halogen, (C$_1$-C$_6$)alkyl, aryl and hetero(C$_3$-C$_8$) cycloalkyl which may be optionally substituted by one or more halogen atoms or oxo and wherein R$_8$ is (C$_1$-C$_6$)alkyl optionally substituted by halogen;
R$_2$ is (CH$_2$)$_m$—W—W'-M-R$_6$, wherein:
m=0 to 4;
W is a single bond or is selected from the group consisting of —O—, carbonyl or thiocarbonyl;
W' is absent, NH or is aryl;
M is absent or is selected from the group consisting of (C$_1$-C$_6$)alkylsulfanyl and (C$_1$-C$_6$)alkylsulfinyl;
R$_6$ is selected from the group consisting of H, linear or branched (C$_1$-C$_6$)alkyl, (C$_3$-C$_8$)cycloalkyl, hetero (C$_3$-C$_8$)cycloalkyl, aryl and heteroaryl, wherein (C$_3$-C$_8$)cycloalkyl, hetero(C$_3$-C$_8$)cycloalkyl, aryl and heteroaryl are optionally substituted by one or more groups selected from halogen atoms, oxo, OH, CN, COOH, (C$_1$-C$_6$)alkoxy, halo(C$_1$-C$_6$)alkoxy, aryl(C$_1$-C$_6$)alkyl, (C$_1$-C$_6$)alkyl, halo(C$_1$-C$_6$)alkyl, —OCO (C$_1$-C$_6$)alkyl or halogen; —OR$_7$, —OCOR$_7$, —COR$_7$, —COOR$_8$, —CONR$_9$R$_{10}$, —CSNR$_9$R$_{10}$, —S(O)$_2$R$_{11}$ wherein R$_7$, R$_8$ and R$_{11}$ are independently selected from the group consisting of (C$_1$-C$_6$) alkyl, (C$_2$-C$_6$)alkenyl, (C$_3$-C$_8$)cycloalkyl, aryl(C$_1$-C$_6$)alkyl, (C$_1$-C$_6$)alkylheteroaryl, aryl, hetero(C$_3$-C$_8$) cycloalkyl and heteroaryl having 3 to 10 ring atoms wherein at least one ring atom is a heteroatomic group selected from the group consisting of N, NH, S, and O, which groups may be optionally substituted with one or more substituents selected from the group consisting of halogen and (C$_1$-C$_6$)alkyl; R$_9$ and R$_{10}$ are independently selected from the group consisting of (C$_1$-C$_6$)alkyl and (C$_3$-C$_8$)cycloalkyl;
R$_3$ is selected from the group consisting of H and C(O) OR$_{12}$ wherein R$_{12}$ is H or (C$_1$-C$_6$)alkyl;
X and Y are independently selected from the group consisting of H and fluorine.

4. A compound or pharmaceutically acceptable salt according to claim 1, wherein:
R$_1$ is (CH$_2$)$_n$—V—(CH$_2$)$_{n'}$—Z—R$_4$, wherein:
n=1,
n'=0,
Z is —O—,
R$_4$ is (C$_1$-C$_6$)alkylcarbonyl or (C$_1$-C$_6$)alkylcarboxyl;

$R_2$ is $(CH_2)_m$—W—W'-M-$R_6$, wherein:
  m=0 or 1,
  W is a bond, carbonyl or thiocarbonyl,
  W' and M are absent,
  $R_6$ is H, ($C_1$-$C_6$)alkyl, ($C_3$-$C_8$)cycloalkyl, aryl, heteroaryl, or —$OR_7$, wherein $R_7$ is ($C_1$-$C_6$)alkyl or ($C_1$-$C_6$)alkylaryl.

5. A compound or pharmaceutically acceptable salt according to claim 1, wherein:
$R_1$ is $(CH_2)_n$—V—$(CH_2)_{n'}$—Z—$R_4$, wherein:
  n=1,
  n'=0,
  V is absent,
  Z is —O— and
  $R_4$ is ($C_1$-$C_6$)alkylcarbonyl;
$R_2$ is $(CH_2)_m$—W—W'-M-$R_6$, wherein:
  m=0,
  W is carbonyl,
  $R_6$ is —$OR_7$, wherein $R_7$ is ($C_1$-$C_6$)alkylaryl, and
  W' and M are absent.

6. A compound or pharmaceutically acceptable salt according to claim 1, wherein $R_1$ is $(CH_2)_n$—Z—$R_4$, wherein:
  n=0,
  Z is —O—,
  and $R_4$ is ($C_1$-$C_6$)alkyl, wherein one or more hydrogen atoms are substituted by halogen.

7. A compound or pharmaceutically acceptable salt according to claim 1, wherein:
$R_2$ is $(CH_2)_m$—W—W'-M-$R_6$, wherein:
  m=1,
  W is a single bond,
  W' is aryl,
  M is ($C_1$-$C_6$)alkylsulfanyl or ($C_1$-$C_6$)alkylsulfinyl, and
  $R_6$ is aryl optionally substituted by OH.

8. A compound or pharmaceutically acceptable salt according to claim 1, wherein:
$R_1$ is $(CH_2)_n$—V—$(CH_2)_n$—Z—$R_4$, wherein:
  n and n'=0,
  V is absent,
  Z is —O—, and
  $R_4$ is ($C_1$-$C_6$)alkyl, wherein one or more hydrogen atoms are substituted by halogen.

9. A compound or pharmaceutically acceptable salt according to claim 1, wherein:
$R_1$ is $(CH_2)_n$—V—$(CH_2)_n$—Z—$R_4$, wherein:
  n and n'=0,
  V is absent, and
  Z is —$NR_5$, wherein $R_5$ is H or is selected from the group consisting of ($C_1$-$C_6$)alkyl, ($C_3$-$C_8$)cycloalkyl, aryl, aryl($C_1$-$C_6$)alkyl, aryl($C_3$-$C_8$)cycloalkyl, and heteroaryl, optionally substituted by CN.

10. A pharmaceutical composition, comprising a compound or pharmaceutically acceptable salt as defined in claim 1 and one or more pharmaceutically acceptable carriers and/or excipients.

11. A combination comprising a compound or pharmaceutically acceptable salt as defined in claim 1 and one or more active ingredients selected from the group of a β2-agonist, an antimuscarinic agent, a PDE4 inhibitor, a P38 MAP kinase inhibitor, and an IKK2 inhibitor.

12. A device, comprising a pharmaceutical composition according to claim 10, wherein said device is a single-dose dry powder inhaler, a multi-dose dry powder inhaler, a metered dose inhaler, or a soft mist inhaler.

13. A method for the treatment of a disease selected from the group consisting of asthma and chronic obstructive pulmonary disease, comprising administering to a subject in need thereof an effective amount of a compound or pharmaceutically acceptable salt according to claim 1.

14. A method according to claim 13, wherein said disease is asthma.

15. A method according to claim 13, wherein said disease is chronic obstructive pulmonary disease.

\* \* \* \* \*